(12) United States Patent
Cutshall et al.

(10) Patent No.: US 12,110,288 B2
(45) Date of Patent: Oct. 8, 2024

(54) MASP-2 INHIBITORS AND METHODS OF USE

(71) Applicant: Omeros Corporation, Seattle, WA (US)

(72) Inventors: Neil S. Cutshall, Snohomish, WA (US); Jennifer Lynn Gage, Kenmore, WA (US); Do Yeon Kwon, Seattle, WA (US); Thomas L Little, Seattle, WA (US); Markus Metz, Bellevue, WA (US); Peter Kurt Nollert von Specht, Bainbridge Island, WA (US); Jennifer Tsoung, Seattle, WA (US); Jeremiah H. Nguyen, Kent, WA (US); Melinda Davis, Seattle, WA (US); Robert Huerta Lemus, Seattle, WA (US); Santosh Kumar Keshipeddy, Bellevue, WA (US); Sara Rebecca Goldstein, Seattle, WA (US)

(73) Assignee: Omeros Corporation, Seattle, WA (US)

( * ) Notice: Subject to any disclaimer, the term of this patent is extended or adjusted under 35 U.S.C. 154(b) by 319 days.

(21) Appl. No.: 17/112,906

(22) Filed: Dec. 4, 2020

(65) Prior Publication Data
US 2021/0179612 A1 Jun. 17, 2021

Related U.S. Application Data

(60) Provisional application No. 62/943,599, filed on Dec. 4, 2019.

(51) Int. Cl.
| | | |
|---|---|---|
| C07D 471/04 | (2006.01) |
| A61K 31/495 | (2006.01) |
| A61K 31/497 | (2006.01) |
| C07D 239/545 | (2006.01) |
| C07D 401/12 | (2006.01) |
| C07D 401/14 | (2006.01) |
| C07D 403/12 | (2006.01) |
| C07D 405/14 | (2006.01) |
| C07D 491/048 | (2006.01) |
| C07D 495/04 | (2006.01) |
| C07D 519/00 | (2006.01) |

(52) U.S. Cl.
CPC ....... *C07D 471/04* (2013.01); *C07D 239/545* (2013.01); *C07D 401/12* (2013.01); *C07D 401/14* (2013.01); *C07D 403/12* (2013.01); *C07D 405/14* (2013.01); *C07D 491/048* (2013.01); *C07D 495/04* (2013.01); *C07D 519/00* (2013.01)

(58) Field of Classification Search
CPC ......... C07D 471/04; C07D 239/545; C07D 401/12; C07D 401/14; C07D 403/12; C07D 405/14; C07D 491/048; C07D 495/04; C07D 519/00; A61K 31/495; A61K 31/497
See application file for complete search history.

(56) References Cited

U.S. PATENT DOCUMENTS

| | | | |
|---|---|---|---|
| 4,331,647 A | 5/1982 | Goldberg |
| 4,816,567 A | 3/1989 | Cabilly et al. |
| 4,946,778 A | 8/1990 | Ladner |
| 5,211,657 A | 5/1993 | Yamada |
| 5,223,409 A | 6/1993 | Ladner |
| 5,403,484 A | 4/1995 | Ladner |
| 5,552,157 A | 9/1996 | Yagi |
| 5,565,213 A | 10/1996 | Nakamori |
| 5,567,434 A | 10/1996 | Szoka, Jr. |
| 5,571,698 A | 11/1996 | Ladner |
| 5,610,288 A | 3/1997 | Rubenstein |
| 5,693,762 A | 12/1997 | Queen |
| 5,718,709 A | 2/1998 | Considine |
| 5,738,868 A | 4/1998 | Shinkarenko |
| 5,739,119 A | 4/1998 | Galli |
| 5,741,516 A | 4/1998 | Webb |
| 5,759,829 A | 6/1998 | Shewmaker |
| 5,789,573 A | 8/1998 | Baker |
| 5,795,587 A | 8/1998 | Gao |
| 5,801,154 A | 9/1998 | Baracchini |
| 5,866,573 A | 2/1999 | Sanderson |
| 6,649,592 B1 | 11/2003 | Larson |
| 6,653,316 B1 | 11/2003 | South et al. |
| 7,015,230 B1 | 3/2006 | South et al. |
| 7,919,094 B2 | 4/2011 | Schwaeble et al. |
| 8,652,477 B2 | 2/2014 | Schwaeble et al. |
| 8,840,893 B2 | 9/2014 | Schwaeble et al. |
| 8,889,712 B2 | 11/2014 | Borzilleri et al. |

(Continued)

FOREIGN PATENT DOCUMENTS

| | | |
|---|---|---|
| AU | 2013201779 A1 | 4/2013 |
| CL | 202003083 | 5/2019 |

(Continued)

OTHER PUBLICATIONS

Ambrus et al., "Natural Substrates and Inhibitors of Mannan-Binding Lectin-Associated Serine Protease-1 and -2: A Study on Recombinant Catalytic Fragments," *J. Immunol.* 170:1374-1382, 2003.

(Continued)

*Primary Examiner* — Bruck Kifle
(74) *Attorney, Agent, or Firm* — Christensen O'Connor Johnson Kindness PLLC

(57) ABSTRACT

The present disclosure provides, inter alia, compounds with MASP-2 inhibitory activity, compositions of such compounds, and methods of making and using such compounds.

17 Claims, No Drawings

Specification includes a Sequence Listing.

(56) References Cited

U.S. PATENT DOCUMENTS

| | | |
|---|---|---|
| 8,951,522 B2 | 2/2015 | Demopulos et al. |
| 9,011,860 B2 | 4/2015 | Dudler et al. |
| 9,469,608 B2 | 10/2016 | Chobanian |
| 9,475,885 B2 | 10/2016 | Dudler et al. |
| 9,644,035 B2 | 5/2017 | Demopulos et al. |
| 11,299,479 B1 | 4/2022 | Ashcraft |
| 11,584,714 B2 | 2/2023 | Cutshall |
| 11,661,418 B2 | 5/2023 | Cutshall |
| 12,030,853 B2 | 7/2024 | Cutshall et al. |
| 2002/0019369 A1 | 2/2002 | Li |
| 2002/0119992 A1 | 8/2002 | Selnick et al. |
| 2004/0072862 A1 | 4/2004 | Bitler |
| 2005/0004031 A1 | 1/2005 | Subasinghe |
| 2006/0002937 A1 | 1/2006 | Schwaeble |
| 2007/0172483 A1 | 7/2007 | Schwaeble |
| 2013/0266560 A1 | 10/2013 | Demopulos et al. |
| 2013/0344073 A1 | 12/2013 | Schwaeble et al. |
| 2015/0166675 A1 | 6/2015 | Demopulos et al. |
| 2015/0315141 A1 | 11/2015 | Chobanian et al. |
| 2017/0137537 A1 | 5/2017 | Demopulos et al. |
| 2017/0166660 A1 | 6/2017 | Schwaeble et al. |
| 2017/0189525 A1 | 7/2017 | Brunskill et al. |
| 2017/0253667 A1 | 9/2017 | Brunskill et al. |
| 2017/0267781 A1 | 9/2017 | Demopulos et al. |
| 2017/0283508 A1 | 10/2017 | Demopulos et al. |
| 2018/0105604 A1 | 4/2018 | Brunskill et al. |
| 2019/0367452 A1 | 12/2019 | Cutshall |
| 2021/0171461 A1 | 6/2021 | Cutshall et al. |
| 2021/0171512 A1 | 6/2021 | Cutshall et al. |
| 2021/0171531 A1 | 6/2021 | Cicirelli et al. |
| 2023/0145071 A1 | 5/2023 | Cutshall |
| 2024/0092788 A1 | 3/2024 | Cutshall et al. |

FOREIGN PATENT DOCUMENTS

| | | |
|---|---|---|
| CL | 202103105 | 5/2019 |
| CL | 202000610 | 11/2020 |
| CN | 1127509 | 7/1996 |
| CN | 1127509 A | 7/1996 |
| CN | 104661676 A | 5/2015 |
| EP | 0321201 | 6/1989 |
| EP | 0321201 B1 | 12/1994 |
| JP | 20014515922 A | 9/2001 |
| JP | 2004516286 A | 6/2004 |
| JP | 2007-535474 A | 12/2007 |
| RU | 2014133019 A | 2/2016 |
| WO | 1988004300 | 6/1988 |
| WO | 1991011465 | 8/1991 |
| WO | 1994029335 | 12/1994 |
| WO | 1994029336 A1 | 12/1994 |
| WO | 1995023609 A1 | 9/1995 |
| WO | 99/61442 A1 | 12/1999 |
| WO | 9961442 | 12/1999 |
| WO | 2000039124 | 7/2000 |
| WO | 2002050056 A1 | 9/2000 |
| WO | 00/69834 A1 | 11/2000 |
| WO | 0069834 | 11/2000 |
| WO | 2001079195 A2 | 10/2001 |
| WO | 2001087854 | 11/2001 |
| WO | 0250056 A1 | 6/2002 |
| WO | 2000055188 A1 | 6/2002 |
| WO | 03/029224 A1 | 4/2003 |
| WO | 03029224 | 4/2003 |
| WO | WO2003028729 A2 | 4/2003 |
| WO | 2004009664 | 1/2004 |
| WO | 2004032834 | 4/2004 |
| WO | 2005002627 A2 | 1/2005 |
| WO | 2006/101860 A1 | 9/2006 |
| WO | 2006101860 | 9/2006 |
| WO | 2008/085608 A1 | 7/2008 |
| WO | 2008085608 | 7/2008 |
| WO | 2010141406 A2 | 12/2010 |
| WO | 2012007777 A1 | 1/2012 |
| WO | 2012139081 | 10/2012 |
| WO | 2012151481 A1 | 11/2012 |
| WO | 2013106643 A2 | 7/2013 |
| WO | 2013180834 A3 | 12/2013 |
| WO | WO2014057068 A1 | 4/2014 |
| WO | 2015103317 A1 | 7/2015 |
| WO | 2017/173290 A1 | 10/2017 |
| WO | 2017173290 | 10/2017 |
| WO | 2018/045054 A1 | 3/2018 |
| WO | 2018045054 | 3/2018 |
| WO | 2019036460 A1 | 2/2019 |
| WO | 2019055590 A1 | 3/2019 |
| WO | 2019/186164 A1 | 10/2019 |
| WO | 2019186164 | 10/2019 |
| WO | 2019211585 A1 | 11/2019 |
| WO | 2019231933 A2 | 12/2019 |
| WO | 2022035997 A1 | 2/2022 |

OTHER PUBLICATIONS

Berge et al., "Pharmaceutical salts," *J. Pharm. Sci.* 66(1):1-19, Jan. 1977.

Berthoux et al., "Predicting the Risk for Dialysis or Death in IgA Nephropathy," *J. Am. Soc. Nephrol.* 22:752-761, 2011.

Goto et al., "A scoring system to predict renal outcome in IgA nephropathy: a nationwide 10-year prospective cohort study," *Nephrol. Dial. Transplant.* 24:3068-3074, Jun. 10, 2009.

Ho et al., "Blood and Marrow Transplant Clinical Trials Network Toxicity Committee Consensus Summary: Thrombotic Microangiopathy after Hematopoietic Stem Cell Transplantation," *Biology of Blood and Marrow Transplantation* 11:571-575, 2005.

Kozarcanin et al., "The lectin complement pathway serine proteases (MASPs) represent a possible crossroad between the coagulation and complement system in thromboinflammation," *Journal of Thrombosis & Haemostasis* 14:531-545, 2015.

Lange et al., "Orally active thrombin inhibitors. Part 2: Optimization of the P2-moiety," *Biorganic & Medicinal Chemistry Letters* 16:2648-2653, Feb. 3, 2006.

Noris et al., "Genetic Atypical Hemolytic-Uremic Syndrome," *GeneReviews®*, eds. Adam et al., University of Washington, Seattle, WA, Nov. 16, 2007, 32 pages.

Parlow et al., "Design, Parallel Synthesis, and Crystal Structures of Pyrazinone Antithrombotics as Selective Inhibitors of the Tissue Factor VIIa Complex," *Journal of Medicinal Chemistry* 46(19):4050-4062, 2003.

Peterlin-Masic et al., "Metabolism-Directed Optimisation of Antithrombotics: The Prodrug Principle," *Curr. Pharm. Des.* 12(1):73-91, 2006.

Pétursson, "Protecting Groups in Carbohydrate Chemistry," *Journal of Chemical Education* 74(11):1297, Nov. 1997.

Rambaldi et al., "Endothelial injury and thrombotic microangiopathy in COVID-19: Treatment with the lectin-pathway inhibitor narsoplimab," *Immunobiology* 225(152001):1-10, 2020.

Reich et al., "Remission of Proteinuria Improves Prognosis in IgA Nephropathy," *J. Am. Soc. Nephrol.* 18:3177-3183, 2007.

Ricklin et al., "Complement—a key system for immune surveillance and homeostasis," *Nat. Immunol.* 11(9):785-797, Sep. 2010.

Sanderson et al., "Azaindoles: Moderately Basic P1 Groups for Enhancing the Selectivity of Thrombin Inhibitors," *Bioorganic & Medicinal Chemistry Letters* 13:795-798, 2003.

Schwaeble et al., "Targeting of mannan-binding lectin-associated serine protease-2 confers protection from myocardial and gastrointestinal ischemia/reperfusion injury," *PNAS* 108(18):7523-7528, May 3, 2011.

Staas et al., "Discovery of potent, selective 4-fluoroproline-based thrombin inhibitors with improved metabolic stability," *Bioorganic & Medicinal Chemistry* 14(20):6900-6916, Jul. 25, 2006.

Trost et al., eds., "Comprehensive Organic Synthesis: Selectivity, Strategy & Efficiency in Modern Organic Chemistry" vol. 1, Pergamon Press, Oxford, United Kingdom, 1991.

Vorup-Jensen et al., "Distinct Pathways of Mannan-Binding Lectin (MBL)- and C1-Complex Autoactivation Revealed by Reconstitution of MBL with Recombinant MBL-Associated Serine Protease-2," *J. Immunol.* 165(4):2093-2100, 2000.

(56) References Cited

OTHER PUBLICATIONS

Wyatt et al., "IgA Nephropathy," N. Engl. J. Med. 368(25):2402-2414, Jun. 20, 2013.
Zipfel et al., "Deletion of Complement Factor H-Related Genes CFHR1 and CFHR3 Is Associated with Atypical Hemolytic Uremic Syndrome," PLoS Genet. 3(3):0387-0392, e41, Mar. 2007.
Courtenay-Luck, N.S., "Genetic Manipulation of Monoclonal Antibodies," in Monoclonal Antibodies: Production, Engineering and Clinical Application, Ritter et al., (eds.) p. 166, Cambridge University Press, (1995).
Kelley, R.F., "Engineering Therapeutic Antibodies," in Protein Engineering: Principles and Practice, Cleland et al., (eds.) John Wiley & Sons, Inc., pp. 399-434, (1996).
Baines et al., "Purification of Immunoglobulin G, (IgG)," in Methods in Molecular Biology vol. 10: Immunochemical Protocols, Chapter 8, pp. 79-105, (1992).
Matsushita, M., et al., "The role of ficolins in innate immunity," Immunobiology, 205(4-5):490-497, (2002).
Tezel, G., et al., "Oxidative stress and the regulation of complement activation in human glaucoma" Invest Ophthalmol Vis Sci 51:5071-5082, (2010).
Harlow, E., et al., Antibodies: A Laboratory Manual, Cold Spring Harbor Laboratory, New York, (1988).
Heja, et al., "Monospecific Inhibitors Show That Both Mannan-binding Lectin-associated Serine Protease-1 (MASP-1) and -2 Are Essential for Lectin Pathway Activation and Reveal Structural Plasticity of MASP-2," The Journal of Biological Chemistry, 287(24): 20290-20300 (2012).
Risitano, A.M., et al., "Complement fraction 3 binding on erythrocytes as additional mechanism of disease in paroxysmal nocturnal hemoglobinuria patients treated by eculizumab," Blood 113(17):4094-100, (2009).
Teh, C., et al., "M-ficolin is expressed on monocytes and is a lectin binding to N-acetyl-D-glucosamine and mediates monocyte adhesion and phagocytosis of Escherichia coli," Immunology 101:225-232, (2000).
Hansen, et al, "Collectin 11 (CL-11, CL-K1) is a MASP-1/3-associated plasma collectin with microbial-binding activity," J. Immunol 185(10):6096-6104, (2010).
Jack, D.L., et al., "Mannose-binding lectin enhances phagocytosis and killing of Neisseria meningitidis by human macrophages" J Leukoc Biol., 77(3):328-36, (2005).
Aoyagi et al., "Role of L-ficolin/mannose-binding lectin-associated serine protease complexes in the opsonophagocytosis of type III group B streptococci," J Immunol, 174(1):418-25(2005).
Degn, S.E., et al., "MAp19, the alternative splice product of the MASP2 gene," J Immunol. Methods, 373(1-2):89-101, (2011).
Guessous, F., et al., "Shiga toxin 2 and lipopolysaccharide induce human microvascular endothelial cells to release chemokines and factors that stimulate platelet function," Infect. Immun., 73(12): 8306-8316, (2005).
Kaufman, R.J., et al., "Improved vectors for stable expression of foreign genes in mammalian cells by use of the untranslated leader sequence from EMC virus," Nucleic Acids Research 19:4485-90, (1991).
Kaufman, R.J., "Selection and coamplification of heterologous genes in mammalian cells,"Methods in Enzymology, 185:537-66, (1990).
Maniatis, A., et al., "Intermediate-dose melphalan for refractory myeloma," Blood 74(3):1177, (1989).
Shea, K.J., "Molecular Imprinting of Synthetic Network Polymers: The De Novo synthesis of Macromolecular Binding and Catalytic Sties," Trip 2(5):166-173, (1994).
Colligan, "Production of Monoclonal Antibosies," Current Protocols in Immunology, vol. 1., John Wiley & Sons, pp. 2.5.1-2.6.7, (1991).
Gal et al., "A true autoactivating enzyme. Structural insight into mannose-binding lectin-associated serine protease-2 activations," J. Biol. Chem. 280(39):33435-44, (2005).
Reichmann, L., et al., "Reshaping human antibodies for therapy," Nature 332:323-329, (1988).
Lee, W.A., "Permeation enhancers for the nasal delivery of protein and peptide therapeutics," Biopharm. 3:22-25, (1990).
Yoshihiro, I., et al., "An Insulin-Releasing System that is Responsive to Glucose," J. Controlled Release 10:195-203, (1989).
Green, J.A., et al., "Production of polyclonal antisera," In: Immunochemical protocols. Methods in molecular biology, vol. 10. Humana Press, Totowa, N.J., p. 1, (1992).
King, L.A., et al., "Propagation, titration and purification of AcMNPV in cell culture," The Baculovirus Expression System: A Laboratory Guide, Chapman and Hall Ltd., London, pp. 106-126, (1992).
Gastoldi, S., et al., "C5a/C5aR interaction mediates complement activation and thrombosis on endothelial cells in atypical hemolytic uremic syndrome (aHUS)," Immunobiology 217(11):1145-1146, (2012).
Abagyan, R., et al., "Biased probability Monte Carlo conformational searches and electrostatic calculations for peptides and proteins," J Mol Biol 235(3):983-1002 (1994).
Abagyan, R., et al., "ICM—A new method for protein modeling and design: Applications to docking and structure prediction from the distorted native conformation," Journal of Computational Chemistry 15(5):488-506 (1994).
An, J., et al., "Pocketome via comprehensive identification and classification of ligand binding envelopes," Mol Cell Proteomics 4(6):752-761 (2005).
Biela, A., et al., "Ligand binding stepwise disrupts water network in thrombin: enthalpic and entropic changes reveal classical hydrophobic effect," J Med Chem 55(13):6094-6110 (2012).
Brady, G. P., Jr., et al., "Fast prediction and visualization of protein binding pockets with PASS," J Comput Aided Mol Des 14(4):383-401 (2000).
Brylinski, M., et al., "Prediction of functional sites based on the fuzzy oil drop model," PLoS Comput Biol 3(5):e94 (2007).
Brylinski, M., et al., "A threading-based method (Findsite) for ligand-binding site prediction and functional annotation," Proc Natl Acad Sci U S A 105(1):129-134 (2008).
Chang, D. T., et al., "MEDock: a web server for efficient prediction of ligand binding sites based on a novel optimization algorithm," Nucleic Acids Res 33(Web Server issue):W233-238 (2005).
Del Carpio, C. A., et al., "A new approach to the automatic identification of candidates for ligand receptor sites in proteins: (I). Search for pocket regions," J Mol Graph 11(1):23-29, 42 (1993).
Delaney, J. S., "Finding and filling protein cavities using cellular logic operations," J Mol Graph 10(3):174-177, 163 (1992).
Donner, A., "The XII factor," Science-Business exchange 7:1-4 (2014).
Dundas, J., et al., "CASTp: computed atlas of surface topography of proteins with structural and topographical mapping of functionally annotated residues," Nucleic Acids Res 34(Web Server issue):W116-118 (2006).
Emsley, P., et al., "Features and development of Coot," Acta Crystallogr D Biol Crystallogr 66(Pt 4):486-501 (2010).
Fernández-Recio, J., "Prediction of protein binding sites and hot spots," Wiley Interdiscip Rev Comput Mol Sci 1(5):680-698 (2011).
Fukunishi, Y., et al., "Prediction of ligand-binding sites of proteins by molecular docking calculation for a random ligand library," Protein Sci 20(1):95-106 (2011).
Gelb, M. H., et al., "Substituted isatoic anhydrides: selective inactivators of trypsin-like serine proteases," J Med Chem 29(4):585-589 (1986).
Glaser, F., et al., "ConSurf: identification of functional regions in proteins by surface-mapping of phylogenetic Information," Bioinformatics 19(1):163 164 (2003).
Goodford, P. J., "A computational procedure for determining energetically favorable binding sites on biologically important macromolecules," J Med Chem 28(7):849-857 (1985).
Greene, J., et al., "Chemical Function Queries for 3D Database Search," J Chem Inf Comput Sci 34(6):1297-1308 (1994).
Grutter, M. G., et al., "Crystal structure of the thrombin-hirudin complex: a novel mode of serine protease inhibition," EMBO J 9(8):2361-2365 (1990).

(56) References Cited

OTHER PUBLICATIONS

Halgren, T., "New method for fast and accurate binding-site identification and analysis," Chem Biol Drug Des 69(2):146-148 (2007).
"Hedstrom, L., "Serine protease mechanism and specificity," Chem Rev 102(12):4501-4524 (2002)."
Hendlich, M., et al., "Ligsite: automatic and efficient detection of potential small molecule-binding sites in proteins," J Mol Graph Model 15(6):359-363, 389 (1997).
Huang, B., et al., "LIGSITEcsc: predicting ligand binding sites using the Connolly surface and degree of conservation," BMC Struct Biol 6:19 (2006).
Katz, B. A., et al., "Design of potent selective zinc-mediated serine protease inhibitors," Nature 391(6667):608-612 (1998).
Sandhu, U.S., "Protein engineering of antibodies," Crit. Rev. Biotech. 12:437-462, (1992).
Ravetch, J.V., et al., "Fc receptors," Annu. Rev. Immunol. 9:457-492, (1991).
Rosenblatt, J., et al., "The Effect of Collagen Fiber Size Distribution on the Release Rate of Proteins from Collagen Matrices by Diffusion," J. Controlled Release 9:195, (1989).
Porter, R.R., "The hydrolysis of rabbit y-globulin and antibodies with crystalline papain," Biochem. J. 73:119, (1959).
Merrifield, R.B., "Solid Phase Peptide Synthesis. I. The Synthesis of a Tetrapeptide," in J. Amer. Chem. Soc. 85:2149-2154, (1963).
Presta, L.G., "Antibody engineering," Curr. Op. Struct. Biol. 2:593-596, (1992).
Lee, V.H.L., "Enzymatic Barriers to Peptide and Protein Absorption," Crit. Rev. Ther. Drug Carrier Sys. 5(2):69-97, (1988).
Yamakawa, I., et al., "Sustained release of insulin by double-layered implant using poly(D,L-lactic acid)," J. Pharm. Sci. 79:505, (1990).
Ohman, E.M., et al., "Early clinical experience with integrelin, an inhibitor of the platelet glycoprotein IIb/IIIa integrin receptor," European Heart J. 16:50-55, (1995).
Pack, P., et al., "Improved bivalent miniantibodies, with identical avidity as whole antibodies, produced by high cell density fermentation of *Escherichia coli*," Bio/Technology 11:1271, (1993).
Zhang, L., et al., "A discrete site modulates activation of I domains. Application to integrin alphaMbeta2," J. Biol. Chem. 271(47):29953-57, (1996).
Taylor, L.D., et al., "Human immunoglobulin transgenes undergo rearrangement, somatic mutation and class switching in mice that lack endogenous IgM," Int. Immun. 6:579, (1994).
Takakura, Y., et al., "Control of pharmaceutical properties of soybean trypsin inhibitor by conjugation with dextran. I: Synthesis and characterization," J. Pharm. Sci. 78:117, (1989).
Van de Winkel, J.G., et al., "Human IgG Fc receptor heterogeneity: molecular aspects and clinical implications," Immunol. Today 14:215-221, (1993).
Vaughan, T.J., et al., "Human antibodies by design," Nature Biotechnical 16:535-539, (1998).
Scatchard, G., "The Attraction of Proteins for Small Molecules and Ions," NY Acad. Sci. 51:660-672, (1949).
Green, L.L., et al., "Antigen-specific human monoclonal antibodies from mice engineered with human Ig heavy and ight chain YACs," Nature Genet. 7:13-21, (1994).
Glover, G.I., et al., "Synthetic peptide inhibitors of complement serine proteases—I. Identification of functionally equivalent protease inhibitor sequences in serpins and inhibition of C1s and D," Mol. Immunol. 25:1261, (1988).
Fedor, M.J., et al., "Substrate sequence effects on "hammerhead" RNA catalytic efficiency," Proc. Natl. Acad. Sci. USA 87:1668-1672, (1990).
Duncan, A.R., et al., "The binding site for C1q on IgG," Nature 332:738-740, (1988).
Dodds, A.W., "Small-scale preparation of complement components C3 and C4," Methods Enzymol. 223:46, (1993).
Haseloff, J., et al., "Simple RNA enzymes with new and highly specific endoribonuclease activities," Nature 334:585-591, (1988).

Matsushita, M., et al., "Activation of the classical complement pathway by mannose-binding protein in association with a novel C1s-like serine protease," J. Exp. Med. 176(6):1497-2284, (2000).
Morgan, B.P., "Clinical complementology: recent progress and future trends," Eur. J. Clinical Investig. 24(4):219-228, (1994).
Itakura, K., et al., "Synthesis and use of synthetic oligonucleotides," Annu. Rev. Biochem. 53:323, (1984).
Kuntz, I.D., et al., "Structure-based strategies for drug design and discovery," Science 257:1078, (1992).
Holmskov, U., et al., "Collections and ficolins: humoral lectins of the innate immune defense," Annu. Rev. Immunol. 21:547-578, (2003).
Ikeda, K., et al., "Serum lectin with known structure activates complement through the classical pathway," J. Biol. Chem. 262:7451-7454, (1987).
Jensen, J., et al., "Taming of transposable elements by homology-dependent gene silencing," Nat. Genet. 21(2):209-12, (1999).
Lloyd, B.H., et al., "Determination of optimal sites of antisense oligonucleotide cleavage within TNFalpha mRNA," Nucleic Acids Res. 29:3665-3673, (2001).
DesJarlais, R.L., et al., "Structure-based design of nonpeptide inhibitors specific for the human immunodeficiency virus 1 protease," PNAS 87:6644-6648, (1990).
Bae, Y.H., et al., "Insulin Permeation Through Thermo-Sensitive Hydrogels," J. Controlled Release 9:271, (1989).
Asano, M., et al., "In Vivo Characteristics of Low Molecular Weight Copoly(L-Lactice Acid/Glycolic Acid) Formulations with Controlled Release of Luteinizing Hormone-Releasing Hormone Agonist," J. Controlled Release 9:111-112, (1989).
Kohler, G., et al., "Continuous cultures of fused cells secreting antibody of predefined specificity," Nature 256:495, (1975).
Kuntz, I.D., et al., "A geometric approach to macromolecule-ligand interactions," J. Mol. Biol. 161:269-288, (1982).
Kuhlman, et al., "The human mannose-binding protein functions as an opsonin," J. Exp. Med. 169:1733, (1989).
Losman, M.J., et al., "Baboon anti-idiotype antibodies mimic a carcinoembryonic antigen epitope," Int. J. Cancer 46:310, (1990).
Lonberg, N., et al., "Antigen-specific human antibodies from mice comprising four distinct genetic modifications," Nature 368:856, (1994).
Marks, J.D., et al., "By-passing immunization. Human antibodies from V-gene libraries displayed on phage," J. Mol. Biol. 222:581-597, (1991).
Matsushita et al., "A novel human serum lectin with collagen- and fibrinogen-like domains that functions as an opsonin," J. Biol. Chem. 271(5):2448-54, (1996).
Mariani, M., et al., "A new enzymatic method to obtain high-yield F(ab)2 suitable for clinical use from mouse IgGI," Mol. Immunol. 28:69-71, (1991).
Morrison, S.L., et al., "Chimeric human antibody molecules: mouse antigen-binding domains with human constant region domains," Proc. Nat'l Acad. Sci. USA 81:6851-6855, (1984).
Murayama, O., et al., "Novel peptide ligands for integrin alpha 6 beta 1 selected from a phage display library," J. Biochem. 120:445-51, (1996).
Nisonoff, A., et al., "Separation of univalent fragments from the bivalent rabbit antibody molecule by reduction of disulfide bonds," Arch. Biochem. Biophys. 89:230-244, (1960).
Scherr, M., et al., "Rapid determination and quantitation of the accessibility to native RNAs by antisense bligodeoxynucleotides in murine cell extracts," Nucleic Acids Res. 26:5079-5085, (1998).
Isaacs, J.D., et al., "Therapy with monoclonal antibodies. An in vivo model for the assessment of therapeutic potential," J. Immunol. 148(10):3062-3071, (1992).
Whitlow, M., et al., "Single-chain Fv Proteins and Their Fusion Proteins," Methods: A Companion to Methods in Enzymology 2:97-105, (1991).
Larrick, J.W., et al., "PCR Amplification of Antibody Genes," Methods: A Companion to Methods in Enzymology 2:106-110, (1991).
Jones, P.T., et al., "Replacing the complementarity-determining regions in a human antibody with those from a mouse," Nature 321:522-525, (1986).

(56) References Cited

OTHER PUBLICATIONS

Ward et al., "Genetic Manipulation and Expression of Antibodies," in Monoclonal Antibodies: Principles and Applications, Birch et al., (eds.) p. 137, Wiley-Liss, Inc., (1995).
E-EROS Encyclopedia of Reagents for Organic Synthesis; "N-hydroxyacetamide"—preparations, properties and applications; Published Apr. 15, 2001; pp. 1-4, Conference 2008.
Shirk et al.; "Inhibitors of Factor VIIa/Tissue Factor"; Arteriosclerosis, Thrombosis, and Vascular Biology; Sep. 1, 2007; pp. 1895-1900; vol. 27, Issue 9.
Trujillo et al.; "Design, synthesis, and biological evaluation of pyrazinones containing novel P1 needles as inhibitors of TF/VIIa"; Bioorganic & Med Chem Letters; Aug. 15, 2007; pp. 4568-4574; vol. 17, Issue 16.
Chen, C.B., et al., "Stoichiometry of complexes between mannose-binding protein and its associated serine proteases. Defining functional units for complement activation," J. Biol. Chem., 276(28):25894-25902, (2001).
Feinberg, H., et al., "Crystal structure of the CUB1-EGF-CUB2 region of mannose-binding protein associated serine protease-2," EMBO J. 22:2348-2359, (2003).
Lynch, N.J., et al., "L-ficolin specifically binds to lipoteichoic acid, a cell wall constituent of Gram-positive bacteria, and activates the lectin pathway of complement," J. Immunol. 172:1198-1202, (2004).
Stover, C.M., et al., "Two constituents of the initiation complex of the mannan-binding lectin activation pathway of complement are encoded by a single structural gene," J. Immunol. 162:3481-3490, (1999).
Stover, C.M., et al., "The rat and mouse homologues of MASP-2 and MAp19, components of the lectin activation bathway of complement," J. Immunol. 163:6848-6859, (1999).
Thiel, S., et al., "A second serine protease associated with mannan-binding lectin that activates complement," Nature 386:506-510, (1997).
Thiel, S., et al., "Interaction of C1q and mannan-binding lectin (MBL) with C1r, C1s, MBL-associated serine proteases 1 and 2, and the MBL-associated protein MAp19," J. Immunol. 165:878-887, (2000).
Thielens, N.M., et al., "Interaction properties of human mannan-binding lectin (MBL)-associated serine proteases-1 and 2, MBL-associated protein 19, and MBL," J. Immunol. 166:5068-5077, (2001).
Matsushita, M., et al., "Cutting edge: complement-activating complex of ficolin and mannose-binding lectin-associated serine protease," J. Immunol. 164:2281-2284, (2000).
Rodrigues, M.L., et al., "Engineering Fab' fragments for efficient F(ab)2 formation in Escherichia coli and for improved in vivo stability," J. Immunol. 151(12):6954-6961, (1998).
Riedermann, N.C., et al., "Complement in ischemia reperfusion injury," Am. J. Pathol. 162:363-367, (2003).
Matsushita, M., et al., "Activation of the lectin complement pathway by H-ficolin (Hakata antigen)," J. Immunol. 168(7):3502-3506, (2002).
Stengaard-Pedersen, K., et al., "Inherited deficiency of mannan-binding lectin-associated serine protease 2," New England J. Med. 349:554-560, (2003).
Takahashi, M., et al., "A truncated form of mannose-binding lectin-associated serine protease (MASP)-2 expressed by alternative polyadenylation is a component of the lectin complement pathway," Int. Immunol. 11:859-863, (1999).
Moller-Kristensen, M., et al., "Levels of mannan-binding lectin-associated serine protease-2 in healthy individuals," J. Immunol Methods 282:159-167 (2003).
Dahl, M.R., et al., "MASP-3 and its association with distinct complexes of the mannan-binding lectin complement activation pathway," Immunity 15:127-35, (2001).
Petersen, S.V., et al., "An assay for the mannan-binding lectin pathway of complement activation," J. Immunol. Methods 257:107-116, (2001).

Liszewski, M.K., et al., "The Complement System," in Fundamental Immunology, Third Edition, Raven Press, Ltd., New York, (1993).
Collard, C.D., et al., "Complement activation after oxidative stress: role of the lectin complement pathway," Am J. Pathol 156(6):1549-56, (2000).
Lu, J., et al., "Collectins and ficolins: sugar pattern recognition molecules of the mammalian innate immune system," Biochim Biophys Acta 1572:387-400, (2002).
Jordan et al., "Inhibition of mannose-binding lectin reduces postischemic myocardial reperfusion injury," Circulation 104(12):1413-1418, (2001).
Maynard, Y., et al., "Characterization of a mannose and N-acetylglucosamine-specific lectin present in rat hepatocytes," J. Biol. Chem. 257:3788-3794, (1982).
Lee, R.T., et al., "Multivalent ligand binding by serum mannose-binding protein," Archiv. Biochem. Biophys. 299:129-136, (1992).
Collard et al., "Endothelial oxidative stress activates the lectin complement pathway: role of cytokeratin 1," Am. J. Pathol. 159(3):1045-1054, (2001).
Ji, Y.H., et al., "Activation of the C4 and C2 components of complement by a proteinase in serum bactericidal factor, Ra reactive factor," J. Immunol. 150:571-578, (1993).
Kilpatrick, D.C., et al., "Mannan-binding lectin: clinical significance and applications," Biochim Biophys Acta 1572:401-413, (2002).
Weis, W.I., et al., "Structure of a C-type mannose-binding protein complexed with an oligosaccharide," Nature 360:127-134, (1992).
Kalli, K.R., et al., "Therapeutic uses of recombinant complement protein inhibitors," Springer Semin. Immunopathol. 15:417-431, (1994).
Wallis, R., et al., "Localization of the serine protease-binding sites in the collagen-like domain of mannose-binding protein: indirect effects of naturally occurring mutations on protease binding and activation," J. Biol. Chem. 279:14065-73, (2004).
Wallis, R., et al., "Interaction of mannose-binding protein with associated serine proteases: effects of naturally occurring mutations," J. Biol. Chem. 275:30962-30969, (2000).
Sim, R.B., et al., "Innate Immunity," Biochem. Soc. Trans. 28:545-550, (2000).
Cech, T.R., et al., "Biological catalysis by RNA," Ann. Rev. Biochem. 55:599-629, (1986).
Clackson, T., et al., "Making antibody fragments using phage display libraries," Nature 352:624-628, (1991).
Chen, P.F., et al., "Development of the non-palindromic adaptor polymerase chain reaction (NPA-PCR) for the amplification of alpha- and beta-chain T-cell receptor cDNAs," Scand. J. Immunol. 35:539-549, (1992).
Bird, et al., "Single-chain antigen-binding proteins," Science 242(4877):423-426, (1988).
Climie, S., et al., "Chemical synthesis of the thymidylate synthase gene," Proc. Nat'l Acad. Sci. USA 87(2):633, (1990).
Carter, P., et al., "Humanization of an anti-p185HER2 antibody for human cancer therapy," Proc. Nat'l. Acad. Sci. USA 89(10):4285-4289, (1992).
Altschul, S.F., et al., "Gapped Blast and PSI-Blast: a new generation of protein database search programs," Nucl. Acids Res. 25:3389-3402, (1997).
Makino, K., "A Microcapsule Self-Regulating Delivery System for Insulin," J. Controlled Release 12:235-239, (1990).
Lee, V.H.L., "Protease Inhibitors and Penetration Enhancers as Approaches to Modify Peptide Absorption," J. Controlled Release 13:213, (1990).
Jolliffe, L.K., et al., "Humanized antibodies: enhancing therapeutic utility through antibody engineering," Int'l Rev. Immunol. 10:241-250, (1993).
Jackson, D.Y., et al., "Potent alpha 4 beta 1 peptide antagonists as potential anti-inflammatory agents," J. Med. Chem. 40:3359-68, (1997).
Hori, R., et al., "Enhanced bioavailability of subcutaneously injected insulin coadministered with collagen in rats and humans," Pharm. Res. 6:813 (1989).

(56) References Cited

OTHER PUBLICATIONS

Daha, M.R., et al., "C3 nephritic factor (C3NeF): stabilization of fluid phase and cell-bound alternative pathway convertase," J. Immunol. 116(1):1-7, (1976).
Greenspan, N.S., et al., "Idiotypes: structure and immunogenicity," FASEB J. 7(5):437-444, (1993).
DeBoer, A.G., et al., "Rectal Absorption Enhancement of Peptide Drugs," J. Controlled Release 13:241, (1990).
Fuertges, F., et al., "The Clinical Efficacy of Poly(ethylene Glycol)-modified Proteins," J. Controlled Release 11:139, (1990).
Singer, I.I., et al., "Optimal humanization of 1B4, an anti-CD18 murine monoclonal antibody, is achieved by correct choice of human V-region framework sequences," J. Immun. 150:2844, (1993).
Siegert, C.E., et al., "The relationship between serum titers of autoantibodies to C1q and age in the general population and in patients with systemic lupus erythematosus," Clin. Immunol. Immunopathol. 67:204-9, (1993).
Schwaeble, W., et al., "The mannan-binding lectin-associated serine proteases (MASPs) and MAp19: four components of the lectin pathway activation complex encoded by two genes," Immunobiology 205:455-466, (2002).
Kenawy, H. I., et al., "Complement-Coagulation Cross-Talk: A Potential Mediator of the Physiological Activation of Complement by Low pH," Front Immunol 6:215 (2015).
Kleywegt, G. J., et al., "Detection, delineation, measurement and display of cavities in macromolecular structures," Acta Crystallogr D Biol Crystallogr 50(Pt 2):178-185 (1994).
Laskowski, R. A., et al., "LigPlot+: multiple ligand-protein interaction diagrams for drug discovery," J Chem Inf Model 51(10):2778-2786 (2011).
Laskowski, R. A., "Surfnet: a program for visualizing molecular surfaces, cavities, and intermolecular interactions," J Mol Graph 13(5):323-330, 307-328 (1995).
Laurie, A. T., et al., "Q-SiteFinder: an energy-based method for the prediction of protein-ligand binding sites," Bioinformatics 21(9):1908-1916 (2005).
Levitt, D. G., et al., "Pocket: a computer graphics method for identifying and displaying protein cavities and their surrounding amino acids," J Mol Graph 10(4):229-234 (1992).
Lin, C., et al., "Discovery and development of VX-950, a novel, covalent, and reversible inhibitor of hepatitis C virus NS3.4A serine protease," Infect Disord Drug Targets 6(1):3-16 (2006).
Moake, J. L., Merck Manual—Hematology and Oncology: Overview of Thrombotic Disorders [updated Oct. 17, 2019]. Available from: https://www.merckmanuals.com/professional/hematology-and-oncology/thrombotic- disorders/overview-of-thrombotic-disorders.
Nayal, M., et al., "On the nature of cavities on protein surfaces: application to the identification of drug-binding sites," Proteins 63(4):892-906 (2006).
Ni-NTA Superflow Cartridge Handbook: For manual or FPLC™ purification of His-tagged proteins: Qiagen; 2007. 32 p.
Pedregosa, F., et al., "Scikit-learn: Machine Learning in Python," Journal of Machine Learning Research 12:2825-2830 (2011).
Peters, K. P., et al., "The automatic search for ligand binding sites in proteins of known three-dimensional structure using only geometric criteria," J Mol Biol 256(1):201-213 (1996).
Pettersen, E. F., et al., "UCSF Chimera—a visualization system for exploratory research and analysis," J Comput Chem 25(13):1605-1612 (2004).
Powers, J. C., et al., "Irreversible inhibitors of serine, cysteine, and threonine proteases," Chem Rev 102(12):4639-4750 (2002).
Protein Data Bank [Internet]. 3TVJ—Catalytic fragment of MASP-2 in complex with its specific inhibitor developed by directed evolution on SGCI scaffold. 2011 [cited Oct. 22, 2019]. Available from: https://www.rcsb.org/structure/3tvj.
Ramot, Y., et al., "Drug-induced thrombosis-experimental, clinical, and mechanistic considerations," Toxicol Pathol 35(2):208-225 (2007).
Renne, T., et al., "In vivo roles of factor XII," Blood 120(22):4296-4303 (2012).
Schechter, I., et al., "On the size of the active site in proteases. I. Papain," Biochem Biophys Res Commun 27(2):157-162 (1967).
Smoum, R., et al., "Boron containing compounds as protease inhibitors," Chem Rev 112(7):4156-4220 (2012).
Uniprot.org [Internet]. Identifier: O00187, Mannan-binding lectin serine protease 2. 2019 [cited Oct. 22, 2019]. Available from: https://www.uniprot.org/uniprot/O00187.
Venkatachalam, C. M., et al., "LigandFit: a novel method for the shape-directed rapid docking of ligands to protein active sites," J Mol Graph Model 21(4):289-307 (2003).
Verdonk, M. L., et al., "SuperStar: a knowledge-based approach for identifying interaction sites in proteins," J Mol Biol 289(4):1093-1108 (1999).
Weisel, M., et al., "PocketPicker: analysis of ligand binding-sites with shape descriptors," Chem Cent J 1:7 (2007).
Weitz, J. I., et al., "Factors XI and XII as Targets for New Anticoagulants," Front Med (Lausanne) 4:19 (2017).
Young, W. B., et al., "Generation of potent coagulation protease inhibitors utilizing zinc-mediated chelation," Bioorg Med Chem Lett 16(3):710-713 (2006).
SciFinder; Chemical Abstracts Service: Columbus, OH; RN 1223890-82-1 [accessed Nov. 27, 2019]. Available from: https://scifinder.cas.org.
SciFinder; Chemical Abstracts Service: Columbus, OH; RN 1242003-50-4 [accessed Nov. 27, 2019]. Available from: https://scifinder.cas.org.
Zadlo-Dobrowolska et al., "Enzymatic Ugi Reaction with Amines and Cyclic Imines," Chem.Eur. J., 22:16684-16689 (2016).
Harmat et al., (2004), ""The Structure of MBL-associated Serine Protease-2 Reveals that Identical Substrate Specificities of C1s and MASP-2 are Realized Through Different Sets of Enzyme-Substrate Interactions"", JMB, 342(5): , XP004844933, https://www.dropbox.com/s/6eto0ib57oqe8pq/D5.pdf?dl=0.
Szakacs et al., (Apr. 5, 2019), ""Novel MASP-2 inhibitors developed via directed evolution of human TFPI1 are potent lectin pathway inhibitors"", J. Biol. Chem., 294(20):8227-8237, XP055727499, DOI: http://dx.doi.org/10.1074/jbc.RA119.008315.
Hedstrom, L., "Serine protease mechanism and specificity," Chem Rev 102(12):4501-4524 (2002).
U.S. Appl. No. 62/688,611, filed Jun. 22, 2018, Demopulos et al.
Ronn R et al, (2006), "Exploration of acyl sulfonamides as carboxylic acid replacements in protease inhibitors of the hepatitis C virus full-length NS3", Bioorganic, Elsevier, Amsterdam, NL, 14(2):544-559 , XP027992303, https://www.dropbox.com/s/qzqalozouacfevl/D11.pdf?dl=0.
Nurbo et al., Bioorganic & Medicinal Chemistry (2008), 16(10), 5590-5605 and Supplementary Material on pages S1-S8. (Year: 2008).
Clark J,E, Dudler T, Marber M,S, et al. Cardioprotection by an anti-MASP-2 antibody in a murine model of myocardial infarction. Open Heart 2018;5:e000652. doi:10.1136/ openhrt-2017-000652.
Orsini, F. et al., "Mannan binding lectin-associated serine protease-2 (MASP-2) critically contributes to post-ischemis brain injury independent of MASP-1," Journal of Neuroinflammation (2016)13:213; DOI 10.1186s/12974-016-0684-6.
Asgari, E. et al., "Mannan-binding lectin-associated serine protease 2 is critical for the development of renal ischemia reperfusion injury and mediates tissue injury in the absence of complement C4," The FASEB Journal Research Communication; May 19, 2014; pp. 3996-4003.
Alghadban, S. et al., "Absence of the Lectin Activation Pathway of the Complement Ameliorates Proteinuria-Induced Renal Injury," Front. Immunol. 10:2238; doi: 10.3389/fimmu.2019.02238.
Banda, N. K. et al., "Deconstructing the Lectin Pathway in the Pathogenesis of Experimental Inflammatory Arthritis: Essential Role of the Lectin Ficolin B and Mannose-Binding Protein-Associated Serine Protease 2," J Immunol (2017) 199 (5): 1835-1845; https://doi.org/10.4049/jimmunol.1700119.
Elhadad, S. et al. "MASP2 levels are elevated in thrombotic microangiopathies: association with microvascular endothelial cell injury and suppression by anti-MASP2 antibody narsoplimab," Clinical and Experimental Immunology, 203: 96-104.

(56) References Cited

OTHER PUBLICATIONS

Belcher, J. D. et al., "MASP-2 and MASP-3 inhibitors block complement activation, inflammation, and microvascular stasis in a murine model of vaso-occlusion in sickle cell disease," Translational Research, Nov. 2022; pp. 1-12.
Khaled, MD, S. K. et al., "Narsoplimab, a Mannan-Binding Lectin-Associated Serine Protease-2 Inhibitor, for the Treatment of Adult Hematopoietic Stem-Cell Transplantation-Associated Thrombotic Microangiopathy," Journal of Clinical Oncology; vol. 40, Issue 22; pp. 2247-2459.
Lafayette, R. A. et al., "Safety, Tolerability and Efficacy of Narsoplimab, a Novel MASP-2 Inhibitor for the Treatment of IgA Nephropathy," Kidney International Reports (2020) 5, 2032-2041.
Lafayette MD, R. A. et al. "Long-Term Phase 2 Efficacy of the MASP-2 Inhibitor Narsoplimab for Treatment of Severe IgA Nephropathy," ASN (2021).
Nurbo et al., Bioorganic & Medicinal Chemistry (2008), 16(10), 5590-5605 and Supplementary Material on pp. S1-S8. (Year: 2008).
Belikov, V.G., "Pharmaceutical Chemistry", textbook, 2007, Moscow, "MEDpress-Inform", pp. 27-29.
Dyson G. and P. Mei, "Chemistry of synthetic drugs", translation from English, M: "Mir", 1964, pp. 12-19).
Kümmererer, K. Pharmaceuticals in the environment, Annual Review of Environment and Resources, 2010, V.35, p. 57-75, doi: 10.1146/annurev-environ-052809-16122.
Alexeev, V.V., Optical isomerism and pharmacologic activity of drugs. Soros Educational Journal, 1998, pp. 49-55.

MASP-2 INHIBITORS AND METHODS OF USE

STATEMENT REGARDING SEQUENCE LISTING

The sequence listing associated with this application is provided in text format in lieu of a paper copy and is hereby incorporated by reference into the specification. The name of the text file containing the sequence listing is 700128_424_SEQUENCE_LISTING. The text file is 6.0 KB, was created on Dec. 3, 2020, and is being submitted via EFS-Web with the filing of the specification.

TECHNICAL FIELD

The present disclosure is directed generally to compositions and methods that are useful in the field of medicine. More specifically, the disclosure provides synthetic inhibitors of mannan-binding lectin-associated serine protease-2 (MASP-2), including inhibitors that selectively inhibit MASP-2 over thrombin, compositions thereof, and methods for the manufacture and use thereof.

BACKGROUND

The complement system plays a role in the inflammatory response and becomes activated because of tissue damage or microbial infection. Complement activation must be tightly regulated to ensure selective targeting of invading microorganisms and avoid self-inflicted damage (Ricklin et al., Nat. Immunol. 11:785-797, 2010). Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and generally requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

Mannan-binding lectin-associated serine protease-2 (MASP-2) has been shown to be required for the function of the lectin pathway, one of the principal complement activation pathways (Vorup-Jensen et al., J. Immunol 165:2093-2100, 2000; Ambrus et al., J Immunol. 170: 1374-1382, 2003; Schwaeble et al., PNAS 108:7523-7528, 2011). Importantly, inhibition of MASP-2 does not appear to interfere with the antibody-dependent classical complement activation pathway, which is a critical component of the acquired immune response to infection. As described in U.S. Pat. No. 9,011,860 (assigned to Omeros Corporation), which is hereby incorporated by reference, discloses a fully human monoclonal antibody targeting human MASP-2 has been generated which binds to human MASP-2 with high affinity and blocks the lectin pathway complement activity and is therefore useful to treat various lectin complement pathway-associated diseases and disorders.

MASP-2-dependent complement activation has been implicated as contributing to the pathogenesis of numerous acute and chronic disease states. Therefore, a need exists for compounds that are suitable for administration/treatment of subject suffering from MASP-2 complement pathway-associated diseases and disorders, including diseases that are not suitably or efficiently treated with large molecule biologic inhibitors.

BRIEF SUMMARY

One embodiment provides a compound having the following Structure (I):

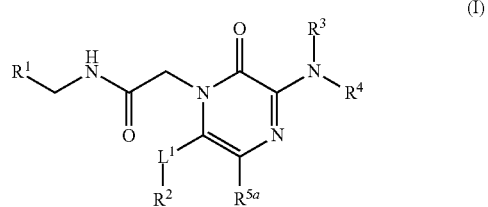

or a stereoisomer, tautomer, or pharmaceutically acceptable salt thereof, wherein $R^1$, $R^2$, $R^3$, $R^4$, $R^{5a}$, and $L^1$ are as defined below.

Another embodiment provides a compound having the following Structure (II):

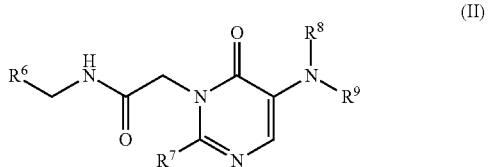

or a stereoisomer, tautomer, or pharmaceutically acceptable salt thereof, wherein $R^6$, $R^7$, $R^8$, and $R^9$ are as defined below.

Another embodiment provides a compound having the following Structure (III):

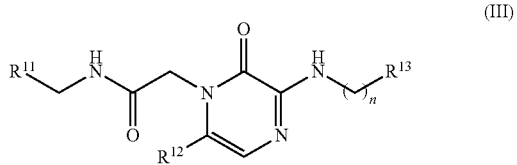

or a stereoisomer, tautomer, or pharmaceutically acceptable salt thereof, wherein $R^{11}$, $R^{12}$, $R^{13}$, and n are as defined below.

Another embodiment provides a compound having the following Structure (IV):

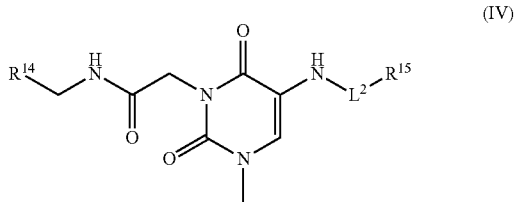

or a stereoisomer, tautomer, or pharmaceutically acceptable salt thereof, wherein $R^{14}$, $R^{15}$, and $L^2$ are as defined below.

Additional embodiments of the present disclosure provide a pharmaceutical composition comprising a compound of Structure (I), (II), (III), or (IV), or a stereoisomer, tautomer, or pharmaceutically acceptable salt thereof, and at least one pharmaceutically acceptable carrier or excipient.

The compounds of Structures (I), (II), (III), and (IV) are useful in the treatment of MASP-2-associated diseases and disorders, and in the manufacture of medicaments for treating MASP-2-associated diseases and disorders. Accordingly, other embodiments of the disclosure provide methods of treating a MASP-2-associated disease and disorder comprising administering to a patient a therapeutically effective amount of a compound of Structure (I), (II), (III), or (IV), or a stereoisomer, tautomer, or pharmaceutically acceptable salt thereof.

These and other aspects, objects and embodiments will become more apparent when read with the detailed description and figures which follow.

DETAILED DESCRIPTION

I. Definitions

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter of the present disclosure, suitable methods and materials are described below. In addition, the materials, methods, and examples are illustrative only and not intended to be limiting.

In certain embodiments herein, reference is made to features and aspects of the disclosure, including method steps. All possible combinations of such features and aspects within the embodiments of the disclosure are included, at least to the extent that such combinations are non-contradictory. For example, if an embodiment presents aspects A, B, and C, it is understood that this also discloses embodiments including both aspects A and B, both aspects B and C, and both aspects A and C, as well as an embodiment with aspects A, B, and C.

The terms "a," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art.

The terms "about" and "approximately" refer to an acceptable degree of error for the quantity measured given the nature or precision of the measurements. Typical, exemplary degrees of error are within ±20 percent (%); preferably, within ±10%; and more preferably, within ±5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written support for a claim limitation of, e.g., "0.98X." Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated. When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11 mg/kg" is equivalent to "about 7, about 9, or about 11 mg/kg."

The term "MASP-2" refers to mannan-binding lectin-associated serine protease-2. Human MASP-2 protein with UniProt accession code O00187 (SEQ ID NO:1). The Serine Protease Domain ('B-chain'=Mannan-binding lectin serine protease 2 B chain, based on UniProtKB—O00187 (MASP-2 HUMAN)) includes residues 445 to 686 (or consists of residues 445 to 686).

The term "MASP-2-dependent complement activation" refers to MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n.

The term "MASP-2-dependent complement-associated disease or disorder" refers to a disease or disorder that is associated with MASP-2-dependent complement activation.

The term "MASP-2-associated disease or disorder" refers to a disease or disorder that is associated with activation or activity of MASP-2, including MASP-2-dependent complement-associated disease or disorders, and wherein inhibition of MASP-2 is or is expected to be therapeutically beneficial.

The term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

The term "classical pathway" refers to complement activation that is triggered by an antibody bound to a foreign particle and requires binding of the recognition molecule C1q.

Amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile), leucine (Leu), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either His, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further sub-classed as follows: by "uncharged hydrophilic" amino acid is meant either Ser, Thr, Asn or Gln. By "acidic" amino acid is meant either Glu or Asp. By "basic" amino acid is meant either Lys, Arg or His.

The term "conservative amino acid substitution" is illustrated by a substitution among amino acids within each of the following groups:
  (1) glycine, alanine, valine, leucine, and isoleucine;
  (2) phenylalanine, tyrosine, and tryptophan;
  (3) serine and threonine;

(4) aspartate and glutamate;
(5) glutamine and asparagine; and
(6) lysine, arginine and histidine.

The term "a subject" includes all mammals, including without limitation, humans, non-human primates, dogs, cats, horses, sheep, goats, cows, rabbits, pigs, and rodents.

"Mammal" includes humans and both domestic animals such as laboratory animals and household pets, (e.g., cats, dogs, swine, cattle, sheep, goats, horses, rabbits), and non-domestic animals such as wildlife and the like.

The terms "small molecule" and "small organic molecule" refers to a small carbon-containing molecule that has a molecular weight of about 2500 daltons or lower. In some embodiments, a small molecule has a molecular weight of about 2000 daltons or lower. In some embodiments, a small molecule has a molecular weight of about 1500 daltons or lower. In some embodiments, a small molecule has a molecular weight of about 1000 daltons or lower. In some embodiments, a small molecule has a molecular weight of about 750 daltons or lower. In some embodiments, a small molecule has a molecular weight of about 500 daltons or lower. In some embodiments, a small molecule has a molecular weight of about 50 daltons or greater. In some embodiments, a small molecule has a molecular weight of about 75 daltons or greater. In some embodiments, a small molecule has a molecular weight of about 100 daltons or greater. In some embodiments, a small molecule has a molecular weight of about 150 daltons or greater. In some embodiments, a small molecule has a molecular weight of about 250 daltons or greater. In some embodiments, small molecules may have a molecular weight in the range from about 50 daltons to about 500 daltons, from about 50 daltons to about 750 daltons, from about 50 daltons to about 1000 daltons, from about 50 daltons to about 1500 daltons, from about 50 daltons to about 2000 daltons, or from about 50 daltons to about 2500 daltons. When the term "compound" is used herein, the term is explicitly intended to include small molecule compounds as defined herein (including any of the embodiments thereof).

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. In some embodiments, a disease is a pathological condition of an organ, a body part, or a system resulting from various causes, such as infection, genetic defect, or environmental stress that is characterized by an identifiable group of symptoms.

"Therapeutically effective amount," "effective amount," or "effective dose" refers to that amount of a compound of the disclosure that, when administered to a mammal (e.g., a human), is sufficient to effect treatment, as defined below, of a disease or condition in the mammal, preferably a human. The amount of a compound of the disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

The term "subcutaneous administration" refers to administration of a formulation under all layers of the skin of a subject.

The term "histidine" specifically includes L-histidine unless otherwise specified.

The term "isotonic" refers to a formulation that has essentially the same osmotic pressure as human blood. Isotonic formulations will generally have an osmotic pressure from about 250 to about 350 mOsmol/L. Isotonicity can be measured using a vapor pressure or freezing point depression osmometer, for example.

The term "hypertonic" refers to a formulation with an osmotic pressure above that of human (i.e., greater than 350 mOsm/L).

The term "hydrogen-bonding" is a partially electrostatic attraction between a hydrogen (H) which is bound to a more electronegative atom such as nitrogen (N) or oxygen (O) and another adjacent atom bearing a lone pair of electrons. For example, when it is stated that the nitrogen acts as a "hydrogen bond donor" it means that a hydrogen (H) bound to a nitrogen (N) is donated by the nitrogen as it electrostatically attracted to or accepted by an adjacent atom bearing a lone pair of electrons such as an oxygen. Similarly, when it is stated that an oxygen acts as a "hydrogen bond acceptor," it means that a hydrogen (H) bound to a more electronegative atom such as nitrogen (N) is electrostatically attracted to or "accepted by" an adjacent atom such as oxygen bearing a lone pair of electrons. Sometimes the hydrogen bonded atoms are called out without explicitly stating the origin and presence of an intermediate hydrogen atom. The term "hydrogen bonding" is used wherever LigPlot+ software predicts a hydrogen bonding interaction using its algorithm and applied parameters of 3.35 Å for maximum distance between hydrogen bond donor and acceptor. Not all hydrogen bonds may actually be in place simultaneously; this is evident for atoms that are shown to form 4 putative hydrogen bonds, where however, at any given time only 3 hydrogen bonds are chemically possible. In general, although crystal structures such as the co-crystal structural information herein does not directly show or detect hydrogen bonding, the software used to describe the co-crystal does predict such H-bonding exists. Therefore, throughout the disclosure when a H-bond is present and described, it may be said to be "predicted" by software to be present.

The term ionic bonding includes a type of chemical bond that involves the electrostatic attraction between oppositely charged ions, and is the primary interaction occurring in ionic compounds.

The term "van der Waals" interaction includes weak, short-range electrostatic attractive forces between uncharged molecules, arising from the interaction of permanent or transient electric dipole moments. As determined by LigPlot+ software employing models derived from the corresponding crystallographic MASP-2 compound co-structures, such interactions include all contacts that are computed using non-bonded contact parameters between hydrophobic to any contacts for interactions with a maximum contact distance of 3.90 Å.

The term "π-π interaction" or "π-π stacking" interaction includes attractive, non-covalent interactions between aromatic rings that are oriented either roughly parallel or roughly perpendicular (such as in "edge-face" interactions) to each other, since they contain π-bonds.

Typically, the active site of serine proteases such as MASP-2 is shaped as a cleft where the polypeptide substrate or inhibitor binds. Schechter and Berger labeled amino acid residues from the N to C terminus of the polypeptide substrate as follows: Pi, . . . , P3, P2, P1, P1', P2', P3', . . . , Pj) and their respective binding sub-sites Si, . . . , S3, S2, S1, S1', S2', S3', . . . , Sj. The cleavage is catalyzed between P1 and P1' (Schechter, I. & Berger, A. On the size of the active site in proteases. I. Papain. Biochem. Biophys. Res. Commun. 27 (1967)).

The term "binding site" is an area on the protein wherein a small molecule can interact with, such as a region on the surface of MASP-2. The binding site or region may not or only partially overlap with the active site, but nevertheless render the MASP-2 molecule less active or inactive.

The term "or" refers to an alternative and should in general be construed non-exclusively. For example, a claim to "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The group "A or B" is equivalent to the group "selected from the group consisting of A and B."

The linking term "comprising" or "comprise" is not closed. For example, "a composition comprising A" must include at least the component A, but it may also include one or more other components (e.g., B; B and C; B, C, and D; and the like). The term "comprising" therefore should in general be construed as not excluding additional ingredients. For example, a claim to "a composition comprising A" would cover compositions that include A and B; A, B, and C; A, B, C, and D; A, B, C, D, and E; and the like.

The term "hypertonic" refers to a formulation with an osmotic pressure above that of human (i.e., greater than 350 mOsm/KglHhO).

The term "agent" refers to a compound or mixture of compounds that, when added to a composition, tend to produce an effect on the composition's properties. For example, a composition comprising a thickening agent is likely to be more viscous than an otherwise identical comparative composition that lacks the thickening agent.

A "synthetic" compound means a compound that is not naturally occurring and that has been synthesized by humans. Reference to a compound herein may be understood to include reference to synthetic compounds, unless the context indicates otherwise.

The expressions, "ambient temperature" and "room temperature," as used herein, are understood in the art, and refer generally to a reaction temperature, e.g., a reaction temperature, that is about the temperature of the room in which the reaction is carried out, e.g., a temperature from about 20° C. to about 30° C.

At various places in the present specification, certain features of the compounds are disclosed in groups or in ranges. It is specifically intended that such a disclosure include each and every individual sub-combination of the members of such groups and ranges. For example, the terms "$C_{1-6}$ alkyl" and "$C_1$-$C_6$ alkyl" are specifically intended to individually disclose (without limitation) methyl, ethyl, $C_3$ alkyl, $C_4$ alkyl, $C_5$ alkyl, and $C_6$ alkyl.

The term "substituted" means that an atom or group of atoms formally replaces hydrogen as a "substituent" attached to another group. The term "substituted", unless otherwise indicated, refers to any level of substitution, e.g., mono-, di-, tri-, tetra-, penta-, or higher substitution, where such substitution is permitted (e.g., results in a stable compound). The substituents are independently selected, and substitution may be at any chemically accessible position. It is to be understood that substitution at a given atom is limited by valency. The phrase "optionally substituted" means substituted or unsubstituted. The term "substituted" means that at least hydrogen atom is replaced with a substituent. A single divalent substituent, e.g., oxo, can replace two hydrogen atoms.

The terms "$C_{n-m}$" and "$C_n$-$C_m$" where n and m are integers indicates a group that contains from n to m carbon atoms. Examples include $C_{1-4}$, $C_{1-6}$, and the like. The term is intended to expressly disclose every member in the range, i.e., $C_n$, $C_{n+1}$, $C_{n+2}$ . . . $C_{m-2}$, $C_{m-1}$, $C_m$. For example, $C_{1-6}$ is intended to disclose $C_1$, $C_2$, $C_3$, $C_4$, $C_5$, and $C_6$. As used herein, "$C_{n-m}$" means the same as "$C_n$-$C_m$".

The term "n-membered," where n is an integer (e.g., 6-membered), typically describes the number of ring-forming atoms in a moiety where the number of ring-forming atoms is n. The term "n-m membered" wherein n and m are integers (e.g., 6-10 membered) describes a range where the number of ring forming atoms is from n to m. For example, piperidinyl is an example of a 6-membered heterocyclyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. In certain specific embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_pR^{102}$ (where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. In certain embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_pR^{102}$ where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl.

"Alkynyl" refers to a straight-chain or branched hydrocarbon group corresponding to an alkyl group as defined above having one or more triple carbon-carbon bonds. An alkynyl group formally corresponds to an alkyne with one C—H bond replaced by the point of attachment of the alkyl group to the remainder of the compound. The term "$C_{n-m}$ alkynyl" and "$C_n$-$C_m$ alkynyl" refer to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms. Unless indicated otherwise, alkynyl groups are optionally substituted.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. In some embodiments, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{100}$, —$OC(O)R^{100}$, —$N(R^{100})_2$, —$C(O)R^{100}$, —$C(O)OR^{100}$, —$C(O)N(R^{100})_2$, —$N(R^{20})C(O)OR^{102}$, —$N(R^{100})C(O)R^{102}$, —$N(R^{102})S(O)_pR^{102}$ (where p is 1 to 2), —$S(O)_pOR^{102}$ (where p is 1 to 2), —$S(O)_tR^{102}$ (where t is 0 to 2), and —$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; and each $R^{102}$ is alkyl, haloalkyl, cycloalkyl, cycloalkylalkyl, aryl, arylalkyl, heterocyclyl, heterocyclylalkyl, heteroaryl, or heteroarylalkyl.

The term "hydroxyalkyl" refers to an alkyl group as defined above in which one or more of the hydrogen atoms has been replaced by a hydroxy group (i.e., —OH). The term "$C_{n-m}$ hydroxyalkyl" refers to a $C_{n-m}$ alkyl group having n to m carbon atoms and from at least one hydroxy group. In some embodiments, the hydroxyalkyl group comprises one hydroxy group. In certain aspects, the hydroxyalkyl group comprises two or more hydroxy groups (e.g., a "dihydroxyalkyl"), each on the same or a different carbon atom(s). In certain aspects, the hydroxyalkyl group has 1, 2, 3, 4, 5, 6, or more hydroxy groups. Examples may include, but are not limited to, hydroxymethyl, 2-hydroxyethyl, and 1-hydroxyethyl.

"Aminylalkyl" refers to an alkyl group as defined above in which one or more hydrogen atoms have been replaced by an aminyl group (i.e., —$NR^{100}R^{101}$ wherein $R^{100}$ and $R^{101}$ are each independently hydrogen, alkyl, alkenyl, or alkynyl as defined herein). In some embodiments, the aminylalkyl comprises one aminyl group. In some embodiments, the aminyl group is —$NH_2$.

"Carboxyalkyl" refers to an alkyl group as defined above in which one or more hydrogen atoms have been replaced by a carboxy group (i.e., —C(O)OH). In some embodiments, the carboxyalkyl comprises one carboxy group.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, ace-phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, an aryl group may be optionally substituted by one or more substituents independently selected from the group consisting of alkyl, alkenyl, halo, haloalkyl, haloalkenyl, cyano, nitro, aryl, arylalkyl, cycloalkyl, cycloalkylalkyl, heterocyclyl, heterocyclylalkyl, heteroaryl, heteroarylalkyl, —$R^{101}$—$OR^{100}$, —$R^{101}OC(O)R^{100}$, —$R^{101}$—$N(R^{100})_2$, —$R^{101}$—$N(R^{100})$—$R^{103}$—$OR^{100}$, —$R^{101}$—$C(O)R^{100}$, —$R^{101}$—$C(O)OR^{100}$, —$R^{101}$—$C(O)N(R^{100})_2$, —$R^{101}$—$N(R^{100})C(O)OR^{102}$, —$R^{101}$—$N(R^{100})C(O)R^{102}$, —$R^{101}$—$N(R^{100})S(O)_pR^{102}$ (where p is 1 to 2), —$R^{101}$—N=C(OR^{100})R^{100}$, —$R^{101}$—$S(O)_pOR^{102}$ (where p is 1 to 2), —$R^{101}$—$S(O)_tR^{102}$ (where t is 0 to 2), and —$R^{101}$—$S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain. In some embodiments an aryl group has the following structure:

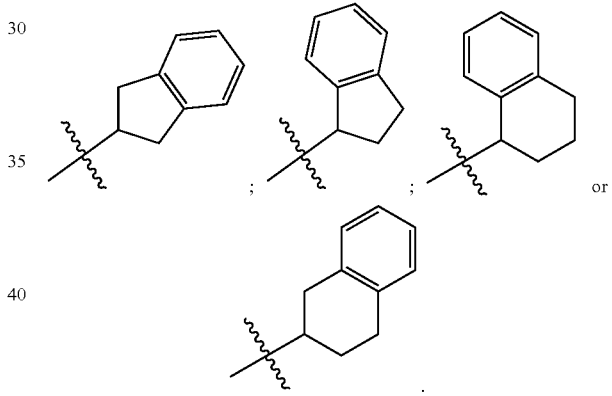

"Arylalkyl" or "aralkyl" refers to a group of formula -alkylene-aryl wherein the alkylene group and aryl groups are as defined herein, respectively. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is $C_{6-10}$ aryl-$C_{1-3}$ alkyl. In some embodiments, arylalkyl is phenyl-$C_{1-3}$ alkyl. Examples include, but are not limited to, benzyl, 1-phenylethyl, 4-methylbenzyl, and 1,1,-dimethyl-1-phenylmethyl. In some embodiments, arylalkyl is optionally substituted benzyl.

"Aryloxy" refers to a group with the formula —O-aryl wherein aryl is a group as defined above. In some embodiments, the aryloxy group is —O—$C_{6-10}$ aryl. In some embodiments, the aryloxy is a substituted or unsubstituted phenyloxy (i.e., —O—$C_6$ aryl).

"Arylalkoxy" refers to a group with the formula -alkoxy-aryl wherein alkoxy and aryl are groups as defined above, respectively. In some embodiments, arylalkoxy is $C_{6-10}$ aryl-$C_{1-3}$ alkoxy. In some embodiments, arylalkoxy is $C_{6-10}$ aryl-$C_{1-4}$ alkoxy. In some embodiments, arylalkoxy is $C_{6-10}$ aryl-$C_{1-3}$ alkoxy. In some embodiments, arylalkoxy is phenyl-$C_{1-3}$ alkoxy (e.g., methoxy).

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. In some embodiments, a cycloalkyl group may be optionally substituted by one or more substituents independently selected from the group consisting of alkyl, alkenyl, halo, haloalkyl, haloalkenyl, cyano, nitro, oxo, aryl, arylalkyl, cycloalkyl, cycloalkylalkyl, heterocyclyl, heterocyclylalkyl, heteroaryl, heteroarylalkyl, $-R^{101}-OR^{100}$, $-R^{101}-OC(O)-R^{100}$, $-R^{101}-N(R^{100})-R^{103}-OR^{100}$, $-R^{101}-N(R^{100})_2$, $-R^{101}-C(O)R^{100}$, $-R^{101}-C(O)OR^{100}$, $-R^{101}-C(O)N(R^{100})_2$, $-R^{101}-N(R^{100})C(O)OR^{102}$, $-R^{101}-N(R^{100})C(O)R^{102}$, $-R^{101}-N(R^{100})S(O)_pR^{102}$ (where p is 1 to 2), $-R^{101}-N=C(OR^{100})R^{100}$, $-R^{101}-S(O)_pOR^{102}$ (where p is 1 to 2), $-R^{101}-S(O)_tR^{102}$ (where t is 0 to 2), and $-R^{101}-S(O)_pN(R^{100})_2$ (where p is 1 to 2) where each $R^{100}$ is independently hydrogen, alkyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain.

"Cycloalkylalkyl" refers to a radical of the formula $-R^{100}R^{101}$ where $R^{100}$ is an alkylene chain as defined above and $R^{101}$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Alkoxy" refers to a radical group having the following formula "—O-alkyl," wherein the alkyl group is as defined herein above. Example alkoxy groups include methoxy, ethoxy, propoxy (e.g., n-propoxy and isopropoxy), t-butoxy, and the like. In some embodiments, the alkyl group has 1 to 6, 1 to 4, or 1 to 3 carbon atoms. Unless indicated otherwise, alkoxy groups are optionally substituted.

"Alkoxyalkyl" refers to a radical having the following formula "-alkylene-O-alkyl," wherein the alkylene and alkyl groups are as defined herein above, respectively. In some embodiments, the alkoxyalkyl group comprises one —O-alkyl group. In some embodiments, the alkoxyalkyl group comprises two or more alkoxy groups. Examples may include, but are not limited to, methoxymethyl, ethoxymethyl, 3-ethoxy ethyl, and 1-m ethoxy ethyl. Unless indicated otherwise, alkoxyalkyl groups are optionally substituted.

"Oxo" refers to a =O group. For example, an oxo connected to a carbon atom forms a carbonyl group (i.e., C=O). Alternatively, when an oxo group is attached to a heteroatom, for example, a sulfoxide, sulfone group, an A-oxide group is formed.

"Sulfido" refers to a =S group.

"Amino" refers to a $-NH_2$ group.

"Carbamyl" refers to a $-C(O)NH_2$ group.

"Carboxy" refers to a $-C(O)OH$ group.

"Carbonyl" refers to a C(=O) group, which also may be written as C(O).

"Cyano" or "nitrile" refers to a $-C\equiv N$ group, which also may be written as —CN.

"Nitro" refers to a $-NO_2$ group.

"Hydroxy" or "hydroxyl" refers to an —OH group.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

The term "haloalkoxy", employed alone or in combination with other terms, refers to a group of formula —O-haloalkyl, wherein the haloalkyl group is as defined above. Example haloalkoxy groups include trifluoromethoxy, difluoromethoxy, pentafluoroethoxy, and the like.

"Heterocyclyl" refers to a stable 3- to 18-membered non-aromatic ring radical which consists of two to twelve carbon atoms and from one to six heteroatoms selected from the group consisting of nitrogen, oxygen, and sulfur. Unless stated otherwise specifically in the specification, the heterocyclyl radical may be a monocyclic, bicyclic, tricyclic, or tetracyclic ring system, which may include fused, bridged, and spiro ring systems; and the nitrogen, carbon, or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, 3-azabicyclo[3.1.0]hexan-3-yl, l-azaspiro[3.3]heptan-1-yl, 5-azaspiro[2.3]hexan-5-yl, 2-oxa-6-azaspiro[3.3]heptan-6-yl, 1-oxa-6-azaspiro[3,4]octan-6-yl, 1-oxa-6-azaspiro[3.3]heptan-6-yl, 6-oxa-1-azaspiro[3.3]heptan-1-yl, 6-azaspiro[3.4]octan-6-yl, 7-oxa-2-azaspiro[3.5]nonan-2-yl, 2,6-diazaspiro[3.3]heptan-2-yl, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxothiomorpholinyl. In certain embodiments, a heterocyclyl group may be optionally substituted by one or more substituents selected from the group consisting of alkyl, alkenyl, halo, haloalkyl, haloalkenyl, cyano, oxo, thioxo, nitro, aryl, arylalkyl, cycloalkyl, cycloalkylalkyl, heterocyclyl, heterocyclylalkyl, heteroaryl, heteroaryl alkyl, $-R^{101}-OR^{100}$, $-R^{101}-OC(O)-R^{100}$, $-R^{101}-N(R^{100})-R^{103}-OR^{100}$, $-R^{101}-N(R^{100})_2$, $-R^{101}-C(O)R^{100}$, $-R^{101}-C(O)OR^{100}$, $-R^{101}-C(O)N(R^{100})_2$, $-R^{101}-N(R^{100})C(O)OR^{102}$, $-R^{101}-N(R^{100})C(O)R^{102}$, $-R^{101}-N(R^{100})S(O)_pR^{102}$ (where p is 1 to 2), $-R^{101}-N=C(OR^{100})R^{102}$, $-R^{101}-S(O)_pOR^{102}$ (where p is 1 to 2), $-R^{101}-S(O)_tR^{102}$ (where t is 0 to 2), and $-R^{101}-S(O)_pN(R^{100})_2$ (where p is 1 to 2) where each $R^{100}$ is independently hydrogen, alkyl, alkenyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, alkenyl, haloalkyl, cycloalkyl, cycloalkylalkyl, aryl, arylalkyl, heterocyclyl, heterocyclylalkyl, heteroaryl or heteroarylalkyl, and each $R^{103}$ is a direct bond or a straight or branched alkylene chain.

"Heterocyclylalkyl" refers to a radical of the formula —$R^{100}R^{101}$ where $R^{100}$ is an alkylene chain as defined above and $R^{101}$ is a heterocyclyl radical as defined above, and if the heterocyclyl is a nitrogen-containing heterocyclyl, the heterocyclyl may be attached to the alkyl radical at the nitrogen atom. In some embodiments, the alkylene chain of the heterocyclylalkyl radical may be optionally substituted as defined above for an optionally substituted alkylene chain. In some embodiments, the heterocyclyl part of the heterocyclylalkyl radical may be optionally substituted as defined above for an optionally substituted heterocyclyl group.

"Heteroaryl" refers to a 4- to 14-membered ring system radical comprising hydrogen atoms, one to thirteen carbon atoms, one to six heteroatoms selected from the group consisting of nitrogen, oxygen, and sulfur, and at least one aromatic ring. For purposes of this disclosure, the heteroaryl radical may be a monocyclic, bicyclic, tricyclic, or tetracyclic ring system, which may include fused or bridged ring systems; and the nitrogen, carbon, or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). In certain embodiments, a heteroaryl group may be optionally substituted by one or more substituents selected from the group consisting of alkyl, alkenyl, halo, haloalkyl, haloalkenyl, cyano, oxo, thioxo, nitro, thioxo, aryl, arylalkyl, cycloalkyl, cycloalkylalkyl, heterocyclyl, heterocyclylalkyl, heteroaryl, heteroarylalkyl, —$R^{101}$—$OR^{100}$, —$R^{101}$—OC(O)—$R^{100}$, —$R^{101}$—N($R^{100}$)—$R^{103}$—$OR^{100}$, —$R^{101}$—N($R^{100}$)$_2$, —$R^{101}$—C(O)$R^{100}$, —$R^{101}$—C(O)$OR^{100}$, —$R^{101}$—C(O)N($R^{100}$)$_2$, —$R^{101}$—N($R^{100}$)C(O)$OR^{102}$, —$R^{101}$—N($R^{100}$)C(O)$R^{100}$C(O)$R^{102}$, —$R^{101}$—N($R^{100}$)S(O)$_p R^{102}$ (where p is 1 to 2), —$R^{101}$—N=C($OR^{100}$)$R^{100}$, —$R^{101}$—S(O)$_p OR^{102}$ (where p is 1 to 2), —$R^{101}$—S(O)$_t R^{102}$ (where t is 0 to 2), and —$R^{101}$—S(O)$_p N(R^{100})_2$ (where p is 1 to 2) where each $R^{100}$ is independently hydrogen, alkyl, alkenyl, haloalkyl, cycloalkyl, cycloalkylalkyl, aryl, arylalkyl, heterocyclyl, heterocyclylalkyl, heteroaryl or heteroarylalkyl; each $R^{101}$ is independently a direct bond or a straight or branched alkylene chain; each $R^{102}$ is alkyl, alkenyl, haloalkyl, cycloalkyl, cycloalkylalkyl, aryl, arylalkyl, heterocyclyl, heterocyclylalkyl, heteroaryl, or heteroarylalkyl, and each $R^{103}$ is a direct bond or a straight or branched alkylene chain. Preferably, the optional substituents on an optionally substituted bicyclic heteroaryl group for $R^1$ herein are halo. Preferably, the optional substituents on an optionally substituted monocyclic heteroaryl group for $R^1$ herein are alkyl. The term "heteroaryl" includes, e.g., the following structures:

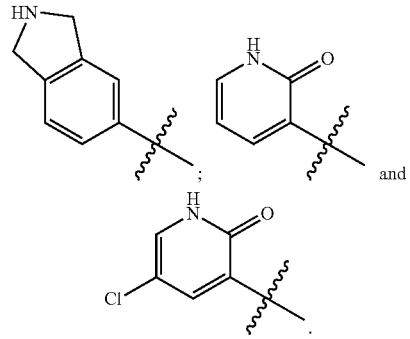

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —$R^{100}R^{101}$ where $R^{100}$ is an alkylene chain as defined above and $R^{101}$ is a heteroaryl radical as defined above. When specifically stated in the specification, the heteroaryl part of the heteroarylalkyl radical may be optionally substituted as defined above for an optionally substituted heteroaryl group. In some specific embodiments, the alkylene chain part of the heteroarylalkyl radical may be optionally substituted as defined above for an optionally substituted alkylene chain.

The compounds and methods of the present disclosure are also meant to encompass all pharmaceutically acceptable compounds of Structures (I), (II), (III), and (IV) being isotopically-labelled by having one or more atoms replaced by an atom having a different atomic mass or mass number.

Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radio-labelled compounds could be useful to help determine or measure the effectiveness of the compounds, by characterizing, for example, the site or mode of action or binding affinity. Certain isotopically-labelled compounds of Structures (I), (II), (III), or (IV), for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. In one embodiment, the compounds of Structures (I), (II), (III), or (IV) are enriched with deuterium. Such deuterated compounds can be achieved by methods known to one skilled in the art, such as exchanging protons with deuterium or by synthesizing the molecule with enriched starting materials.

Substitution with positron emitting isotopes, such as $^{11}$C, $^{18}$F, $^{15}$O, and $^{13}$N, can be useful in Positron Emission Topography (PET) studies for examining substrate receptor occupancy. Isotopically-labeled compounds of Structures (I), (II), (III), or (IV) can generally be prepared by conventional techniques known to those skilled in the art or by processes analogous to those described in the Examples and Preparations as set out below using an appropriate isotopically-labeled reagent in place of the non-labeled reagent previously employed.

This disclosure is also meant to encompass the in vivo metabolic products of the disclosed compounds. Such products may result from, for example, the oxidation, reduction, hydrolysis, amidation, esterification, and the like of an administered compound, primarily due to enzymatic processes. Accordingly, this disclosure includes compounds produced by a process comprising contacting a compound of this disclosure with a mammal for a period of time sufficient to yield a metabolic product thereof. Such products are typically are identified by administering a radio-labelled compound in a detectable dose to an animal, such as rat, mouse, guinea pig, monkey, or to human, allowing sufficient time for metabolism to occur, and isolating its conversion products from the urine, blood, or other biological samples.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substituents on the functional group are also "optionally substituted" and so on, for the purposes of this disclosure, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline, and caffeine.

Often crystallizations produce a solvate of the compound of the disclosure (e.g., a compound of Structure (I), (II), (III), or (IV)). As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate, and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents, or excipients therefor.

"Treating" or "treatment" as used herein covers the treatment of the disease or condition of interest in a mammal, preferably a human, having the disease or condition of interest, and includes:
  (a) preventing the disease or condition from occurring in a mammal, in particular, when such mammal is predisposed to the condition but has not yet been diagnosed as having it;

(b) inhibiting the disease or condition, i.e., arresting the disease or condition's development;
(c) relieving (or ameliorating) the disease or condition, i.e., causing regression of the disease or condition; or
(d) relieving (or ameliorating) the symptoms resulting from the disease or condition, e.g., without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the disclosure, or their pharmaceutically acceptable salts may contain one or more stereocenter and may thus give rise to enantiomers, diastereomers, and other stereoisomeric forms that may be defined, in terms of absolute stereochemistry, as (R)- or (S)- or, as (D)- or (Z)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres giving rise to geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes enantiomers, which refers to two stereoisomers whose molecules are non-superimposable mirror images of one another. See, e.g., Smith, M. B. and J. March, March's Advanced Organic Chemistry: Reactions, Mechanisms, and Structure, 6th edition (Wiley, 2007), for a detailed description of the structure and properties of enantiomers and stereoisomers.

A "tautomer" refers to a proton shift from one atom of a molecule to another atom of the same molecule. The present disclosure includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemBioDraw Ultra Version 14.0 software program. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

At certain places, the definitions or embodiments may refer to specific rings (e.g., an azetidine ring, a pyridine ring, etc). Unless otherwise indicated, these rings can be attached to any ring member provided that the valency of the atom is not exceeded.

When any two groups or two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different). Unless otherwise indicated, if two or more groups having the same definition are present, but the definition provides for alternatives, it should be understood that each occurrence of the same group is independently selected from the possible alternatives. For example, if two or more $R^a$ groups are present in a compound, and the definition of $R^a$ provides that $R^a$ can be A, B, or C, then it should be understood that each $R^a$ group present in the compound is independently chosen from A, B, and C, so that the $R^a$ groups present in the compound can be the same or different.

Compounds, and salts thereof, including pharmaceutically acceptable salts, can be found together with other substances such as water and solvents (e.g., hydrates and solvates) or can be isolated. When in the solid state, the compounds described herein, and salts thereof may occur in various forms and may, e.g., take the form of solvates, including hydrates. The compounds may be in any solid-state form, such as a polymorph or solvate, so unless clearly indicated otherwise, reference to compounds and salts thereof should be understood as encompassing any solid-state form of the compound.

In some embodiments, the compounds described herein or salts thereof, are substantially isolated. "Substantially isolated" means the compound is at least partially or substantially separated from the environment in which it was formed or detected. Partial separation can include, e.g., a composition enriched in the compounds of the disclosure. Substantial separation can include compositions containing at least about 50%, at least about 60%, at least about 70%, at least about 80%, at least about 90%, at least about 95%, at least about 97%, or at least about 99% by weight of the compounds of the disclosure, or salt thereof.

The following abbreviations may be used herein and, unless otherwise noted, have the meanings indicated below:

μ (micro); ° C. (degrees Celsius); Ac (acetyl); ACN (acetonitrile); anhyd (anhydrous); aq (aqueous); atm (atmosphere(s)); Bn (benzyl); Boc (tert-butoxycarbonyl); Bu (butyl); calcd (calculated); Cbz (benzyloxycarbonyl); chrom. (chromatography); CPME (cyclopentyl methyl ether); $CH_2Cl_2$ (dichloromethane); concd (concentrated); conc (concentration); DCC (N,N'-dicyclohexylcarbodiimide); DIAD (Diisopropyl azodicarboxylate); DIEA (N,N-diisopropylethylamine); DMAP (4-(N,N-dimethylamino) pyridine); DMF (dimethylformamide); DMSO (dimethylsulfoxide); EDC (N-(3-dimethylaminopropyl)-N'-ethylcarbodiimide hydrochloride); equiv (equivalent); ES (electrospray); Et (ethyl); Et$_2$O (diethyl ether); g (gram(s)); h (hour(s)); HATU (N-[(Dimethylamino)-1H-1,2,3-triazolo-[4,5-b]pyridin-1-ylmethylene]-N-methylmethanaminium hexafluorophosphate A-oxide); HBTU (O-(Benzotriazol-1-yl)-N,N,N',N'-tetramethyl-O-(1H-benzotriazol-1-yl)uronium hexafluorophosphate); HPLC (high-performance liquid chromatography); HOBt (1-hydroxybenzotriazole hydrate); L (liter(s)); m (milli); m- (meta); M (molar); MeCN (acetonitrile); min (minute(s)); mL (milliliter); mol (mole; molecular (as in mol wt)); Ms (methanesulfonyl); MS (mass spectrometry); MW (molecular weight); NBS (A-bromosuccinimide); NCS (A-chlorosuccinimide); NIS (N-iodosuccinimide); NHS (A-hydroxysuccinimide); NMM (4-methylmorpholine); NMR (nuclear magnetic resonance); o- (ortho); obsd (observed); p-(para); Ph (phenyl); Phth (Phthalimide); ppt (precipitate); Pr (propyl); psi (pounds per square inch); temp (temperature); TFA (trifluoroacetic acid); THF (tetrahydrofuran); TPP (triphenylphosphine); and Tr (trityl). Other abbreviations may also be used and have the meanings that would be understood by the person having skill in the art.

II. Compounds

In certain aspects, the present disclosure provides a compound having the following Structure (I):

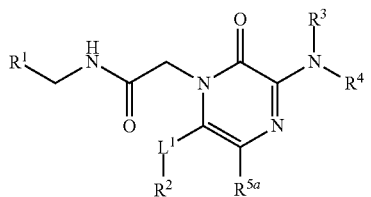

or a stereoisomer, tautomer, or pharmaceutically acceptable salt thereof, wherein:

$R^1$ is a substituted or unsubstituted heteroaryl;

$R^2$ is a substituted or unsubstituted aryl or a substituted or unsubstituted heteroaryl;

$R^3$ is hydrogen or alkyl;

$R^4$ is alkyl, a substituted or unsubstituted arylalkyl, a heterocyclyl substituted with substituents selected from the group consisting of a substituted or unsubstituted phenyl or a substituted or unsubstituted pyridinyl, or $R^3$ and $R^4$, together with the nitrogen and carbon to which they are attached, respectively, form an optionally substituted 4-10 membered heterocyclyl;

$R^{5a}$ is hydrogen or halo;

$L^1$ is a direct bond, —CH$_2$—, —S(O)$_t$—, NR$^{5b}$, —O—, —C=C—, or —C≡C—;

t is 0, 1, or 2; and $R^{5b}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C=O)heterocyclyl, (C=O)Oheterocyclyl, a substituted or unsubstituted aryl, a substituted or unsubstituted heteroaryl, a substituted or unsubstituted cycloalkyl, a substituted or unsubstituted heterocyclyl, a substituted or unsubstituted arylalkyl, a substituted or unsubstituted heteroarylalkyl, a substituted or unsubstituted cycloalkylalkyl, or a substituted or unsubstituted heterocyclylalkyl, provided that:

A) $R^2$ does not have one of the following structures:

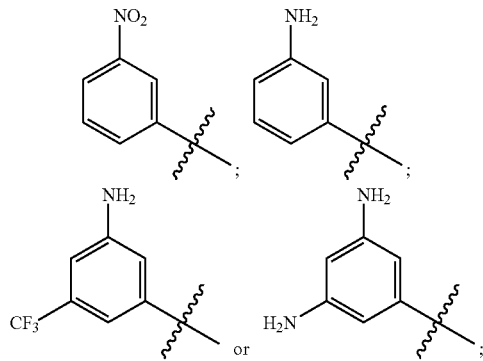

B) $R^1$ does not have one of the following structures:

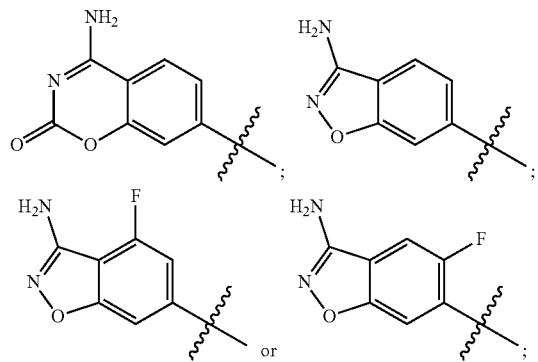

and

C) when $R^2$ is unsubstituted phenyl, $R^1$ does not have one of the following structures:

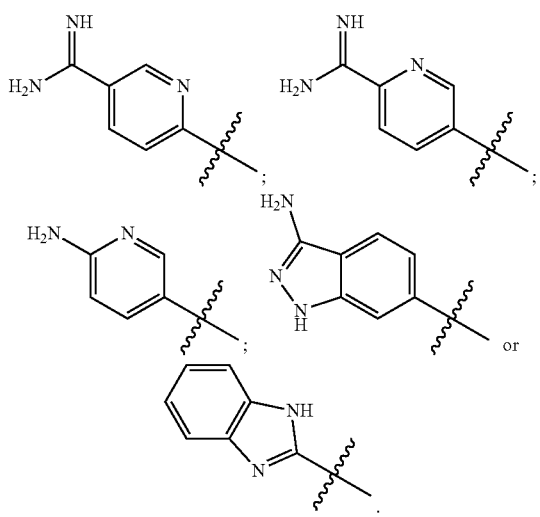

In some embodiments, $R^1$ is a substituted or unsubstituted 5-10 membered heteroaryl. In certain embodiments, $R^1$ is a substituted or unsubstituted pyridinyl, a substituted or unsubstituted pyrrolopyridinyl, or a substituted or unsubstituted benzoimidazolyl.

In some specific embodiments, $R^1$ is substituted with one or more of $R^{1a}$, $R^{1b}$, $R^{1c}$, $R^{1d}$, and $R^{1e}$ wherein $R^{1a}$, $R^{1b}$, $R^{1c}$, $R^{1d}$, and $R^{1e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxyalkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^c$, $C(=NOR^a)NR^bR^c$, $C(=NOC(O)R^a)NR^bR^c$, $C(=NR^a)N(R^b)C(O)OR^c$, $N(R^a)C(=NR^b)NR^cR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{6-10}$ cycloalkyl, and substituted or unsubstituted 4-10 membered heterocyclyl, wherein $R^a$, $R^b$, $R^c$, and $R^d$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain specific embodiments, $R^{1a}$, $R^{1b}$, $R^{1c}$, $R^{1d}$, or $R^{1e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NR^fR^g$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{1a}$, $R^{1b}$, $R^{1c}$, $R^{1d}$, or $R^{1e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{6-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^1$ has one of the following structures:

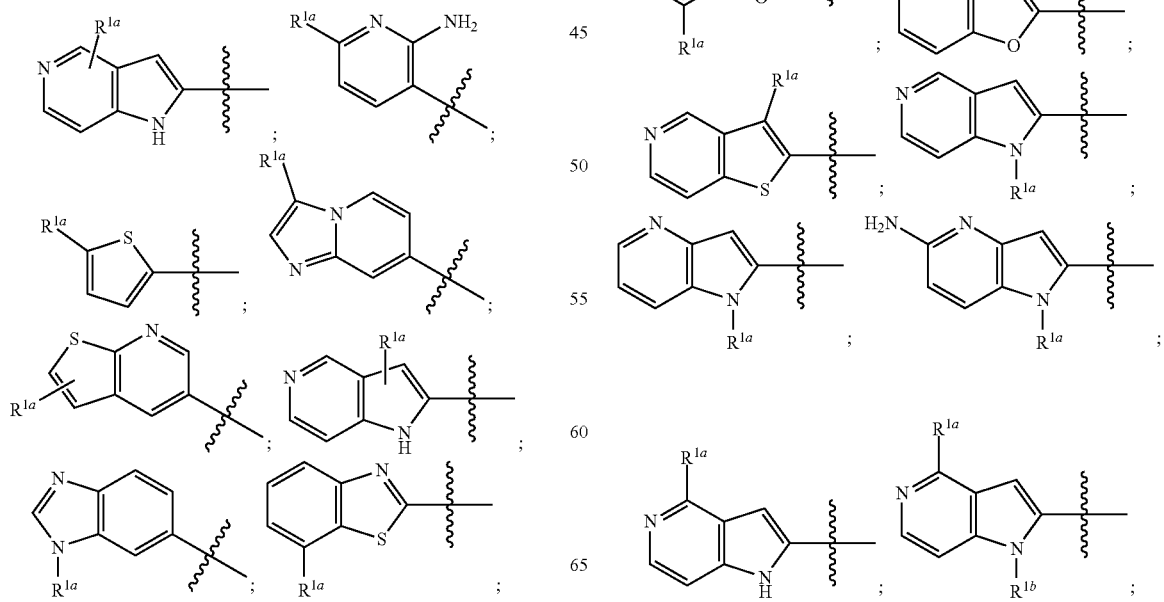

-continued
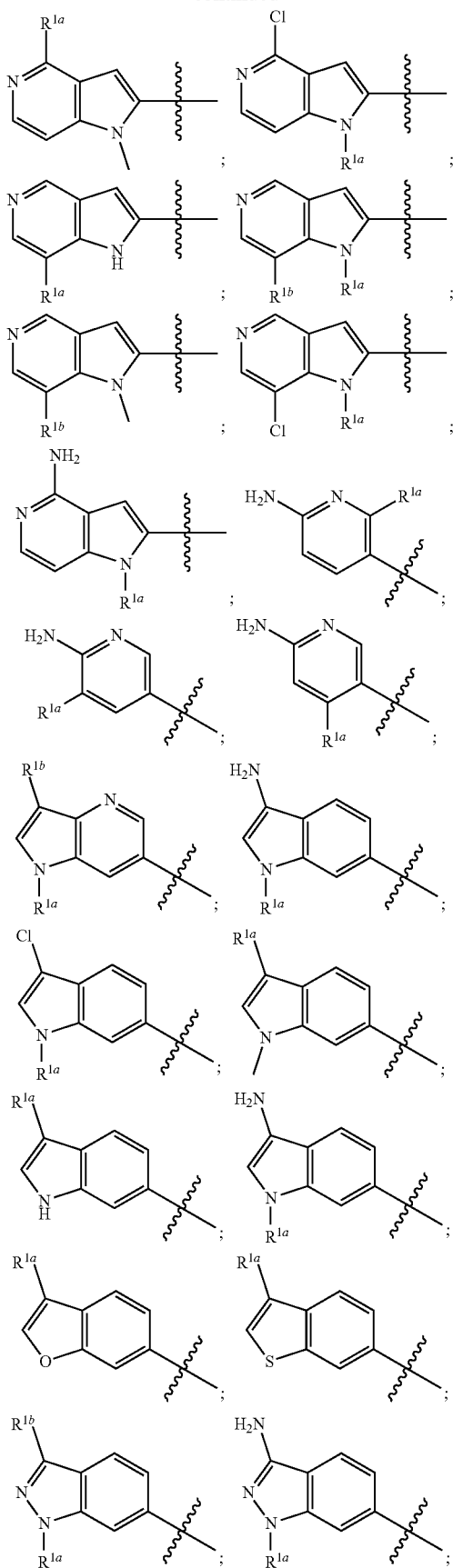
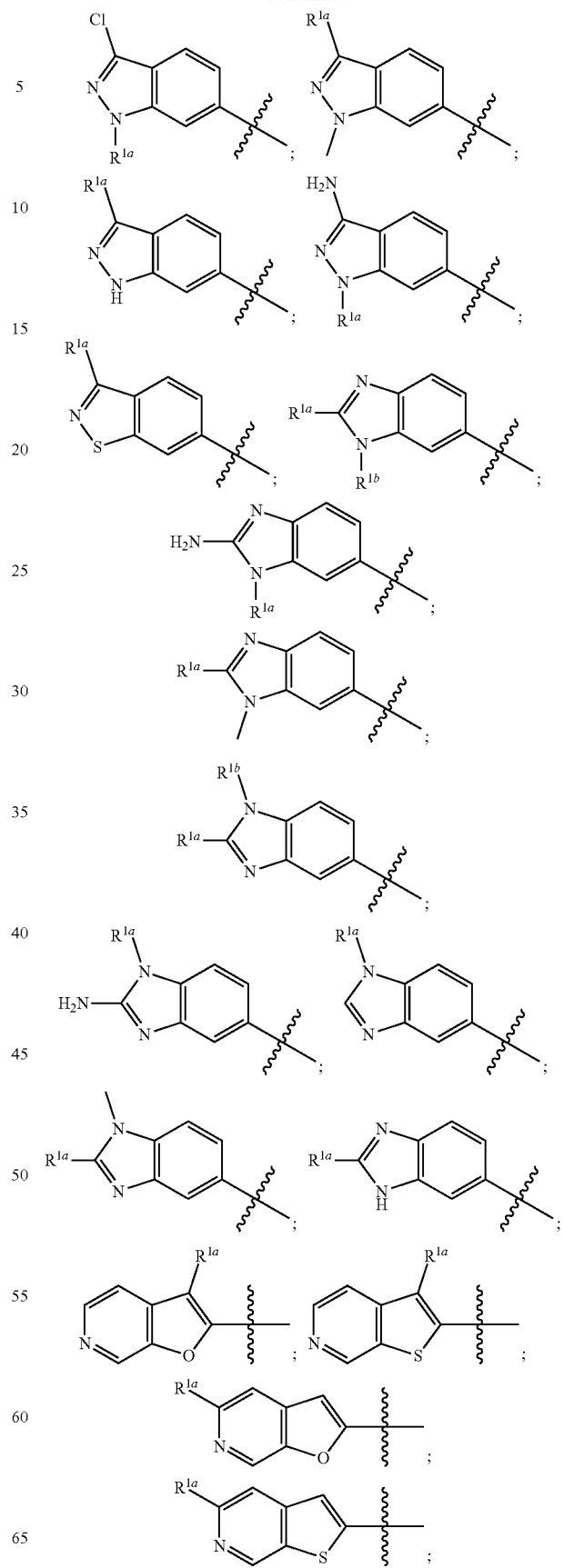

-continued

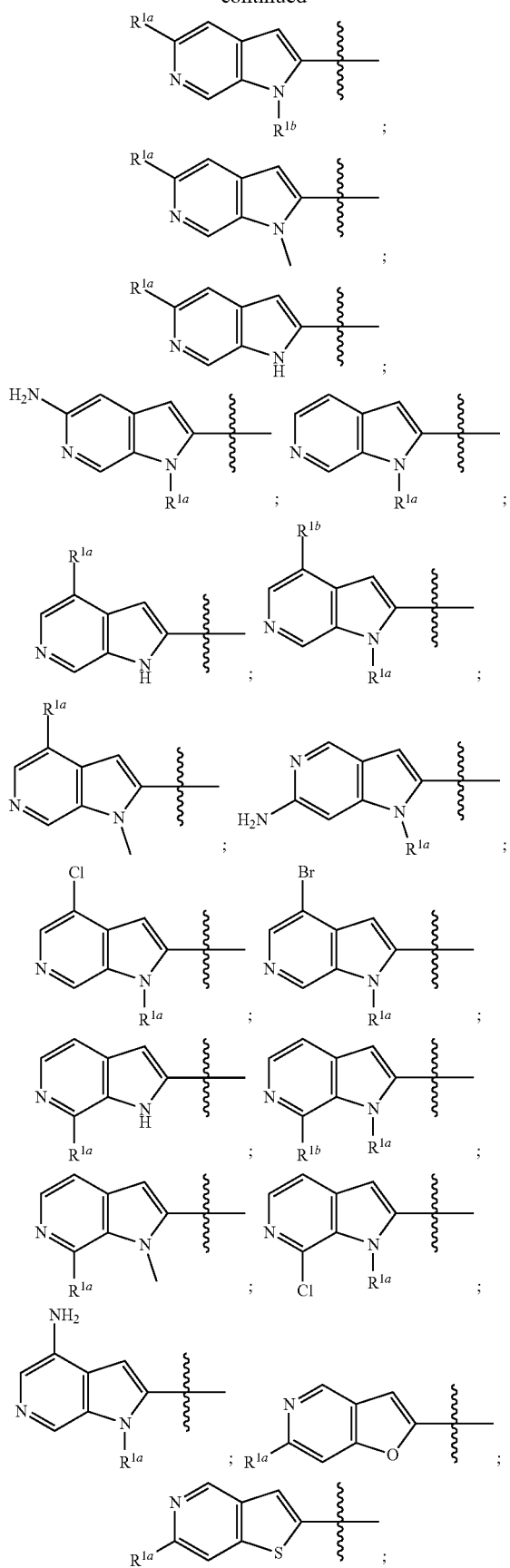

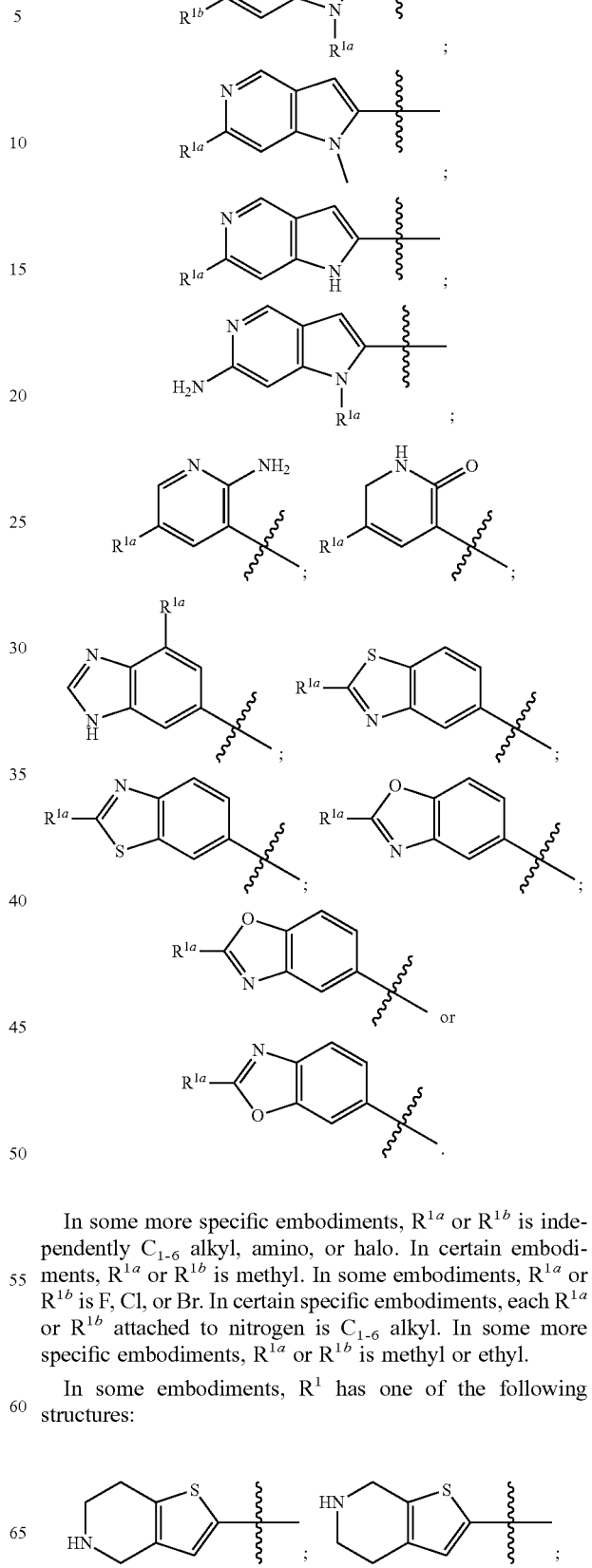

In some more specific embodiments, $R^{1a}$ or $R^{1b}$ is independently $C_{1-6}$ alkyl, amino, or halo. In certain embodiments, $R^{1a}$ or $R^{1b}$ is methyl. In some embodiments, $R^{1a}$ or $R^{1b}$ is F, Cl, or Br. In certain specific embodiments, each $R^{1a}$ or $R^{1b}$ attached to nitrogen is $C_{1-6}$ alkyl. In some more specific embodiments, $R^{1a}$ or $R^{1b}$ is methyl or ethyl.

In some embodiments, $R^1$ has one of the following structures:

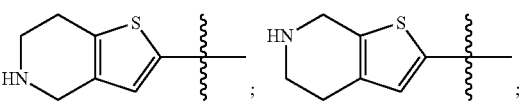

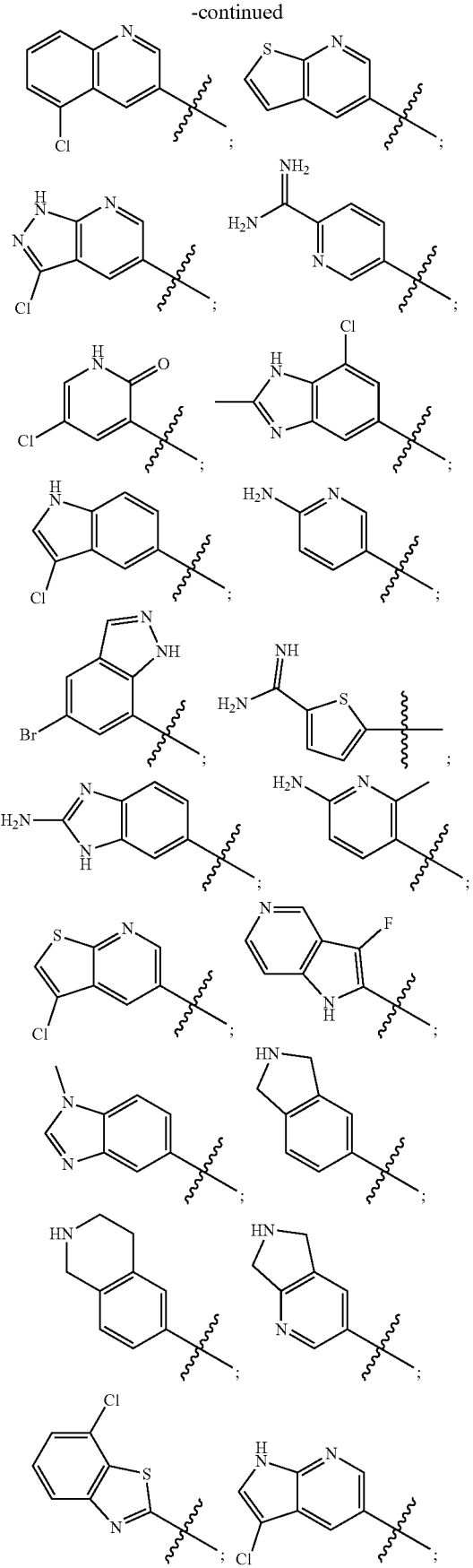
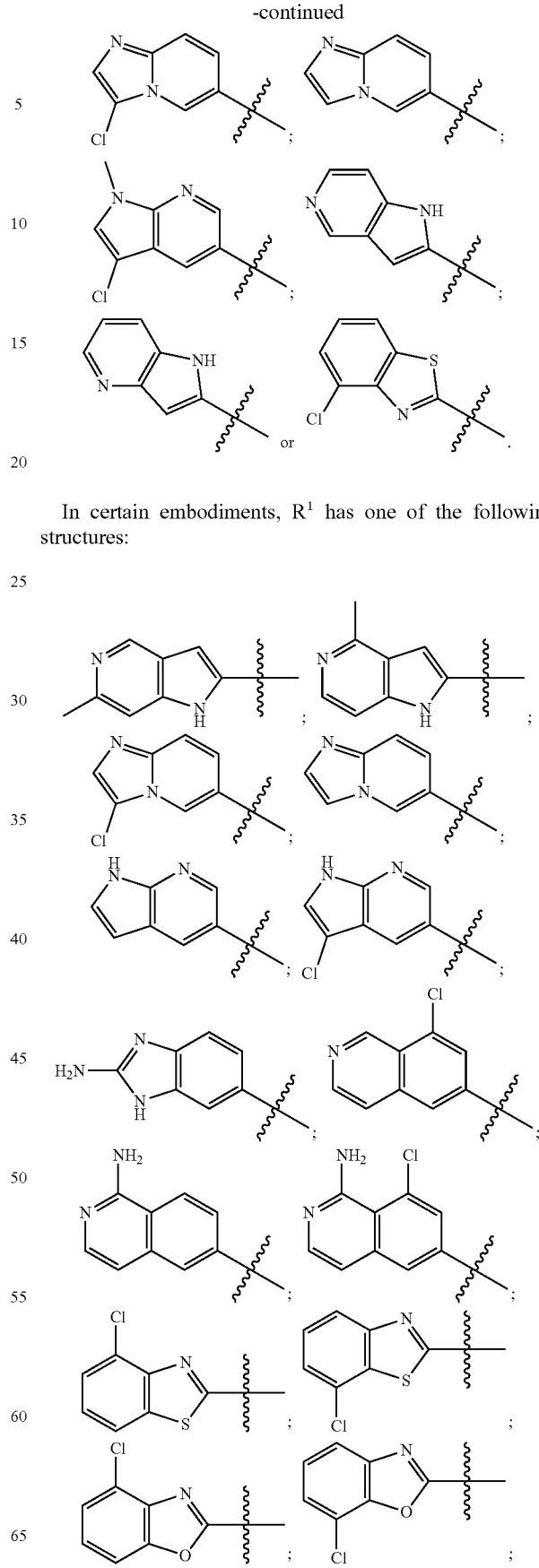
In certain embodiments, $R^1$ has one of the following structures:

-continued
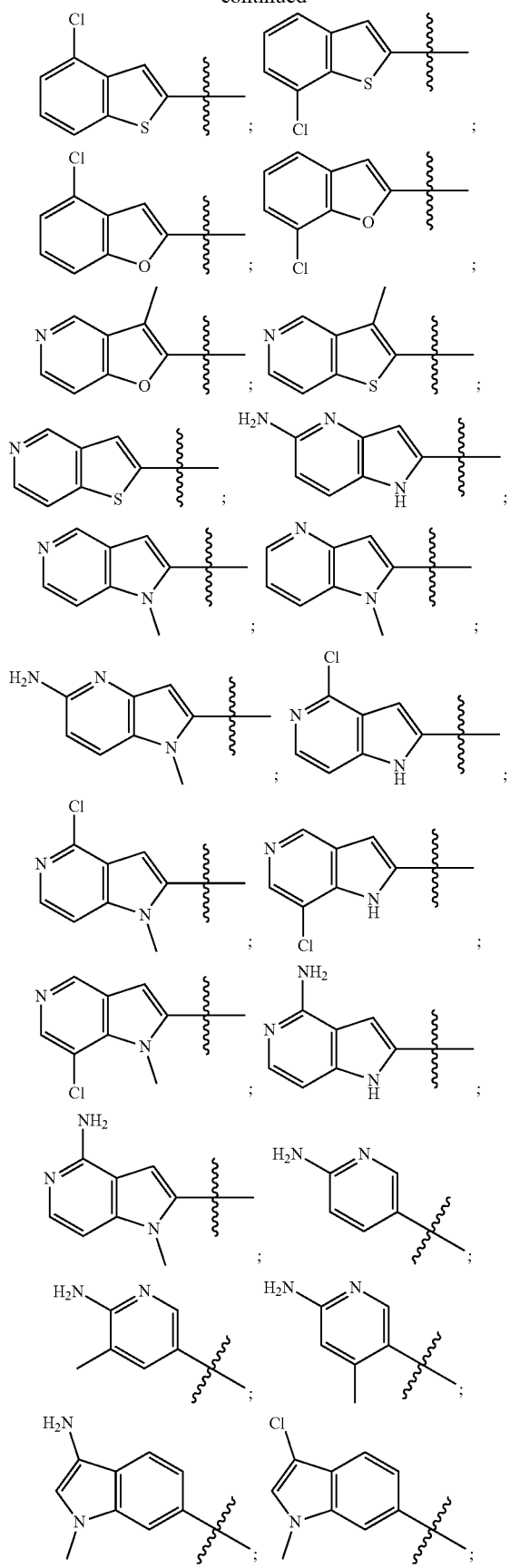
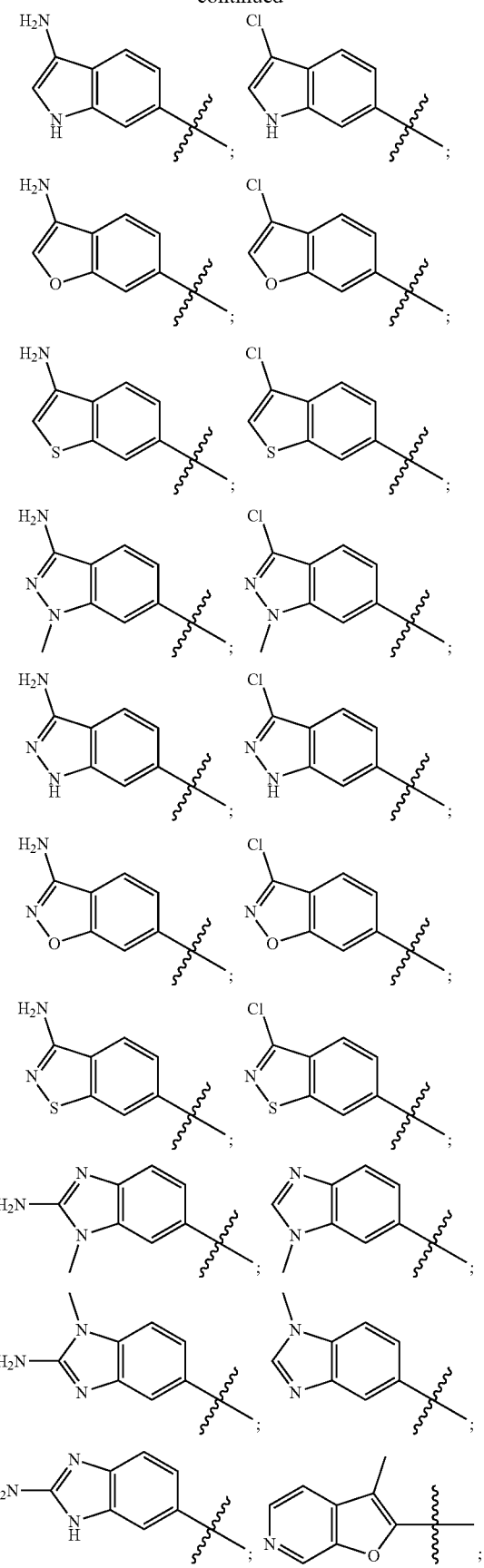

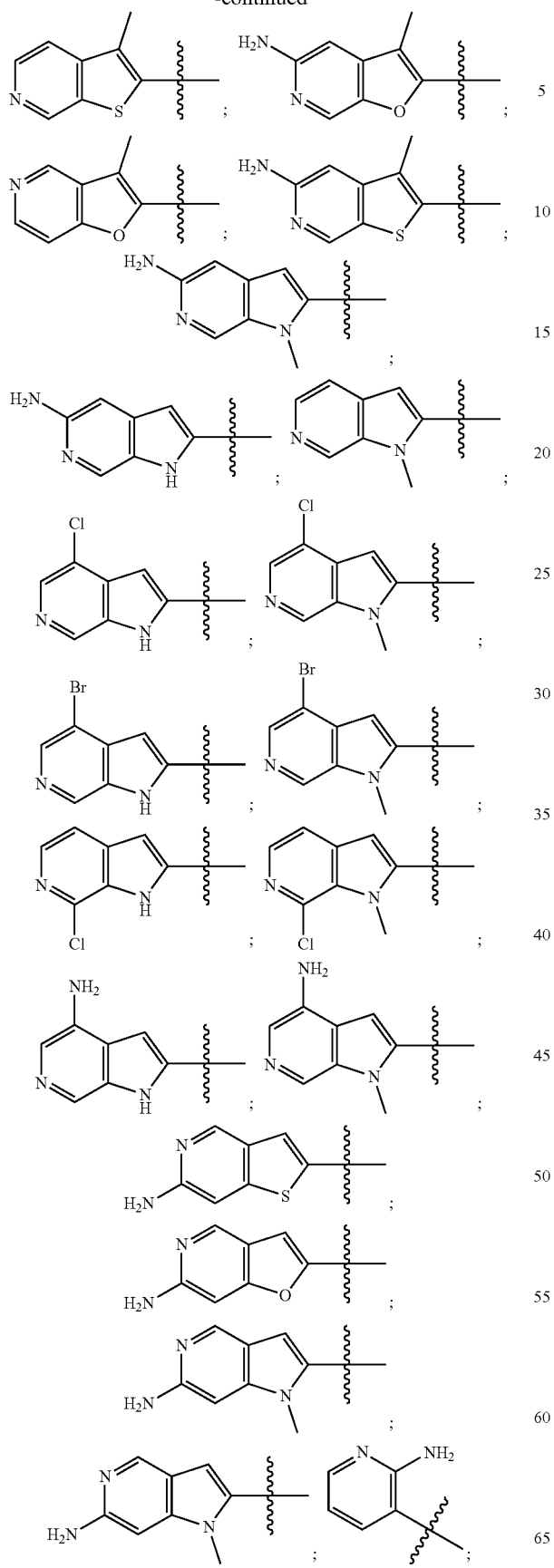
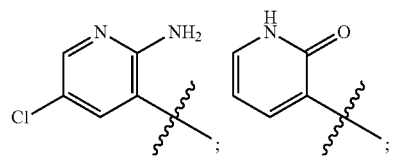
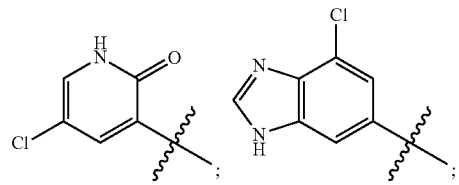
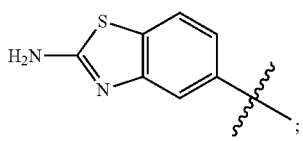
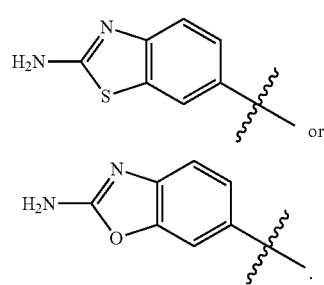
In certain embodiments, R¹ has one of the following structures:
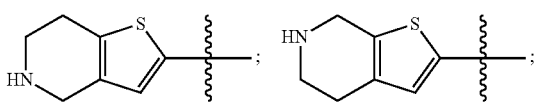
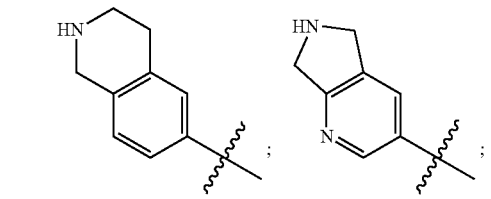
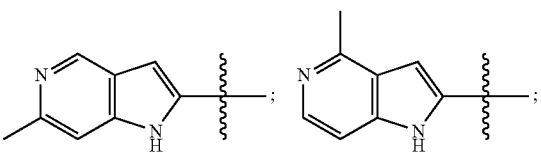
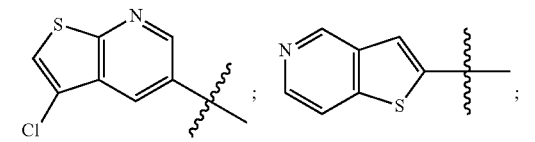
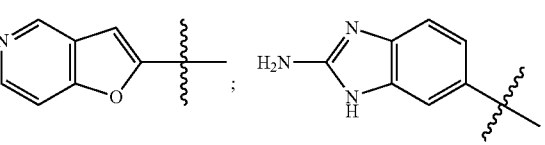

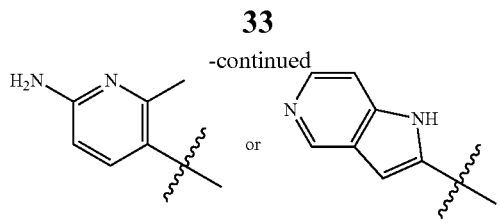

In some embodiments, $R^2$ is a substituted or unsubstituted 6-10 membered aryl. In certain embodiments, $R^2$ is a substituted or unsubstituted phenyl. In some specific embodiments, $R^1$ is an unsubstituted phenyl. In certain specific embodiments, $R^2$ is substituted with one or more of $R^{2a}$, $R^{2b}$, $R^{2c}$, $R^{2d}$, or $R^{2e}$ wherein $R^{2a}$, $R^{2b}$, $R^{2c}$, $R^{2d}$, and $R^{2e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxyalkyl, phosphate, phosphonalkyl, phosphoalkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^c$, $C(=NOR^a)NR^bR^c$, $C(=NOC(O)R^a)NR^bR^c$, $C(=NR^a)N(R^b)C(O)OR^c$, $N(R^a)C(=NR^b)NR^cR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^a$, $R^b$, $R^c$, and $R^d$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^{2a}$, $R^{2b}$, $R^{2c}$, $R^{2d}$, or $R^{2e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NR^fR^g$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{2a}$, $R^{2b}$, $R^{2c}$, $R^{2d}$, or $R^{2e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some specific embodiments, $R^2$ has one of the following structures:

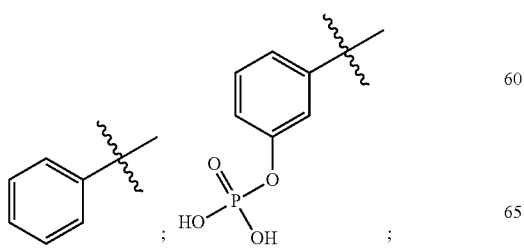

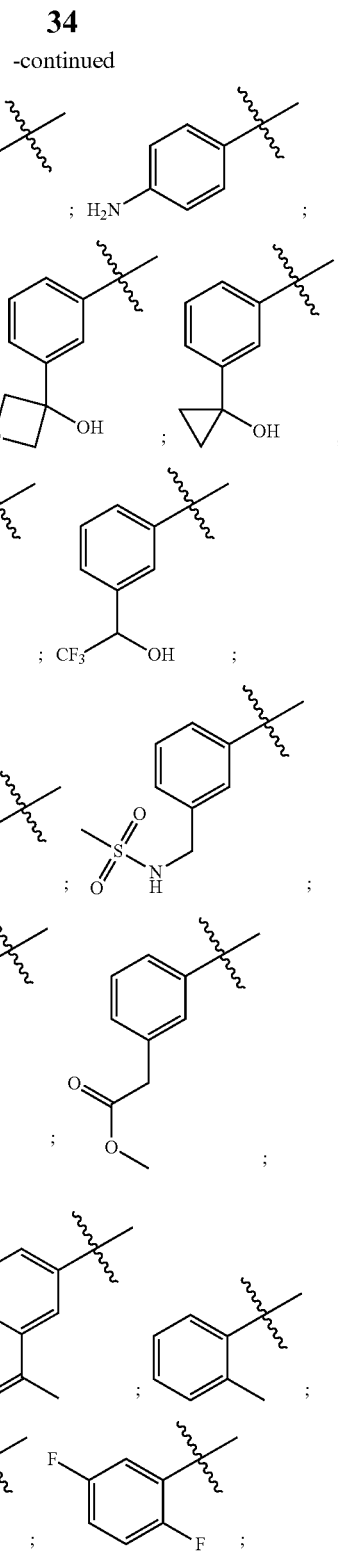

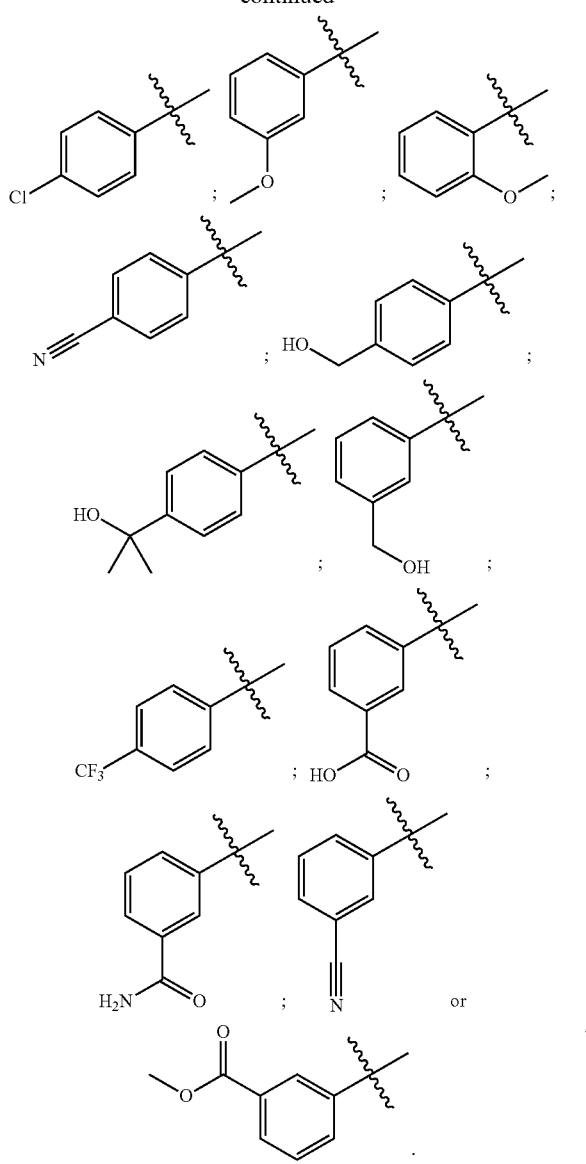
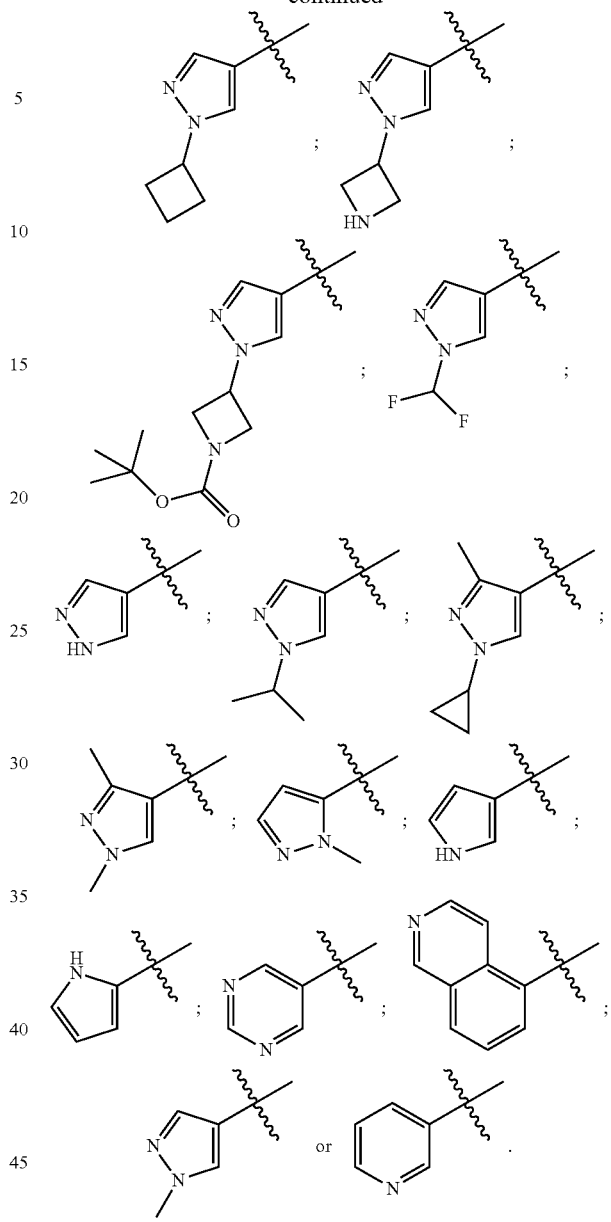
In some embodiments, R² has one of the following structures:
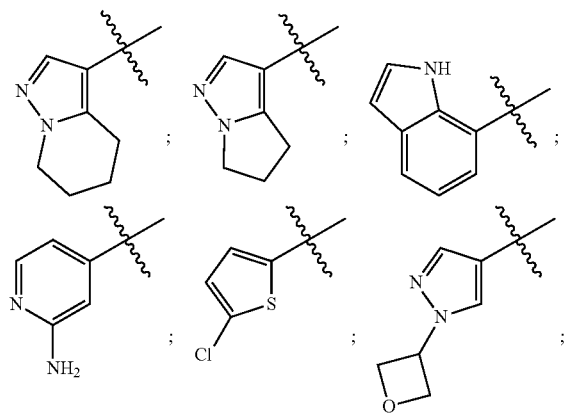
In some embodiments, R² has one of the following structures:
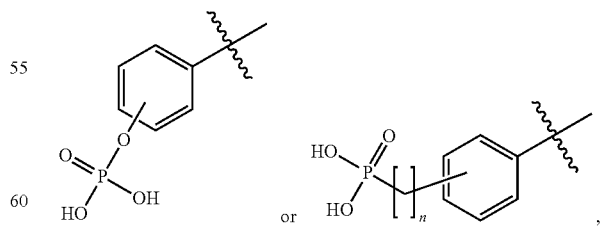
wherein
n is 1, 2, 3, 4, 5, or 6.
In some embodiments, R² is a substituted or unsubstituted pyridinyl, a substituted or unsubstituted pyrrolyl, a substituted or unsubstituted pyrimidinyl, a substituted or unsubstituted isoquinolinyl, a substituted or unsubstituted pyrazolyl, a substituted or unsubstituted pyrrolopyridinyl, or a substituted or unsubstituted benzoimidazolyl. In certain embodiments, $R^2$ is a substituted or unsubstituted pyridinyl, a substituted or unsubstituted pyrrolyl, a substituted or unsubstituted pyrimidinyl, a substituted or unsubstituted isoquinolinyl, or a substituted or unsubstituted pyrazolyl. In certain embodiments, $R^1$ is an unsubstituted pyridinyl, an unsubstituted pyrrolyl, an unsubstituted pyrimidinyl, or an unsubstituted isoquinolinyl.

In some embodiments, $R^2$ is substituted with one or more of $R^{2a}$, $R^{2b}$, $R^{2c}$, $R^{2d}$, or $R^{2e}$ wherein $R^{2a}$, $R^{2b}$, $R^{2c}$, $R^{2d}$, and $R^{2e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxy alkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^c$, $C(=NOR^a)NR^bR^c$, $C(=NOC(O)R^a)NR^bR^c$, $C(=NR^a)N(R^b)C(O)OR^c$, $N(R^a)C(=NR^b)NR^cR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^a$, $R^b$, $R^c$, and $R^d$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^{2a}$, $R^{2b}$, $R^{2c}$, $R^{2d}$, or $R^{2e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NR^fR^g$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{2a}$, $R^{2b}$, $R^{2c}$, $R^{2d}$, or $R^{2e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some specific embodiments, $R^2$ has the following structure:

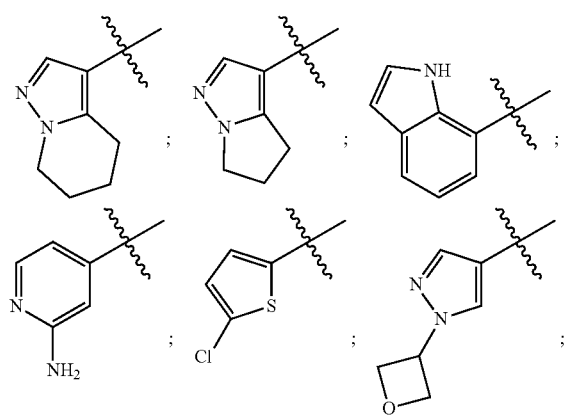

-continued

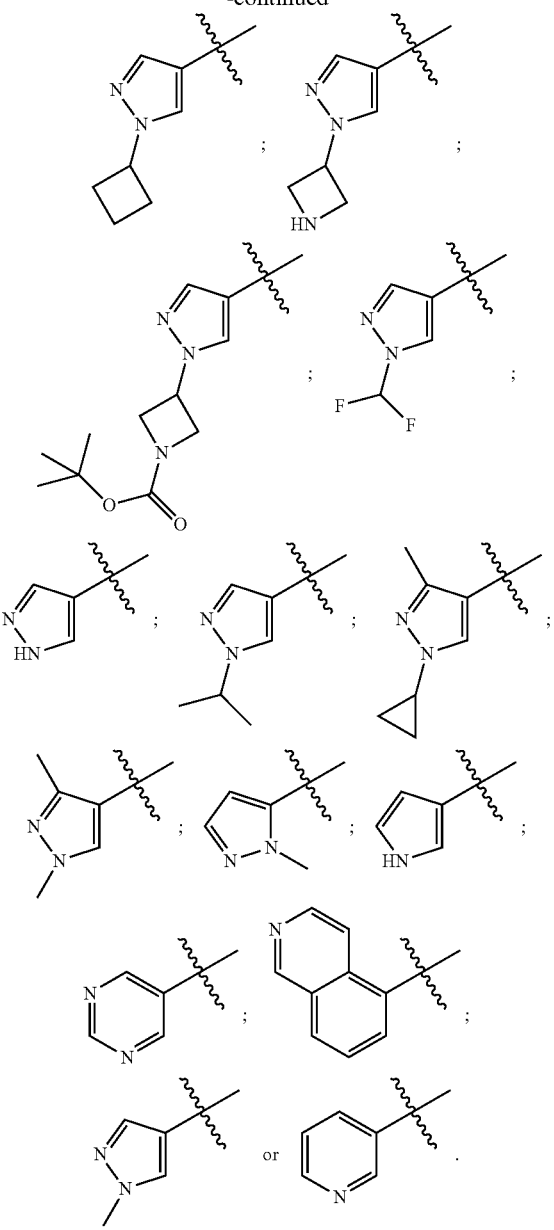

In some embodiments, $R^3$ is hydrogen. In certain embodiments, $R^3$ is methyl.

In some specific embodiments, $R^3$ and $R^4$, together with the nitrogen to which they are attached form an optionally substituted 4-10 membered heterocyclyl. In some more specific embodiments, $R^3$ and $R^4$, together with the nitrogen to which they are attached form an unsubstituted 4-6 membered heterocyclyl. In certain more specific embodiments, $R^3$ and $R^4$, together with the nitrogen to which they are attached form an unsubstituted 5-membered ring. In some embodiments, $R^3$ and $R^4$, together with the nitrogen to which they are attached form an unsubstituted 6-membered ring. In certain specific embodiments, $R^3$ and $R^4$, together with the nitrogen to which they are attached form an unsubstituted pyrrolidinyl ring. In some embodiments, $R^3$ and $R^4$, together with the nitrogen to which they are attached form one of the following structures:

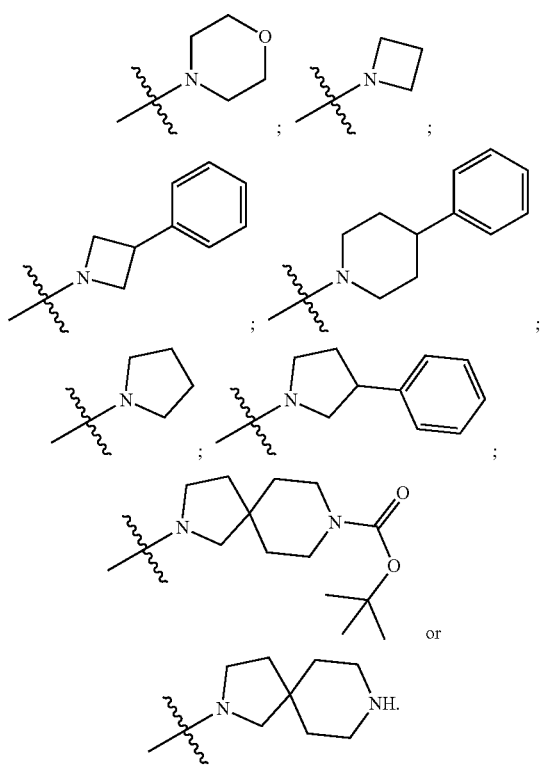

In more specific embodiments, R⁴ is methyl or has one of the following structures:

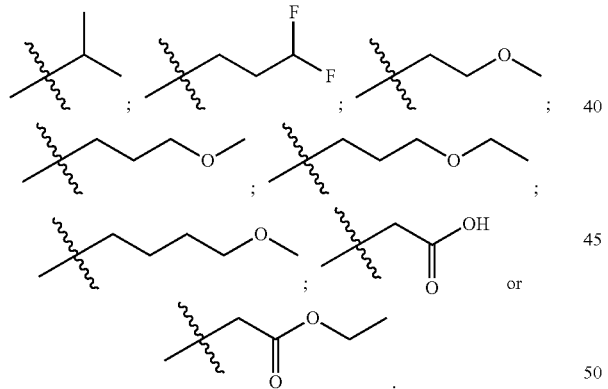

In certain specific embodiments, R⁴ is a substituted or unsubstituted arylalkyl. In some embodiments, R⁴ is substituted. In some embodiments, the arylalkyl is substituted with one or more substituents selected from the group consisting of alkyl, alkoxy, halo, haloalkyl, cycloalkyl, heterocyclyl, hydroxyl, carboxy, and combinations thereof. In some more specific embodiments, the arylalkyl is substituted with one or more substituents selected from the group consisting of methyl, fluoro, chloro, trifluoromethyl, methoxy, cyclopropyl, cyclobutyl, oxetanyl, tetrahydrofuranyl, hydroxyl, carboxy, and combinations thereof. In some embodiments, R⁴ is unsubstituted. In some more specific embodiments, R⁴ is benzyl or phenethyl. In some embodiments, R⁴ is benzyl. In certain specific embodiments, R⁴ is phenethyl.

In some embodiments, R⁴ has the following structure:

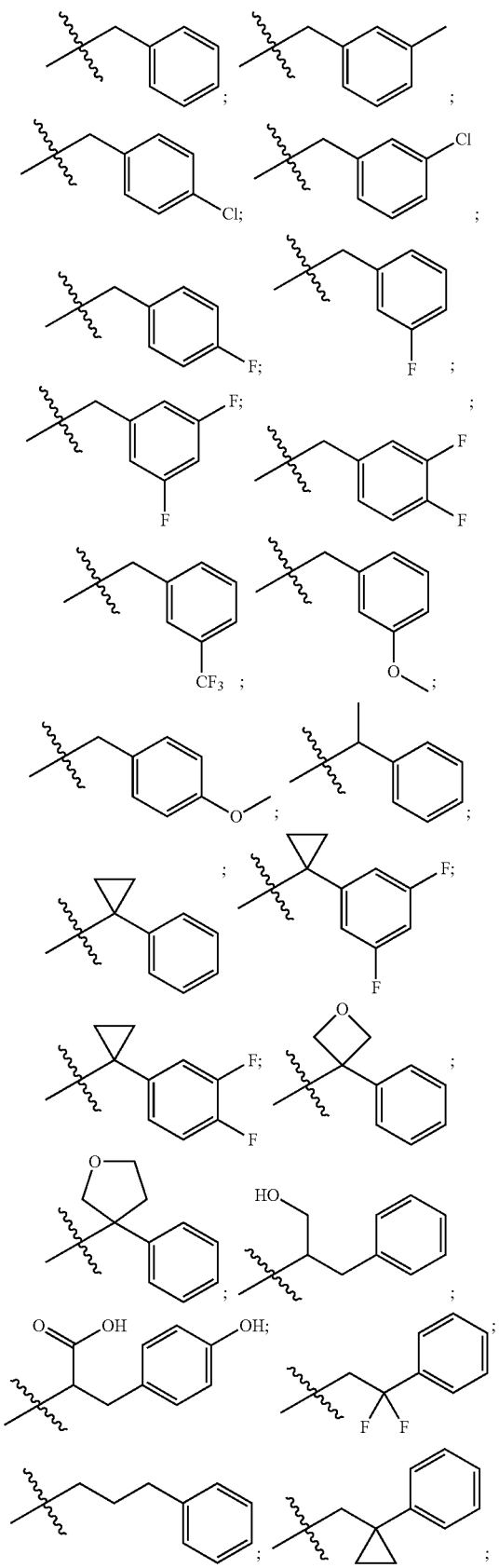

-continued

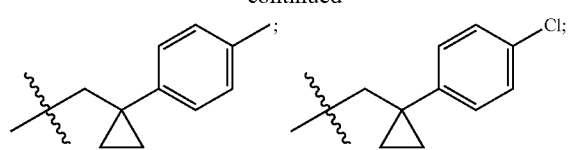
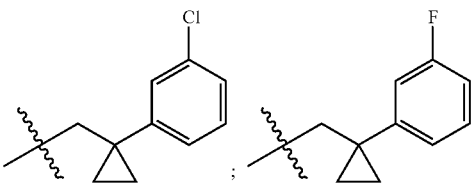
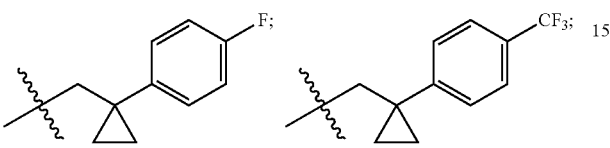
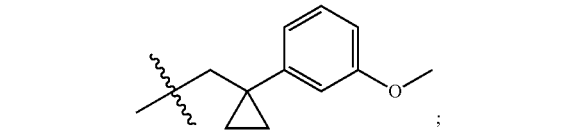
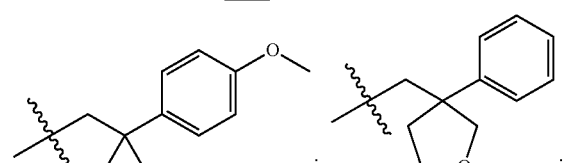
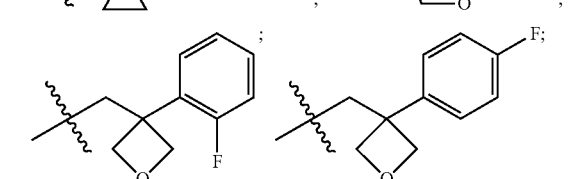
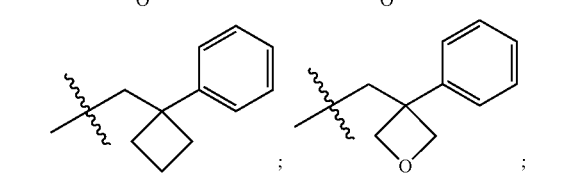
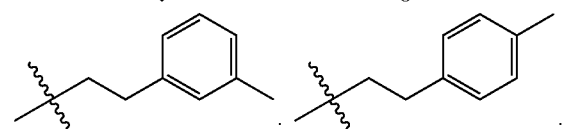
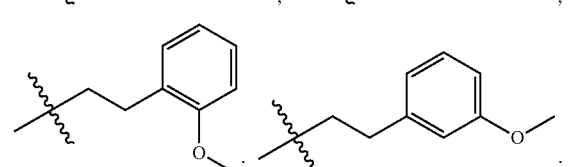
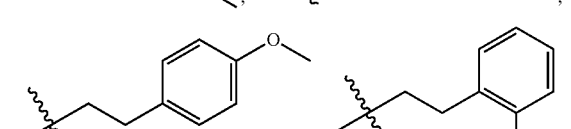
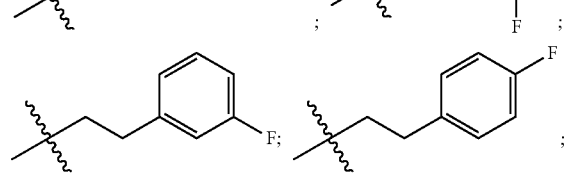

-continued

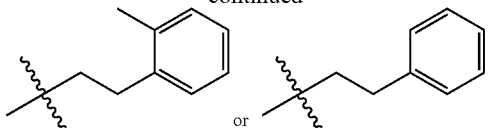

In some embodiments, $R^4$ has one of the following structures:

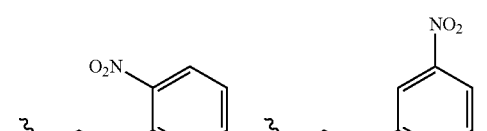

In some embodiments, $R^4$ is a heterocyclyl substituted with substituents selected from the group consisting of a substituted or unsubstituted phenyl or a substituted or unsubstituted pyridinyl. In some more specific embodiments, $R^4$ is a 4-6 membered heterocyclyl ring. In some embodiments, $R^4$ comprises oxygen. In certain embodiments, $R^4$ has one of the following structures:

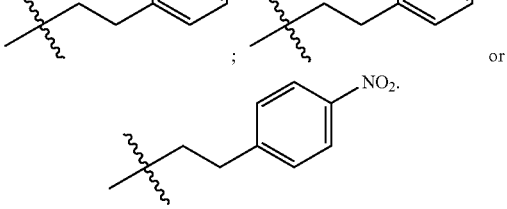

In some embodiments, $L^1$ is a direct bond, —$CH_2$—, or —C≡C—. In some embodiments, $L^1$ is a direct bond. In certain embodiments, $L^1$ is —$CH_2$—. In some specific embodiments, $L^1$ is —C≡C—.

In certain embodiments, $R^{5a}$ is hydrogen. In some embodiments, $R^{5a}$ is halo. In some specific embodiments, $R^{5a}$ is F, Br, or Cl. In more specific embodiments, $R^{5a}$ is Cl.

Another embodiment provides a compound having the following Structure (II):

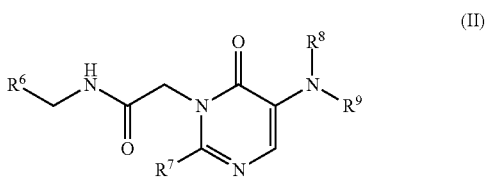

(II)

or a stereoisomer, tautomer, or pharmaceutically acceptable salt thereof, wherein:

$R^6$ is a substituted or unsubstituted aryl or a substituted or unsubstituted heteroaryl;

$R^7$ is alkyl, —$NR^{10a}R^{10b}$, —$SR^{10c}$, a substituted or unsubstituted aryl, or a substituted or unsubstituted heteroaryl;

$R^8$ is hydrogen, alkyl, haloalkyl, cycloalkyl, or a substituted or unsubstituted arylalkyl;

$R^9$ is alkyl, a substituted or unsubstituted —$S(O)_2$-arylalkyl, a substituted or unsubstituted arylalkyl, a substituted or unsubstituted heteroarylalkyl, or $R^8$ and $R^9$, together with the nitrogen to which they are attached, form an optionally substituted 4-10 membered heterocyclyl;

$R^{10a}$, $R^{10b}$, and $R^{10c}$ are each independently hydrogen, alkyl, haloalkyl, or cycloalkyl;

provided that:

A) when $R^7$ is unsubstituted phenyl, 3-((methylsulfonyl)amino)phenyl, 2-methylphenyl, 3-(dimethylamino)phenyl, 3-(methylamino)phenyl, 3-methylphenyl, 3-aminomethylphenyl, 3-aminophenyl, unsubstituted pyridinyl, 3-(methylamino)-2-thienyl, 3,4-diamino-2-thienyl, 3-((methylsulfonyl)amino)-2-thienyl, 3-amino-2-thienyl, 3-amino-5-5 (aminocarbonyl)phenyl, or has one of the following structures:

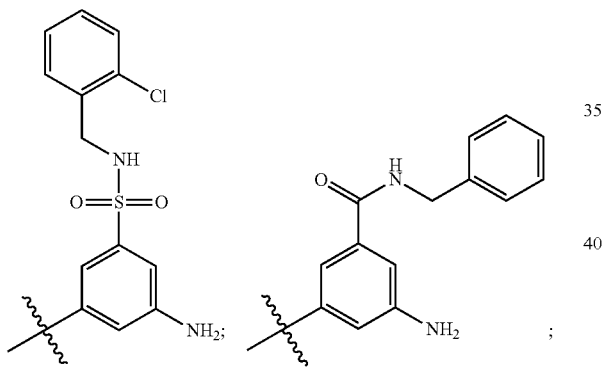

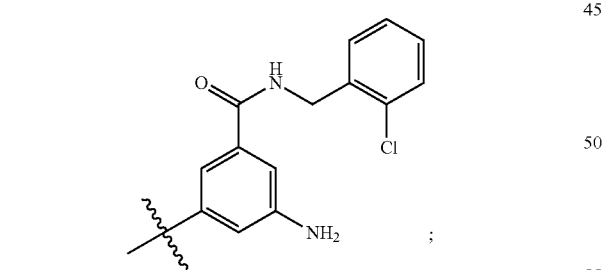

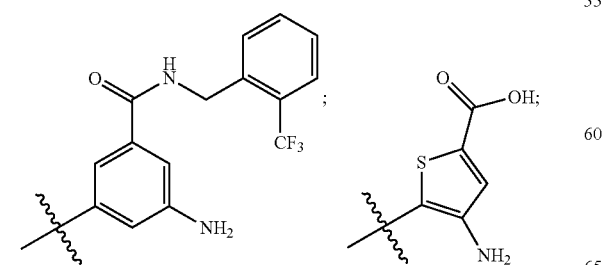

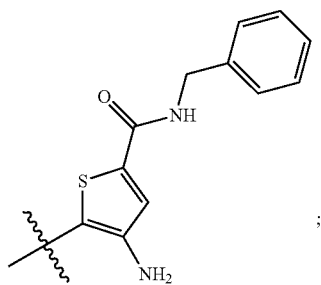

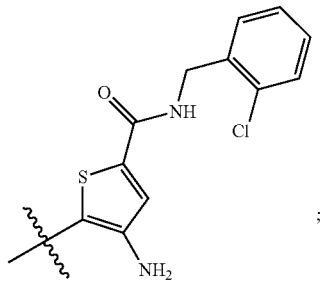

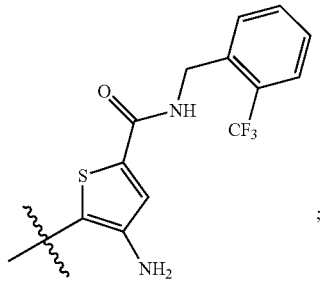

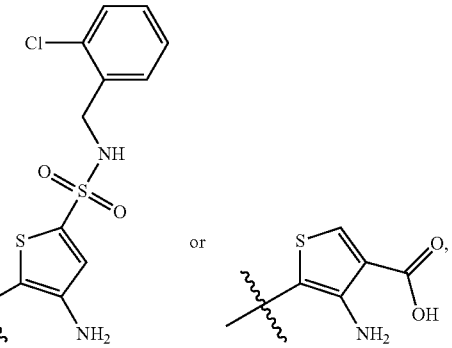

$R^6$ does not have the following structure:

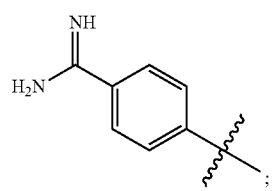 [SMILES: *c1ccc(C(=N)N)cc1]

and

B) when $R^7$ is unsubstituted phenyl, $R^6$ does not have the following structure:

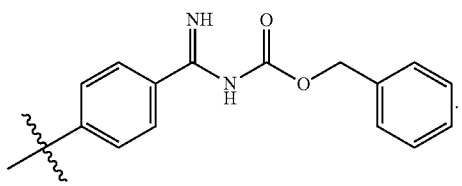 [SMILES: *c1ccc(C(=N)NC(=O)OCc2ccccc2)cc1]

In some embodiments, $R^6$ is a substituted or unsubstituted aryl. In certain embodiments, $R^6$ is a substituted or unsubstituted $C_6$-$C_{10}$ aryl. In some more specific embodiments, $R^6$ is a substituted or unsubstituted phenyl. In some embodiments, $R^6$ is a substituted phenyl.

In some embodiments, $R^6$ is phenyl substituted with one or more of $R^{6a}$, $R^{6b}$, $R^{6c}$, $R^{6d}$, or $R^{6e}$ wherein $R^{6a}$, $R^{6b}$, $R^{6c}$, $R^{6d}$, and $R^{6e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxyalkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^c$, $C(=NOR^a)NR^bR^c$, $C(=NOC(O)R^a)NR^bR^c$, $C(=NR^a)N(R^b)C(O)OR^c$, $N(R^a)C(=NR^b)NR^cR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^a$, $R^b$, $R^c$, and $R^d$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In certain embodiments, $R^{6a}$, $R^{6b}$, $R^{6c}$, $R^{6d}$, or $R^{6e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NR^fR^g$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{6a}$, $R^{6b}$, $R^{6c}$, $R^{6d}$, or $R^{6e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^6$ is phenyl substituted with at least one substituent selected from the group consisting of halo, haloalkyl, $C(=NR^a)NR^bR^c$, alkyl, and 5-10 membered heteroaryl. In some more specific embodiments, $R^6$ is substituted with at least one substituent selected from the group consisting of —C(=NH)NH$_2$, chloro, fluoro, methyl, and

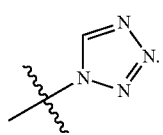 [SMILES: *n1cnnn1]

In some embodiments, $R^6$ has one of the following structures:

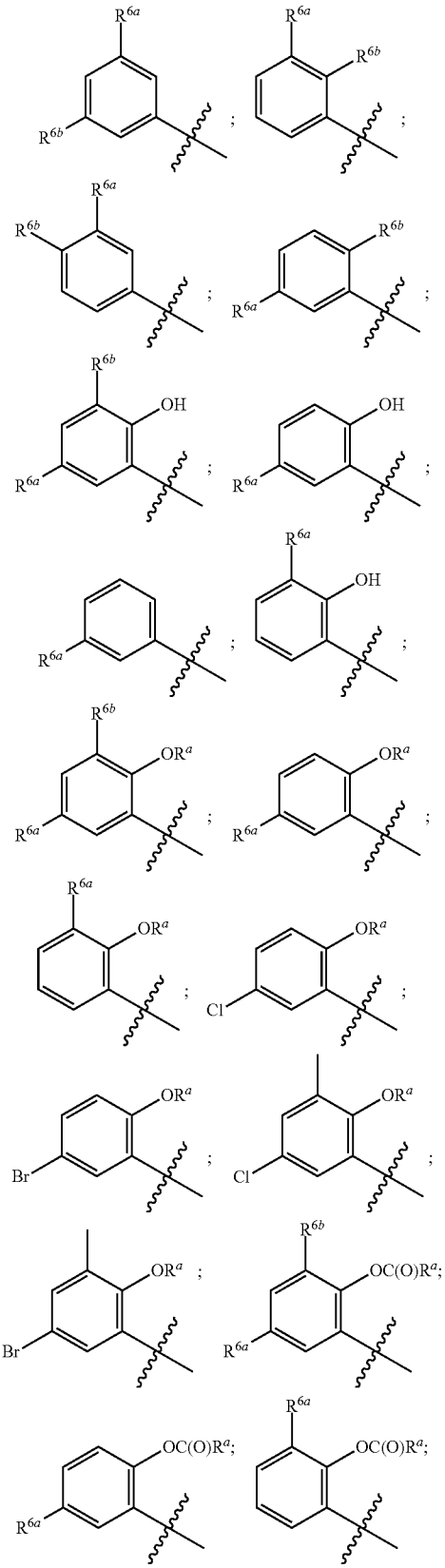

-continued

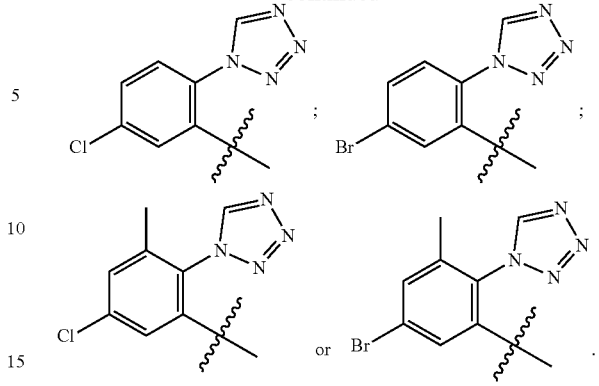

In some embodiments, R⁶ has one of the following structures:

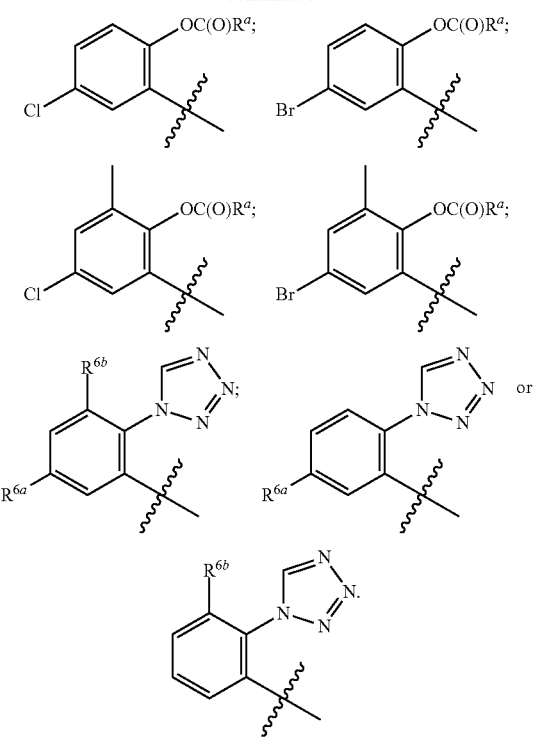

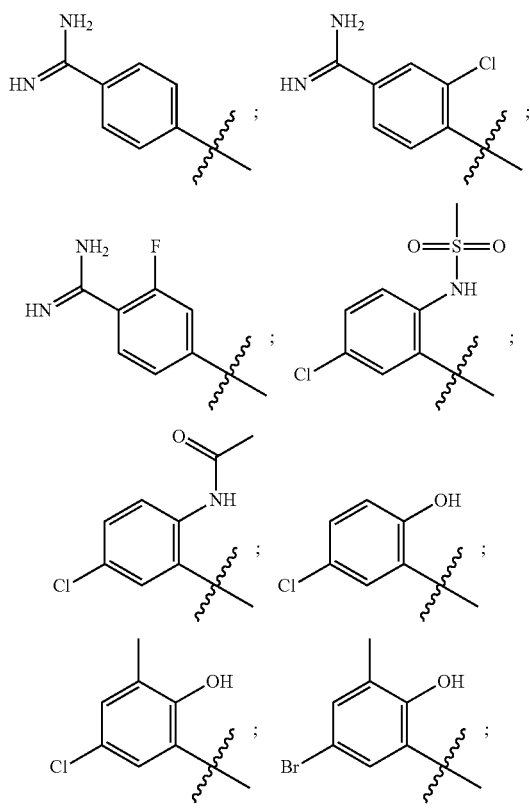

In certain embodiments, $R^6$ is an unsubstituted phenyl.

In some other embodiments, $R^6$ is a substituted or unsubstituted heteroaryl. In some more specific embodiments, $R^6$ is a substituted or unsubstituted 5-10 membered heteroaryl. In some embodiments, $R^6$ is a substituted or unsubstituted pyridinyl, a substituted or unsubstituted pyrrolopyridinyl, a substituted or unsubstituted imidazopyridinyl, a substituted or unsubstituted thienopyridinyl, a substituted or unsubstituted benzoimidazolyl, a substituted or unsubstituted isoindolinyl, or a substituted or unsubstituted benzothiazolyl.

In more specific embodiments, $R^6$ is a heteroaryl substituted with one or more of $R^{6a}$, $R^{6b}$, $R^{6c}$, $R^{6d}$, or $R^{6e}$ wherein $R^{6a}$, $R^{6b}$, $R^{6c}$, $R^{6d}$, and $R^{6e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxyalkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^c$, $C(=NOR^a)NR^bR^c$, $C(=NOC(O)R^a)NR^bR^c$, $C(=NR^a)N(R^b)C(O)OR^c$, $N(R^a)C(=NR^b)NR^cR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^a$, $R^b$, $R^c$, and $R^d$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some specific embodiments, $R^{6a}$, $R^{6b}$, $R^{6c}$, $R^{6d}$, or $R^{6e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NR^fR^g$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{6a}$, $R^{6b}$, $R^{6c}$, $R^{6d}$, or $R^{6e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^6$ has one of the following structures:
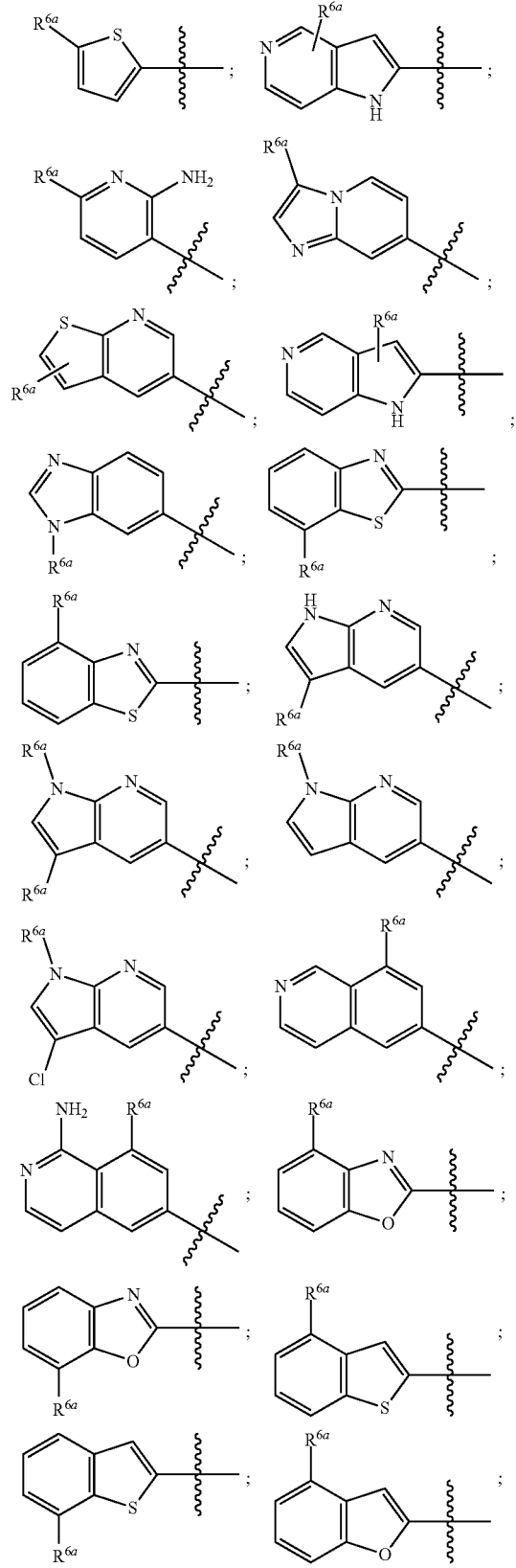
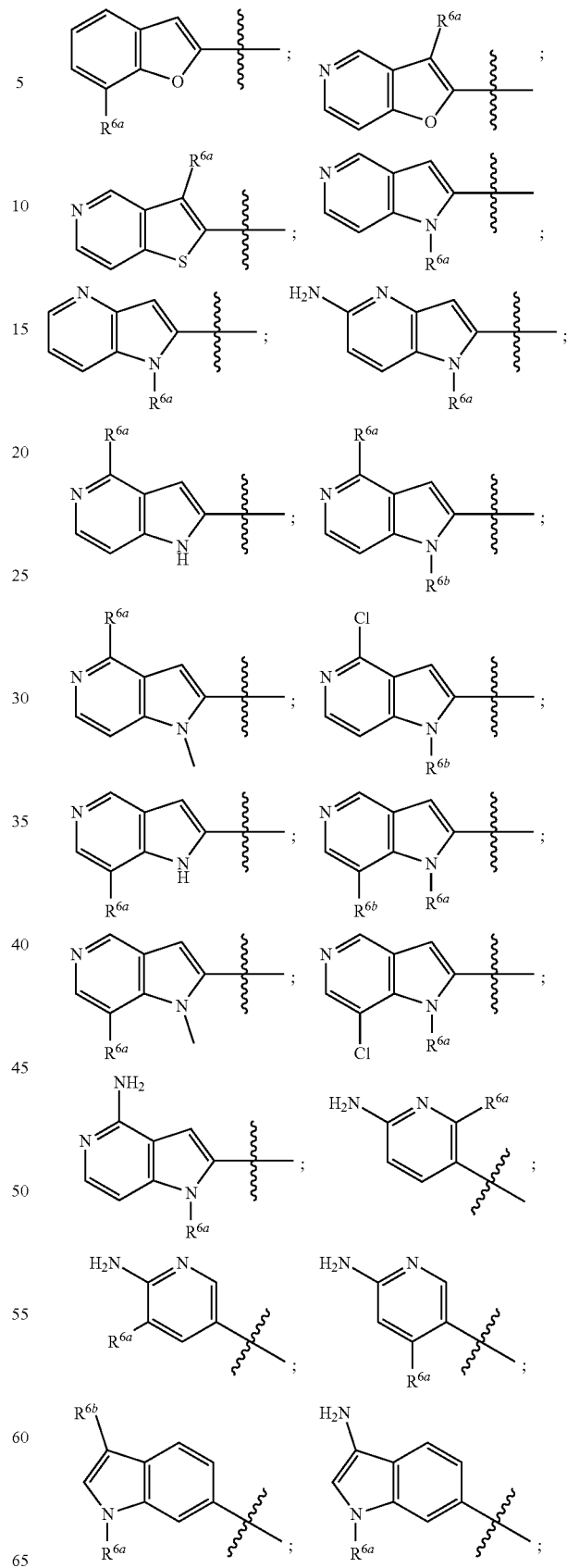

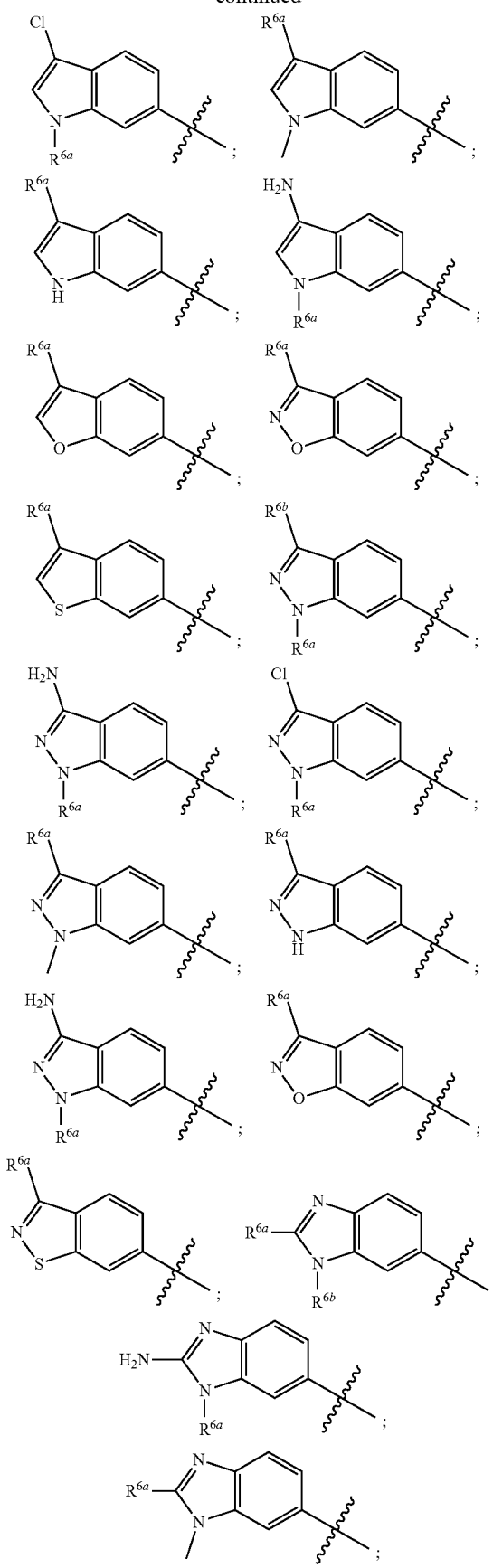
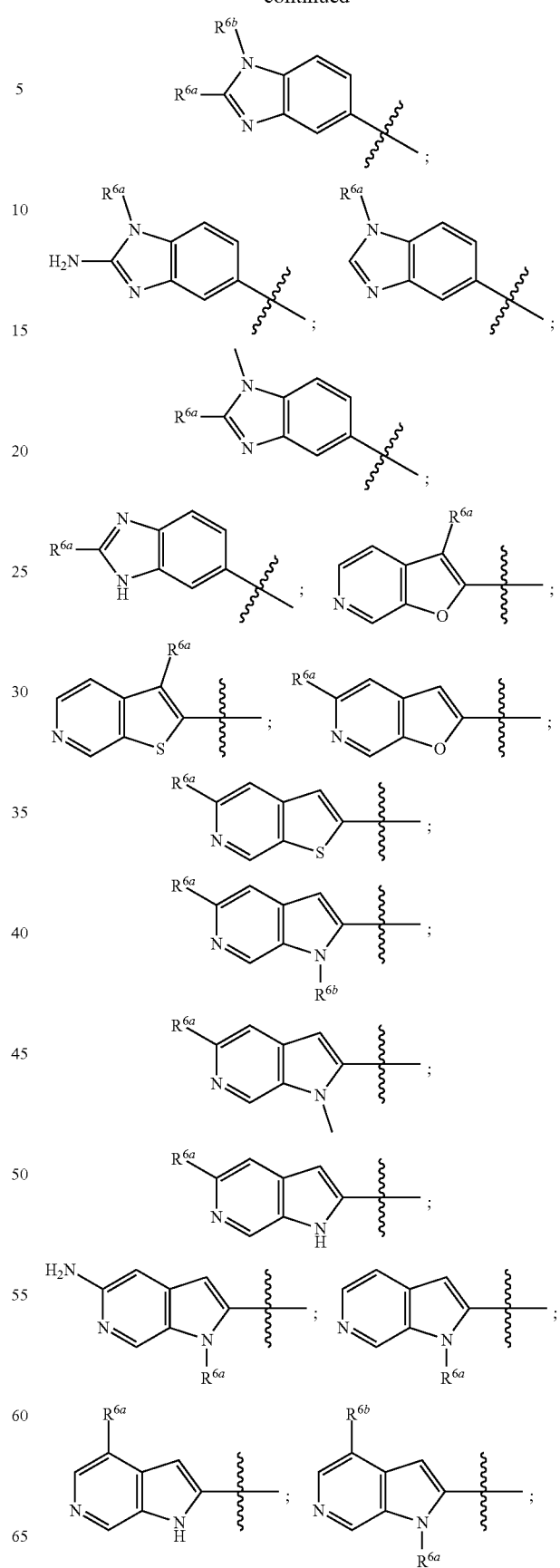

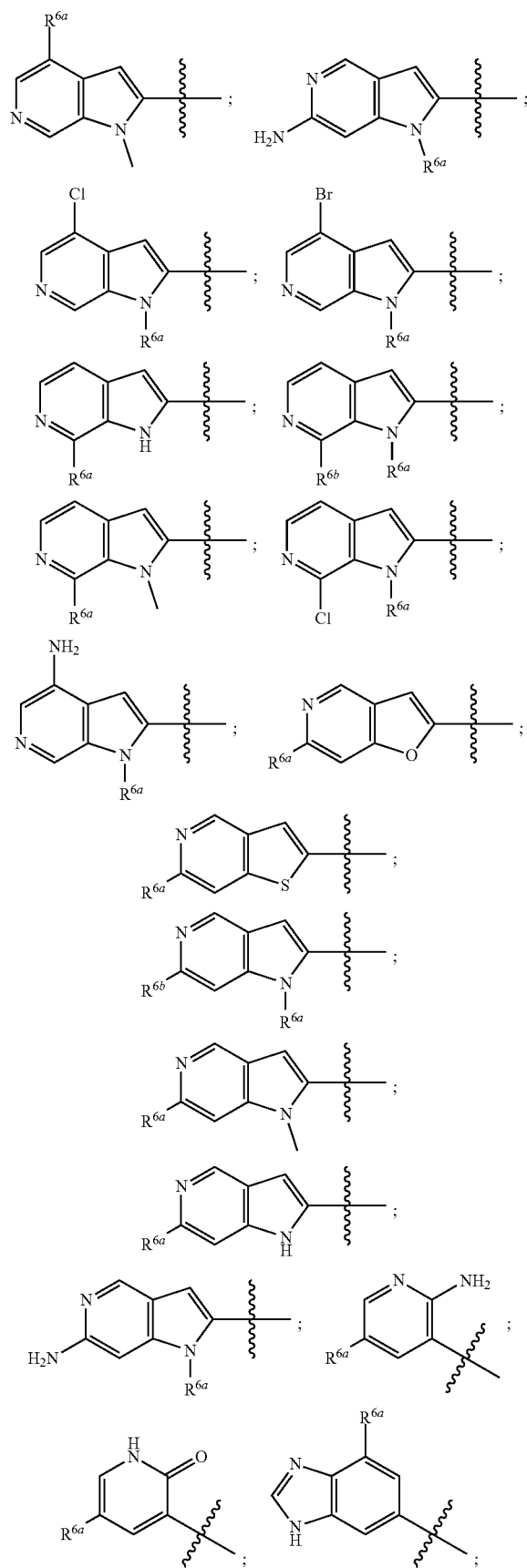

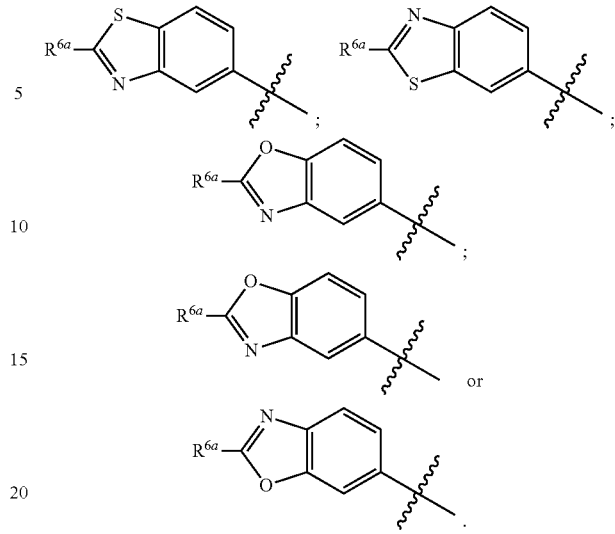

In some embodiments, $R^{6a}$ or $R^{6b}$ is independently $C_{1-6}$ alkyl, $C_{1-6}$ deuterated alkyl, amino, or halo. In certain embodiments, $R^{6a}$ or $R^{6b}$ is methyl. In some specific embodiments, $R^{6a}$ or $R^{6b}$ is F, Cl, or Br. In some embodiments, each $R^{6a}$ or $R^{6b}$ attached to nitrogen is $C_{1-6}$ alkyl. In more specific embodiments, $R^{6a}$ or $R^{6b}$ is methyl or ethyl.

In some embodiments, $R^6$ has one of the following structures:

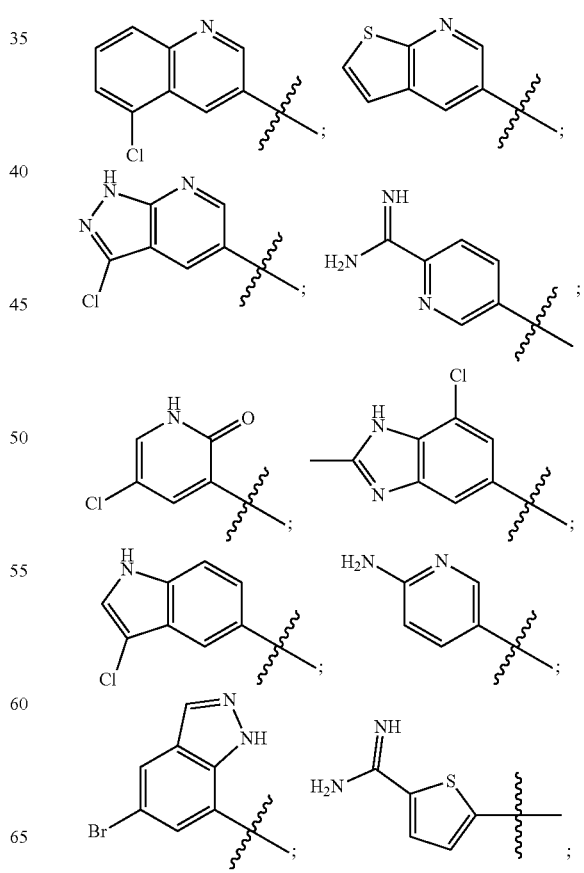

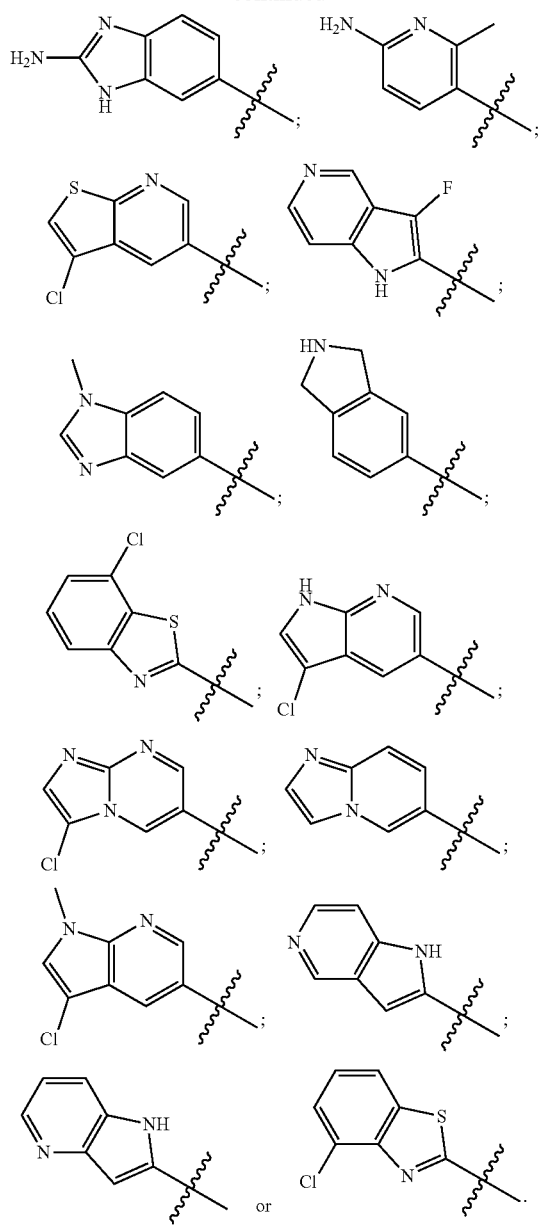
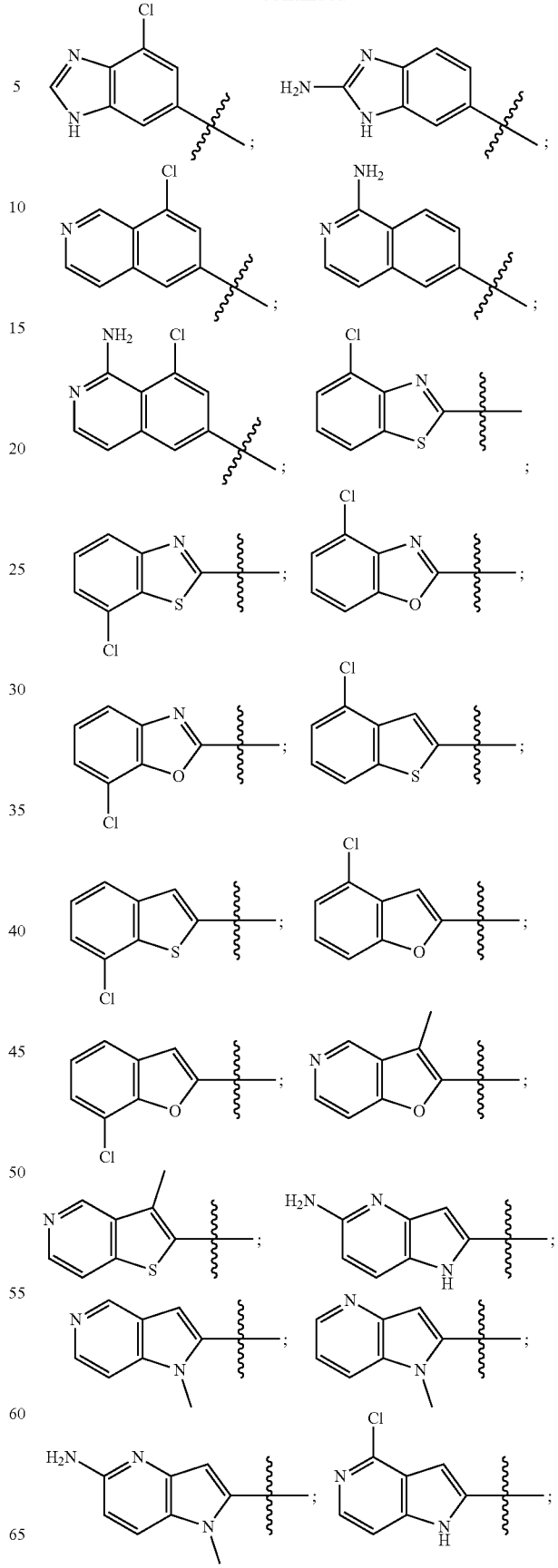
In certain embodiments, $R^6$ has one of the following structures:
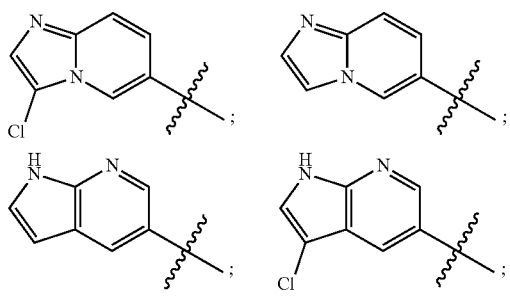

-continued
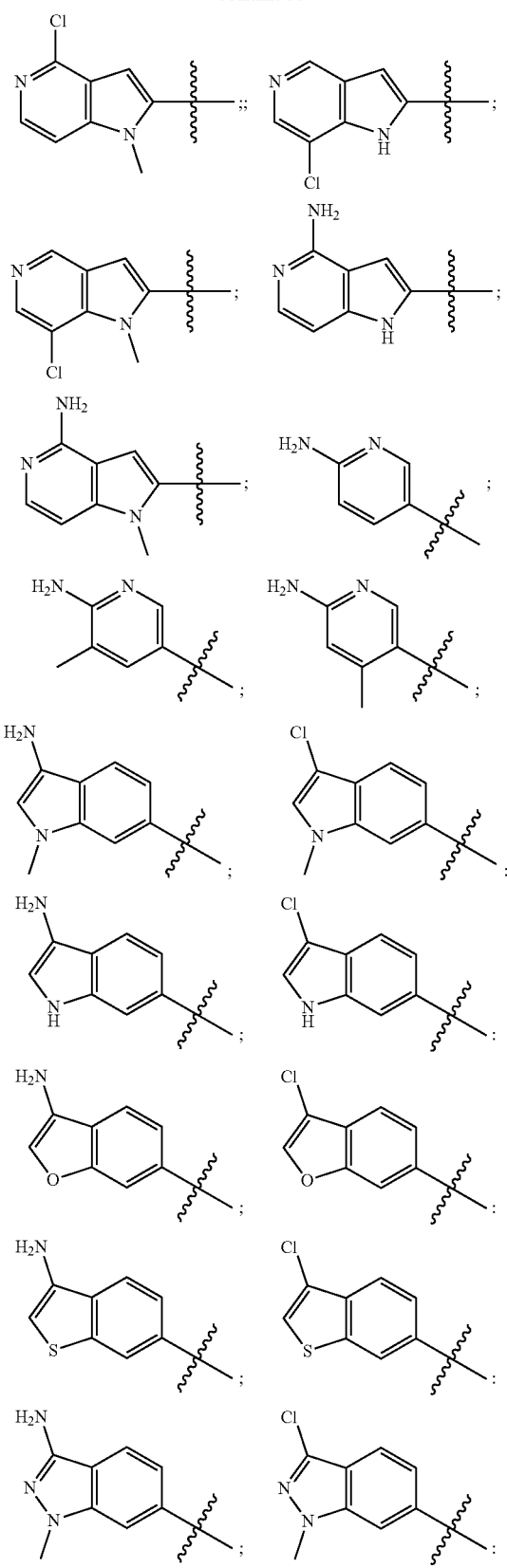
-continued
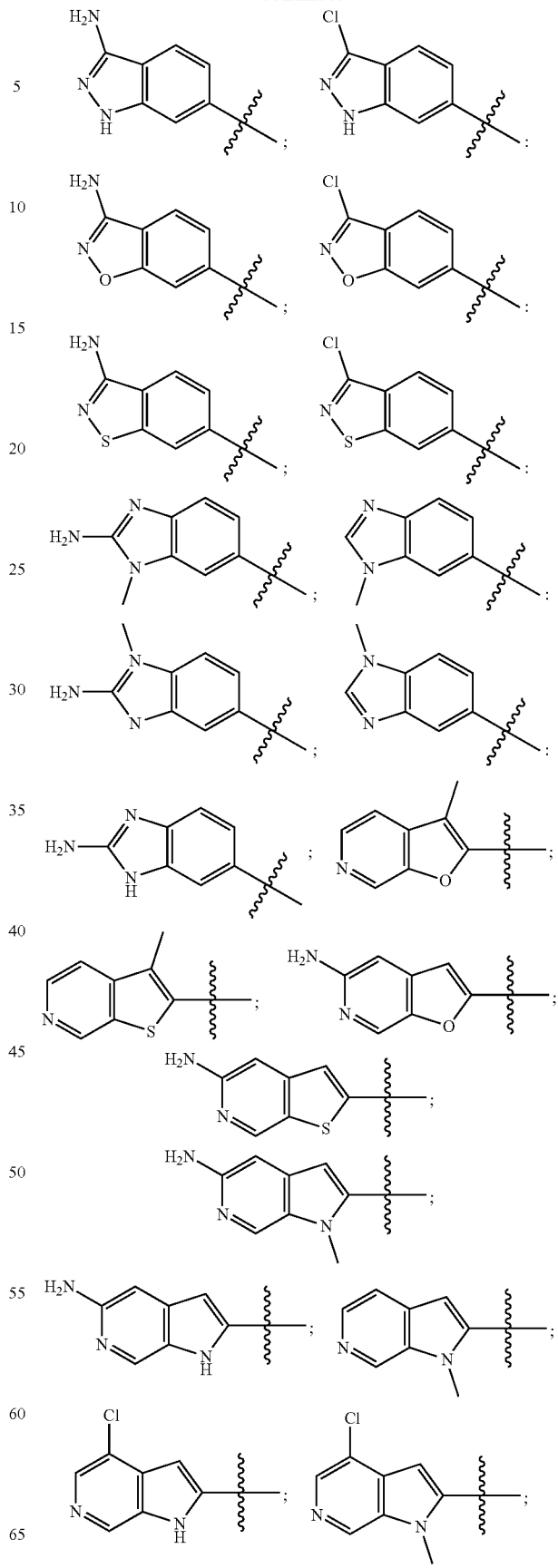

-continued
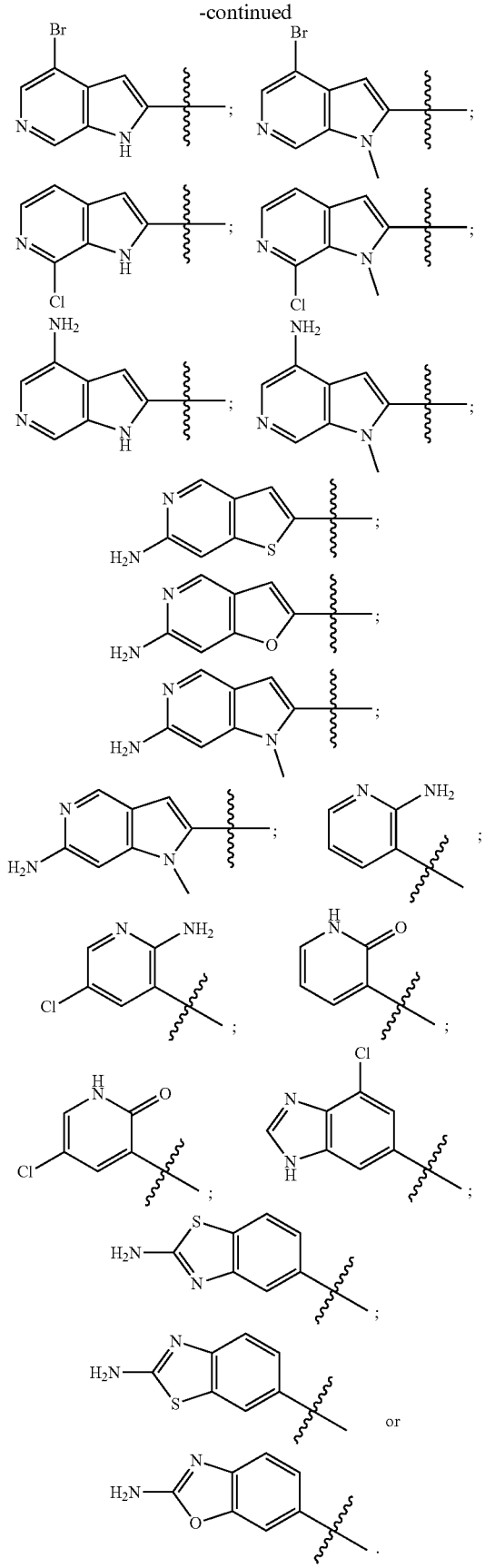
or
In some more specific embodiments, R has one of the following structures:
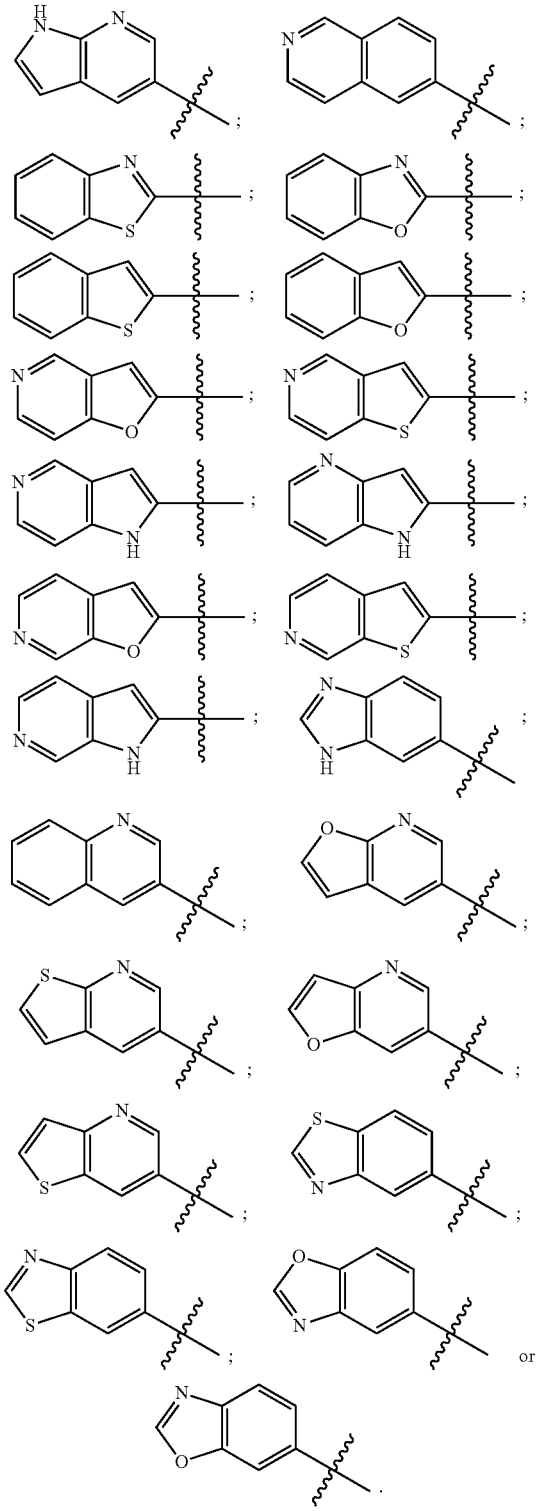
or
In some embodiments, $R^7$ is $C_1$-$C_6$ alkyl. In more specific embodiments, $R^7$ is methyl. In more embodiments, $R^7$ is $-NR^{10a}R^{10b}$ or $-SR^{10c}$. In certain embodiments, $R^7$ has one of the following structures:

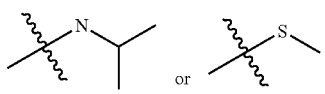

In some embodiments, $R^7$ is a substituted or unsubstituted aryl. In certain embodiments, $R^7$ is an unsubstituted phenyl.

In some embodiments, $R^8$ is hydrogen, an unsubstituted arylalkyl, or $C_1$-$C_6$ alkyl. In more specific embodiments, $R^8$ is hydrogen, —$CH_3$, or has one of the following structures:

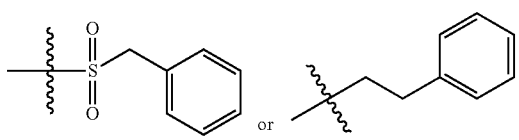

In certain embodiments, $R^9$ is a substituted or unsubstituted arylalkyl. In some specific embodiments, $R^9$ is an unsubstituted arylalkyl. In certain specific embodiments, $R^9$ has the following structure:

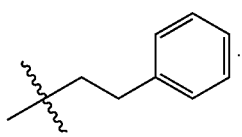 [SMILES: *CCc1ccccc1]

In certain embodiments, $R^9$ is a substituted or unsubstituted heteroarylalkyl. In more specific embodiments, $R^9$ is an unsubstituted heteroarylalkyl. In still more specific embodiments, $R^9$ has one of the following structures:

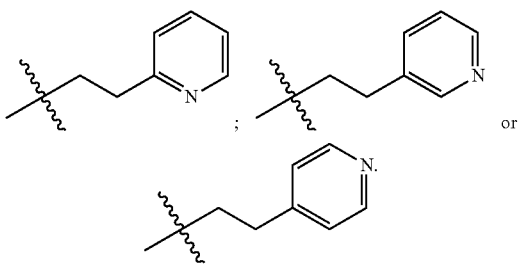

In certain embodiments, $R^8$ and $R^9$, together with the nitrogen to which they are attached form an optionally substituted 4-7 membered heterocyclyl. In certain embodiments, $R^8$ and $R^9$, together with the nitrogen to which they are attached, form an optionally substituted 4, 5, or 6 membered heterocyclyl. In some embodiments, $R^8$ and $R^9$, together with the nitrogen to which they are attached, forms one of the following structures:

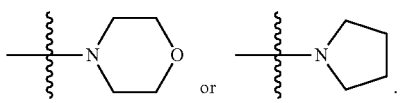 [SMILES: *N1CCOCC1 ; *N1CCCC1]

Another embodiment provides a compound having the following Structure (III):

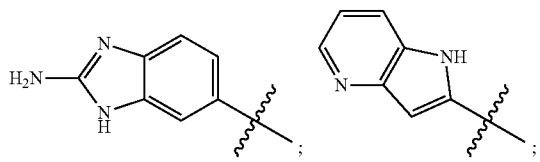

or a stereoisomer, tautomer, or pharmaceutically acceptable salt thereof, wherein:

$R^{11}$ has one of the following structures:

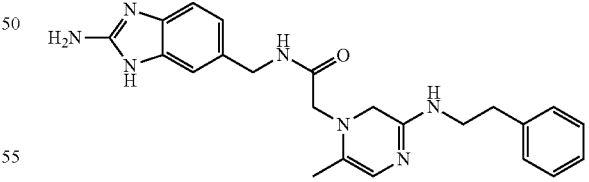

$R^{12}$ is methyl, alkoxy, or halo;

$R^{13}$ is a substituted or unsubstituted aryl; and n is 1 or 2 provided that:

the compound of Structure (III) does not have the following structure:

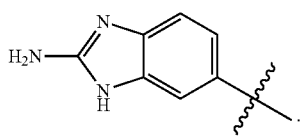 [SMILES: *c1ccc2nc(N)[nH]c2c1]

In some embodiments, $R^{11}$ has the following structure:

In certain embodiments, R$^{11}$ has the following structure:

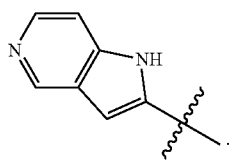 [SMILES: *c1cc2cnccc2[nH]1]

In some embodiments, R$^{12}$ is methyl. In certain embodiments, R$^{12}$ is halo or butoxy. In more specific embodiments, R$^{12}$ is Br.

In some embodiments, n is 1. In certain embodiments, n is 2.

In some embodiments, R$^{13}$ is a substituted or unsubstituted phenyl. In certain embodiments, R$^{13}$ is an unsubstituted phenyl.

Still another embodiment provides a compound having the following Structure (IV):

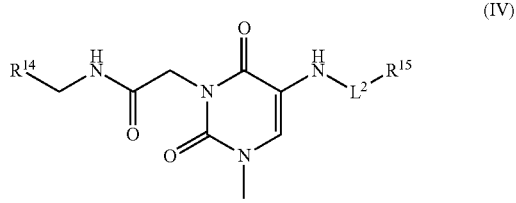

(IV)

or a stereoisomer, tautomer, or pharmaceutically acceptable salt thereof, wherein:

R$^{14}$ is a substituted or unsubstituted aryl or a substituted or unsubstituted heteroaryl;

R$^{15}$ is a substituted or unsubstituted arylalkyl, or a substituted or unsubstituted heteroarylalkyl;

L$^2$ is a direct bond, —C(=O), or —S(=O)$_t$—; and t is 0, 1, or 2.

In some embodiments, R$^{14}$ is a substituted or unsubstituted aryl. In certain embodiments, R$^{14}$ is a substituted or unsubstituted C$_6$-C$_{10}$ aryl. In some specific embodiments, R$^{14}$ is a substituted or unsubstituted phenyl. In certain specific embodiments, R$^{14}$ is a substituted phenyl.

In some embodiments, R$^{14}$ is phenyl substituted with one or more of R$^{14a}$, R$^{14b}$, R$^{14c}$, R$^{14d}$, or R$^{14e}$ wherein R$^{14a}$, R$^{14b}$, R$^{14c}$, R$^{14d}$, and R$^{14e}$ are each independently selected from the group consisting of C$_{1-6}$ alkyl, C$_{1-6}$ deuterated alkyl, C$_{2-6}$ alkenyl, C$_{2-6}$ alkynyl, halo, C$_{1-6}$ haloalkyl, aminylalkyl, hydroxyalkyl, cyano, nitro, OR$^a$, SR$^a$, C(O)R$^a$, C(O)NR$^a$R$^b$, C(O)OR$^a$, OC(O)R$^a$, OC(O)OR$^a$, OC(O)NR$^a$R$^b$, NR$^a$R$^b$, N(R$^a$)C(O)R$^b$, N(R$^a$)C(O)NR$^b$R$^c$, N(R$^a$)C(O)OR$^b$, C(=NR$^a$)NR$^b$R$^c$, C(=NOR$^a$)NR$^b$R$^c$, C(=NOC(O)R$^a$)NR$^b$R$^c$, C(=NR$^a$)N(R$^b$)C(O)OR$^c$, N(R$^a$)C(=NR$^b$)NR$^c$R$^d$, S(O)R$^a$, S(O)NR$^a$R$^b$, S(O)$_2$R$^a$, N(R$^a$)S(O)$_2$R$^b$, S(O)$_2$NR$^a$R$^b$, oxo, substituted or unsubstituted C$_{6-10}$ aryl, substituted or unsubstituted C$_{6-10}$ arylalkyl, substituted or unsubstituted C$_{6-10}$ aryloxy, substituted or unsubstituted C$_{6-10}$ arylalkoxy, substituted or unsubstituted 5-10 membered heteroaryl, substituted or unsubstituted C$_{3-10}$ cycloalkyl, and substituted or unsubstituted 4-10 membered heterocyclyl, wherein R$^a$, R$^b$, R$^c$, and R$^d$, are, at each occurrence, independently selected from the group consisting of hydrogen, C$_{1-6}$ alkyl, C$_{2-6}$ alkenyl, C$_{2-6}$ alkynyl, hydroxyl, C$_{1-6}$ alkoxy, aryl, arylalkyl, C$_{1-6}$ haloalkyl, C$_{1-6}$ haloalkoxy, C$_{1-6}$ hydroxyalkyl, cycloalkyl, heterocyclyl, and heteroaryl.

In certain embodiments, R$^{14a}$, R$^{14b}$, R$^{14c}$, R$^{14d}$, or R$^{14e}$ is optionally substituted with one or more substituents selected from the group consisting of halo, CN, OR$^e$, SR$^e$, C(O)R$^e$, C(O)NR$^e$R$^f$, C(O)OR$^e$, OC(O)R$^e$, OC(O)NR$^e$R$^f$, NR$^e$R$^f$, NR$^e$C(O)R$^f$, NR$^e$C(O)NR$^f$R$^g$, NR$^e$C(O)OR$^f$, C(=NR$^e$)NR$^f$R$^g$, NR$^e$C(=NR$^f$)NR$^g$R$^h$, S(O)R$^e$, S(O)NR$^e$R$^f$, S(O)$_2$R$^e$, NR$^e$S(O)$_2$R$^f$, S(O)$_2$NR$^e$R$^f$ and oxo when R$^{14a}$, R$^{14b}$, R$^{14c}$, R$^{14d}$, or R$^{14e}$ is a substituted C$_{6-10}$ aryl, a substituted C$_{6-10}$ arylalkyl, a substituted C$_{6-10}$ aryloxy, a substituted C$_{6-10}$ arylalkoxy, a substituted 5-10 membered heteroaryl, a substituted C$_{3-10}$ cycloalkyl, and a substituted 4-10 membered heterocyclyl, wherein R$^e$, R$^f$, R$^g$, and R$^h$ are, at each occurrence, independently selected from the group consisting of hydrogen, C$_{1-6}$ alkyl, C$_{2-6}$ alkenyl, C$_{2-6}$ alkynyl, hydroxyl, C$_{1-6}$ alkoxy, aryl, arylalkyl, C$_{1-6}$ haloalkyl, C$_{1-6}$ haloalkoxy, C$_{1-6}$ hydroxyalkyl, cycloalkyl, heterocyclyl, and heteroaryl.

In some specific embodiments, R$^{14}$ is phenyl substituted with at least one substituent selected from the group consisting of halo, alkyl, hydroxy, amino, and C(=NR$^a$)NR$^b$R$^c$. In more specific embodiments, R$^{14}$ has one of the following structures:

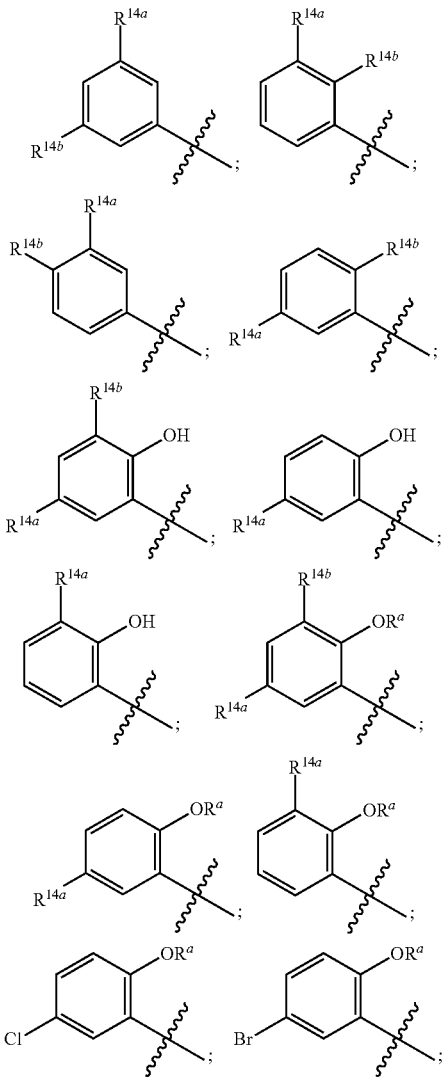

-continued

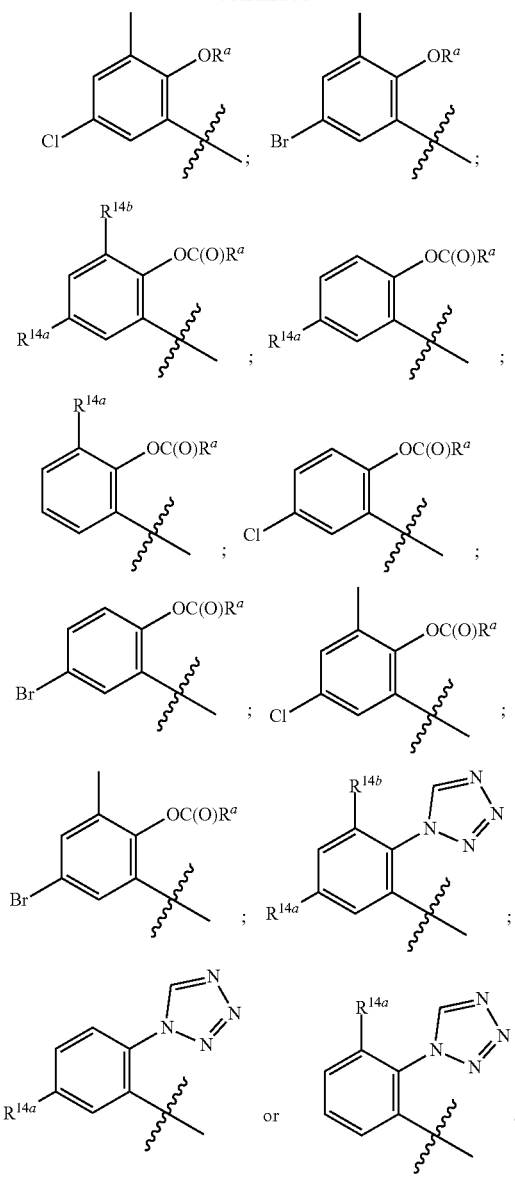

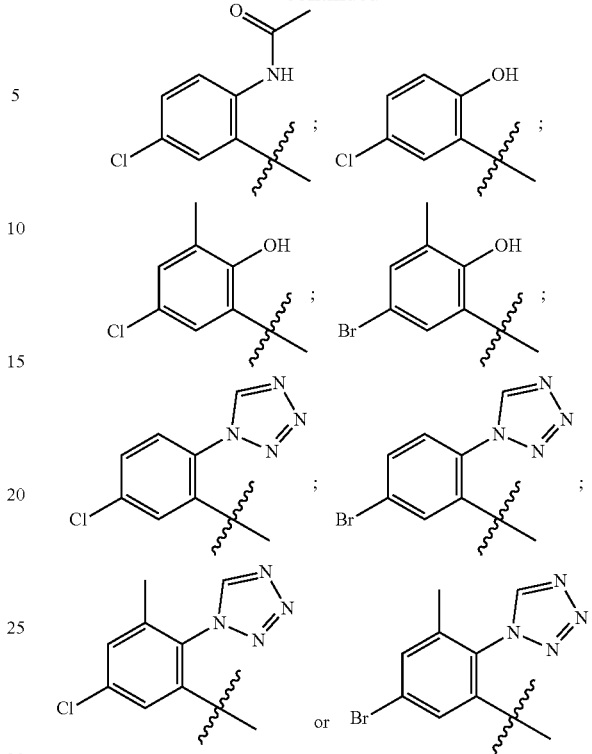

In some embodiments, R¹⁴ has one of the following structures:

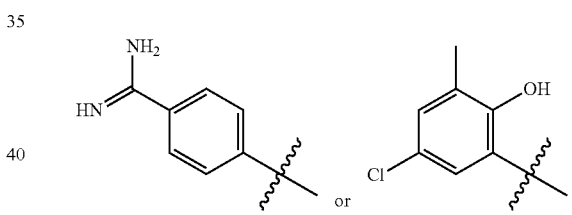

In some embodiments, R¹⁴ is an unsubstituted phenyl.

In certain embodiments, R¹⁴ is a substituted or unsubstituted heteroaryl. In some more specific embodiments, R¹⁴ is a substituted or unsubstituted 5-10 membered heteroaryl. In certain embodiments, R¹⁴ is a substituted or unsubstituted pyridinyl, a substituted or unsubstituted pyrrolopyridinyl, a substituted or unsubstituted imidazopyridinyl, a substituted or unsubstituted thienopyridinyl, a substituted or unsubstituted benzoimidazolyl, a substituted or unsubstituted isoindolinyl, or a substituted or unsubstituted benzothiazolyl.

In some embodiments, R¹⁴ is a heteroaryl substituted with one or more of $R^{14a}$, $R^{14b}$, $R^{14c}$, $R^{14d}$, or $R^{14e}$ wherein $R^{14a}$, $R^{14b}$, $R^{14c}$, $R^{14d}$, and $R^{14e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxyalkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^c$, $C(=NOR^a)NR^bR^c$, $C(=NOC(O)R^a)NR^bR^c$, $C(=NR^a)N(R^b)C(O)OR^c$, $N(R^a)C(=NR^b)NR^cR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or

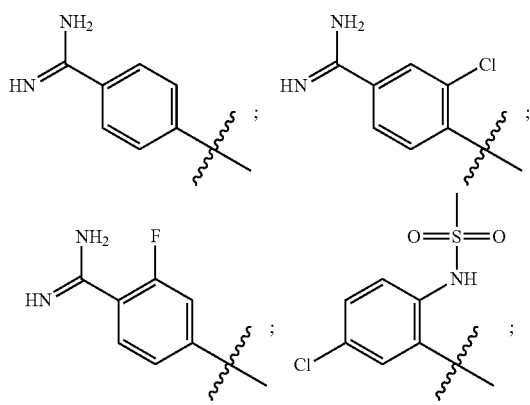

unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^a$, $R^b$, $R^c$, and $R^d$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some specific embodiments, $R^{14a}$, $R^{14b}$, $R^{14c}$, $R^{14d}$, or $R^{14e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NR^fR^g$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{14a}$, $R^{14b}$, $R^{14c}$, $R^{14d}$, or $R^{14e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl.

In some embodiments, $R^{14}$ has one of the following structures:

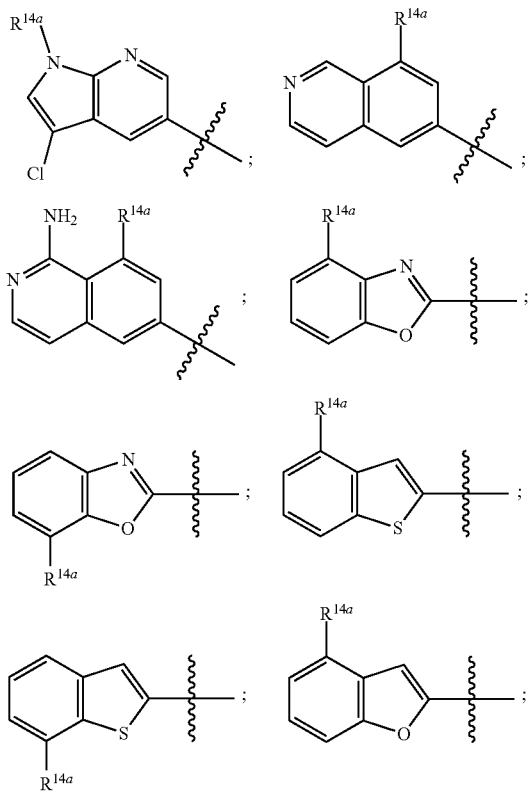

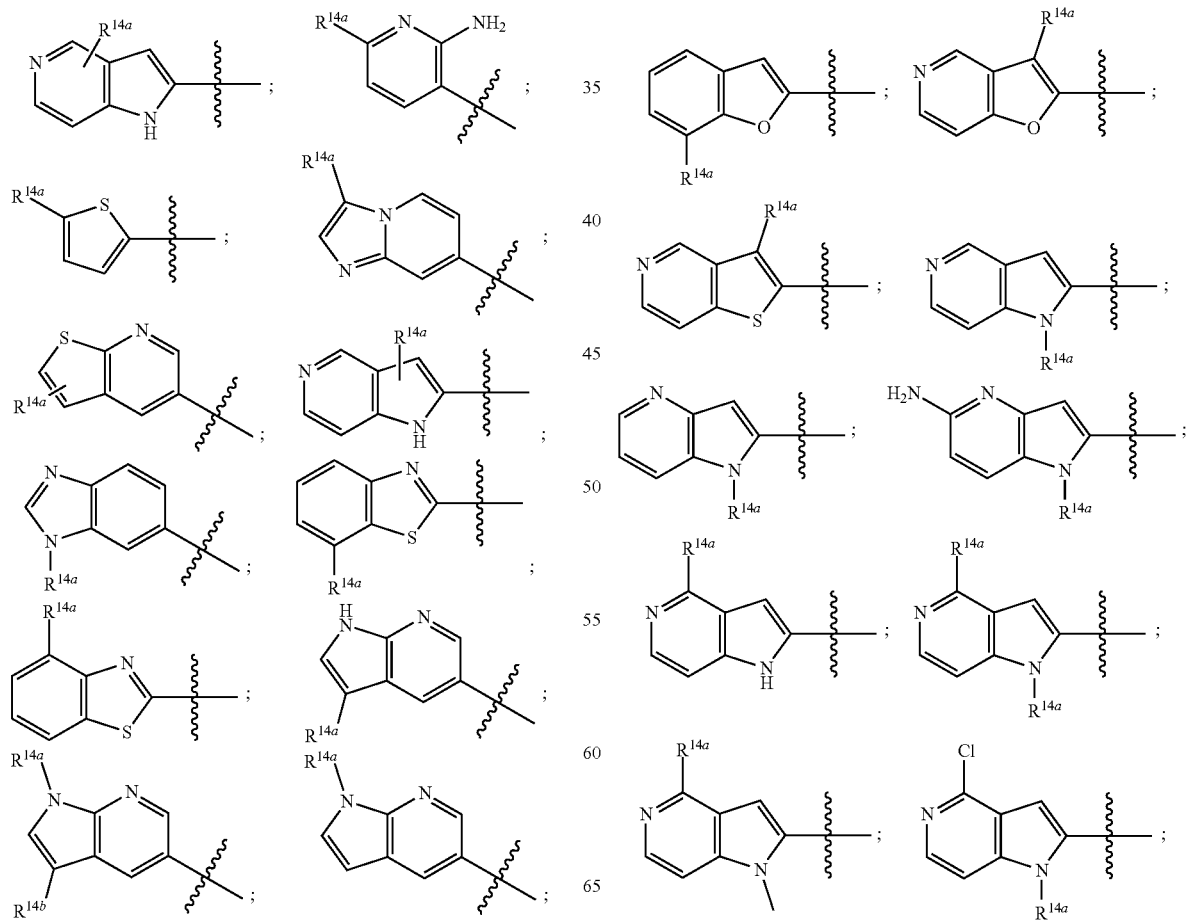

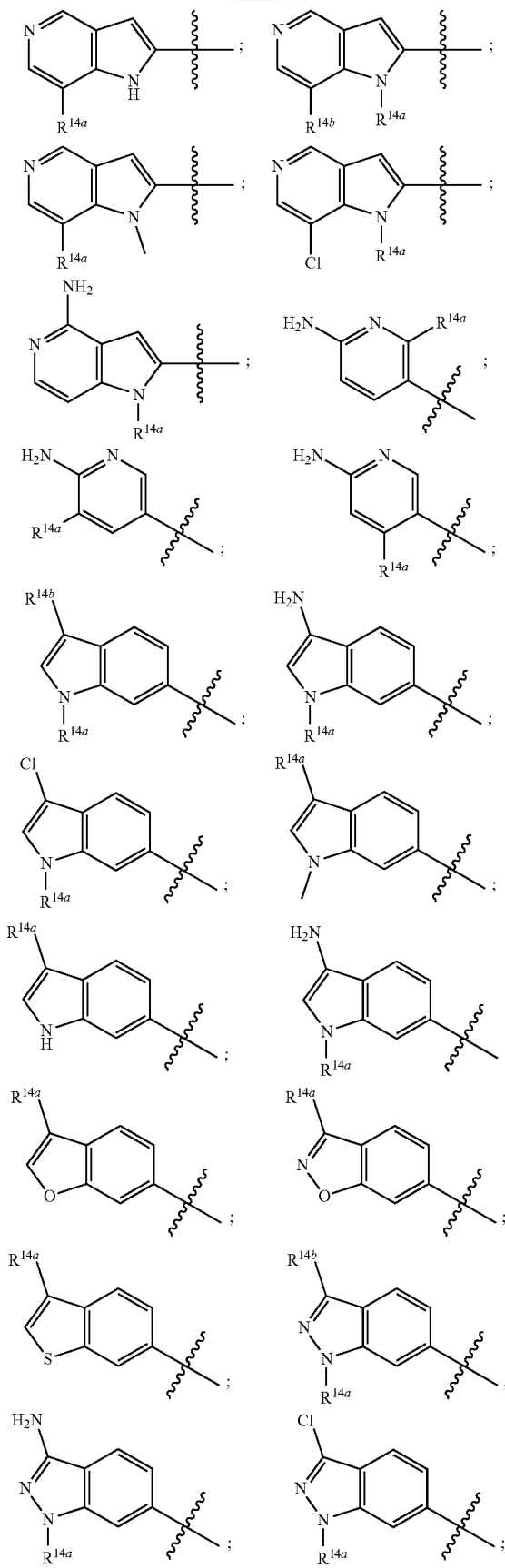
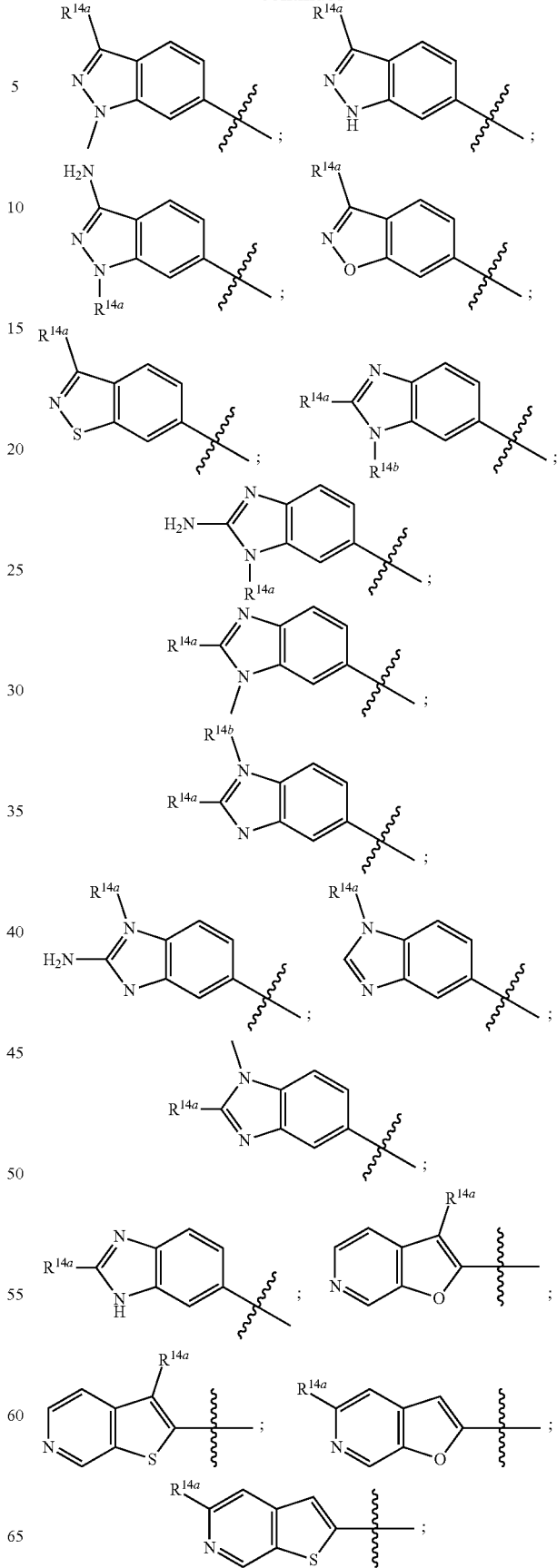

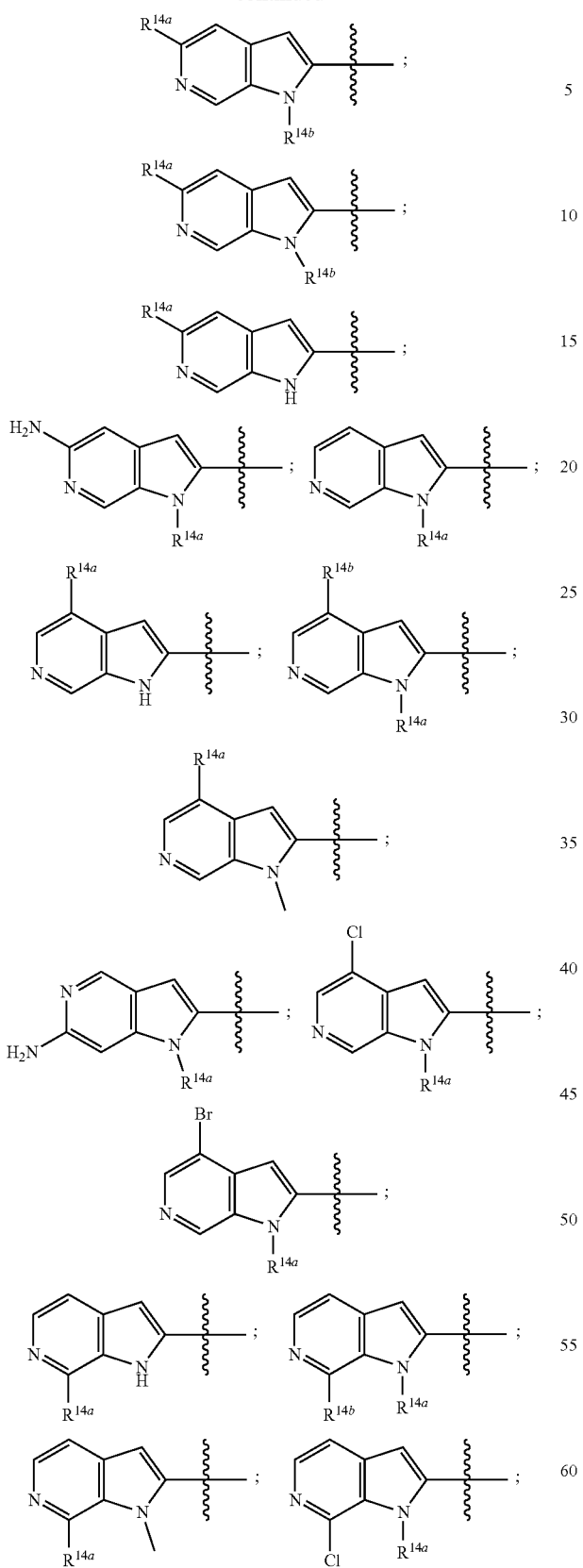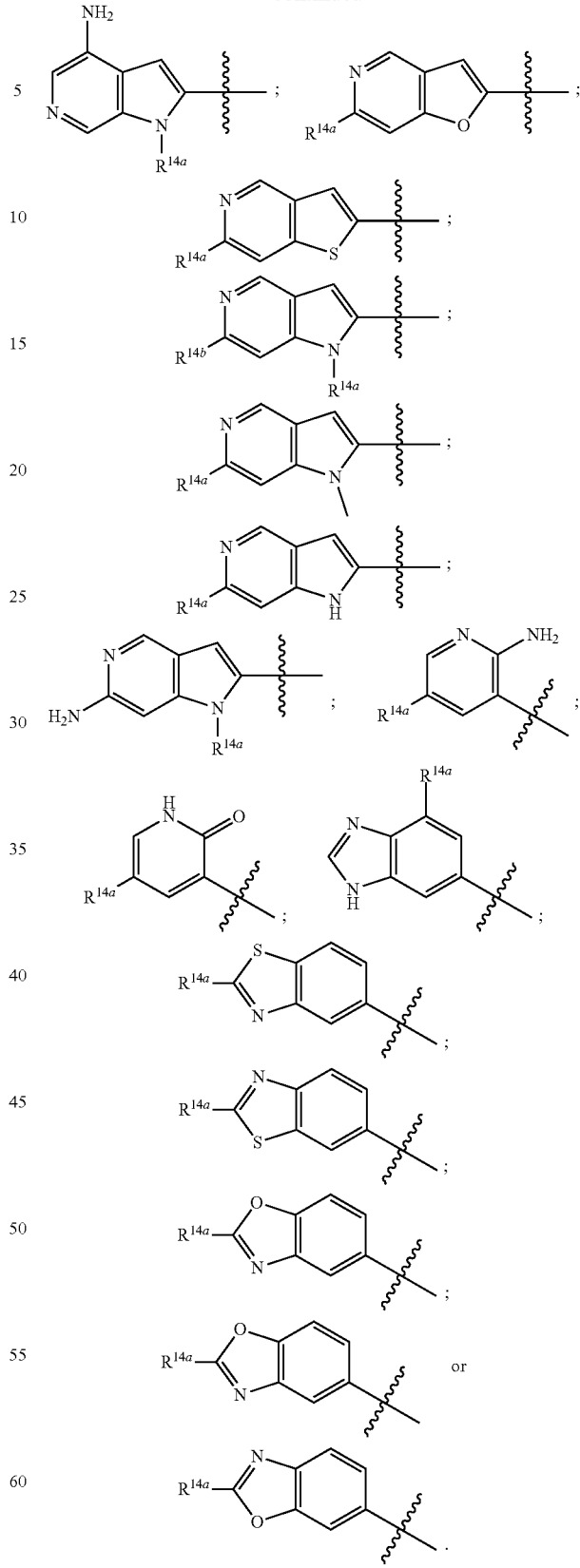
In more specific embodiments, $R^{14a}$ or $R^{14b}$ is independently $C_{1-6}$ alkyl, amino, or halo. In some embodiments, $R^{14a}$ or $R^{14b}$ is methyl. In certain embodiments, $R^{14a}$ or $R^{14b}$ is F, Cl, or Br. In some embodiments, each $R^{14a}$ or $R^{14b}$ attached to nitrogen is $C_{1-6}$ alkyl. In some embodiments, $R^{14a}$ or $R^{14b}$ is methyl or ethyl.
In some embodiments, $R^{14}$ has one of the following structures:
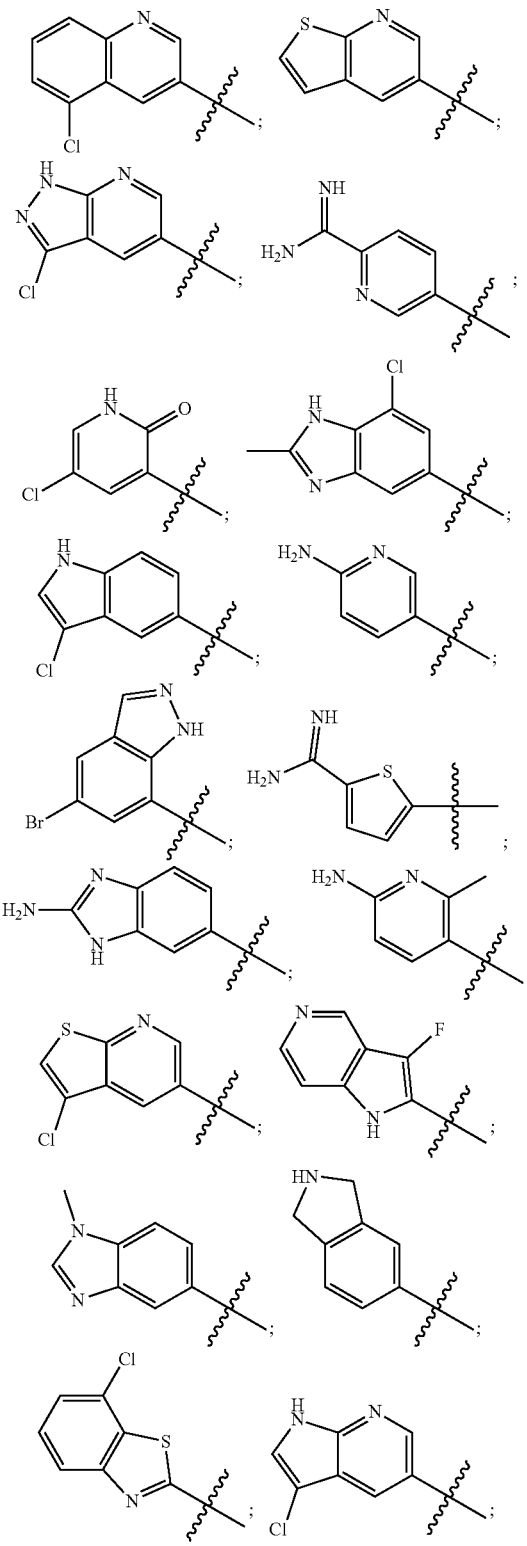
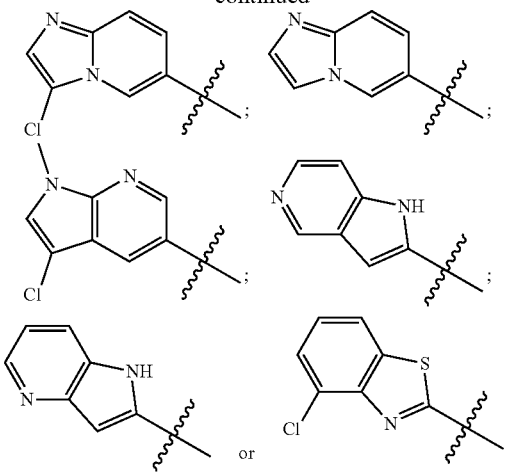
In more specific embodiments, $R^{14}$ has one of the following structures:
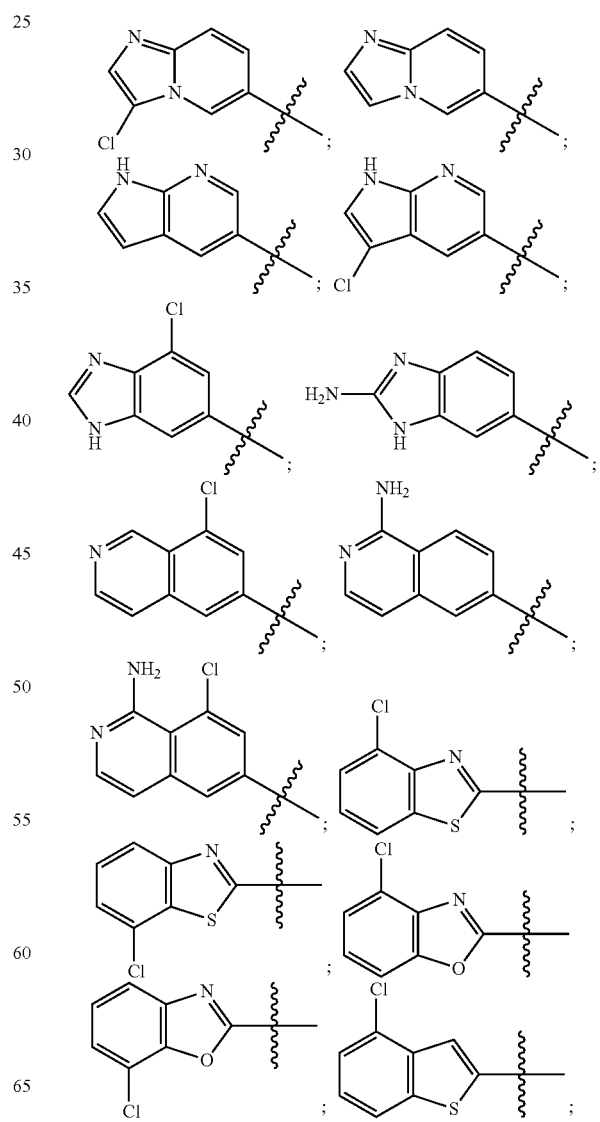

-continued
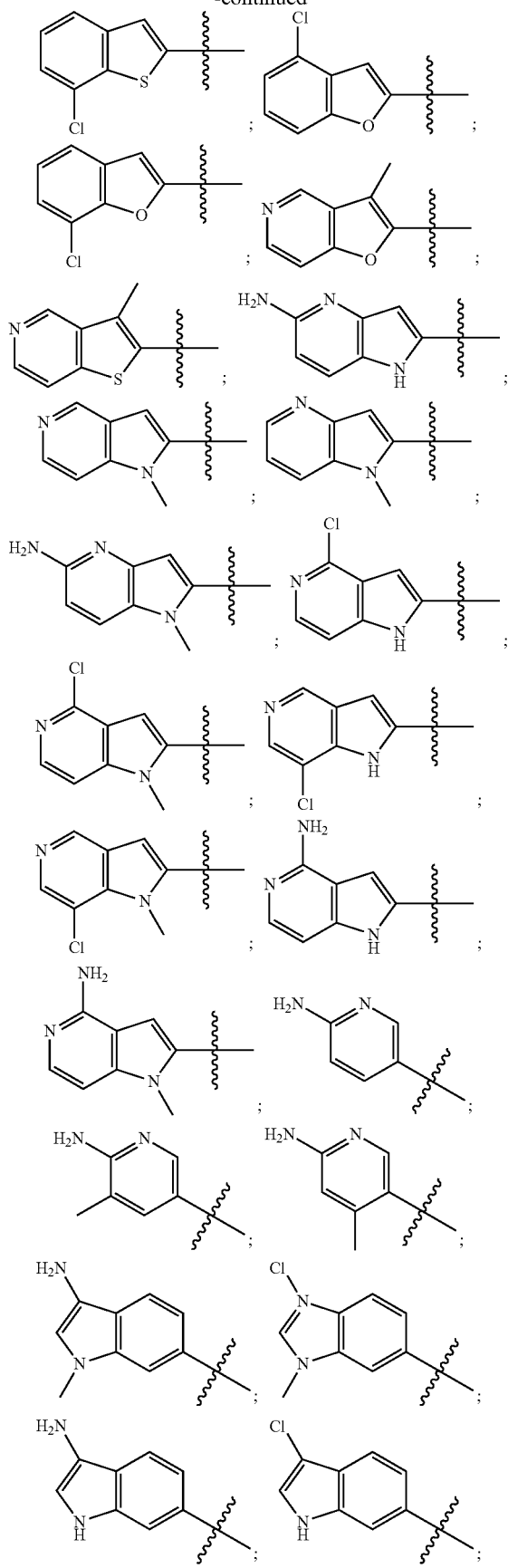
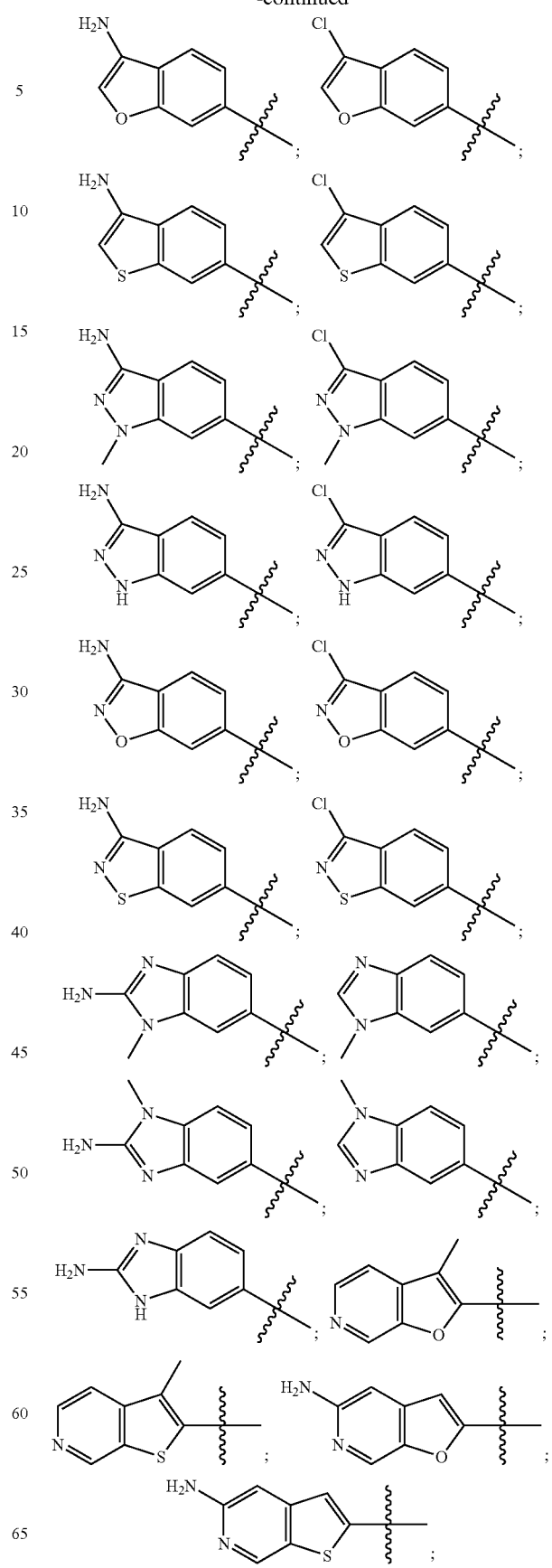

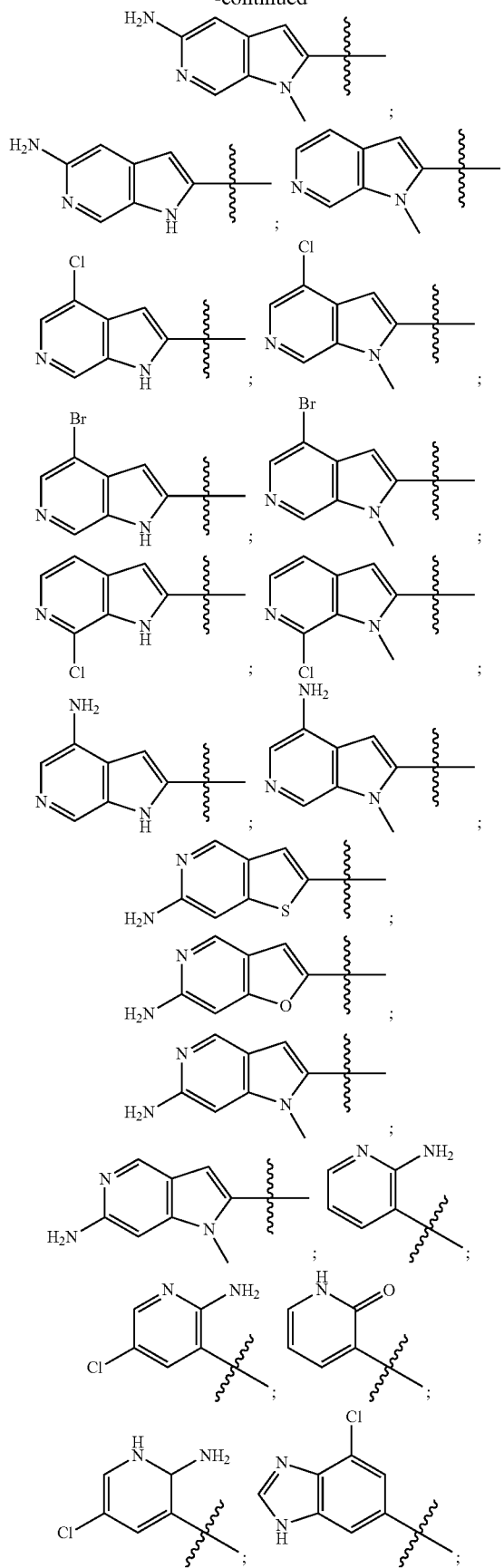
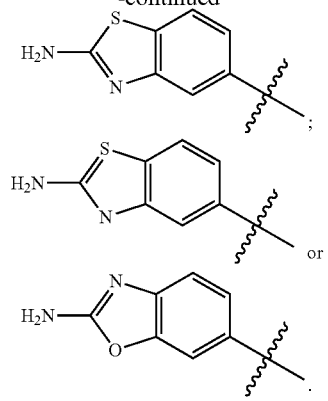
In some embodiments, $R^{14}$ has one of the following structures:
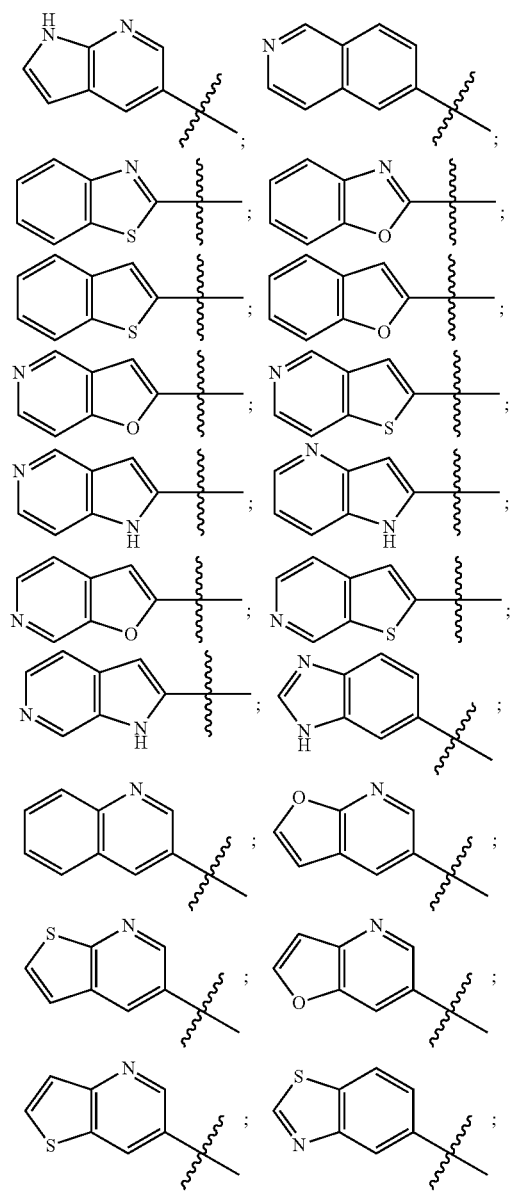

-continued

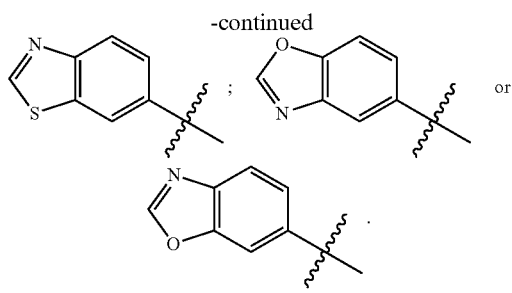

In some embodiments, $R^{15}$ is a substituted or unsubstituted arylalkyl. In certain embodiments, $R^{15}$ is an unsubstituted arylalkyl. In some more specific embodiments, $R^{15}$ has one of the following structures:

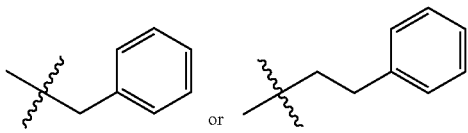

In some more specific embodiments, $R^{15}$ is a substituted or unsubstituted heteroarylalkyl.

In certain embodiments, $R^{15}$ is an unsubstituted heteroarylalkyl. In some embodiments, $R^{15}$ has one of the following structures:

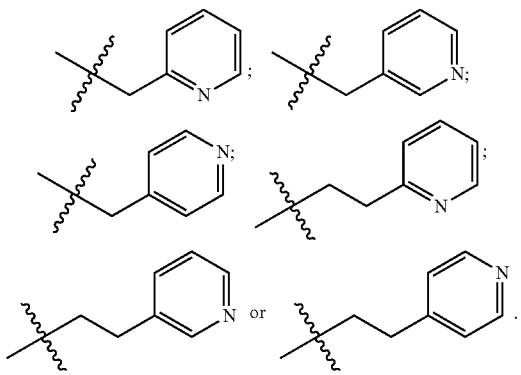

In certain embodiments, $L^2$ is a direct bond. In some embodiments, $L^2$ is —C(=O)—. In certain embodiments, $L^2$ is —S(=O)$_2$—. In some embodiments, $L^2$ is —S—. In still other embodiments, $L^2$ is —S(O)—.

In some embodiments, the compounds of Structure (I), (II), (III), or (IV), and embodiments thereof, can be in the form of a salt such as a pharmaceutically acceptable salt.

The compounds of Structure (I), (II), (III), or (IV), and embodiments thereof, are useful as inhibitors of MASP-2 and for therapeutic use. The compounds of Structure (I), (II), (III), or (IV), and embodiments thereof, are useful in the treatment of MASP-2-associated diseases and disorders, and in the manufacture of medicaments for treating MASP-2-associated diseases and disorders. The present disclosure also provides methods of treating a MASP-2-associated disease and disorder comprising administering to a patient a therapeutically effective amount of a compound of Structure (I), (II), (III), or (IV), or an embodiment thereof, optionally in the form of a salt.

In some embodiments the compound Structure (I), (II), (III), or (IV) or an embodiment thereof is provided in the form of a pharmaceutical composition comprising the compound or a salt thereof, such as a pharmaceutically acceptable salt, and at least one pharmaceutically acceptable carrier or excipient.

In certain aspects, the compound is one or more selected from the compounds of Structure (I), (II), (III), or (IV) set forth in the Examples, including the compounds listed in Table 1, (e.g., compounds with selectivity for MASP-2 over thrombin). In certain aspects, one or more of the variables defining the compounds of Structure (I), (II), (III), or (IV) is selected from the corresponding substituents in the compounds of Structure (I), (II), (III), or (IV) in the Examples including the compounds listed in Table 1, preferably, those of the compounds with selectivity for MASP-2 over thrombin.

In certain aspects, the disclosure sets forth a stereochemically pure enantiomer or diastereomer (e.g., an optically active compound with one or more stereocenter(s)). Unless specifically indicated otherwise, for any compound with one or more stereocenters is intended to include and to describe both the pure (+) and (−) enantiomers, any other diastereomers, mixtures that are enriched in an enantiomer or diastereomer (e.g., 10%, 20%, 30%, 40%, 50%, 60%, 70% 75%, 80%, 85, 90%, or 95% enantiomeric or diastereomeric excess), and a racemic mixture of enantiomers or diastereomers.

Certain embodiments provide a pharmaceutically acceptable salt of the indicated chemical structure (e.g., a hydrohalide, such as a hydrochloride or dihydrochloride). Examples of pharmaceutically acceptable salts are set forth in, e.g., Burge, S. M. et al., J. Pharm. Sci 1977, 66, 1-19. They include chlorides, bromides, iodides, formates, acetates, propionates, oxalates, malonates, succinates, fumarates, maleates, tartrates, citrates, benzoates, phthalates, sulfonates, aryl sulfonates, alkylsulfonates, salts of fatty acids, and the like. Salts can be prepared by a variety of methods known to the skilled artisan, including a precipitation with the conjugate acid or base (e.g., treatment with gaseous HCl or an HCl solution).

In certain embodiments provide a prodrug. A prodrug is a compound that is converted to a biologically active form under physiological conditions, often by hydrolysis, oxidation, or reduction (e.g., ester to acid form; carbamate to amino or hydroxy group; hydroxyamidine to amidine) Exemplary prodrugs are set forth in, e.g., Tilley, J. W., "Prodrugs of Benzamide," *Prodrugs* 2007, 191-222; Peterlin-Masic et al. *Curr. Pharma. Design* 2006, 12, 73-91. Prodrugs for the amidine group include amidoximes, O-alkylamidoximes, acylamidines, carbamates, 1,2,4-oxadiazolin-4-ones, and the like.

In certain aspects, the compound is useful for selectively inhibiting MASP-2 over thrombin, the method comprising administering the compound as described herein. In certain aspects, the selectivity ratio of MASP-2 Thrombin is at least 1.1:1, 1.25:1, 1.5:1, 1.75:1, 2:1,3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, or 30:1. In certain aspects, the selectivity ratio of MASP-2 Thrombin is at least 40:1, 50:1, 60:1, 70:1, 80:1, 90:1, 100:1, 125:1, 150:1, 175:1, 200:1, 250:1, 300:1, 350:1, 400:1, 500:1, 600:1, 700:1, 800:1, 900:1, 1000:1, 2000:1, 3000:1, 4000:1, 5000:1, 7500:1, 10,000:1, 25,000:1, or 50,000:1 or greater.

III. Synthesis

Compounds described herein, including salts thereof, can be prepared using known organic synthesis techniques and can be synthesized according to any of numerous possible synthetic routes, such as those illustrated in the Examples below.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, Protecting Group Chemistry, (Oxford University Press, 2000); Smith et al., March's Advanced Organic Chemistry: Reactions, Mechanisms, and Structure, 6th Ed. (Wiley, 2007); Peturssion et al., "Protecting Groups in Carbohydrate Chemistry," *J. Chem. Educ.*, 1997, 77(11), 1297; and Wuts et al, Protective Groups in Organic Synthesis, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high-performance liquid chromatography (HPLC) or thin layer chromatography (TLC).

The particular synthetic methods used in the Examples provide general guidance in connection with preparing the compounds of the disclosure. One skilled in the art would understand that the preparations can be modified or optimized using general knowledge of organic chemistry to prepare various compounds within the scope of the present disclosure.

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the disclosure may be synthesized and that a broad repertoire of synthetic organic reactions is available to be potentially employed in synthesizing compounds of the disclosure. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry*, Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II* (Pergamon Press, 1996); Smith et al., *March's Advanced Organic Chemistry; Reactions, Mechanisms, and Structure*, 6th Ed. (Wiley, 2007); Trost et al. (Ed.), *Comprehensive Organic Synthesis* (Pergamon Press, 1991).

IV. Methods of Treatment

In another aspect, the present disclosure provides a method of treating a patient suffering from, or at risk for developing a MASP-2-associated disease or disorder such as a MASP-2-dependent complement-associated disease or disorder comprising administering a small molecule inhibitor of MASP-2.

The compound can be any small molecule inhibitor of MASP-2. In some embodiments, the compound can be a small molecule inhibitor of MASP-2 that binds to the serine protease domain of MASP-2. In some embodiments, the compound can be a small molecule inhibitor such as a synthetic small molecule inhibitor of MASP-2. In some embodiments, the compound can be a small molecule inhibitor of MASP-2 that binds to the catalytic, substrate-binding region of MASP-2. In some embodiments, the compound selectively inhibits MASP-2 relative to thrombin. For example, in some embodiments, the compound is a compound of Structure (I), (II), (III), or (IV) as described in any of the foregoing embodiments.

As described in U.S. Pat. Nos. 7,919,094; 8,840,893; 8,652,477; 8,951,522, 9,011,860, 9,475,885, 9,644,035, U.S. Patent Application Publication Nos. US 2013/0344073, US 2013/0266560, US 2015/0166675, US 2017/0137537, US 2017/0166660, US 2017/0189525, US 2017/0267781, US 2017/0283508, US 2017/0253667, US 2018/0105604, and PCT Publication Nos. WO 2018/045054, WO 2019/036460 and co-pending U.S. Patent Application Ser. No. 62/688,611 (each of which is assigned to Omeros Corporation, the assignee of the instant application, each of which is hereby incorporated by reference), MASP-2-dependent complement activation has been implicated as contributing to the pathogenesis of numerous acute and chronic disease states. For example, as described in U.S. Pat. No. 8,951,522, the primary function of the complement system, a part of the innate immune system, is to protect the host against infectious agents, however, inappropriate or over-activation of the complement system can lead to serious disease, such as thrombotic microangiopathies (TMAs, including aHUS, TTP and HUS) in which endothelial damage as well as fibrin and platelet-rich thrombi in the microvasculature lead to organ damage. The lectin pathway plays a dominant role in activating complement in settings of endothelial cell stress or injury and preventing the activation of MASP-2 and the lectin pathway halts the sequence of enzymatic reactions that lead to the formation of the membrane attack complex, platelet activation and leukocyte recruitment. As described in U.S. Pat. No. 8,652,477, in addition to initiation of the lectin pathway, MASP-2 can also activate the coagulation system and is capable of cleaving prothrombin to thrombin.

Accordingly, in some embodiments, the method comprises administering to a patient suffering from or at risk for developing a MASP-2-dependent complement-associated disease or disorder an amount of a compound of the disclosure in an amount sufficient to inhibit MASP-2 dependent complement activation in the mammalian subject to thereby treat the disease or disorder. In some embodiments, the method can further comprise, prior to administering a compound of the disclosure to the patient, determining that the patient is afflicted with the lectin complement-associated disease or disorder.

In some embodiments, the MASP-2-dependent complement-associated disease or disorder is selected from the group consisting of a thrombotic microangiopathy (TMA), a renal condition, an inflammatory reaction resulting from tissue or organ transplantation, an ischemia reperfusion injury, a complication associated with diabetes, a cardiovascular disease or disorder, an inflammatory gastrointestinal disorder, a pulmonary disorder, an ophthalmic disease or disorder, disseminated intravascular coagulation, graft-versus-host disease, veno-occlusive disease, diffuse alveolar hemorrhage, or similar, as well as combinations thereof.

In some embodiments, the MASP-2-dependent complement-associated disease or disorder is a thrombotic microangiopathy (TMA) including thrombotic thrombocytopenic purpura (TTP), refr+actory TTP, Upshaw-Schulman Syndrome (USS), hemolytic uremic syndrome (HUS), atypical hemolytic syndrome (aHUS), non-Factor H-dependent atypical hemolytic syndrome, aHUS secondary to an infection, plasma therapy-resistant aHUS, a TMA secondary to cancer, a TMA secondary to chemotherapy, a TMA secondary to transplantation, or a TMA associated with hematopoietic stem cell transplant.

In some embodiments, the method comprises administering to a patient suffering from or at risk for developing graft-versus-host disease (GVHD), including acute GVHD, chronic GVHD or steroid-resistant GVHD an amount of a compound of the disclosure in an amount sufficient to inhibit MASP-2 dependent complement activation in the mammalian subject to thereby treat the disease or disorder. In some embodiments, the subject suffering from or at risk for developing GVHD has previously undergone, is undergoing, or will undergo a hematopoietic stem cell transplant.

In some embodiments, the method comprises administering to a patient suffering from, or at risk for developing diffuse alveolar hemorrhage (DAH) an amount of a compound of the disclosure in an amount sufficient to inhibit MASP-2 dependent complement activation in the mammalian subject to thereby treat the disease or disorder. In some embodiments, the subject suffering from, or at risk for developing DAH has previously undergone, is undergoing, or will undergo a hematopoietic stem cell transplant.

In some embodiments, the method comprises administering to a patient suffering from, or at risk for developing veno-occlusive disease (VOD) an amount of a compound of the disclosure in an amount sufficient to inhibit MASP-2 dependent complement activation in the mammalian subject to thereby treat the disease or disorder. In some embodiments, the subject suffering from, or at risk for developing VOD has previously undergone, is undergoing, or will undergo a hematopoietic stem cell transplant.

In some embodiments, the method comprises administering to a patient suffering from, or at risk for developing idiopathic pneumonia syndrome (IPS) an amount of a compound of the disclosure in an amount sufficient to inhibit MASP-2 dependent complement activation in the mammalian subject to thereby treat the disease or disorder. In some embodiments, the subject suffering from, or at risk for developing IPS has previously undergone, is undergoing, or will undergo a hematopoietic stem cell transplant.

In some embodiments, the method comprises administering to a patient suffering from, or at risk for developing capillary leak syndrome (CLS) an amount of a compound of the disclosure in an amount sufficient to inhibit MASP-2 dependent complement activation in the mammalian subject to thereby treat the disease or disorder. In some embodiments, the subject suffering from, or at risk for developing CLS has previously undergone, is undergoing, or will undergo a hematopoietic stem cell transplant.

In some embodiments, the method comprises administering to a patient suffering from, or at risk for developing engraftment syndrome (ES) an amount of a compound of the disclosure in an amount sufficient to inhibit MASP-2 dependent complement activation in the mammalian subject to thereby treat the disease or disorder. In some embodiments, the subject suffering from, or at risk for developing ES has previously undergone, is undergoing, or will undergo a hematopoietic stem cell transplant.

In some embodiments, the method comprises administering to a patient suffering from, or at risk for developing fluid overload (FO) an amount of a compound of the disclosure in an amount sufficient to inhibit MASP-2 dependent complement activation in the mammalian subject to thereby treat the disease or disorder. In some embodiments, the subject suffering from, or at risk for developing FO has previously undergone, is undergoing, or will undergo a hematopoietic stem cell transplant.

In some embodiments, the method comprises administering to a patient suffering from any of the above-referenced diseases or conditions an amount of a compound as disclosed in PCT Application No. PCT/US19/34225, which is hereby incorporated in its entirety.

In some embodiments, the MASP-2-dependent complement-associated disease or disorder is a renal condition including mesangioproliferative glomerulonephritis, membranous glomerulonephritis, membranoproliferative glomerulonephritis (mesangiocapillary glomerulonephritis), acute post infectious glomerulonephritis (poststreptococcal glomerulonephritis), C3 glomerulopathy, cryoglobulinemic glomerulonephritis, pauci-immune necrotizing crescentic glomerulonephritis, lupus nephritis, Henoch-Schonlein purpura nephritis, IgA nephropathy, and the like, as well as combinations thereof.

In some embodiments, the MASP-2-dependent complement-associated disease or disorder is renal fibrosis (e.g., tubulointerstitial fibrosis) and/or proteinuria in a subject suffering from or at risk for developing chronic kidney disease, chronic renal failure, glomerular disease (e.g., focal segmental glomerulosclerosis), an immune complex disorder (e.g., IgA nephropathy, membranous nephropathy), lupus nephritis, nephrotic syndrome, diabetic nephropathy, tubulointerstitial damage and glomerulonepthritis (e.g., C3 glomerulopathy), or a disease or condition associated with proteinuria, including, but not limited to, nephrotic syndrome, pre-eclampsia, eclampsia, toxic lesions of kidneys, amyloidosis, collagen vascular diseases (e.g., systemic lupus erythematosus), dehydration, glomerular diseases (e.g., membranous glomerulonephritis, focal segmental glomerulonephritis, C3 glomerulopathy, minimal change disease, lipoid nephrosis), strenuous exercise, stress, benign orthostatis (postural) proteinuria, focal segmental glomerulosclerosis, IgA nephropathy (i.e., Berger's disease), IgM nephropathy, membranoproliferative glomerulonephritis, membranous nephropathy, minimal change disease, sarcoidosis, Alport's syndrome, diabetes mellitus (diabetic nephropathy), drug-induced toxicity (e.g., NSAIDS, nicotine, penicillamine, lithium carbonate, gold and other heavy metals, ACE inhibitors, antibiotics (e.g., adriamycin), opiates (e.g., heroin), or other nephrotoxins); Fabry's disease, infections (e.g., HIV, syphilis, hepatitis A, B or C, poststreptococcal infection, urinary schistosomiasis); aminoaciduria, Fanconi syndrome, hypertensive nephrosclerosis, interstitial nephritis, sickle cell disease, hemoglobinuria, multiple myeloma, myoglobinuria, organ rejection (e.g., kidney transplant rejection), ebola hemorrhagic fever, Nail patella syndrome, familial Mediterranean fever, HELLP syndrome, systemic lupus erythematosus, Wegener's granulomatosis, Rheumatoid arthritis, Glycogen storage disease type 1, Goodpasture's syndrome, Henoch-Schonlein purpura, urinary tract infection which has spread to the kidneys, Sjogren's syndrome and post-infections glomerulonepthritis.

In some embodiments, the MASP-2-dependent complement-associated disease or disorder is an inflammatory reaction resulting from tissue or solid organ transplantation, including allotransplantation or xenotransplantation of whole organs (e.g., kidney, heart, liver, pancreas, lung, cornea, and the like) or tissue grafts (e.g., valves, tendons, bone marrow, and the like).

In some embodiments, the MASP-2-dependent complement-associated disorder is an ischemia reperfusion injury (I/R), including myocardial I/R, gastrointestinal I/R, renal I/R, and I/R following an aortic aneurism repair, I/R associated with cardiopulmonary bypass, cerebral I/R, stroke, organ transplant or reattachment of severed or traumatized limbs or digits; revascularization to transplants and/or replants, and hemodynamic resuscitation following shock, surgical procedures, or similar, as well as combinations thereof.

In some embodiments, the MASP-2-dependent complement-associated disease or disorder is a complication associated with non-obese diabetes (Type-1 diabetes or Insulin-dependent diabetes mellitus) and/or complications associated with Type-1 or Type-2 (adult onset) diabetes including diabetic angiopathy, diabetic neuropathy, diabetic retinopathy, diabetic macular edema, and the like, as well as combinations thereof.

In some embodiments, the MASP-2-dependent complement-associated disease or disorder is a cardiovascular disease or disorder, including Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease; dilated cardiomyopathy; diabetic angiopathy; Kawasaki's disease (arteritis); venous gas embolus (VGE); and inhibition of restenosis following stent placement, rotational atherectomy, percutaneous transluminal coronary angioplasty (PTCA), and the like as well as combinations thereof.

In some embodiments, the MASP-2-dependent complement-associated disease or disorder is an inflammatory gastrointestinal disorder, including pancreatitis, diverticulitis and bowel disorders including Crohn's disease, ulcerative colitis, irritable bowel syndrome, inflammatory bowel disease (IBD), or similar, as well as combinations thereof.

In some embodiments, the MASP-2-dependent complement-associated disease or disorder is a pulmonary disorder, including acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, aspiration pneumonia, bronchiolitis obliterans syndrome, idiopathic pulmonary fibrosis, acute lung injury secondary to burn, non-cardiogenic pulmonary edema, transfusion-related respiratory depression, emphysema, and the like, as well as combinations thereof.

In some embodiments, the MASP-2-dependent complement-associated disease or disorder is an extracorporeal exposure-triggered inflammatory reaction and the method comprises treating a subject undergoing an extracorporeal circulation procedure. In some embodiments, the extracorporeal circulation procedure includes hemodialysis, plasmapheresis, leukopheresis, extracorporeal membrane oxygenation (ECMO), heparin-induced extracorporeal membrane oxygenation LDL precipitation (HELP), cardiopulmonary bypass (CPB), and the like.

In some embodiments, the MASP-2-dependent complement-associated disease or disorder is selected from inflammatory or non-inflammatory arthritides and other musculoskeletal disorders, e.g., osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy, systemic lupus erythematosus (SLE), or similar, as well as combinations thereof.

In some embodiments, the MASP-2-dependent complement-associated disease or disorder is a skin disorder; for example, psoriasis, autoimmune bullous dermatoses, eosinophilic spongiosis, bullous pemphigoid, epidermolysis bullosa acquisita, atopic dermatitis, herpes gestationis, and other skin disorders. In some embodiments, the MASP-2-dependent complement-associated disease or disorder is a thermal burn, chemical burn, or combinations thereof, including capillary leakage caused thereby.

In some embodiments, the MASP-2-dependent complement-associated disease or disorder is a peripheral nervous system (PNS) and/or central nervous system (CNS) disorder or injury including multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD), Alzheimer's disease (AD), Miller-Fisher syndrome, cerebral trauma and/or hemorrhage, traumatic brain injury, demyelination, meningitis, or similar, as well as combinations thereof.

In some embodiments, the MASP-2-dependent complement-associated disease or disorder is sepsis or a condition resulting from sepsis including severe sepsis, septic shock, acute respiratory distress syndrome resulting from sepsis, hemolytic anemia, systemic inflammatory response syndrome, hemorrhagic shock, or the like, as well as combinations thereof.

In some embodiments, the MASP-2-dependent complement-associated disease or disorder is a urogenital disorder including painful bladder disease, sensory bladder disease, chronic abacterial cystitis and interstitial cystitis, male and female infertility, placental dysfunction and miscarriage, pre-eclampsia, or similar, as well as combinations thereof.

In some embodiments, the MASP-2-dependent complement-associated disease or disorder is an inflammatory reaction in a subject being treated with chemotherapeutics and/or radiation therapy, including for the treatment of cancerous conditions.

In some embodiments, the MASP-2-dependent complement-associated disease or disorder is an angiogenesis-dependent cancer, including a solid tumor(s), blood borne tumor(s), high-risk carcinoid tumors, tumor metastases, and the like, including combinations thereof.

In some embodiments, the MASP-2-dependent complement-associated disease or disorder is an angiogenesis-dependent benign tumor, including hemangiomas, acoustic neuromas, neurofibromas, trachomas, carcinoid tumors, pyogenic granulomas, or similar, as well as combinations thereof.

In some embodiments, the MASP-2-dependent complement-associated disease or disorder is an endocrine disorder including Hashimoto's thyroiditis, stress, anxiety, other potential hormonal disorders involving regulated release of prolactin, growth or insulin-like growth factor, adrenocorticotropin from the pituitary, or similar, as well as combinations thereof.

In some embodiments, the MASP-2-dependent complement-associated disease or disorder is an ophthalmic disease or disorder including age-related macular degeneration, glaucoma, endophthalmitis, and the like, as well as combinations thereof.

In some embodiments, the MASP-2-dependent complement-associated disease or disorder is an ocular angiogenic disease or condition including age-related macular degeneration, uveitis, ocular melanoma, corneal neovascularization, primary pterygium, HSV stromal keratitis, HSV-1-induced corneal lymphangiogenesis, proliferative diabetic retinopathy, diabetic macular edema, retinopathy of prematurity, retinal vein occlusion, corneal graft rejection, neovascular glaucoma, vitreous hemorrhage secondary to proliferative diabetic retinopathy, neuromyelitis optica, rubeosis, or similar, as well as combinations thereof.

In some embodiments, the MASP-2-dependent complement-associated disease or disorder is disseminated intravascular coagulation (DIC) or other complement mediated coagulation disorder, including DIC secondary to sepsis, severe trauma, including neurological trauma (e.g., acute head injury; see Kumura et al, *Acta Neurochirurgica* 55:23-28 (1987), infection (e.g., bacterial, viral, fungal, parasitic), cancer, obstetrical complications, liver disease, severe toxic reaction (e.g., snake bite, insect bite, transfusion reaction), shock, heat stroke, transplant rejection, vascular aneurysm, hepatic failure, cancer treatment by chemotherapy or radiation therapy, burn, or accidental radiation exposure.

In some embodiments, the MASP-2-dependent complement-associated disease or disorder is selected from the group consisting of acute radiation syndrome, dense deposit disease, Degos Disease, Catastrophic Antiphospholipid Syndrome (CAPS), Behcet's disease, cryoglobulinemia, paroxysmal nocturnal hemoglobinuria (PNH), cold agglutinin disease, and combinations thereof.

In some embodiments, the MASP-2-dependent complement-associated disease or disorder is selected from the group consisting of aHUS, HSCT-TMA, IgAN, Lupus Nephritis (LN), and combinations thereof.

In some embodiments, the method comprises administering to a patient suffering from, or at risk for developing a disease, disorder or condition associated with fibrin-induced activation of the complement system and the associated activation of the coagulation and/or contact systems an amount of a compound according to any one of the foregoing embodiments (e.g., a compound of Structure (I), (II), (III), or (IV)) in an amount sufficient to inhibit MASP-2 dependent complement activation in the mammalian subject to thereby treat the disease or disorder. In some embodiments, the subject is suffering from, or at risk of developing, a disease, disorder or condition associated with complement-related inflammation, excessive coagulation or contact system activation initiated by fibrin or activated platelets. In some embodiments, the subject is suffering from a disease or disorder selected from the group consisting of arterial thrombosis, venous thrombosis, deep vein thrombosis, post-surgical thrombosis, restenosis following coronary artery bypass graft and/or an interventional cardiovascular procedure (e.g., angioplasty or stent placement), atherosclerosis, plaque rupture, plaque instability, restenosis, hypotension, acute respiratory distress syndrome (ARDS), systemic inflammatory response syndrome (SIRS), disseminated intravascular coagulation (DIC), veno-occlusive disease (VOD), thrombotic microangiopathy, lupus nephritis, superficial thrombophlebitis, Factor V Leiden mutation, ischemic/reperfusion injury, human immunodeficiency virus (HIV) infection, undergoing hormone-replacement therapy (HRT), Alzheimer's disease and/or suffering from a hypercoagulable state.

In some embodiments, the subject is suffering from, or at risk for developing an acquired hypercoagulable state due to at least one or more of the following: undergoing therapy with a drug selected from the group consisting of 5-FU, GM-CSF, cisplatin, heparin, COX-2 inhibitor, contrast media, corticosteroids and antipsychotics; venous stasis (immobilization, surgery, etc.), antiphospholipid syndrome, cancer (promyelocytic leukemia, lung, breast, prostate, pancreas, stomach and colon tumors), tissue injury due to trauma or surgery, presence of a catheter in a central vein, acquired deficiency of a protein involved in clot formation (e.g., protein C), paroxysmal nocturnal hemoglobinuria (PNH), elevated levels of homocysteine, heart failure, presence of a mechanical valve, pulmonary hypertension with in situ thrombosis, atrial fibrillation, heparin-induced thrombocytopenia (HIT), heparin-induced thrombocytopenia and thrombosis (HITT), Kawasaki disease with in situ thrombus, Takayasu arteritis with in situ thrombus, thrombophilia of metastatic cancer, elevated Factor VIII levels, pregnancy, inflammatory bowel disease (IBD), or due to a genetic defect that causes or increases the risk of developing, a hypercoagulable state, such as a genetic defect selected from the group consisting of a Prothrombin 20210 gene mutation, an MTHFR mutation, a deficiency of protein C, a deficiency of protein S, a deficiency of protein A, a deficiency of protein Z, an antithrombin deficiency, and a genetic disorder producing thrombophilia.

In some embodiments, the subject is suffering from, or at risk for developing, a disease or disorder that is amenable to treatment with a kallikrein inhibitor. In some embodiments, the subject is suffering from, or at risk for developing a disease or disorder amenable to treatment with a kallikrein inhibitor is selected from the group consisting of hereditary angioedema, diabetic macular edema and bleeding during cardiopulmonary bypass. In some embodiments, the subject is suffering from, or at risk for developing, a disease or disorder that is amenable to treatment with a thrombin inhibitor, such as arterial thrombosis, venous thrombosis, pulmonary embolism, atrial fibrillation, heparin-induced thrombocytopenia, conversion from one anticoagulant to another, or off-label use for extracorporeal circuit patency of continuous renal replacement therapy (CRRT) in critically ill patients with HIT (maintenance).

In some embodiments, the subject has previously experienced, is currently suffering from, or is at risk for developing atrial fibrillation and the MASP-2 inhibitory compound (e.g., a compound of Structure (I), (II), (III), or (IV)) is administered in an amount sufficient to reduce the risk of stroke in said subject. In some embodiments, the subject is suffering from, or at risk for developing, a disease or disorder that is amenable to treatment with a factor XII inhibitor, such as deep vein thrombosis (both primary prophylaxis and extended therapy), pulmonary embolism, non-valvular atrial fibrillation, prevention of recurrent ischemia after acute coronary syndrome in subjects with or without atrial fibrillation, end-stage renal disease, cerebral ischemia, angina, or to reduce or prevent clotting associated with medical devices (e.g., valves, small caliber grafts, etc.) and/or extracorporeal circuits.

In some embodiments, the subject has previously experienced, is currently suffering from, or is at risk for developing nonvalvular atrial fibrillation and the MASP-2 inhibitory compound (e.g., a compound of Structure (I), (II), (III), or (IV)) is administered in an amount sufficient to reduce the risk of stroke and/or embolism in said subject. In some embodiments, the subject has an acquired disease or disorder that increases the propensity for thromboembolism, such as a disease or disorder selected from the group consisting of atherosclerosis, antiphospholipid antibodies, cancer (e.g., promyelocytic leukemia, lung, breast, prostate, pancreatic, stomach and colon), hyperhomocysteinemia, infection, tissue injury, venous stasis (such as due to surgery, orthopedic or paralytic immobilization, heart failure, pregnancy, or obesity) and a subject taking oral contraceptives that contain estrogen.

In some embodiments, the subject is in need of anticoagulant therapy and the MASP-2 inhibitory compound (e.g., a compound of Structure (I), (II), (III), or (IV)) is used as a replacement for standard anticoagulant therapy (e.g., Warfarin). In some embodiments, the subject has a condition that normally prohibits standard anticoagulant therapy, such as CNS amyloid angiopathy. In some embodiments of the method, the MASP-2 inhibitory compound is administered as a bridging agent peri operatively in a subject otherwise on standard anti coagulation therapy. In some embodiments, the subject has sickle cell disease which is a vaso-occlusive disorder involving activation of platelets.

Atypical hemolytic uremic syndrome (aHUS) is part of a group of conditions termed "Thrombotic microangiopathies." In the atypical form of HUS (aHUS), the disease is associated with defective complement regulation and can be either sporadic or familial. Familial cases of aHUS are associated with mutations in genes coding for complement activation or complement regulatory proteins, including complement factor H, factor I, factor B, membrane cofactor CD46 as well as complement factor H-related protein 1(CFHR1) and complement factor H-related protein 3 (CFHR3). (Zipfel, P. F., et al., PloS Genetics 3(3):e41 (2007)). The unifying feature of this diverse array of genetic mutations associated with aHUS is a predisposition to enhanced complement activation on cellular or tissue surfaces. A subject is a risk for developing aHUS upon the onset of at least one or more symptoms indicative of aHUS (e.g., the presence of anemia, thrombocytopenia and/or renal insufficiency) and/or the presence of thrombotic microangiopathy in a biopsy obtained from the subject. The determination of whether a subject is at risk for developing aHUS comprises determining whether the subject has a genetic predisposition to developing aHUS, which may be carried out by assessing genetic information (e.g. from a database containing the genotype of the subject), or performing at least one genetic screening test on the subject to determine the presence or absence of a genetic marker associated with aHUS (i.e., determining the presence or absence of a genetic mutation associated with aHUS in the genes encoding complement factor H (CFH), factor I (CFI), factor B (CFB), membrane cofactor CD46, C3, complement factor H-related protein 1 (CFHR1), or THBD (encoding the anticoagulant protein thrombodulin) or complement factor H-related protein 3 (CFHR3), or complement factor H-related protein 4 (CFHR4)) either via genome sequencing or gene-specific analysis (e.g., PCR analysis), and/or determining whether the subject has a family history of aHUS. Methods of genetic screening for the presence or absence of a genetic mutation associated with aHUS are well established, for example, see Noris M et al. "Atypical Hemolytic-Uremic Syndrome," 2007 Nov. 16 [Updated 2011 Mar. 10], In: Pagon R A, Bird T D, Dolan C R, et al., editors. GeneReviews™, Seattle (Wash.): University of Washington, Seattle.

Hematopoietic stem cell transplant-associated TMA (HSCT-TMA) is a life-threatening complication that is triggered by endothelial injury. The kidney is the most commonly affected organ, though HSCT-TMA can be a multi-system disease that also involves the lung, bowel, heart, and brain. The occurrence of even mild TMA is associated with long-term renal impairment. Development of post-allogeneic HSCT-associated TMA differs in frequency based on varying diagnostic criteria and conditioning and graft-versus-host disease prophylaxis regimens, with calcineurin inhibitors being the most frequent drugs implicated (Ho V T et al., Biol Blood Marrow Transplant, 11(8):571-5, 2005).

Immunoglobulin A nephropathy (IgAN) is an autoimmune kidney disease resulting in intrarenal inflammation and kidney injury. IgAN is the most common primary glomerular disease globally. With an annual incidence of approximately 2.5 per 100,000, it is estimated that 1 in 1400 persons in the U.S. will develop IgAN. As many as 40% of patients with IgAN will develop end-stage renal disease (ESRD). Patients typically present with microscopic hematuria with mild to moderate proteinuria and variable levels of renal insufficiency (Wyatt R. J., et al., N Engl J Med 36S(25):2402-4, 2013). Clinical markers such as impaired kidney function, sustained hypertension, and heavy proteinuria (over 1 g per day) are associated with poor prognosis (Goto M et al., Nephrol Dial Transplant 24(10):3068-74, 2009; Berthoux F. et al., J Am Soc Nephrol 22(4):752-61, 2011). Proteinuria is the strongest prognostic factor independent of other risk factors in multiple large observational studies and prospective trials (Coppo R. et al., J Nephrol 18(5):503-12, 2005; Reich H. N., et al., J Am Soc Nephrol 18(12):3177-83, 2007). It is estimated that 15-20% of patients reach ESRD within 10 years of disease onset if left untreated (D'Amico G., Am J Kidney Dis 36(2):227-37, 2000). The diagnostic hallmark of IgAN is the predominance of IgA deposits, alone or with IgG, IgM, or both, in the glomerular mesangium.

A main complication of systemic lupus erythematosus (SLE) is nephritis, also known as lupus nephritis, which is classified as a secondary form of glomerulonephritis. Up to 60% of adults with SLE have some form of kidney involvement later in the course of the disease (Koda-Kimble et al., Koda-Kimble and Young's Applied Therapeutics: the clinical use of drugs, 10th Ed, Lippincott Williams & Wilkins: pages 792-9, 2012) with a prevalence of 20-70 per 100,000 people in the U.S. Lupus nephritis often presents in patients with other symptoms of active SLE, including fatigue, fever, rash, arthritis, serositis, or central nervous system disease (Pisetsky D. S. et al., Med Clin North Am 81(1): 113-28, 1997). Some patients have asymptomatic lupus nephritis; however, during regular follow-up, laboratory abnormalities such as elevated serum creatinine levels, low albumin levels, or urinary protein or sediment suggest active lupus nephritis.

V. Compositions, Dosage, and Administration

The compounds as described herein (e.g., a compound of Structure (I), (II), (III), or (IV)) can be administered in a manner compatible with the dosage formulation, and in such amount as will be effective or suitable for treatment. The quantity to be administered depends on a variety of factors including, e.g., the age, body weight, physical activity, and diet of the individual, and the desired effect. In certain embodiments, the size of the dose may also be determined by the existence, nature, and extent of any adverse side effects that accompany the administration of the compound in a particular individual.

It will be understood, however, that the specific dose level and frequency of dosage for any particular patient may be varied by a physician and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose may take the form of solid, semi-solid, or liquid forms, preferably in unit dosage forms suitable for simple administration of precise dosages.

As used herein, the term "unit dosage form" refers to physically discrete units suitable as unitary dosages for humans and other mammals, each unit containing a predetermined quantity of an active agent calculated to produce the desired onset, tolerability, and/or efficacious effects, in association with a suitable pharmaceutical excipient (e.g., an ampoule). In addition, more concentrated dosage forms may be prepared, from which the more dilute unit dosage forms may then be produced.

The compounds described herein (e.g., a compound of Structure (I), (II), (III), or (IV)) can be administered to a subject in need of treatment using methods known in the art, such as by oral administration or by injection. The injection can be, e.g., subcutaneous, intravenous, intraperitoneal, or intramuscular. As described herein, parenteral formulations can be prepared in dosage unit form for ease of administration and uniformity of dosage. As used herein the term "unit dosage form" refers to physically discrete units suited as unitary dosages for the subject to be treated; each unit containing a predetermined quantity of active compound calculated to produce the desired therapeutic effect.

The pharmaceutical compositions of the present application comprise a therapeutically effective amount of a compound of the present disclosure ((e.g., a compound of Structure (I), (II), (III), or (IV)) formulated together with one or more pharmaceutically acceptable carriers or excipient. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations include, for example, sterile injectable aqueous or oleaginous suspensions formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished using a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound as disclosed in the foregoing embodiments (e.g., a compound of Structure (I), (II), (III), or (IV)) include ointments, pastes, creams, lotions, gels, powders, solutions, sprays, inhalants, or patches. For example, the active component may be ad-mixed under sterile conditions with a pharmaceutically acceptable carrier or excipient and any needed preservatives or buffers as may be required.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound according to any one of the foregoing embodiments, in such amounts and for such time as is necessary to achieve the desired result. As is well understood in the medical arts a therapeutically effective amount of a compound will be at a reasonable benefit/risk ratio applicable to any medical treatment.

In general, compounds (e.g., compounds of Structure (I), (II), (III), or (IV)) will be administered in therapeutically effective amounts via any of the usual and acceptable modes known in the art, either singly or in combination with one or more other therapeutic agents. A therapeutically effective amount may vary widely depending on the severity of the disease, the age and relative health of the subject, the potency of the compound used and other factors.

In general, satisfactory results are indicated to be obtained systemically at daily dosages of from about 0.03 to 2.5 $mg/kg$ per body weight. An indicated daily dosage in the larger mammal, e.g., humans, is in the range from about 0.5 mg to about 250 mg, about 5 mg to about 150 mg, about 5 mg to about 100 mg, about 10 mg to about 75 mg, about 10 mg to about 50 mg, such as 10, 20, 30, 40, or about 50 mg, conveniently administered, e.g., in divided doses up to four times a day or in retard form. Suitable unit dosage forms for oral administration comprise from ca. 1 to 60 mg active ingredient.

In certain embodiments, a therapeutic amount or dose of the compound (e.g., compounds of Structure (I), (II), (III), or (IV)) may range from about 0.1 $mg/kg$ to about 500 $mg/kg$, alternatively from about 1 $mg/kg$ to about 50 $mg/k$. In general, treatment regimens according to the present application comprise administration to a patient in need of such treatment from about 10 mg to about 1000 mg of the compound (s) per day in single or multiple doses. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds (e.g., compounds of Structure (I), (II), (III), or (IV)) and compositions thereof will be decided by an attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The application also provides for a pharmaceutical combination, e.g., a kit, comprising:

a) a first agent which is a compound of the application as disclosed herein, in free form or in pharmaceutically acceptable salt form, and b) at least one co-agent. The kit can comprise instructions for its administration.

Methods for preparing such dosage forms are known to those skilled in the art (see, e.g., REMINGTON'S PHARMACEUTICAL SCIENCES, 18th ED., Mack Publishing Co., Easton, PA (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, 18th ED., Mack Publishing Co., Easton, PA (1990)).

EXAMPLES

The following examples are provided by way of illustration only and not by way of limitation. Those of skill will readily recognize a variety of noncritical parameters which could be changed or modified to yield essentially similar results.

GENERAL METHODS

If not otherwise stated, chromatography refers to flash chromatography conducted on silica gel. "Amine column" refers to flash chromatography conducted on Redisep Rf Gold high performance amine column.

HPLC purification was performed by one of two methods. Method 1: on a Gilson preparative reverse phase HPLC system with the combination of UV/ELS detectors (254 nm and 280 nm) and ThermoFisher Hypersil GOLD Agilent (21.2×250 mm) 5 µm $C_{18}$ column. Eluents were a mixture of water and acetonitrile (with 0.05% trifluoroacetic acid). Flow rate was typically 20 $mL/min$ with a linear gradient of water in acetonitrile from 2-90% in 45 minutes. The injection volume was from 1 to 3 mL with maximum 20 mg per load. Method 2: on a Waters preparative reverse phase HPLC system with the combination of UV/MS detectors (254 nm and 280 nm) and XBridge Prep (19×50 mm) $C_{18}$ 10 µM OBD column. Eluents were a mixture of water and acetonitrile (with 0.05% trifluoroacetic acid). Flow rate was typically 50 $mL/min$ with a linear gradient of water in acetonitrile from 5-95% in 8 minutes. The injection volume was from 0.2 to 1 mL with maximum 20 mg per load.

Abbreviations

µ micro
° C. degrees Celsius
Ac acetyl
anhyd anhydrous
aq aqueous
atm atmosphere(s)
Bn benzyl
Boc tert-butoxycarbonyl
Bu butyl
calcd calculated
Cbz benzyloxycarbonyl
CPME cyclopentyl methyl ether
concd concentrated
conc concentration
DCC N,N'-dicyclohexylcarbodiimide
DIEA N,N-diisopropylethylamine
DMAP 4-(N,N-dimethylaminojpyridine
DMF dimethylformamide
DMSO dimethylsulfoxide
EDC N-(3-dimethylaminopropyl)-N'-ethylcarbodiimide hydrochloride
equiv equivalent
ES electrospray Et ethyl
Et$_2$O diethyl ether
g gram(s)
h hour(s)
HATU N-[(Dimethylamino)-1H-1,2,3-triazolo-[4,5-b]pyridin-1-ylmethylene]-N-methylmethanaminium hexafluorophosphate N-oxide
HBTU N,N,N',N'-Tetramethyl-O-(1H-benzotriazol-1-yl)uronium hexafluorophosphate, O-(Benzotriazol-1-yl)-
HPLC high-performance liquid chromatography/high-performance liquid chromatography
HOBt 1-hydroxybenzotriazole hydrate
iPrOH iso-propanol
L liter(s)
LiOH lithium hydroxide
m milli
M molar
MeCN acetonitrile
min minute(s)
mL milliliter
mol mole; molecular (as in mol wt)
MS mass spectrometry
MW molecular weight
NBS N-bromosuccinimide
NCS N-chlorosuccinimide
NHS N-hydroxysuccinimide
NMM 4-methylmorpholine
NMR nuclear magnetic resonance
o ortho
obsd observed
p para
Pd-RuPhos-G2 chloro(2-dicyclohexylphosphino-2',6'-diisopropoxy-1,1'-biphenyl)[2-(2'-amino-1,1'-biphenyl)]palladium(II)
Pd-XPhos-G2 chloro(2-dicyclohexylphosphino-2',4',6'-triisopropyl-1,1'-biphenyl)[2-(2'-amino-1,1'-biphenyl)]palladium(II)
Ph phenyl
ppt precipitate
Pr propyl
psi pounds per square inch
RT room temperature (e.g., ~20-23° C.)
temp temperature
TFA trifluoroacetic acid
THF tetrahydrofuran Example 1

Preparation of N-((6-Amino-2-Methylpyridin-3-yl)Methyl)-2-(2-Methyl-6-Oxo-5-((Phenylmethyl)Sulfonamido)Pyrimidin-1(6H)-yl)Acetamide, Trifluoro Acetate (Compound 1)

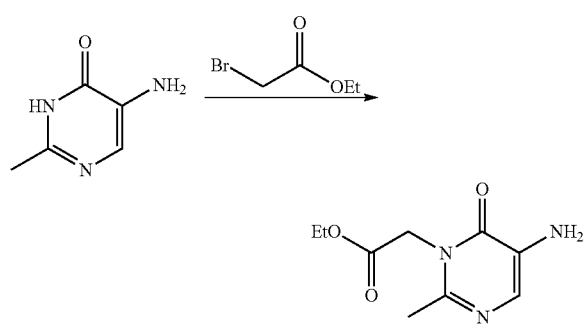

Step 1: A 100 mL RBF was charged with NaH (60% in oil, 440 mg, 11 mmol) and washed ×3 with hexanes under Ar. 5-Amino-2-methylpyrimidin-4(3H)-one (1.25 g, 10 mmol), THF (10 mL) and DMF (5 mL) were then added to the flask and the mixture stirred for 1.5 h at RT. Ethyl bromoacetate (1.33 mL, 12 mmol) was then added neat, and the reaction stirred for 1.5 h at RT. The reaction was then diluted with ethyl acetate, quenched with H$_2$O and separated. The organic layer was washed with 5% aq. LiCl and brine, dried over Na$_2$SO$_4$, filtered through a silica gel plug with ethyl acetate and concentrated to yield a mixture 4:1 mixture of N- vs O-alkylated product (965 mg, 46% yield).

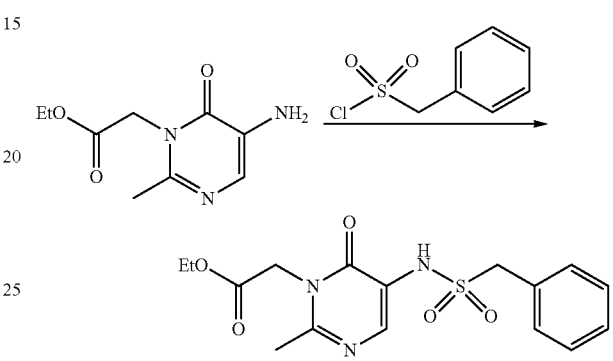

Step 2: Ethyl 2-(5-amino-2-methyl-6-oxopyrimidin-1(6H)-yl)acetate (110 mg, 0.52 mmol) was dissolved in THF (5 mL), cooled to 0° C. and treated with NMM (114 μL, 1.04 mmol). Sulfonyl chloride (109 mg, 0.57 mmol) in THF (5 mL) was added slowly via syringe, and the resulting mixture then stirred at RT for 12 h. The reaction was then diluted with ethyl acetate, and washed with 1N HCl, brine, sat. NaHCO$_3$, dried over Na$_2$SO$_4$ and concentrated. The residue was then purified by chromatography (6-8% MeOH/DCM) to afford ethyl 2-(2-methyl-6-oxo-5-((phenylmethyl)sulfonamido)pyrimidin-1(6H)-yl)acetate as a pale yellow solid (190 mg, quant.)

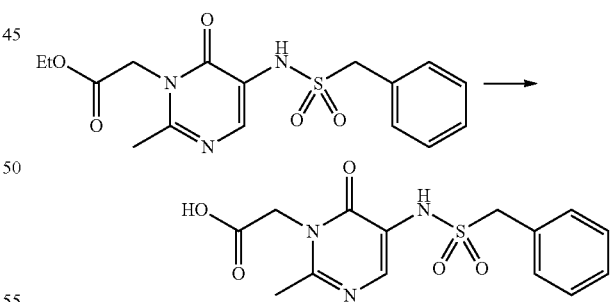

Step 3: Ethyl 2-(2-tri ethyl-6-oxo-5-((phenyl methyl)sulfonamido)pyrimidin-1(6H)-yl)acetate (190 mg, 0.52 mmol) was dissolved in MeOH (5 mL) and treated with 1N NaOH (5 mL). The reaction mixture was stirred at RT for 12 h, then the organics removed in vacuo. The aq. layer was acidified with 1N HCl, then extracted with ethyl acetate (×3). The combined organics were washed with brine, dried over Na$_2$SO$_4$, and concentrated to yield 2-(2-methyl-6-oxo-5-((phenylmethyl)sulfonamido)pyrimidin-1(6H)-yl)acetic acid as a beige solid (39 mg, 22% yield).

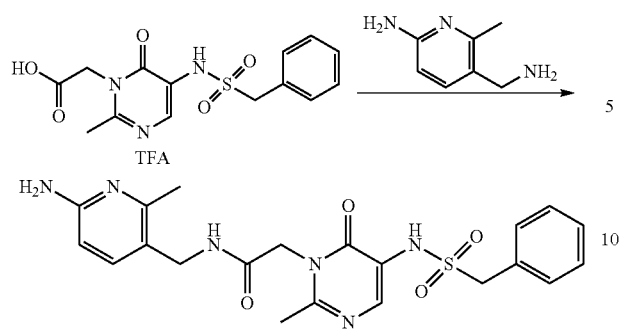

Step 4: 2-(2-methyl-6-oxo-5-((phenylmethyl)sulfonamido)pyrimidin-1(6H)-yl)acetic acid (20 mg, 0.06 mmol) was dissolved in DCM (2 mL) and treated with NHS (8 mg, 0.07 mmol) and DCC (13 mg, 0.063 mmol). After 30 min, 5-(aminomethyl)-6-methylpyridin-2-amine (10 mg, 0.07 mmol) was added and the mixture stirred for 30 min. The reaction was then concentrated, diluted with $H_2O$, filtered and purified by prep-HPLC (35-65% acetonitrile/$H_2O$+ TFA) to afford the title compound as a white solid (12 mg, 35% yield).

Example 2

Preparation of N-((6-Amino-2-Methylpyridin-3-yl)Methyl)-2-(2-Methyl-6-Oxo-5-(Phenethylamino)Pyrimidin-1(6H)-yl)Acetamide, Trifluoroacetate (Compound 2)

Step 1: Ethyl 2-(5-amino-2-methyl-6-oxopyrimidin-1(6H)-yl)acetate (385 mg, 1.8 mmol) and phenylacetaldehyde (213 μL, 2 mmol) were dissolved in 1,2-DCE (5 mL) and cooled to 0° C. A solution of $NaBH_4$ (79 mg, 2.1 mmol), acetic acid (361 μL, 6.3 mmol) and 1,2-DCE (5 mL) was added dropwise to the stirring mixture, then the reaction warmed to RT and stirred for 2 h. Upon completion, sat. $NaHCO_3$ was added to the reaction, then extracted ×3 with DCM. The combined organics were washed with brine, dried over $Na_2SO_4$ and concentrated. The residue was purified by chromatography (90% ethyl acetate/hexanes) to afford ethyl 2-(2-methyl-6-oxo-5-(phenethylamino)pyrimidin-1(6H)-yl)acetate as a yellow solid (138 mg, 24% yield).

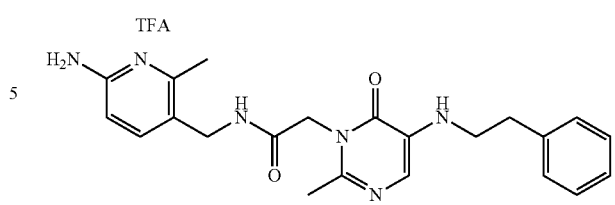

Steps 2-3: The title compound was prepared as a white powder according to steps 3-4 of the procedure for Compound 1 using the appropriate starting materials. Yield=11 mg, 87%.

The following compounds were synthesized according to the procedure described above, substituting the appropriate amine starting material:

| Compound Name | Cmp No. |
|---|---|
| N-((2-Amino-1H-benzo[d]imidazol-6-yl)methyl)-2-(2-methyl-6-oxo-5-(phenethylamino)pyrimidin-1(6H)-yl)acetamide trifluoroacetate | 3 |

Example 3

Preparation of N-((2-Amino-1H-Benzo[d]Imidazol-6-yl)Methyl)-2-(6-Oxo-5-(Phenethylamino)-2-Phenylpyrimidin-1(6H)-yl)Acetamide, Trifluoroacetate (Compound 4)

Step 1: A mixture of tert-butyl 2-(5-bromo-2-(methylthio)-6-oxopyrimidin-1(6H)-yl)acetate (182 mg, 0.5 mmol), $CS_2CO_3$ (326 mg, 1 mmol), Pd(OAc)$_2$ (11 mg, 0.05 mmol) and rac-BINAP (62 mg, 0.1 mmol) were combined in a high pressure flask under an argon atmosphere, and toluene (5 mL) was added under Ar. Phenethylamine (126 μL, 1 mmol) was added, and the reaction stirred at 120° C. for 16 h. The heterogenous mixture was then cooled, filtered through a medium sintered glass funnel, washed with ethyl acetate and the filtrate concentrated. The crude material was purified by chromatography (0-60% ethyl acetate/hexanes) to yield tert-butyl 2-(2-(methylthio)-6-oxo-5-(phenethylamino)pyrimidin-1(6H)-yl)acetate as a white solid (166 mg, 82% yield).

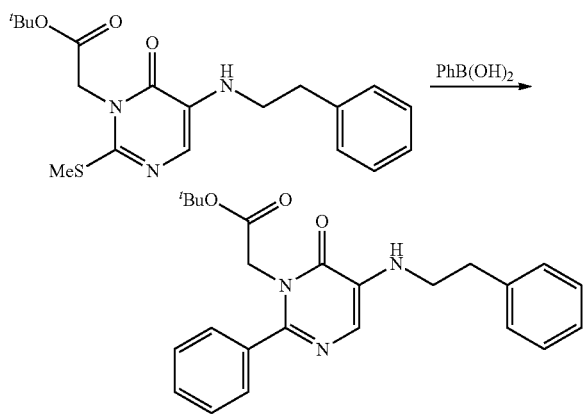

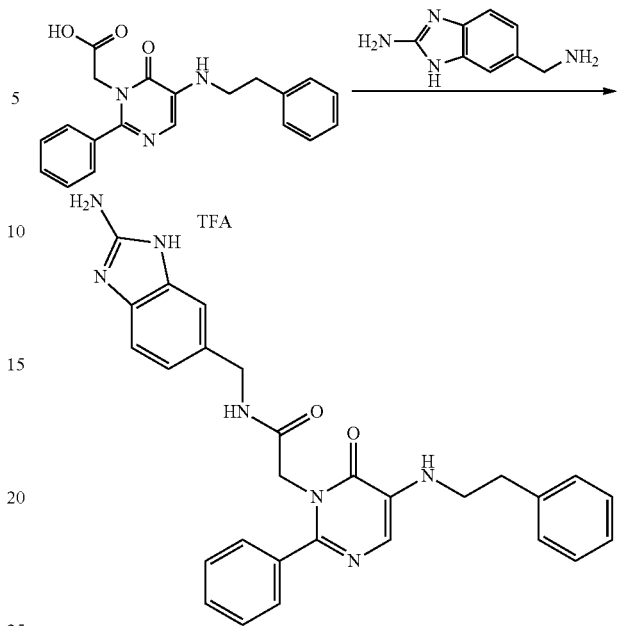

Step 2: A 100 mL pressure flask was charged with tert-butyl 2-(2-(methylthio)-6-oxo-5-(phenethylamino)pyrimidin-1(6H)-yl)acetate (334 mg, 1 mmol), phenylboronic acid (244 mg, 2 mmol), CuTC (419 mg, 2.2 mmol) and Pd(PPh₃)₄ (116 mg, 10 mol %). Under an argon atmosphere, dry THF (15 mL) was added. The reaction was sealed and stirred for 18 h at 55° C. and monitored by LCMS. When the reaction was complete, the mixture was cooled to ambient temperature, ethyl acetate was added, and the mixture was filtered through a medium fritted glass funnel. The filtrate was washed with brine and sat. NaHCO₃. The organic layer was dried over MgSO₄, filtered, and concentrated to a viscous oil. The residue was purified by chromatography (40% ethyl acetate/hexanes) to afford of tert-butyl 2-(6-oxo-5-(phenethylamino)-2-phenylpyrimidin-1(6H)-yl)acetate as a colorless solid (350 mg 78% yield).

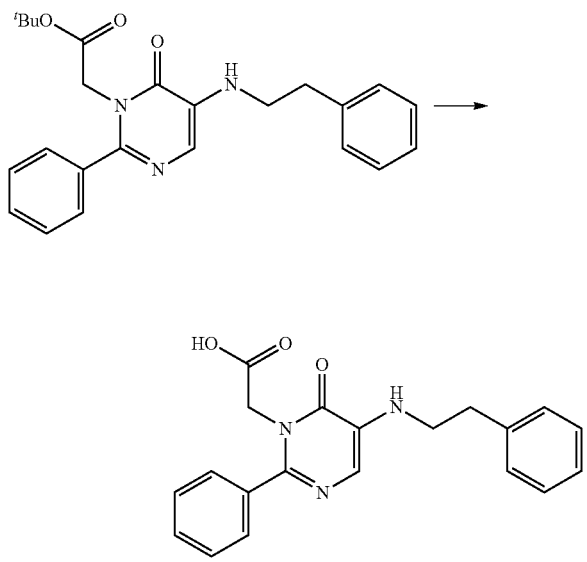 [SMILES: CC(C)(C)OC(=O)Cn1c(-c2ccccc2)ncc(NCCc2ccccc2)c1=O ; O=C(O)Cn1c(-c2ccccc2)ncc(NCCc2ccccc2)c1=O]

Step 3: A 100 mL RBF fitted with a magnetic stir bar was charged with tert-butyl 2-(6-oxo-5-(phenethylamino)-2-phenylpyrimidin-1(6H)-yl)acetate (110 mg, 0.27 mmol), TFA (5 mL) and DCM (10 mL). This mixture was stirred at RT for 5 h and concentrated to afford 2-(6-oxo-5-(phenethylamino)-2-phenylpyrimidin-1(6H)-yl)acetic acid as an yellow foam (75 mg, 80%).

Step 4: A mixture of 2-(6-oxo-5-(phenethylamino)-2-phenylpyrimidin-1(6H)-yl)acetic acid (35 mg, 0.1 mmol), 6-(aminomethyl)-1H-benzo[d]imidazol-2-amine dihydrochloride (31 mg, 0.13 mmol), DIEA (67 μL, 0.39 mmol) and DMF (1 mL) were combined in a 20 mL reaction vial. HBTU (46 mg, 0.12 mmol) was added in a single portion, and the reaction stirred at RT until completion. The mixture was then concentrated and purified by prep-HPLC (H₂O/acetonitrile+TFA) to afford the title compound as a white powder (30 mg, 50% yield).

Example 4

Preparation of N-((2-Amino-1H-Benzo[d]Imidazol-6-yl)Methyl)-2-(2-(Methylthio)-6-Oxo-5-(Phenethylamino)Pyrimidin-1(6H)-yl)Acetamide (Compound 5)

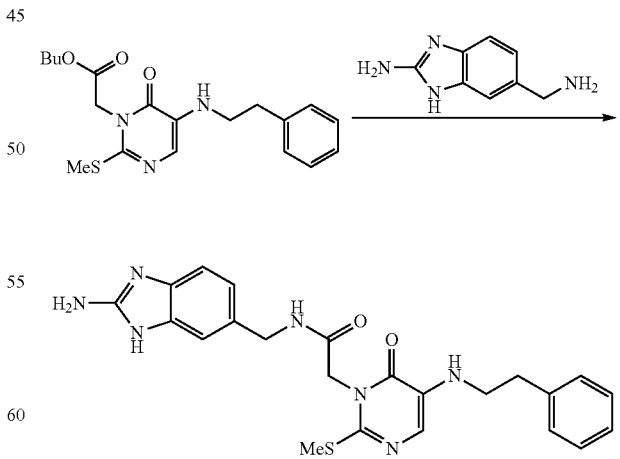

Steps 1-2: The title compound was prepared as a white powder according to steps 3-4 of Example 3 using the appropriate starting materials except with purification by chromatography (MeOH/DCM+NH₃). Yield=5 mg, 54%.

Example 5

Preparation of N-((6-Amino-2-Methylpyridin-3-yl)Methyl)-2-(6-Oxo-5-(Phenethylamino)-2-Phenylpyrimidin-1(6H)-yl)Acetamide (Compound 6)

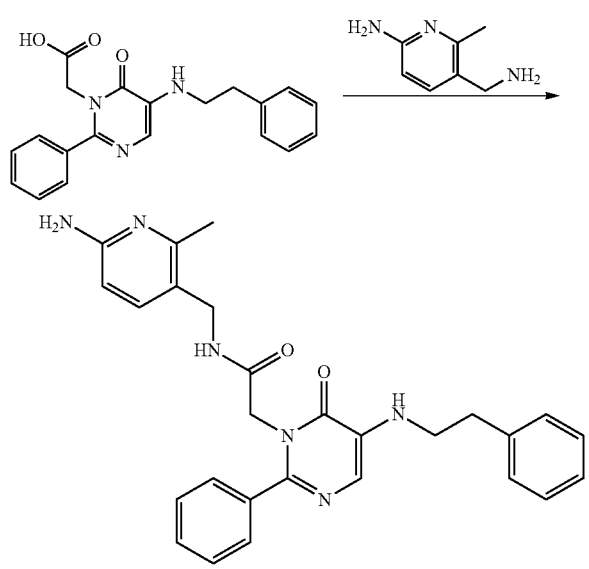

The title compound was prepared as a white fluffy powder according to step 4 of Example 3 using the appropriate starting materials except with purification by chromatography (MeOH/DCM+NH₃). Yield=8 mg, 40%.

Example 6

Preparation of N-((3-Chloro-1H-Pyrrolo[2,3-b]Pyridin-5-yl)Methyl)-2-(6-Methyl-2-Oxo-3-(Phenethylamino)Pyrazin-1(2H)-yl)Acetamide (Compound 7)

The title compound was prepared as a white powder (32 mg, 64% yield) according to step 4 of Example 3 using the appropriate starting materials except with purification by chromatography (MeOH/DCM+NH₃).

Example 7

Preparation of N-((2-Amino-1H-Benzo[d]Imidazol-6-yl)Methyl)-2-(6-Bromo-2-Oxo-3-(Phenethylamino)Pyrazin-1(2H)-yl)Acetamide (Compound 8)

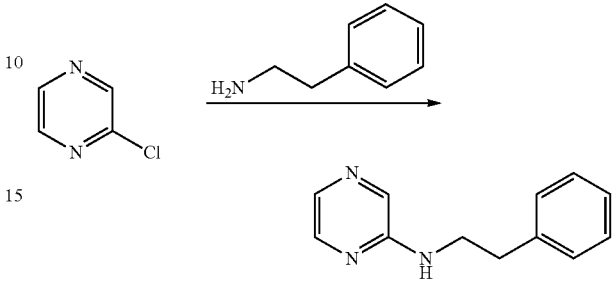

Step 1: A mixture of 2-chloropyrazine (1.34 mL, 15 mmol) and phenethylamine (1.89 mL, 15 mmol) in NMP (5 mL) was heated to 150° C. for 15 min in a microwave reactor. The cooled reaction mixture was poured into ethyl acetate and the organic layer was washed with sat. NaHCO₃, brine (×2), dried over Na₂SO₄, and evaporated to dryness.

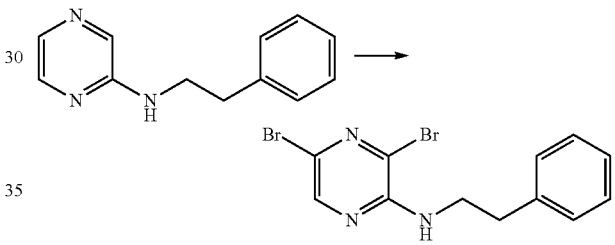

Step 2: To a stirred solution of N-phenethylpyrazin-2-amine (3 g, 15 mmol) in DMSO (30 mL)/H₂O (0.75 mL) at 0° C. was added NBS (6.66 g, 37.5 mmol) in portions. The reaction mixture was then allowed to warm to RT slowly and stirred for 18 h. The reaction mixture was then poured into ice-cold H₂O and extracted with ethyl acetate (×3). Combined organics were washed with sat. NaHCO₃, brine (×2) and dried to provide 3,5-dibromo-N-phenethylpyrazin-2-amine as a brown oil (5.16 g, 97% yield over two steps).

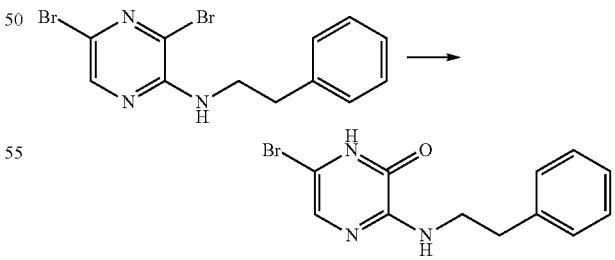

Step 3: KOH (2.25 g, 40 mmol) was added portion-wise to a suspension of 3,5-dibromo-N-phenethylpyrazin-2-amine (2.83 g, 8 mmol) in dioxane (4 mL)/H₂O (40 mL), then the mixture was refluxed for 18 h. An additional 2 equiv. of KOH was added and the mixture refluxed for another 6 h. The reaction was then cooled and filtered through Celite®. The filtrate was acidified with 3N HCl upon which a white precipitate formed and was collected by filtration to obtain 6-bromo-3-(phenethylamino)pyrazin-2(1H)-one (2.25 g, 96% yield).

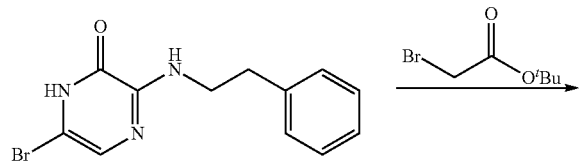

Step 4: To a suspension of calcium hydride (505 mg, 12 mmol) in THF (8 mL) was added 6-bromo-3-(phenethylamino)pyrazin-2(1H)-one (1.465 g, 5 mmol) portion-wise. Reaction mixture was refluxed for 30 min, then cooled to RT. Tert-butyl bromoacetate (886 μL, 6 mmol) in THF (4 mL) was added dropwise to the stirring reaction, then the mixture refluxed for 18 h. Another 0.5 equiv. of tert-butyl bromoacetate was added (369 μL, 2.5 mmol) in THF (2 mL) and the reaction refluxed for another 4 h. Upon cooling, mixture was poured into ice-cold H₂O, and extracted with ethyl acetate (×3). Combined organics were washed with sat. NH₄Cl, brine, dried over MgSO₄ and evaporated to dryness. The crude material was purified by chromatography (20% ethyl acetate/hexanes) to afford of tert-butyl 2-(6-bromo-2-oxo-3-(phenethylamino)pyrazin-1(2H)-yl)acetate as a white solid (904 mg, 44% yield).

Steps 5-6: The title compound was prepared as a white powder (19 mg, 52% yield) according to steps 3-4 of Example 3 using the appropriate starting materials except with purification by chromatography (amine column, 15-20% MeOH/DCM).

Example 8

Preparation of N-((2-Amino-1H-Benzo[d]Imidazol-5-yl)Methyl)-2-(2-Oxo-3-(Phenethylamino)-6-Phenylpyrazin-1(2H)-yl)Acetamide (Compound 9)

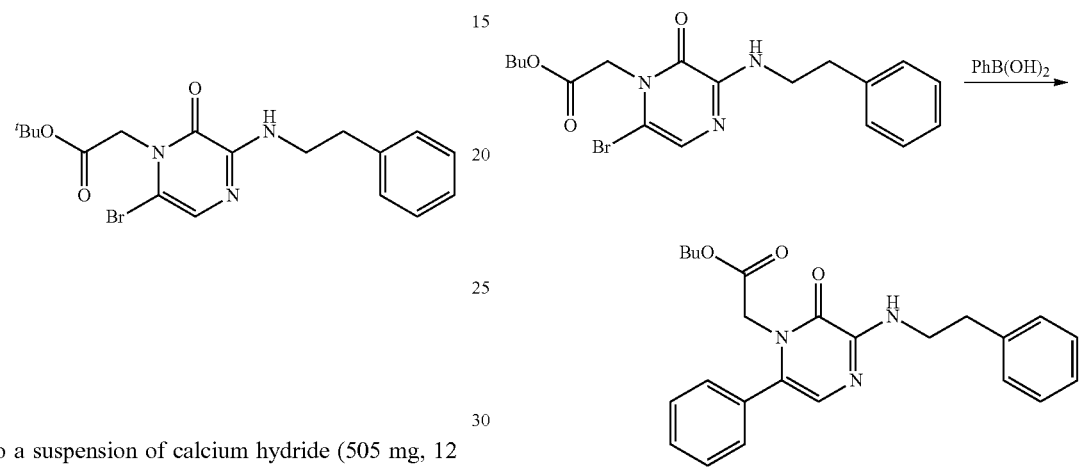

Step 1: A 20 mL pressure vial was charged with tert-butyl 2-(6-bromo-2-oxo-3-(phenethylamino)pyrazin-1(2H)-yl)acetate (163 mg, 0.4 mmol), phenylboronic acid (73 mg, 0.6 mmol), Pd(PPh₃)₄ (46 mg, 0.04 mmol) and Cs₂CO₃ (261 mg, 0.8 mmol). The vial was purged with argon, then THF (2 mL) and H₂O (200 μL) were added and the reaction mixture sealed and stirred at 65° C. for 12 h. Upon completion by LCMS, the mixture was diluted with ethyl acetate, washed with sat. NaHCO₃, brine, dried over MgSO₄ and evaporated to dryness. The crude material was purified by chromatography (35% ethyl acetate/hexanes) to afford tert-butyl 2-(2-oxo-3-(phenethylamino)-6-phenylpyrazin-1(2H)-yl)acetate as a yellow oil (116 mg, 72% yield).

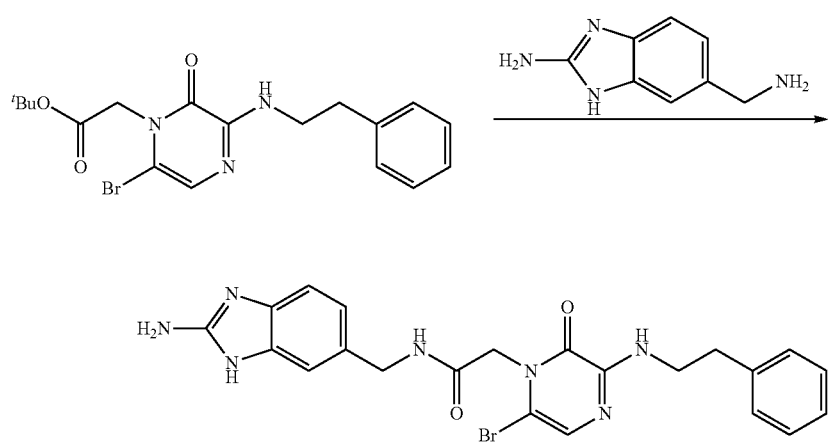

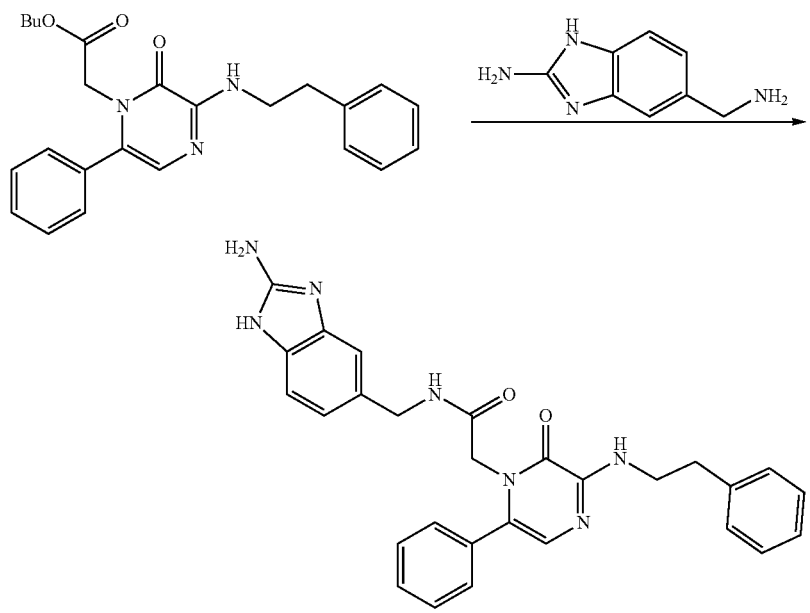

Steps 2-3: The title compound was prepared as a white powder according to steps 3-4 of Example 3 using the appropriate starting materials except with purification by chromatography (amine column, 0-20% MeOH/DCM). Yield=20 mg, 40%.

The following compounds were prepared according to the foregoing procedure using the appropriate boronic acid and amine starting materials:

| Compound Name | Cmp No. |
|---|---|
| N-((6-Amino-2-methylpyridin-3-yl)methyl)-2-(2-oxo-3-(phenethylamino)-6-phenylpyrazin-1(2H)-yl)acetamide | 10 |
| N-((2-Amino-1H-benzo[d]imidazol-6-yl)methyl)-2-(6-(3-cyanophenyl)-2-oxo-3-(phenethylamino)pyrazin-1(2H)-yl)acetamide | 14 |

The following compounds were prepared according to the foregoing procedure using the appropriate boronic acid and amine starting materials and purification via prep-HPLC (acetonitrile/H$_2$O+TFA):

| Compound Name | Cmp No. |
|---|---|
| Methyl 3-(1-(2-(((2-amino-1H-benzo[d]imidazol-6-yl)methyl)amino)-2-oxoethyl)-6-oxo-5-(phenethylamino)-1,6-dihydropyrazin-2-yl)benzoate | 11 |
| N-((2-Amino-1H-benzo[d]imidazol-6-yl)methyl)-2-(2-oxo-3-(phenethylamino)-6-(4-(trifluoromethyl)phenyl)pyrazin-1(2H)-yl)acetamide trifluoroacetate | 12 |
| N-((2-Amino-1H-benzo[d]imidazol-6-yl)methyl)-2-(6-(4-chlorophenyl)-2-oxo-3-(phenethylamino)pyrazin-1(2H)-yl)acetamide trifluoroacetate | 13 |

Example 9

Preparation of 3-(4-(2-(((2-Amino-1H-Benzo[d]Imidazol-6-yl)Methyl)Amino)-2-Oxoethyl)-5-Oxo-6-(Phenethyl Amino)-4,5-Dihydropyridin-3-yl)Benzamide, Trifluoroacetate (Compound 15)

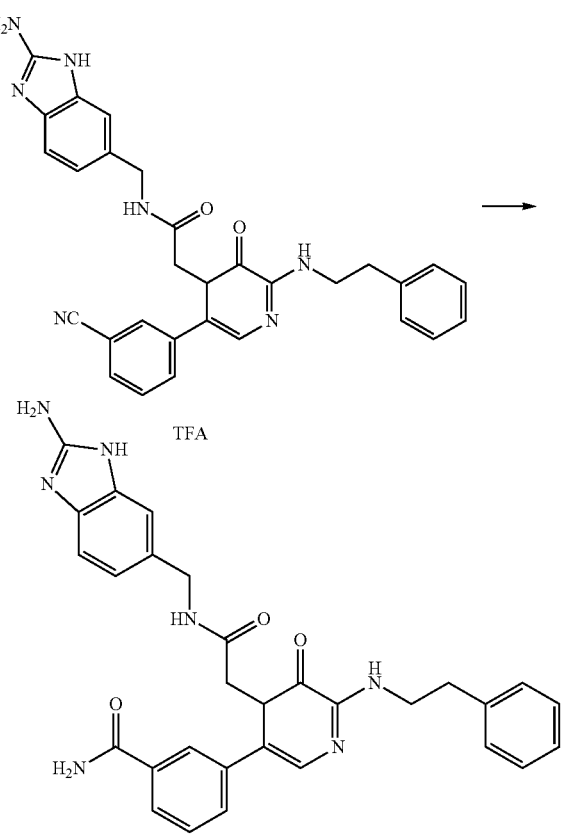

To a stirred solution of urea hydrogen peroxide (38 mg, 0.4 mmol) in H$_2$O (0.25 mL) was added NaOH (9.5 mg, 0.24 mmol). The resulting mixture was cooled in an ice bath before a solution of N-((2-amino-1H-benzo[d]imidazol-6-yl)methyl)-2-(5-(3-cyanophenyl)-3-oxo-2-(phenethylamino)-3,4-dihydropyridin-4-yl)acetamide (35 mg, 0.07 mmol) in EtOH (1 mL) was added. The reaction mixture was stirred vigorously at RT for 2 h. The mixture was diluted with ethyl acetate and washed with H$_2$O, sat. NaHCO$_3$ and brine, then dried over MgSO$_4$ and concentrated in vacuo. The residue was then purified by prep-HPLC (acetonitrile/H$_2$O+TFA) to afford the title compound as a white powder (7.5 mg, 17% yield).

Example 10

Preparation of 3-(4-(2-(((2-Amino-1H-Benzo[d]Imidazol-6-yl)Methyl)Amino)-2-Oxoethyl)-5-Oxo-6-(Phenethyl Amino)-4,5-Dihydropyridin-3-yl)Benzoic Acid, Trifluoroacetate (Compound 16)

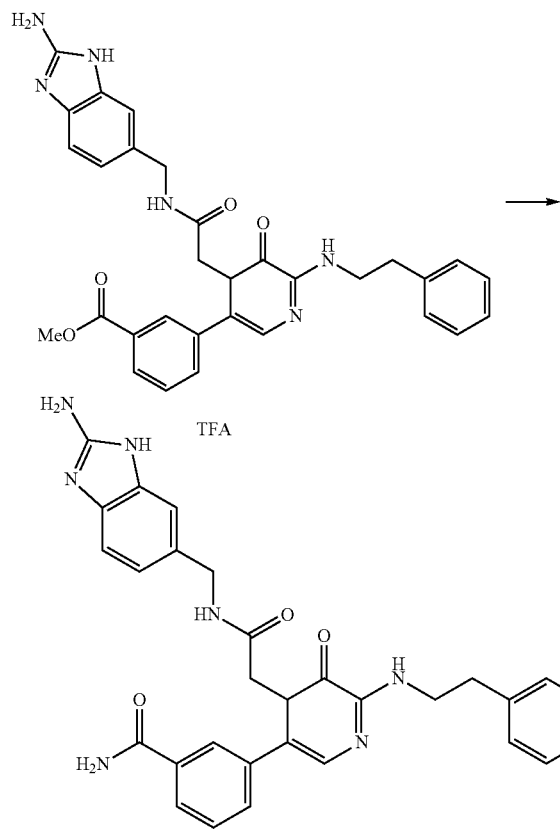

To a stirred solution of methyl 3-(4-(2-(((2-amino-1H-benzo[d]imidazol-6-yl)methyl)amino)-2-oxoethyl)-5-oxo-6-(phenethylamino)-4,5-dihydropyridin-3-yl)benzoate (14 mg, 0.02 mmol) in THF (1 mL) and H$_2$O (1 mL) was added lithium hydroxide (5 mg, 0.2 mmol) and the resulting mixture was stirred at RT overnight. The reaction was then acidified with trifluoroacetic acid and purified by prep-HPLC (acetonitrile/H$_2$O+TFA) to afford the title compound as a white powder (2 mg, 13% yield).

Example 11

Preparation of N-((6-Amino-2-Methylpyridin-3-yl)Methyl)-2-(6-(4-Chlorophenyl)-2-Oxo-3-(Phenethylamino)Pyrazin-1(2H)-yl) Acetamide, Trifluoroacetate (Compound 17)

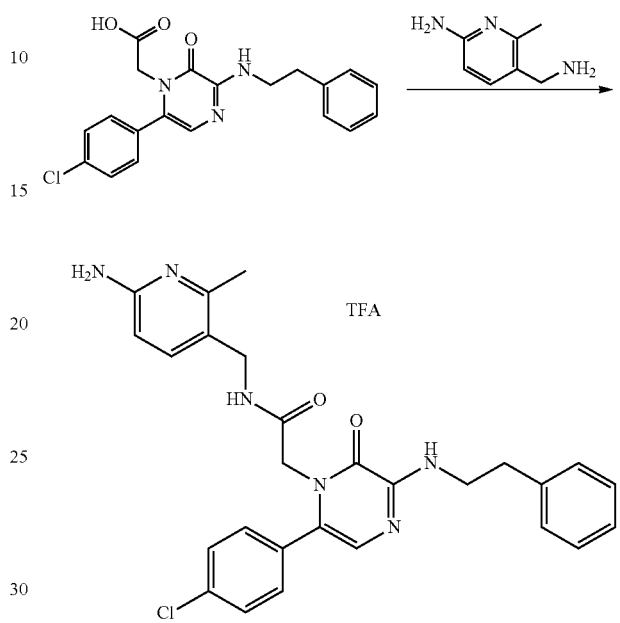

To a stirred solution of 2-(6-(4-chlorophenyl)-2-oxo-3-(phenethylamino)pyrazin-1(2H)-yl)acetic acid (9 mg, 0.02 mmol) in DMF (0.5 mL) was added EDC-HCl (5 mg, 0.025 mmol), HOBt (4 mg, 0.03 mmol) and DIEA (12 μL, 0.07 mmol). The resulting mixture was stirred for 5 minutes, then 5-(aminomethyl)-6-methylpyridin-2-amine (4 mg, 0.03 mmol) was added and stirred at RT for 16 h. The reaction mixture was diluted with H$_2$O and extracted with ethyl acetate (×3). The organic layer was dried over MgSO$_4$ and concentrated. The residue was then purified by prep-HPLC (acetonitrile/H$_2$O+TFA) to afford the title compound as a yellow powder (2.5 mg, 18% yield).

The following compounds were prepared according to the foregoing procedure using the appropriate boronic acid or trifluoroborate salt and amine starting materials:

| Compound Name | Cmp No. |
|---|---|
| N-((1H-Pyrrolo[3,2-c]pyridin-2-yl)methyl)-2-(2-oxo-3-(phenethylamino)-6-phenylpyrazin-1(2H)-yl)acetamide trifluoroacetate | 20 |
| N-((6-amino-2-methylpyridin-3-yl)methyl)-2-(2-oxo-3-(phenethylamino)-6-(pyridin-3-yl)pyrazin-1(2H)-yl) acetamide trifluoroacetate | 18 |
| N-((6-amino-2-methylpyridin-3-yl)methyl)-2-(6-benzyl-2-oxo-3-(phenethylamino)pyrazin-1(2H)-yl)acetamide trifluoroacetate | 19 |

Example 12

Preparation of N-((1H-Pyrrolo[3,2-c]Pyridin-2-yl)Methyl)-2-(2-Oxo-3-(Phenethylamino)-6-(4-(Trifluoromethyl)Phenyl)Pyrazin-1(2H)-yl)Acetamide, Trifluoroacetate (Compound 21)

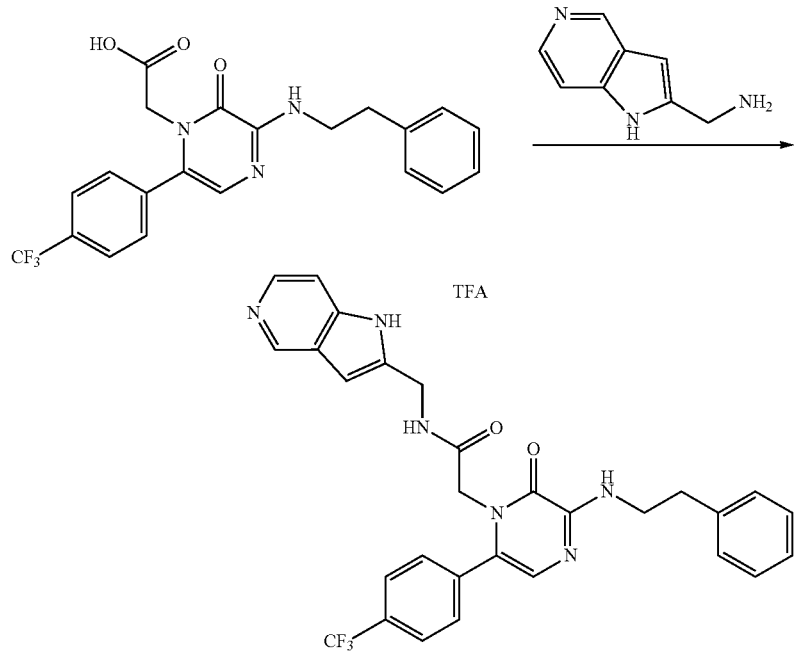

To a solution of 2-(2-oxo-3-(phenethylamino)-6-(4-(trifluoromethyl)phenyl)pyrazin-1(2H)-yl)acetic acid (4.2 mg, 0.01 mmol) in DMF (0.2 mL) was added HATU (4.2 mg, 0.011 mmol) and DIEA (5 µL, 0.03 mmol). After 10 minutes, (1H-pyrrolo[3,2-c]pyridin-2-yl)methanamine (2 mg, 0.012 mmol) was added and the reaction stirred at RT until completion. The reaction mixture was then concentrated, and the residue purified by prep-HPLC (acetonitrile/H$_2$O+ TFA) to afford the title compound as a white powder (2 mg, 30% yield).

The following compounds were prepared according to the foregoing procedure using the appropriate boronic acid and amine starting materials and purification was performed using chromatography (C$_{18}$, acetonitrile/H$_2$O).

| Compound Name | Cmp No. |
|---|---|
| N-((6-Amino-2-methylpyridin-3-yl)methyl)-2-(2-oxo-3-(phenethylamino)-6-(1H-pyrrol-2-yl)pyrazin-1(2H)-yl)acetamide | 22 |
| N-((6-Amino-2-methylpyridin-3-yl)methyl)-2-(2-oxo-3-(phenethylamino)-6-(pyrimidin-5-yl)pyrazin-1(2H)-yl)acetamide | 23 |
| N-((6-Amino-2-methylpyridin-3-yl)methyl)-2-(6-(isoquinolin-5-yl)-2-oxo-3-(phenethylamino)pyrazin-1(2H)-yl)acetamide | 24 |
| N-((6-Amino-2-methylpyridin-3-yl)methyl)-2-(6-(1-methyl-1H-pyrazol-4-yl)-2-oxo-3-(phenethylamino)pyrazin-1(2H)-yl)acetamide | 25 |

Example 13

Preparation of N-((6-Amino-2-Methylpyridin-3-yl)Methyl)-2-(2-Oxo-3-(Phenethylamino)-6-(Phenylethynyl)Pyrazin-1(2H)-yl)Acetamide (Compound 26)

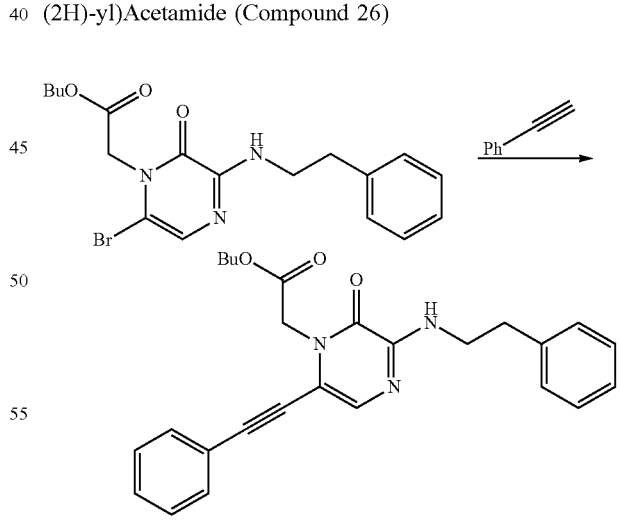

Step 1: A 20 mL pressure vial was charged with tert-butyl 2-(6-bromo-2-oxo-3-(phenethylamino)pyrazin-1(2H)-yl)acetate (28 mg, 0.07 mmol), Pd(PPh$_3$)$_2$Cl$_2$ (2.8 mg, 0.004 mmol) and copper iodide (1.3 mg, 0.007 mmol). The reaction vessel with purged with argon, then DMF (1 mL), DIEA (24 µL, 0.14 mmol) and phenyl acetylene (12 µL, 0.11 mmol) were added and set to stir at 80° C. for 16 h. The reaction mixture was then concentrated and the residue purified by chromatography (20% ethyl acetate/hexanes) to afford tert-butyl 2-(2-oxo-3-(phenethylamino)-6-(phenylethynyl)pyrazin-1(2H)-yl)acetate (19 mg, 62% yield).

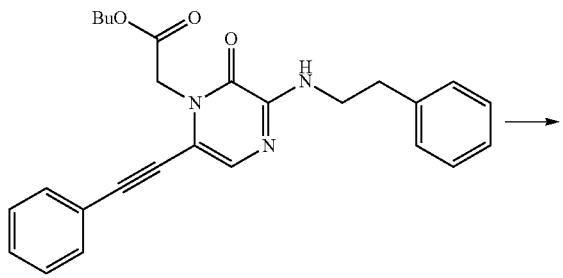

Step 2: 2-(2-oxo-3-(phenethylamino)-6-(phenylethynyl)pyrazin-1(2H)-yl)acetic acid was prepared as a white solid according to step 3 of Example 3 using the appropriate starting materials.

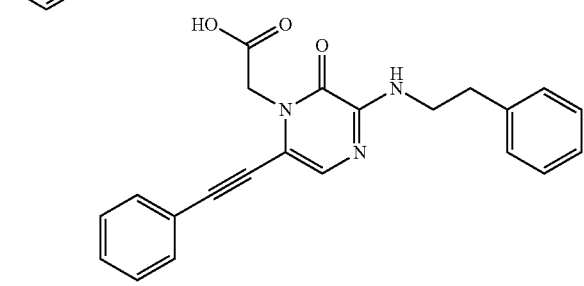

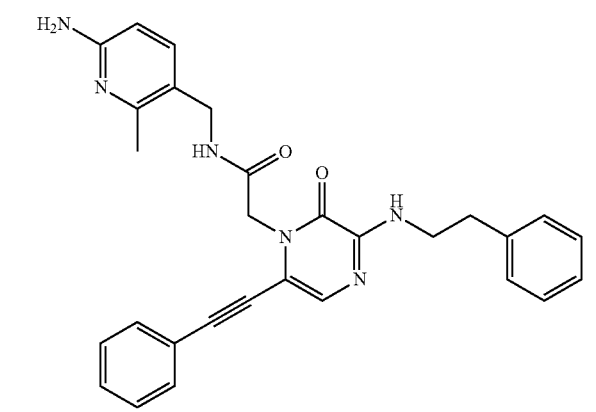

Step 3: A 20 mL reaction vial was charged with 2-(2-oxo-3-(phenethylamino)-6-(phenylethynyl)pyrazin-1(2H)-yl) acetic acid (16 mg, 0.043 mmol), HOBt (6.4 mg, 0.047 mmol), DCM (0.5 mL) and DMF (0.5 mL). DCC (31 mg, 0.052 mmol) was added in a single portion, followed by 5-(aminomethyl)-6-methylpyridin-2-amine (6.5 mg, 0.047 mmol) and NMM (14 μL, 0.13 mmol) after 10 mins. The reaction mixture was then stirred at RT until completion, filtered through Celite® (i.e., diatomaceous earth) with DCM and concentrated. The resulting residue was purified by chromatography (amine column, 0-20% MeOH/DCM) to afford the title compound as a yellow powder (13.6 mg, 64% yield).

Example 14

Preparation of N-((6-Amino-2-Methylpyridin-3-yl)Methyl)-2-(6-(4-Cyanophenyl)-2-Oxo-3-(Phenethyl Amino)Pyrazin-1(2H)-yl)Acetamide (Compound 27)

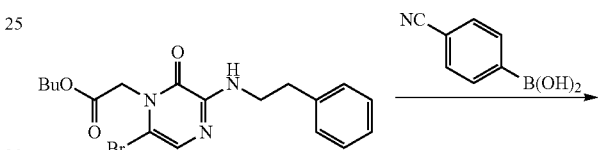

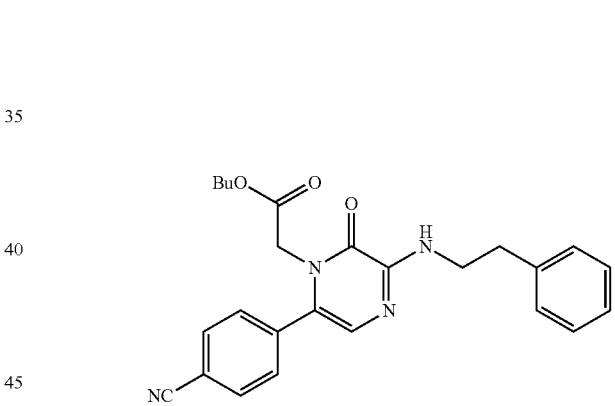

Step 1: A 20 mL pressure vial was charged with tert-butyl 2-(6-bromo-2-oxo-3-(phenethylamino)pyrazin-1(2H)-yl)acetate (41 mg, 0.1 mmol), 4-cyanophenylboronic acid (22 mg, 0.15 mmol), Pd(dppf)$_2$Cl$_2$ (7.3 mg, 0.01 mmol) and Cs$_2$CO$_3$ (65 mg, 0.2 mmol). The vial was purged with argon, then THF (1 mL) and H$_2$O (100 μL) were added and the reaction mixture stirred at 55° C. for 12 h. Upon completion by LCMS, the mixture was evaporated to dryness. The crude material was purified by chromatography (ethyl acetate/hexanes) to afford tert-butyl 2-(6-(4-cyanophenyl)-2-oxo-3-(phenethylamino)pyrazin-1(2H)-yl)acetate as a yellow oil (40 mg, 96% yield).

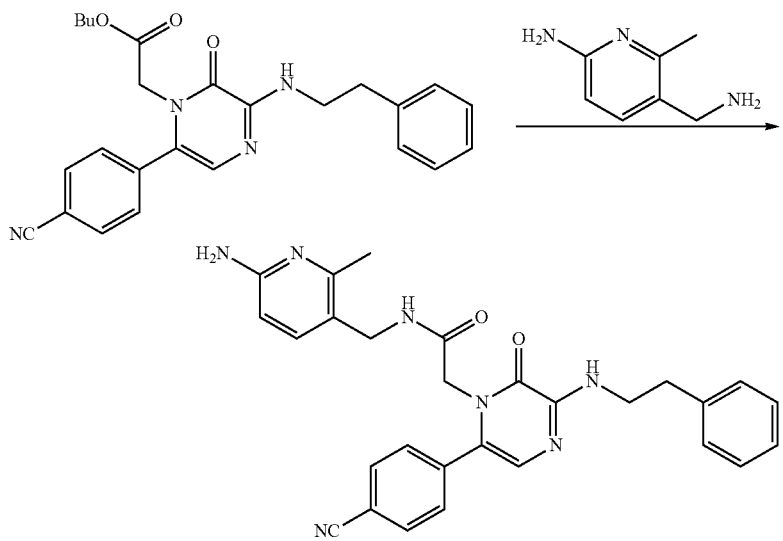

Steps 2-3: The title compound was prepared as a white powder according to steps 2-3 of Example 13 using the appropriate starting materials except with purification by reverse-phase chromatography (C18, acetonitrile/H$_2$O). Yield=13 mg, 28%.

The following compounds were prepared according to the foregoing procedure using the appropriate boronic acid starting materials and purification using chromatography (MeOH/DCM):

| Compound Name | Cmp No. |
|---|---|
| N-((6-Amino-2-methylpyridin-3-yl)methyl)-2-(6-(2-chlorophenyl)-2-oxo-3-(phenethylamino)pyrazin-1(2H)-yl)acetamide | 29 |

The following compounds were prepared according to the foregoing procedure using an appropriate boronic acid starting material, purification using chromatography (MeOH/DCM+NH$_3$), treatment of the purified product with aqueous hydrochloric acid, and lyophilization to yield the hydrochloride salt as a white powder:

| Compound Name | Cmp No. |
|---|---|
| N-((6-Amino-2-methylpyridin-3-yl)methyl)-2-(6-(2-methoxyphenyl)-2-oxo-3-(phenethylamino)pyrazin-1(2H)-yl)acetamide hydrochloride | 28 |
| 3-(1-(2-(((6-Amino-2-methylpyridin-3-yl)methyl)amino)-2-oxoethyl)-6-oxo-5-(phenethylamino)-1,6-dihydropyrazin-2-yl)benzamide hydrochloride | 30 |

Example 15

Preparation of N-((6-Amino-2-Methylpyridin-3-yl)Methyl)-2-(6-(4-Aminophenyl)-2-Oxo-3-(Phenyethylamino)Pyrazin-1-(2H)-yl)Acetamide (Compound 31)

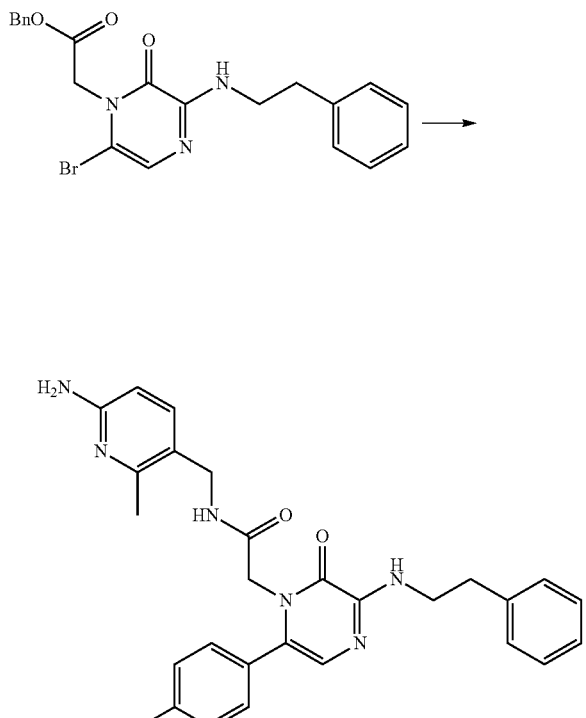

Steps 1-3: N-((6-amino-2-methylpyridin-3-yl)methyl)-2-(6-(4-nitrophenyl)-2-oxo-3-(phenethylamino)pyrazin-1(2H)-yl)acetamide was prepared according to Example 14 using the appropriate starting materials except it was carried to the following step without purification.

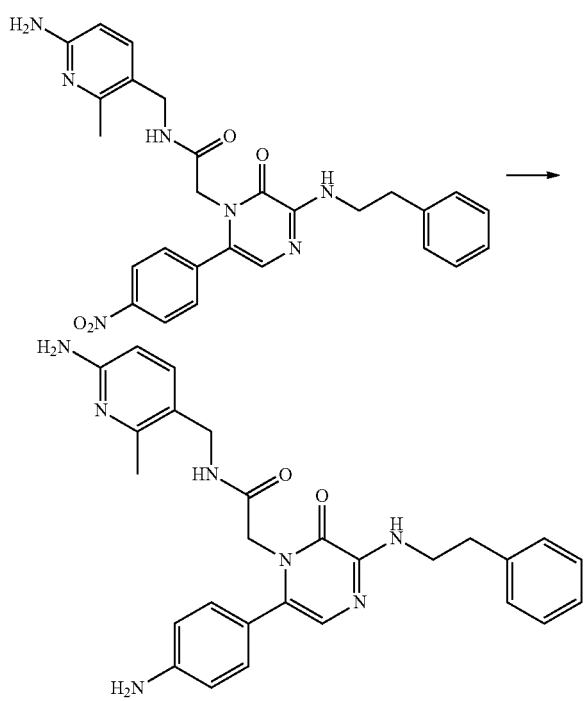

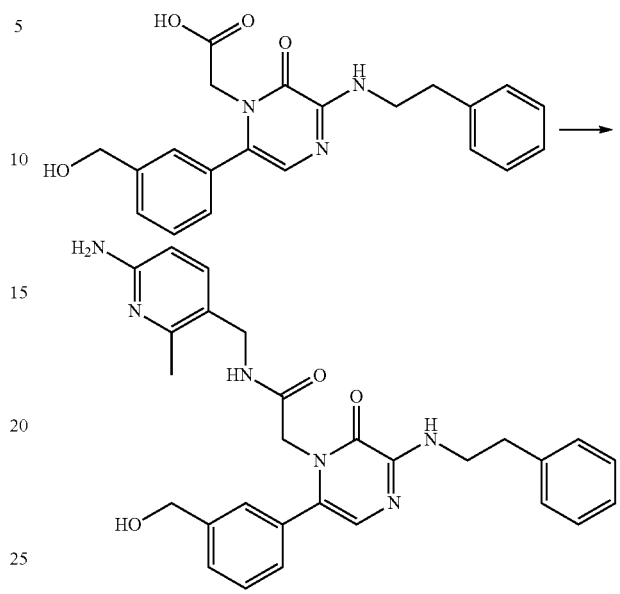

Step 4: A 25 mL round bottom flask was charged with N-((6-amino-2-methylpyridin-3-yl)methyl)-2-(6-(4-nitrophenyl)-2-oxo-3-(phenethylamino)pyrazin-1(277)-yl)acetamide (51 mg, 0.1 mmol), a magnetic stir bar and MeOH. The flask was evacuated and backfilled with argon (×3), then a cat. amount of 10% Pd/C was added. The reaction flask was then evacuated and backfilled with $H_2$ (×3) from a balloon and allowed to stir at RT for 1 h. The reaction was then filtered through a syringe filter (0.2 μm) and concentrated. The residue was then purified by chromatography (10% MeOH/DCM+$NH_3$) to afford the title compound as a white powder (7.7 mg, 17% yield over 3 steps).

Example 16

Preparation of N-((6-Amino-2-Methylpyridin-3-yl)Methyl)-2-(6-(3-(Hydroxymethyl)Phenyl)-2-Oxo-3-(Phenethyl Amino)Pyrazin-1(2H)-yl)Acetamide (Compound 32)

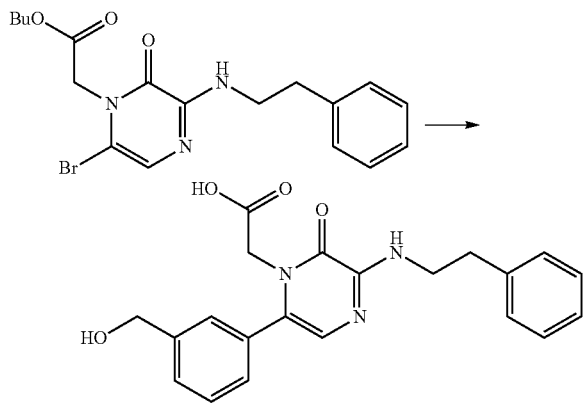

Steps 1-2: 2-(6-(3-(hydroxymethyl)phenyl)-2-oxo-3-(phenethylamino)pyrazin-1(2H)-yl)acetic acid was prepared as a white solid according to steps 1-2 of Example 14 using the appropriate starting materials.

Step 3: A 20 mL reaction vial was charged with 2-(6-(3-(hydroxymethyl)phenyl)-2-oxo-3-(phenethylamino) pyrazin-1(2H)-yl)acetic acid (35 mg, 0.083 mmol), 5-(aminomethyl)-6-methylpyridin-2-amine (16 mg, 0.12 mmol), DCM (1 mL) and DMF (0.5 mL). After 5 mins, HATU (42 mg, 0.11 mmol) and NMM (33 μL, 0.3 mmol) were also added and the reaction allowed to stir at RT for 1 h. The reaction mixture was then evaporated to dryness and the residue purified by chromatography (amine column, 0-15% MeOH/DCM) to afford the title compound as a white powder (31 mg, 67% yield).

The following compounds were prepared according to the foregoing procedure using an appropriate boronic acid starting material:

| Compound Name | Cmp No. |
|---|---|
| N-((6-Amino-2-methylpyridin-3-yl)methyl)-2-(6-(4-(hydroxymethyl)phenyl)-2-oxo-3-(phenethylamino) pyrazin-1(2H)-yl)acetamide | 33 |

Example 17

Preparation of N-((6-Amino-2-Methylpyridin-3-yl)Methyl)-2-(3-Methyl-2,6-Dioxo-5-(Phenethylamino)-3,6-Dihydropyrimidin-1(2H)-yl)Acetamide (Compound 34)

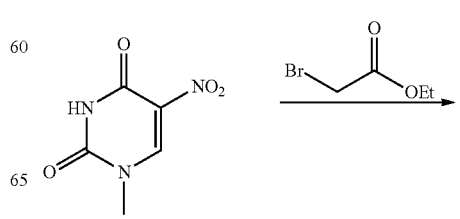

-continued

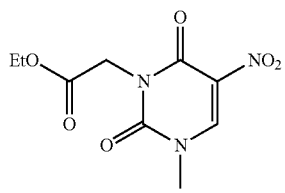

Step 1: A 250 mL RBF was charged with a magnetic stir bar, 1-methyl-5-nitropyrimidine-2,4(1H,3H)-dione (as prepared, e.g., in PCT Publication No. WO 97/46207) (1 g, 5.8 mmol), $K_2CO_3$ (0.883 g, 6.4 mmol) and DMF (12 mL). After 10 min at RT, ethyl bromoacetate (713 µL, 6.4 mmol) was added and the reaction mixture stirred at 40° C. for 5 h. The reaction mixture was diluted with ethyl acetate, washed with $H_2O$ and brine, dried over $MgSO_4$ and concentrated. The residue was purified by chromatography (15% ethyl acetate/DCM) to afford ethyl 2-(3-methyl-5-nitro-2,6-dioxo-3,6-dihydropyrimidin-1(2H)-yl)acetate as a yellow solid (976 mg, 65%).

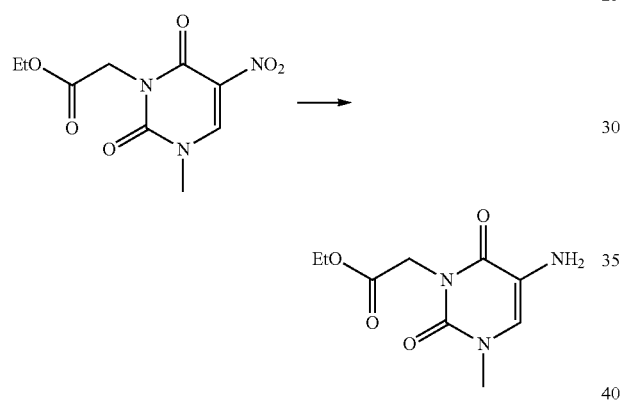

Step 2: In a 100 mL RBF, ethyl 2-(3-methyl-5-nitro-2,6-dioxo-3,6-dihydropyrimidin-1(277)-yl)acetate (514 mg, 2 mmol) was dissolved in a mixture of EtOH (5 mL) and ethyl acetate (5 mL). The flask was evacuated and backfilled with argon (×3), then a cat. amount of 10% Pd/C was added. The reaction flask was then evacuated and backfilled with $H_2$ (×3) from a balloon and allowed to stir at RT for 1 h. The reaction was then filtered through a syringe filter (0.2 µm) and concentrated. The residue was purified by chromatography (3% methanol/DCM+$NH_3$) to afford ethyl 2-(5-amino-3-methyl-2,6-dioxo-3,6-dihydropyrimidin-1(2H)-yl)acetate as a flakey solid (260 mg, 57% yield).

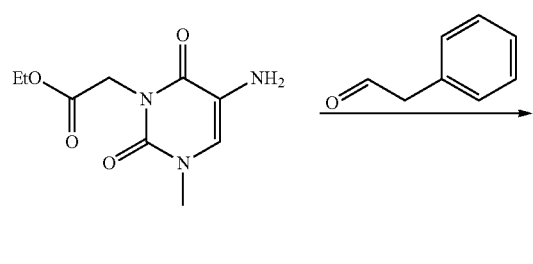

-continued

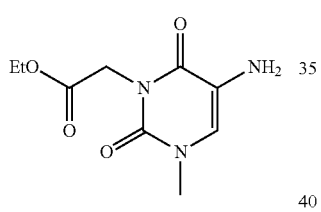

Step 3: A 100 mL RBF was charged with ethyl 2-(5-amino-3-methyl-2,6-dioxo-3,6-dihydropyrimidin-1(2H)-yl)acetate (114 mg, 0.5 mmol) and 1,2-DCE (5 mL). Phenylacetaldehyde (61 µL, 0.55 mmol) and acetic acid (29 µL, 0.5 mmol) were then added to the reaction, and stirred at RT for 10 min. NaBH(OAc)$_3$ (127 mg, 0.6 mmol) was added in a single portion, and the reaction mixture stirred at RT for 4 h. The reaction was then cooled to 0° C. and quenched with 1N NaOH, then extracted with DCM ×2. The combined organics were washed with brine, dried over $MgSO_4$ and purified by chromatography (40% ethyl acetate/DCM) to afford ethyl 2-(3-methyl-2,6-dioxo-5-(phenethylamino)-3,6-dihydropyrimidin-1(2H)-yl)acetate as a white solid (58 mg, 37% yield).

Step 4: To a stirred solution of ethyl 2-(3-methyl-2,6-dioxo-5-(phenethylamino)-3,6-dihydropyrimidin-1(2H)-yl)acetate (58 mg, 0.2 mmol) in MeOH (1 mL) was added 1N NaOH (1 mL) and the resulting mixture stirred at RT for 3 h. MeOH was then removed in vacuo and the aq. layer washed with ethyl acetate (×2). The aq. layer was then acidifed with 1N HCl and extracted with ethyl acetate (*3). The combined organics were dried over $Na_2SO_4$ and concentrated to afford 2-(3-methyl-2,6-dioxo-5-(phenethylamino)-3,6-dihydropyrimidin-1(2H)-yl)acetic acid as a white solid (26 mg, 48% yield).

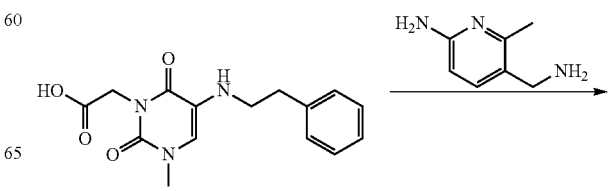

-continued

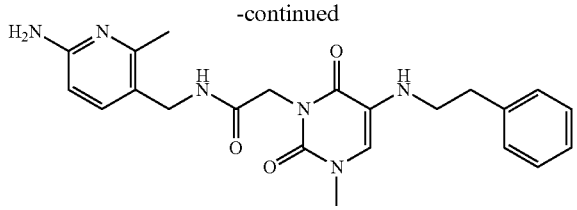

Step 5: The title compound was prepared as a white powder (30 mg, 79% yield) according to step 4 of Example 3 using the appropriate starting materials except with purification by chromatography (15% MeOH/DCM).

The following compounds were prepared according to the foregoing procedure using an appropriate amine starting material and purification by prep-HPLC (45-75% acetonitrile/H₂O+TFA):

| Compound Name | Cmp No. |
|---|---|
| N-(5-Chloro-2-hydroxy-3-methylbenzyl)-2-(3-methyl-2,6-dioxo-5-(phenethylamino)-3,6-dihydropyrimidin-1(2H)-yl)acetamide trifluoroacetate | 35 |

Example 18

Preparation of N-((6-Amino-2-Methylpyridin-3-yl)Methyl)-2-(3-Methyl-2,6-Dioxo-5-((Phenylmethyl)Sulfonamido)-3,6-Dihydropyrimidin-1(2H)-yl)Acetamide, Trifluoroacetate (Compound 36)

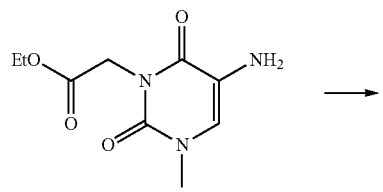

-continued

Steps 1: 2-(3-methyl-2,6-dioxo-5-((phenylmethyl)sulfonamido)-3,6-dihydropyrimidin-1(2H)-yl)acetic acid was prepared as a white solid (82 mg, 89% yield) according to the procedure described in PCT Publication No. WO 97/46207.

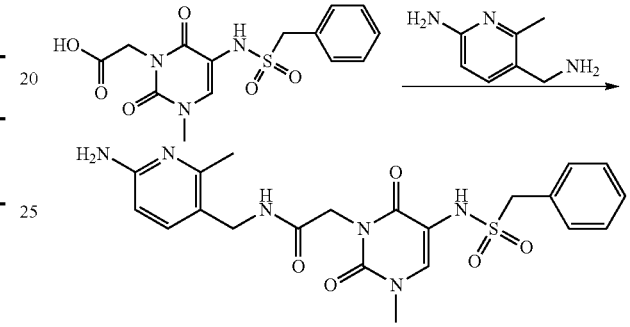

Step 3: The title compound was prepared as a white powder according to step 4 of Example 1 using the appropriate starting materials.

Example 19

Preparation of N-(4-Carbamimidoylbenzyl)-2-(3-Methyl-2,6-Dioxo-5-((Phenylmethyl)Sulfonamido)-3,6-Dihydropyrimidin-1(2H)-yl)Acetamide, Trifluoroacetate (Compound 37)

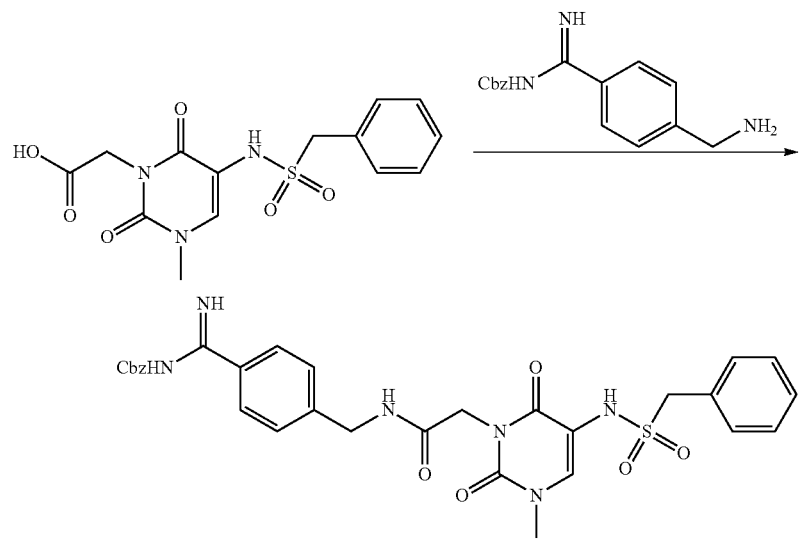

Step 1: Benzyl (imino(4-((2-(3-methyl-2,6-dioxo-5-((phenylmethyl)sulfonamido)-3,6-dihydropyrimidin-1(2H)-yl)acetamido)methyl)phenyl)methyl)carbamate was prepared according to Example 11 using the appropriate starting materials.

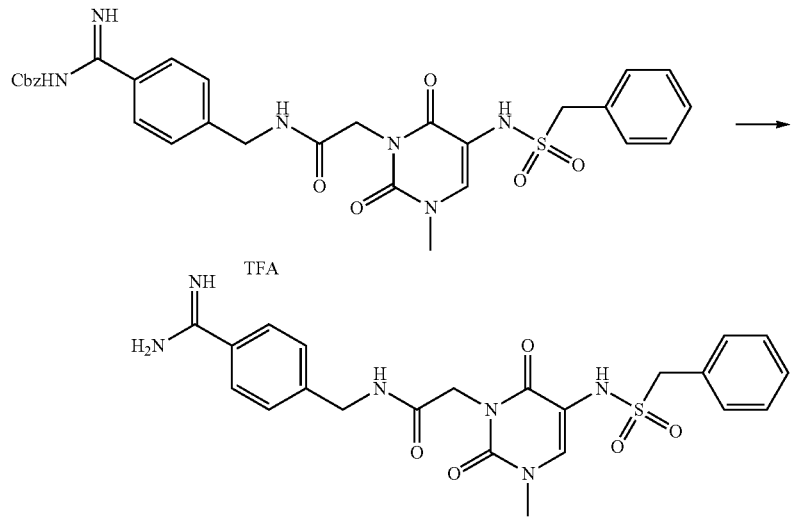

Step 2: Benzyl (imino(4-((2-(3-methyl-2,6-dioxo-5-((phenylmethyl)sulfonamido)-3,6-dihydropyrimidin-1(2H)-yl)acetamido)methyl)phenyl)methyl)carbamate was dissolved in MeOH (2 mL) and purged with Ar. A catalytic amount of 10% Pd/C was added to the reaction mixture, and the flask evacuated and backfilled with $H_2$ ×3, then stirred at RT for 3 h. The reaction mixture was then filtered through a syringe filter (0.2 μm) and concentrated, then the residue purified by prep-HPLC to afford the title compound as a white solid (2 mg, 34% yield).

Example 20

Preparation of 1-(4-(6-Amino-2-Methylpyridin-3-yl)-2-Oxobutyl)-5-Chloro-3-(Methylamino)-6-Phenylpyrazin-2(1H)-One (Compound 38)

-continued

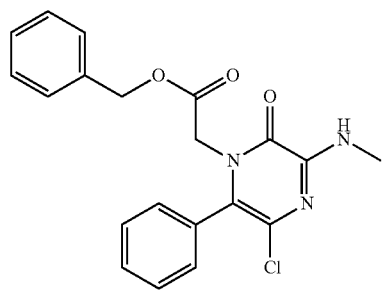

Step 1: A solution of benzyl 2-(3,5-dichloro-2-oxo-6-phenylpyrazin-1(2H)-yl)acetate (300 mg, 0.77 mmol; prepared according to Bioorganic & Medicinal Chemistry Letters, 13(14), 2319-2325; 2003) in methylamine (2M in THF, 5 mL) was stirred at RT for 1 h. After evaporation to dryness, $H_2O$ (5 mL) and ethyl acetate (20 mL) were added and stirred for 10 min. The organic layer was dried over $Na_2SO_4$ and evaporated giving the product as a yellow solid (294 mg, 99% yield).

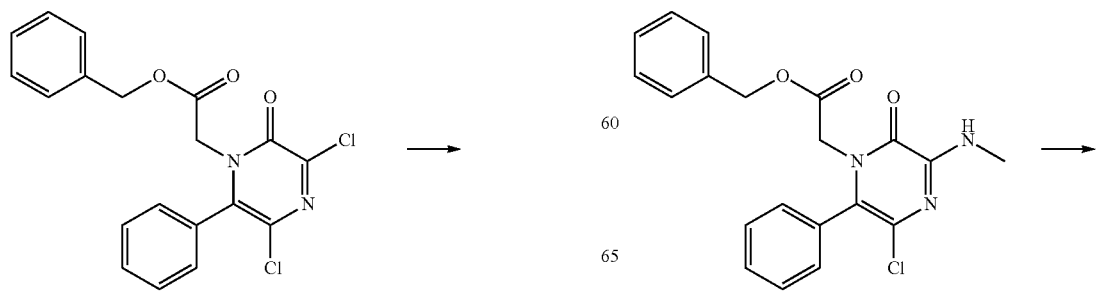

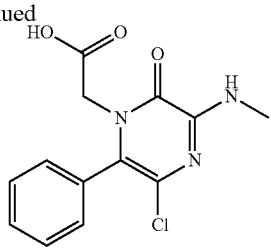

Step 2: A solution of benzyl 2-(5-chloro-3-(methylamino)-2-oxo-6-phenylpyrazin-1(2H)-yl)acetate (294 mg, 0.77 mmol) in MeOH/THF/H$_2$O (2:1:1, 6 mL) containing lithium hydroxide (92 mg, 3.85 mmol) was stirred overnight at RT. After evaporation to dryness, H$_2$O (5 ml) was added with swirling and the pH was adjusted to 3 with the addition of 10% aq. KHSO$_4$. The solution was extracted with CH$_2$Cl$_2$ (2×10 ml), dried over Na$_2$SO$_4$ and evaporated giving the product as a yellow solid (214 mg, 95% yield).

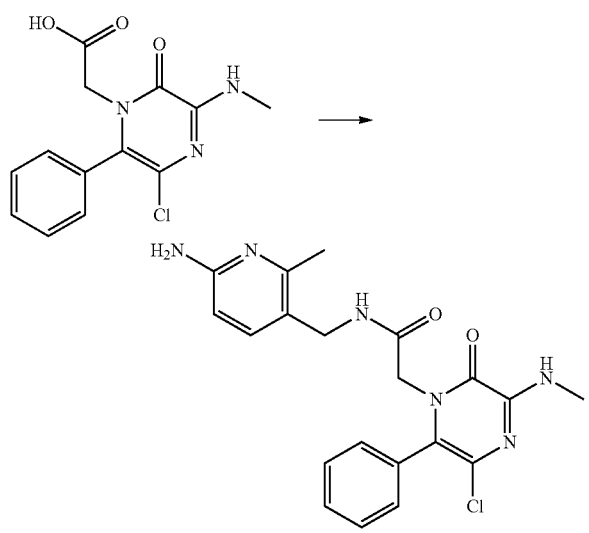

Step 3: To a solution of 2-(5-chloro-3-(methylamino)-2-oxo-6-phenylpyrazin-1(277)-yl)acetic acid (200 mg, 0.68 mmol) in CH$_2$Cl$_2$ was added NHS (86 mg, 0.75 mmol) with stirring until dissolved. DCC (155 mg, 0.75 mmol) was added and stirred at RT for 30 min. The solution was filtered to remove DCU and to the filtrate was added 5-(aminomethyl)-6-methylpyridin-2-amine (0.82 mmol) with stirring at RT overnight. Evaporation to dryness followed by chromatography (3% MeOH—NH$_3$/CH$_2$Cl$_2$) gave product as a yellow solid (147 mg, 51% yield).

The following compounds were prepared according to the foregoing procedure using the appropriate starting materials:

| Compound Name | Cmp No. |
|---|---|
| N-((6-Amino-2-methylpyridin-3-yl)methyl)-2-(5-chloro-3-(dimethylamino)-2-oxo-6-phenylpyrazin-1(2H)-yl)acetamide | 39 |
| N-((6-Amino-2-methylpyridin-3-yl)methyl)-2-(5-chloro-2-oxo-6-phenyl-3-(pyrrolidin-1-yl)pyrazin-1(2H)-yl)acetamide | 40 |

Example 21

Preparation of N-((6-Amino-2-Methylpyridin-3-yl)Methyl)-2-(5-Chloro-2-Oxo-3-(Phenethylamino)-6-Phenylpyrazin-1(2H)-yl)Acetamide (Compound 41)

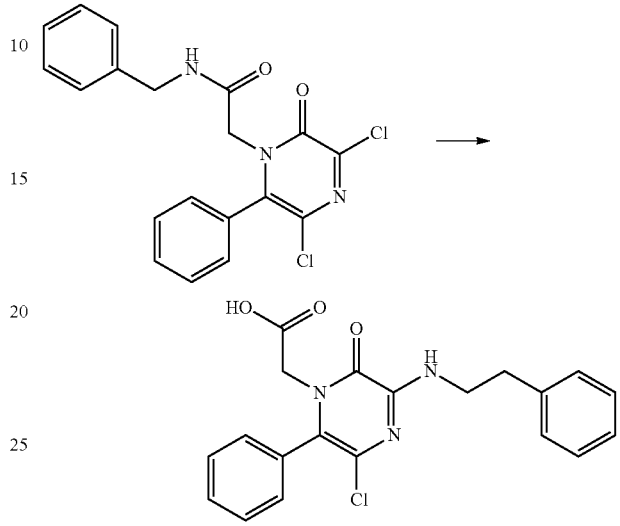

Steps 1-2: 2-(5-chloro-2-oxo-3-(phenethylamino)-6-phenylpyrazin-1(2H)-yl)acetic acid was prepared as a white solid (19 mg, quant.) according to steps 1-2 of Example 20.

Step 3: The title compound was prepared as a white, fluffy powder (32.3 mg, 64% yield) according to Example 12 except for purification by chromatography (methanol/DCM).

The following compounds were prepared according to the foregoing procedure using purification by chromatography (amine column, methanol/DCM):

| Compound Name | Cmp No. |
|---|---|
| N-((6-Amino-2-methylpyridin-3-yl)methyl)-2-(5-chloro-2-oxo-6-phenyl-3-((2-phenyloxetan-3-yl)amino)pyrazin-1(2H)-yl)acetamide | 42 |

Example 22

Preparation of N-((6-Amino-2-Methylpyridin-3-yl)Methyl)-2-(2-Oxo-6-Phenyl-3-(Pyrrolidin-1-yl)Pyrazin-1(2H)-yl) Acetamide (Compound 43)

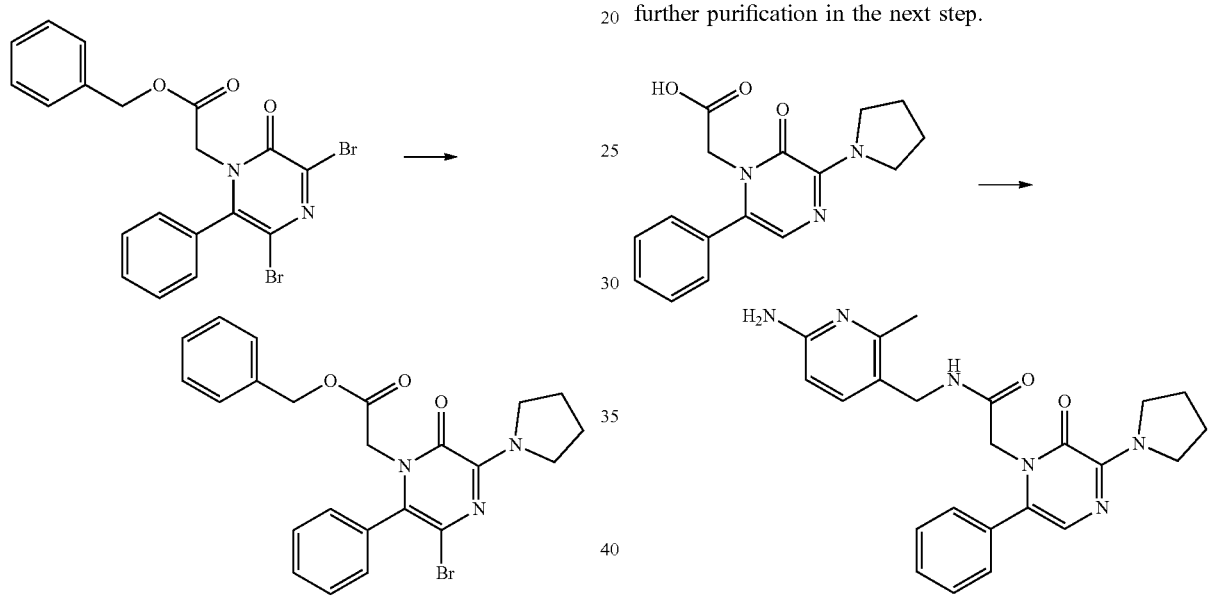

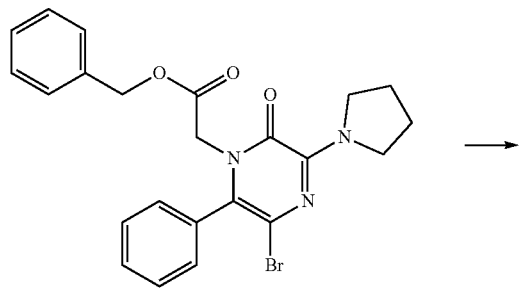

Step 1: To a solution of benzyl 2-(3,5-dibromo-2-oxo-6-phenylpyrazin-1(2H)-yl)acetate (300 mg, 0.63 mmol; prepared according to PCT Int. Appl., 2003029224, 10 Apr. 2003) in THF (5 ml) was added pyrrolidine (134 mg, 1.9 mmol) with stirring overnight at RT. After evaporation to dryness, $H_2O$ (5 mL) and ethyl acetate (20 mL) were added and stirred for 10 min. The organic layer was dried over $Na_2SO_4$ and evaporated giving product as a yellow solid (290 mg, 99% yield).

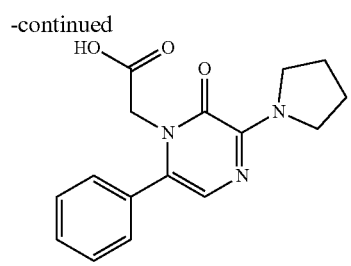

Step 2: A solution of benzyl 2-(5-bromo-2-oxo-6-phenyl-3-(pyrrolidin-1-yl)pyrazin-1(2H)-yl)acetate (290 mg, 0.62 mmol) in ethanol (10 mL) was degassed with a stream of argon for approx. 2-3 min. 10% Pd/C (200 mg) was added and the mixture was hydrogenated at 80 psi for 48 h. The catalyst was removed by filtration and evaporated to dryness giving 179 mg (96%) of a yellow solid that was used without further purification in the next step.

Step 3: To a solution of 2-(2-oxo-6-phenyl-3-(pyrrolidin-1-yl)pyrazin-1(2H)-yl)acetic acid (170 mg, 0.57 mmol) in $CH_2Cl_2$ was added NHS (73 mg, 0.63 mmol) with stirring until dissolved. DCC (133 mg, 0.63 mmol) was added and stirred at RT for 30 min. The solution was filtered to remove DCU and to the filtrate was added 5-(aminomethyl)-6-methylpyridin-2-amine (1.2 equiv, 0.68 mmol) with stirring at RT overnight. Evaporation to dryness followed by chromatography. (3% MeOH—$NH_3$/$CH_2Cl_2$) gave product as a yellow solid (81 mg, 34% yield).

The following compounds were prepared according to the foregoing procedure using appropriate starting materials:

| Compound Name | Cmp No. |
|---|---|
| N-((6-Amino-2-methylpyridin-3-yl)methyl)-2-(3-morpholino-2-oxo-6-phenylpyrazin-1(2H)-yl)acetamide | 44 |
| N-((6-Amino-2-methylpyridin-3-yl)methyl)-2-(3-(methylamino)-2-oxo-6-phenylpyrazin-1(2H)-yl)acetamide | 45 |

Example 23

Preparation of N-((1H-Pyrrolo[3,2-c]Pyridin-2-yl)Methyl)-2-(2-Oxo-6-Phenyl-3-(((3-Phenyloxetan-3-yl)Methyl)Amino)Pyrazin-1(2H)-yl)Acetamide Trifluoroacetate

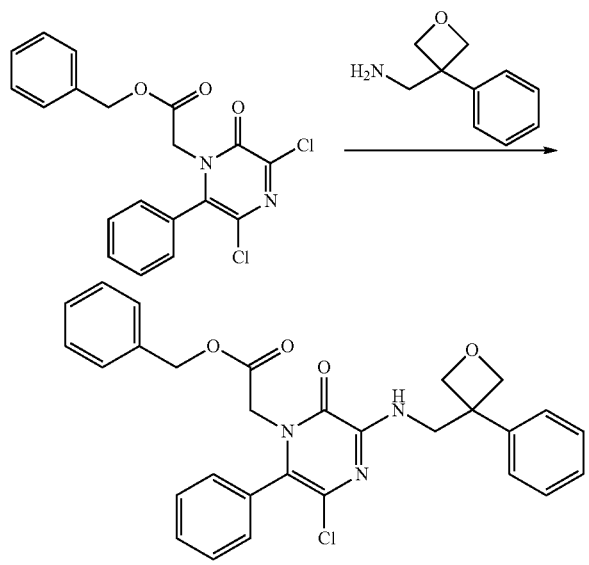

Step 1: To a solution of benzyl 2-(3,5-dichloro-2-oxo-6-phenylpyrazin-1(2H)-yl)acetate (200 mg, 0.54 mmol, prepared according to the procedure described in Bioorganic & Medicinal Chemistry Letters, 13(14), 2319-2325; 2003) in MeCN (5 mL, 0.1 M) was added (3-phenyloxetan-3-yl)methanamine (137 mg, 0.77 mmol) and DIEA (0.27 mL, 1.54 mmol). After stirring for 18 h at 70° C., the reaction mixture was cooled, washed with water, and extracted with EtOAc. The organic layer was dried over anhyd Na$_2$SO$_4$, filtered, and concd under vacuum. The residue was purified by chromatography (0-100% EtOAc-hexanes) to give benzyl 2-(5-chloro-2-oxo-6-phenyl-3-(((3-phenyloxetan-3-yl)methyl)amino)pyrazin-1(2H)-yl)acetate (265 mg, 95% yield).

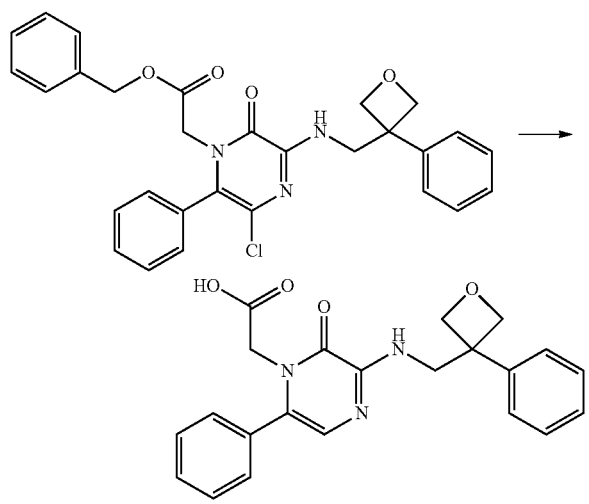

Step 2: A solution of benzyl 2-(5-chloro-2-oxo-6-phenyl-3-(((3-phenyloxetan-3-yl)methyl)amino)pyrazin-1(2H)-yl) acetate (200 mg, 0.39 mmol) in EtOAc (3 mL) and MeOH (3 mL) was degassed with a stream of argon for 1 min. 10% Pd/C (40 mg) was added, a vacuum was pulled for 1 min, and a balloon of EL was added. To the above mixture was added Et$_3$N (0.1 mL, 0.78 mmol) and the reaction was stirred for 16 h at RT. The catalyst was removed by filtration and the solution was evaporated to give 2-(2-oxo-6-phenyl-3-(((3-phenyloxetan-3-yl)methyl)amino)pyrazin-1(2H)-yl) acetic acid (152 mg, 99% yield).

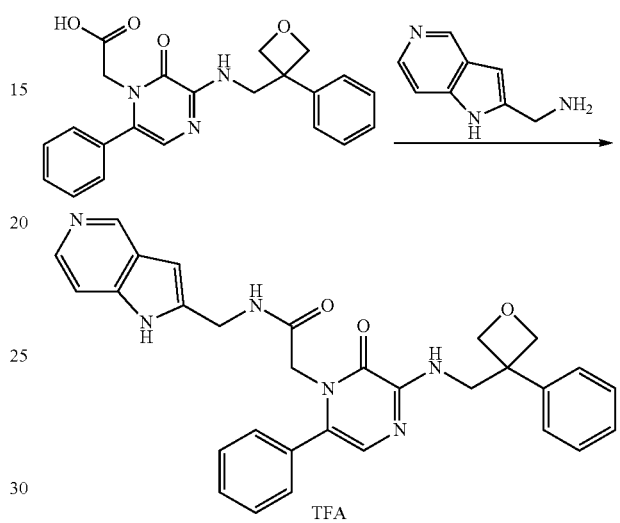

Step 3: To a solution of 2-(2-oxo-6-phenyl-3-(((3-phenyloxetan-3-yl)methyl)amino)pyrazin-1(2H)-yl)acetic acid (95 mg, 0.24 mmol) in DMF (4 mL, 0.06 M) was added (1H-pyrrolo[3,2-c]pyridin-2-yl)methanamine (43 mg, 0.29 mmol) with stirring until dissolved. HATU (92 mg, 0.24 mmol) and DIEA (0.15 mL, 0.88 mmol) were added and the reaction mixture was stirred for 16 h at RT. The reaction mixture was concd and the residue was purified using reverse-phase HPLC to give N-((1H-pyrrolo[3,2-c]pyridin-2-yl)methyl)-2-(2-oxo-6-phenyl-3-(((3-phenyloxetan-3-yl)methyl)amino)pyrazin-1(2H)-yl)acetamide trifluoroacetate (61 mg, 48% yield).

The following compounds were prepared according to the foregoing procedure using the appropriate amine starting materials and purification via reverse-phase HPLC:

| Compound Name | Cmp No. |
|---|---|
| N-((1H-Pyrrolo[3,2-c]pyridin-2-yl)methyl)-2-(3-((2-methoxyethyl)amino)-2-oxo-6-phenylpyrazin-1(2H)-yl)acetamide trifluoroacetate | 120 |
| N-((1H-Pyrrolo[3,2-c]pyridin-2-yl)methyl)-2-(3-((3-methoxypropyl)amino)-2-oxo-6-phenylpyrazin-1(2H)-yl)acetamide trifluoroacetate | 121 |
| N-((1H-Pyrrolo[3,2-c]pyridin-2-yl)methyl)-2-(3-((4-methoxybutyl)amino)-2-oxo-6-phenylpyrazin-1(2H)-yl)acetamide trifluoroacetate | 124 |

Example 24

Preparation of Tert-Butyl 2-(4-(2-(((1H-Pyrrolo[3,2-c]Pyridin-2-yl)Methyl)Amino)-2-Oxoethyl)-3-Oxo-5-Phenyl-3,4-Dihydropyrazin-2-yl)-2,8-Diazaspiro[4.5]Decane-8-Carboxylate (Compound 53)

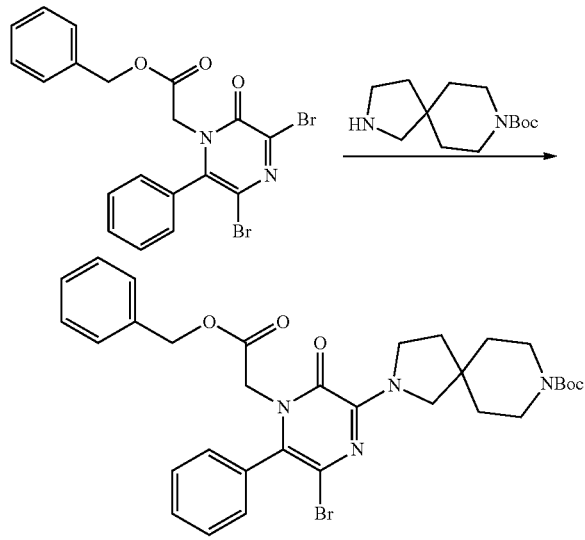

Step 1: tert-Butyl 2-(4-(2-(benzyloxy)-2-oxoethyl)-6-bromo-3-oxo-5-phenyl-3,4-dihydropyrazin-2-yl)-2,8-diazaspiro[4.5]decane-8-carboxylate (258 mg, 97% yield) was synthesized from benzyl 2-(3,5-dibromo-2-oxo-6-phenylpyrazin-1(2H)-yl)acetate (200 mg, 0.42 mmol, prepared according to the procedure described in PCT Int. Appl., 2003029224, 10 Apr. 2003) according to Example 23, step 1.

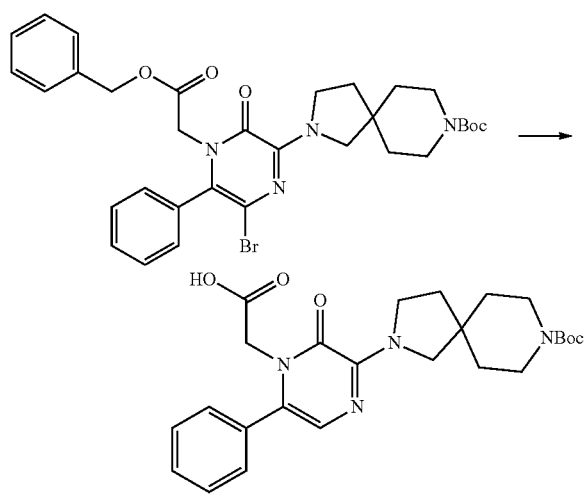

Step 2: 2-(3-(8-(tert-Butoxycarbonyl)-2,8-diazaspiro[4.5]decan-2-yl)-2-oxo-6-phenylpyrazin-1(2H)-yl)acetic acid (177 mg, 90% yield) was synthesized from tert-butyl 2-(4-(2-(benzyloxy)-2-oxoethyl)-6-bromo-3-oxo-5-phenyl-3,4-dihydropyrazin-2-yl)-2,8-diazaspiro[4.5]decane-8-carboxylate (258 mg, 0.4 mmol) according to Example 23, step 2.

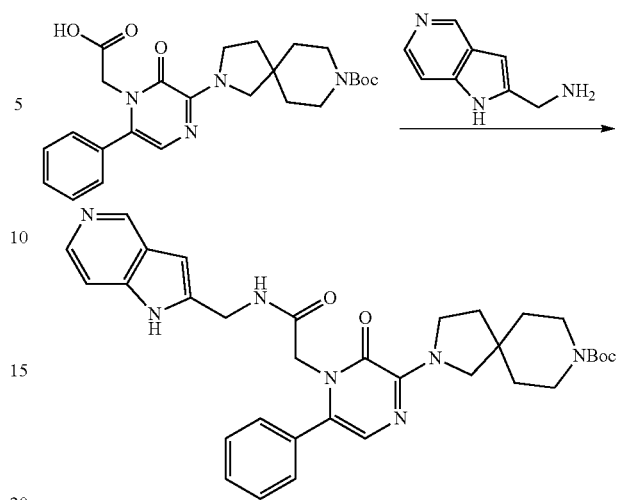

Step 3: tert-Butyl 2-(4-(2-(((1H-pyrrolo[3,2-c]pyridin-2-yl)methyl)amino)-2-oxoethyl)-3-oxo-5-phenyl-3,4-dihydropyrazin-2-yl)-2,8-diazaspiro[4.5]decane-8-carboxylate (34 mg, 30% yield) was synthesized from 2-(3-(8-(tert-butoxycarbonyl)-2,8-diazaspiro[4,5]decan-2-yl)-2-oxo-6-phenylpyrazin-1(2H)-yl)acetic acid (94 mg, 0.2 mmol) except that the crude material was purified by chromatography (0-100% EtOAc-hexanes).

The following compounds were prepared according to the foregoing procedure using the appropriate amine starting materials and purification via reverse-phase HPLC:

| Compound Name | Cmp No. |
|---|---|
| N-((1H-Pyrrolo[3,2-c]pyridin-2-yl)methyl)-2-(2-oxo-6-phenyl-3-((3-phenylpropyl)amino)pyrazin-1(2H)-yl)acetamide trifluoroacetate | 48 |
| N-((1H-Pyrrolo[3,2-c]pyridin-2-yl)methyl)-2-(3-((1-hydroxy-3-phenylpropan-2-yl)amino)-2-oxo-6-phenylpyrazin-1(2H)-yl)acetamide trifluoroacetate | 49 |
| N-((1H-Pyrrolo[3,2-c]pyridin-2-yl)methyl)-2-(2-oxo-6-phenyl-3-(((3-phenyltetrahydrofuran-3-yl)methyl)amino)pyrazin-1(2H)-yl)acetamide trifluoroacetate | 50 |
| N-((1H-Pyrrolo[3,2-c]pyridin-2-yl)methyl)-2-(2-oxo-6-phenyl-3-((3-phenyloxetan-3-yl)amino)pyrazin-1(2H)-yl)acetamide trifluoroacetate | 51 |
| N-((1H-Pyrrolo[3,2-c]pyridin-2-yl)methyl)-2-(2-oxo-6-phenyl-3-(((1-phenylcyclopropyl)methyl)amino)pyrazin-1(2H)-yl)acetamide trifluoroacetate | 52 |
| N-((1H-Pyrrolo[3,2-c]pyridin-2-yl)methyl)-2-(3-((2,2-difluoro-2-phenylethyl)amino)-2-oxo-6-phenylpyrazin-1(2H)-yl)acetamide trifluoroacetate | 128 |
| N-((1H-Pyrrolo[3,2-c]pyridin-2-yl)methyl)-2-(3-(((3-(4-fluorophenyl)oxetan-3-yl)amino)-2-oxo-6-phenylpyrazin-1(2H)-yl)acetamide trifluoroacetate | 55 |
| N-((1H-Pyrrolo[3,2-c]pyridin-2-yl)methyl)-2-(2-oxo-6-phenyl-3-(((1-phenylcyclobutyl)methyl)amino)pyrazin-1(2H)-yl)acetamide trifluoroacetate | 56 |
| N-((1H-Pyrrolo[3,2-c]pyridin-2-yl)methyl)-2-(3-(((1-(4-chlorophenyl)cyclopropyl)methyl)amino)-2-oxo-6-phenylpyrazin-1(2H)-yl)acetamide trifluoroacetate | 57 |
| N-((1H-Pyrrolo[3,2-c]pyridin-2-yl)methyl)-2-(3-(((1-(4-fluorophenyl)cyclopropyl)methyl)amino)-2-oxo-6-phenylpyrazin-1(2H)-yl)acetamide trifluoroacetate | 59 |
| N-((1H-Pyrrolo[3,2-c]pyridin-2-yl)methyl)-2-(2-oxo-6-phenyl-3-(((1-(4-(trifluoromethyl)phenyl)cyclopropyl)methyl)amino)pyrazin-1(2H)-yl)acetamide trifluoroacetate | 60 |
| N-((1H-Pyrrolo[3,2-c]pyridin-2-yl)methyl)-2-(3-(((1-(4-methoxyphenyl)cyclopropyl)methyl)amino)-2-oxo-6-phenylpyrazin-1(2H)-yl)acetamide trifluoroacetate | 61 |

-continued

| Compound Name | Cmp No. |
|---|---|
| N-((1H-Pyrrolo[3,2-c]pyridin-2-yl)methyl)-2-(3-(((3-(2-fluorophenyl)oxetan-3-yl)methyl)amino)-2-oxo-6-phenylpyrazin-1(2H)-yl)acetamide trifluoroacetate | 62 |
| N-((1H-Pyrrolo[3,2-c]pyridin-2-yl)methyl)-2-(2-oxo-6-phenyl-3-(((1-(p-tolyl)cyclopropyl)methyl)amino)pyrazin-1(2H)-yl)acetamide trifluoroacetate | 63 |
| N-((1H-Pyrrolo[3,2-c]pyridin-2-yl)methyl)-2-(3-(((1-(3-fluorophenyl)cyclopropyl)methyl)amino)-2-oxo-6-phenylpyrazin-1(2H)-yl)acetamide | 64 |
| N-((1H-Pyrrolo[3,2-c]pyridin-2-yl)methyl)-2-(2-oxo-6-phenyl-3-((1-phenylcyclopropyl)amino)pyrazin-1(2H)-yl)acetamide trifluoroacetate | 66 |
| N-((1H-Pyrrolo[3,2-c]pyridin-2-yl)methyl)-2-(3-(((1-(3-methoxyphenyl)cyclopropyl)methyl)amino)-2-oxo-6-phenylpyrazin-1(2H)-yl)acetamide trifluoroacetate | 68 |
| N-((1H-Pyrrolo[3,2-c]pyridin-2-yl)methyl)-2-(3-((3,4-difluorobenzyl)amino)-2-oxo-6-phenylpyrazin-1(2H)-yl)acetamide trifluoroacetate | 70 |
| N-((1H-Pyrrolo[3,2-c]pyridin-2-yl)methyl)-2-(3-(((1-(3-chlorophenyl)cyclopropyl)methyl)amino)-2-oxo-6-phenylpyrazin-1(2H)-yl)acetamide trifluoroacetate | 71 |
| N-((1H-Pyrrolo[3,2-c]pyridin-2-yl)methyl)-2-(3-((4-chlorobenzyl)amino)-2-oxo-6-phenylpyrazin-1(2H)-yl)acetamide trifluoroacetate | 73 |
| N-((1H-Pyrrolo[3,2-c]pyridin-2-yl)methyl)-2-(3-((1-(3,4-difluorophenyl)cyclopropyl)amino)-2-oxo-6-phenylpyrazin-1(2H)-yl)acetamide trifluoroacetate | 74 |
| N-((1H-Pyrrolo[3,2-c]pyridin-2-yl)methyl)-2-(3-((3-chlorobenzyl)amino)-2-oxo-6-phenylpyrazin-1(2H)-yl)acetamide trifluoroacetate | 75 |
| Methyl (4-(2-(((1H-pyrrolo[3,2-c]pyridin-2-yl)methyl)amino)-2-oxoethyl)-3-oxo-5-phenyl-3,4-dihydropyrazin-2-yl)-L-tyrosinate trifluoroacetate | 163 |

The following compound was prepared according to the foregoing procedure using the appropriate amine starting materials and purification by chromatography (amine column, MeOH—CH$_2$Cl$_2$):

| Compound Name | Cmp No. |
|---|---|
| Ethyl (4-(2-(((1H-pyrrolo[3,2-c]pyridin-2-yl)methyl)amino)-2-oxoethyl)-3-oxo-5-phenyl-3,4-dihydropyrazin-2-yl)glycinate | 117 |

Example 25

Preparation of N-((1H-Pyrrolo[3,2-c]Pyridin-2-yl)Methyl)-2-(2-Oxo-6-Phenyl-3-(2,8-Diazaspiro[4.5]Decan-2-yl)Pyrazin-1(2H)-yl)Acetamide Di-Trifluoroacetate (Compound 54)

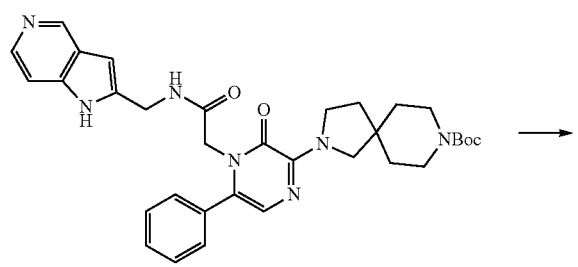

→

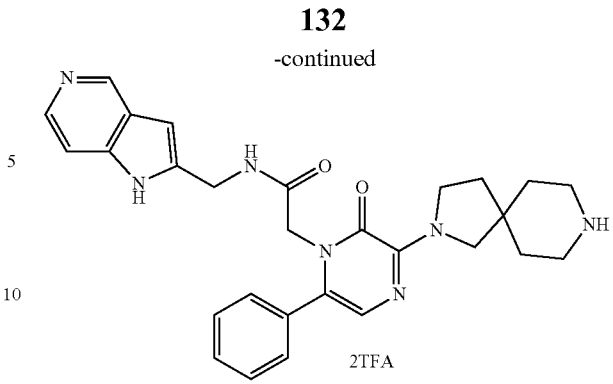

2TFA

To a 0° C. solution of tert-butyl 2-(4-(2-(((1H-pyrrolo[3,2-c]pyridin-2-yl)methyl)amino)-2-oxoethyl)-3-oxo-5-phenyl-3,4-dihydropyrazin-2-yl)-2,8-diazaspiro[4.5]decane-8-carboxylate (34 mg, 0.06 mmol, prepared according to Example 24, steps 1-3) in CH$_2$Cl$_2$ (1.0 mL, 0.06 M) was added 20% TFA in CH$_2$Cl$_2$ (1.0 mL). After stirring for 2 h at RT, the reaction mixture was concd. The crude material was purified using reverse-phase HPLC to give N-((1H-pyrrolo[3,2-c]pyridin-2-yl)methyl)-2-(2-oxo-6-phenyl-3-(2,8-diazaspiro[4.5]decan-2-yl)pyrazin-1(2H)-yl)acetamide di-trifluoroacetate (31 mg, 74% yield).

Example 26

Preparation of N-((1-Methyl-1H-Pyrrolo[3,2-c]Pyridin-2-yl)Methyl)-2-(2-Oxo-3-(Phenethylamino)-6-Phenylpyrazin-1(2H)-yl)Acetamide Trifluoroacetate (Compound 46)

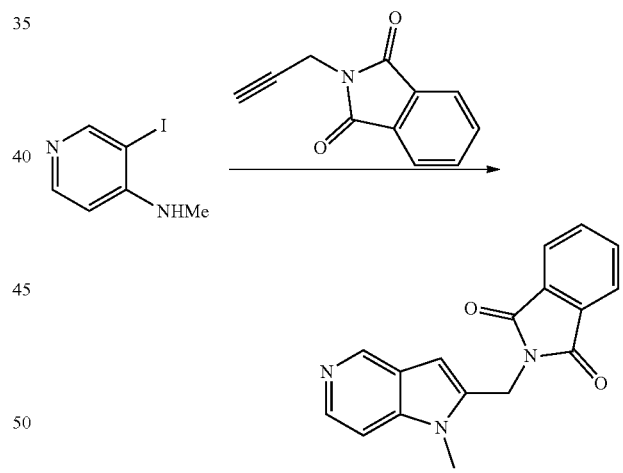

Step 1: To a solution of 3-iodo-N-methylpyridin-4-amine (632 mg, 2.7 mmol) and 2-(prop-2-yn-1-yl)isoindoline-1,3-dione (500 mg, 2.7 mmol) in DMF (10 mL, 0.3 mmol) was added Pd(PPh$_3$)$_2$Cl$_2$ (95 mg, 0.14 mmol), CuI (15 mg, 0.08 mmol), and Et$_3$N (1.5 mL, 10.8 mmol). After stirring for 1.5 h at 100° C., the reaction mixture was cooled to 50° C., and DBU (0.8 mL, 5.4 mmol) was added. After stirring for 30 min for 50° C., the reaction mixture was cooled to RT, diluted with EtOAc, and washed with sat. aq NH$_4$Cl, water, and brine. The organic layer was dried over anhyd NaSO$_4$, filtered, and concd. The crude material was purified by chromatography (0-20% MeOH—CH$_2$Cl$_2$) to give 2-((1-methyl-1H-pyrrolo[3,2-c]pyridin-2-yl)methyl)isoindoline-1,3-dione (62 mg, 8% yield).

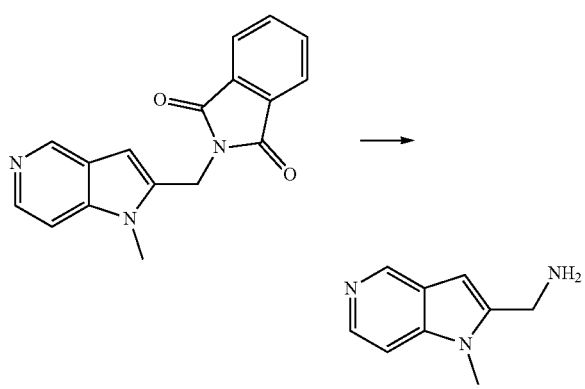

Step 2: 2-((1-Methyl-1H-pyrrolo[3,2-c]pyridin-2-yl)methyl)isoindoline-1,3-dione (62 mg, 0.21 mmol) was dissolved in hydrazine hydrate (80% solution, 0.06 mL). After stirring for 4 h at RT, the reaction mixture was concd under vacuum to yield (1-methyl-1H-pyrrolo[3,2-c]pyridin-2-yl)methanamine (34 mg, 100%). The crude material was used in the next reaction without further purification.

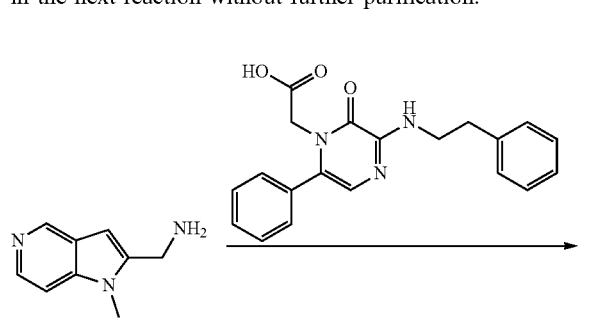

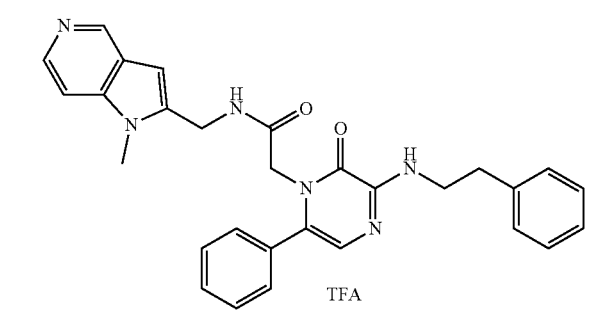

Step 3: N-((1-Methyl-1H-pyrrolo[3,2-c]pyridin-2-yl)methyl)-2-(2-oxo-3-(phenethylamino)-6-phenylpyrazin-1(2H)-yl)acetamide trifluoroacetate was synthesized from (1-methyl-1H-pyrrolo[3,2-c]pyridin-2-yl)methanamine (34 mg, 0.21 mmol) and 2-(2-oxo-3-(phenethylamino)-6-phenylpyrazin-1(2H)-yl)acetic acid (61 mg, 0.17 mmol, prepared according to Example 23, steps 1-2 using 2-phenylethan-1-amine) according to Example 23, step 3.

Example 27

Preparation of N-((6-Methyl-1H-Pyrrolo[3,2-c]Pyridin-2-yl)Methyl)-2-(2-Oxo-3-(Phenethylamino)-6-Phenylpyrazin-1(2H)-yl)Acetamide Trifluoroacetate (Compound 67)

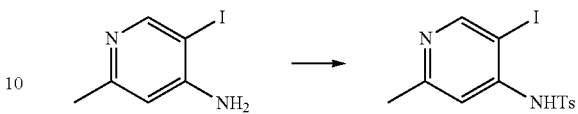

Step 1: To a 0° C. solution of 5-iodo-2-methylpyridin-4-amine (100 mg, 0.43 mmol) in pyridine (5 mL, 0.08 M) was added Ts$_2$O (209 mg, 0.64 mmol) every hour for 4 hours. The reaction mixture was washed with sat. aq NH$_4$Cl and extracted with CH$_2$Cl$_2$. The organic layer was dried over anhyd NaSO$_4$, filtered, and concd. The crude material was purified by chromatography (0-100% EtOAc-hexanes) to give N-(5-iodo-2-methylpyridin-4-yl)-4-methylbenzenesulfonamide (80 mg, 48% yield).

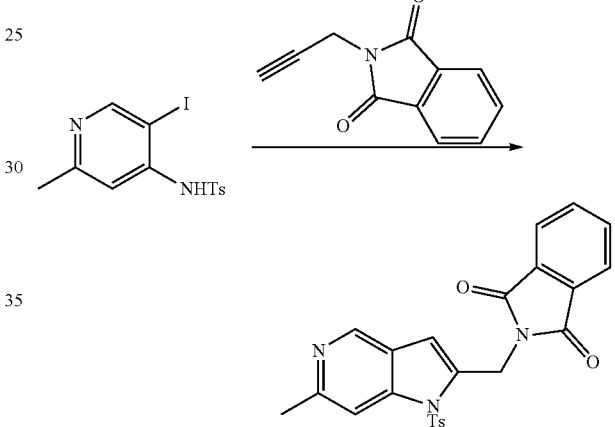

Step 2: 2-((6-Methyl-1-tosyl-1H-pyrrolo[3,2-c]pyridin-2-yl)methyl)isoindoline-1,3-dione was synthesized from N-(5-iodo-2-methylpyridin-4-yl)-4-methylbenzenesulfonamide (269 mg, 0.69 mmol) and 2-(prop-2-yn-1-yl)isoindoline-1,3-dione (642 mg, 3.46 mmol) according to Example 26, step 1.

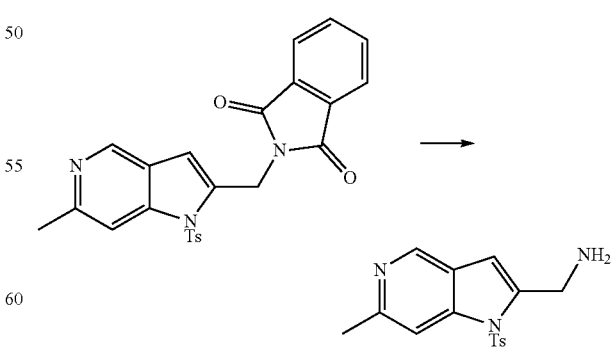

Step 3: (6-Methyl-1-tosyl-1H-pyrrolo[3,2-c]pyridin-2-yl)methanamine was synthesized from 2-((6-methyl-1-tosyl-1H-pyrrolo[3,2-c]pyridin-2-yl)methyl)isoindoline-1,3-dione (120 mg, 0.27 mmol) according to Example 26, step 2.

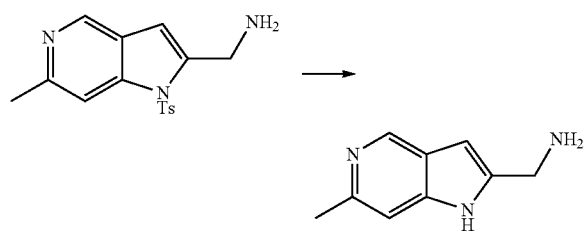 [SMILES: Cc1ccc(S(=O)(=O)n2c(CN)cc3cnc(C)cc32)cc1 ; Cc1cc2[nH]c(CN)cc2cn1]

Step 4: To a solution of (6-methyl-1-tosyl-1H-pyrrolo[3,2-c]pyridin-2-yl)methanamine (80 mg, 0.25 mmol) in THF (3 mL) and MeOH (3 mL) was added $Cs_2CO_3$ (247 mg, 0.76 mmol). After stirring for 16 h at RT, the reaction mixture was concd and the residue was purified using reverse-phase HPLC to give (6-methyl-1H-pyrrolo[3,2-c]pyridin-2-yl)methanamine di-trifluoroacetate (24 mg, 60% yield).

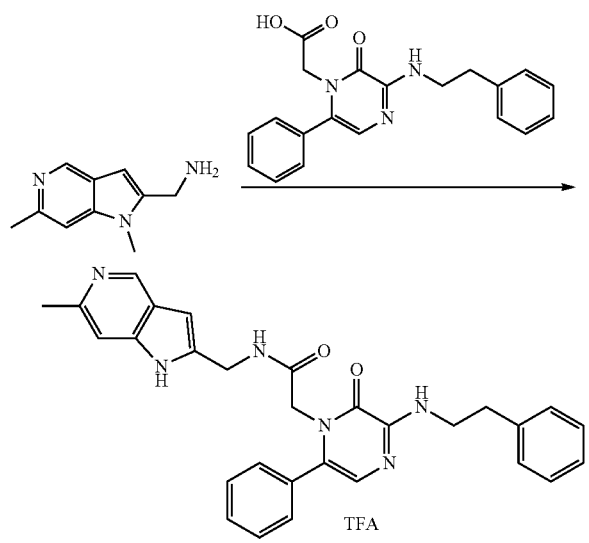

Step 5: N-((6-Methyl-1H-pyrrolo[3,2-c]pyridin-2-yl)methyl)-2-(2-oxo-3-(phenethylamino)-6-phenylpyrazin-1(2H)-yl)acetamide trifluoroacetate was synthesized from (6-methyl-1H-pyrrolo[3,2-c]pyridin-2-yl)methanamine di-trifluoroacetate (24 mg, 0.15 mmol) according to Example 26, step 3.

The following compounds were prepared according to the foregoing procedure using the appropriate amine starting materials and purification via reverse-phase HPLC:

| Compound Name | Cmp No. |
|---|---|
| N-((6-Methyl-1H-pyrrolo[3,2-c]pyridin-2-yl)methyl)-2-(2-oxo-6-phenyl-3-((1-phenylcyclopropyl)amino)pyrazin-1(2H)-yl)acetamide trifluoroacetate | 76 |
| 2-(3-((4-Methoxybenzyl)amino)-2-oxo-6-phenylpyrazin-1(2H)-yl)-N-((6-methyl-1H-pyrrolo[3,2-c]pyridin-2-yl)methyl)acetamide trifluoroacetate | 77 |

The following compound was prepared according to the foregoing procedure using the appropriate iodide starting material and purification via reverse-phase HPLC:

| Compound Name | Cmp No. |
|---|---|
| N-((4-Methyl-1H-pyrrolo[3,2-c]pyridin-2-yl)methyl)-2-(2-oxo-3-(phenethylamino)-6-phenylpyrazin-1(2H)-yl)acetamide trifluoroacetate | 72 |

Example 28

Preparation of N-((1H-Pyrrolo[3,2-c]Pyridin-2-yl)Methyl)-2-(3-(Benzylamino)-2-Oxo-6-Phenylpyrazin-1(2H)-yl)Acetamide Trifluoroacetate (Compound 58)

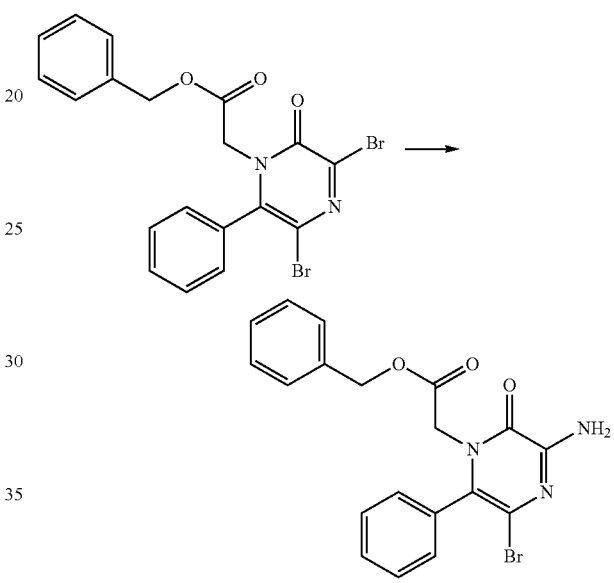

Step 1: A 20 mL sealed tube was charged with benzyl 2-(3,5-dibromo-2-oxo-6-phenylpyrazin-1(2H)-yl)acetate (1.0 g, 2.09 mmol, prepared according to the procedure described in Bioorganic & Medicinal Chemistry Letters, 13(14), 2319-2325; 2003) in THF (10 mL, 0.2 M). $NH_3$ gas was added by bubbling at −78° C. After stirring for 16 h at RT, the reaction mixture was cooled to −78° C. and washed with $H_2O$. The aqueous layer was extracted with EtOAc. The combined organic extracts were dried over anhyd $Na_2SO_4$, filtered, and concd under vacuum to give benzyl 2-(3-amino-5-bromo-2-oxo-6-phenylpyrazin-1(2H)-yl)acetate (745 mg, 86% yield) which was used in the next step without further purification.

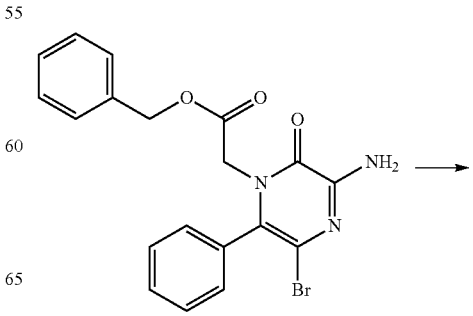

-continued

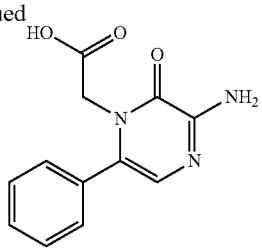

Step 2: 2-(3-Amino-2-oxo-6-phenylpyrazin-1(2H)-yl) acetic acid was synthesized from benzyl 2-(3-amino-5-bromo-2-oxo-6-phenylpyrazin-1(2H)-yl)acetate (866 mg, 2.09 mmol) according to Example 23, step 2.

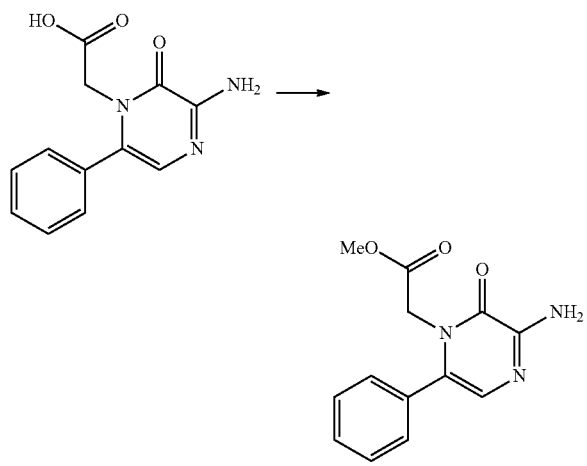

Step 3: To a 0° C. solution of 2-(3-amino-2-oxo-6-phenylpyrazin-1(2H)-yl)acetic acid (171 mg, 0.7 mmol) in MeOH (3 mL, 0.23 M) was added TMSCH$_2$N$_2$ (10% in hexanes, 2.3 mL, 1.4 mmol). After stirring for 1 h at RT, the reaction mixture was concd under vacuum to yield methyl 2-(3-amino-2-oxo-6-phenylpyrazin-1(2H)-yl)acetate (100 mg, 55% yield). The crude material was used in the next reaction without further purification.

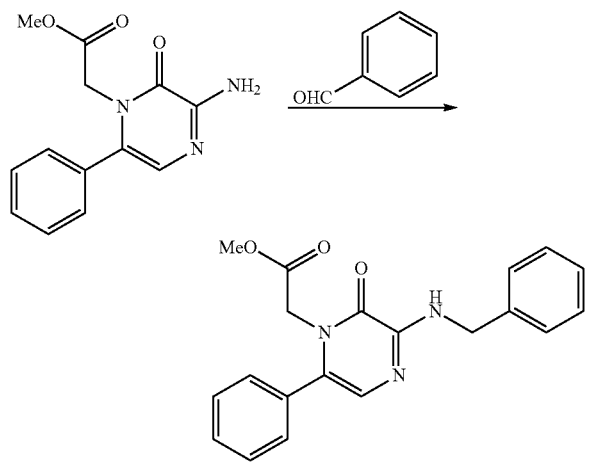

Step 4: To a suspension of methyl 2-(3-amino-2-oxo-6-phenylpyrazin-1(277)-yl)acetate (100 mg, 0.39 mmol) in dichloroethane (3 mL) and acetic acid (3 drops) was added benzaldehyde (0.16 mL, 1.54 mmol). After stirring for 1 h at 70° C., the reaction mixture was concd under vacuum for 10 min on a 40° C. water bath. The crude oil was dissolved in dichloroethane (3 mL) and Na(OAc)$_3$BH (409 mg, 1.93 mmol) was added. After stirring for 30 min at 70° C., the reaction mixture was washed with sat. aq NaHCO$_3$ and extracted with CH$_2$Cl$_2$. The organic layer was dried over anhyd NaSO$_4$, filtered, and concd. The crude material was purified by chromatography (0-100% EtOAc-hexanes) to give methyl 2-(3-(benzylamino)-2-oxo-6-phenylpyrazin-1(2H)-yl)acetate (57 mg, 42% yield).

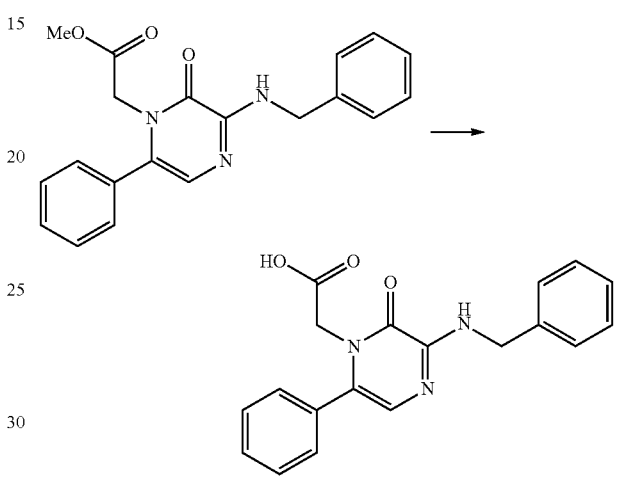

Step 5: To a solution of methyl 2-(3-(benzylamino)-2-oxo-6-phenylpyrazin-1(2H)-yl)acetate (57 mg, 0.16 mmol) in THF (8 mL), MeOH (4 mL), H$_2$O (4 mL) was added LiOH (59 mg, 2.45 mmol). After stirring for 2 h at RT, the reaction mixture was concd, added 10% KHSO$_4$, and extracted with EtOAc. The organic layer was dried over anhyd NaSO$_4$, filtered, and concd under vacuum to yield 2-(3-(benzylamino)-2-oxo-6-phenylpyrazin-1(2H)-yl)acetic acid (56 mg, 98% yield). The crude material was used in the next reaction without further purification.

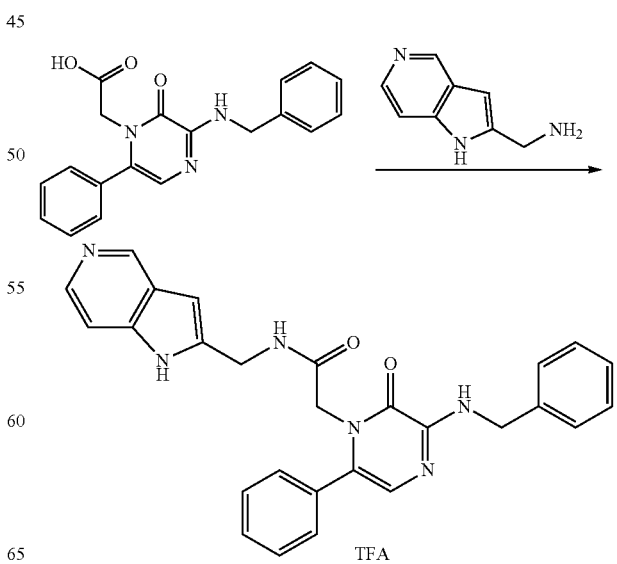

Step 6: N-((1H-Pyrrolo[3,2-c]pyridin-2-yl)methyl)-2-(3-(benzylamino)-2-oxo-6-phenylpyrazin-1(2H)-yl)acetamide trifluoroacetate was synthesized from 2-(3-(benzylamino)-2-oxo-6-phenylpyrazin-1(2H)-yl)acetic acid (56 mg, 0.16 mmol) according to Example 23, step 3.

Example 29

Preparation of 2-(3-(((1-(4-Chlorophenyl)Cyclopropyl)Methyl)Amino)-2-Oxo-6-Phenylpyrazin-1(2H)-yl)-N-((6,7-Dihydro-5H-Pyrrolo[3,4-5]Pyridin-3-yl)Methyl)Acetamide Trifluoroacetate (Compound 69)

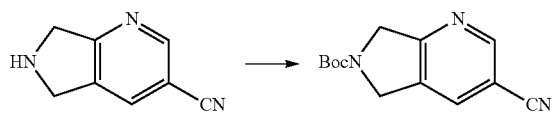 [SMILES: N#Cc1cnc2c(c1)CNC2 ; CC(C)(C)OC(=O)N1Cc2cc(C#N)cnc2C1]

Step 1: To a solution of 6,7-dihydro-5H-pyrrolo[3,4-b]pyridine-3-carbonitrile (200 mg, 1.38 mmol) in CH$_2$Cl$_2$ (7 mL, 0.2 M) was added Boc$_2$O (300 mg, 1.38 mmol) and DMAP (169 mg, 1.38 mmol). After stirring for 1 h at RT, the reaction mixture was concd and the residue was purified by chromatography (0-100% EtOAc-hexanes) to give tert-butyl 3-cyano-5,7-dihydro-6H-pyrrolo[3,4-b]pyridine-6-carboxylate (250 mg, 74% yield).

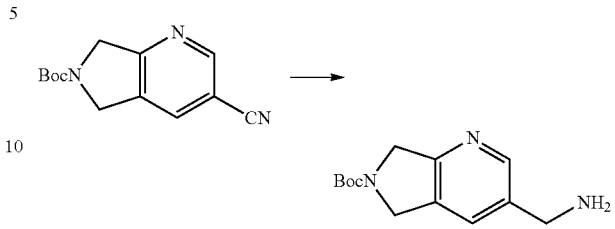

Step 2: A solution of tert-butyl 3-cyano-5,7-dihydro-6H-pyrrolo[3,4-b]pyridine-6-carboxylate (250 mg, 1.02 mmol) in MeOH (3 mL) and 7 N NH$_3$ in MeOH (14 mL) was degassed with a stream of Ar 2 times. Raney nickel (200 mg) was added and a vacuum was pulled for 1 min. A balloon of H$_2$ was added and the reaction mixture was stirred for 16 h at RT. Upon completion, the reaction mixture was degassed with a stream of Ar 2 times. The catalyst was removed by diatomaceous earth filtration and the solution was concd. The residue was taken up in 5% H$_2$O in MeOH, filtered (0.2 μm syringe filter), and the filtrate was concd under vacuum to give N-butyl 3-(aminomethyl)-5,7-dihydro-6H-pyrrolo[3,4-b]pyridine-6-carboxylate (203 mg, 80% yield).

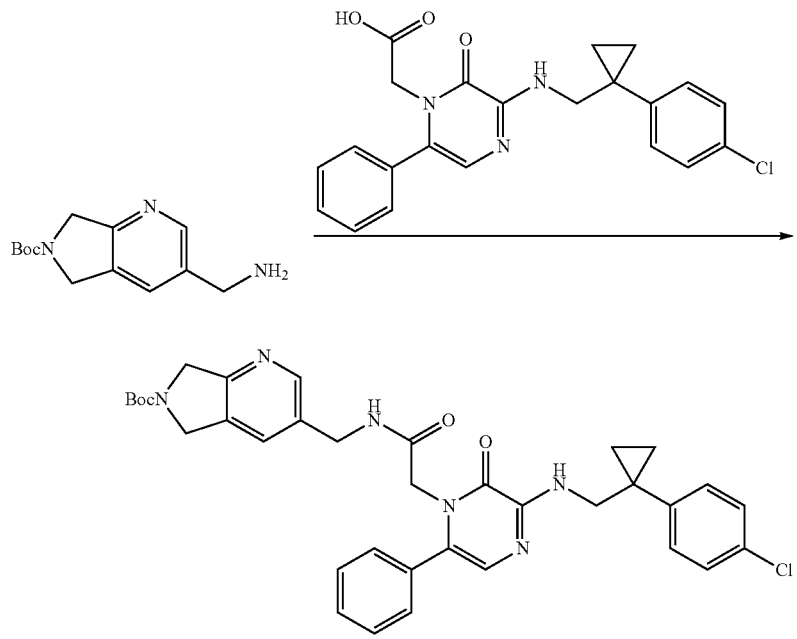

Step 3: tert-Butyl 3-((2-(3-(((1-(4-chlorophenyl)cyclopropyl)methyl)amino)-2-oxo-6-phenylpyrazin-1(2H)-yl)acetamido)methyl)-5,7-dihydro-6H-pyrrolo[3,4b]pyridine-6-carboxylate was synthesized from tert-butyl 3-(aminomethyl)-5,7-dihydro-6H-pyrrolo[3,4-b]pyridine-6-carboxylate (20 mg, 0.08 mmol) and 2-(3-(((1-(4-chlorophenyl)cyclopropyl)methyl)amino)-2-oxo-6-phenylpyrazin-1(2H)-yl)acetic acid (29 mg, 0.07 mmol, prepared according to Example 23, steps 1-2 using (1-(4-chlorophenyl)cyclopropyl)methanamine) according to Example 23, step 3 except that the crude material was purified by chromatography (0-100% EtOAc-hexanes).

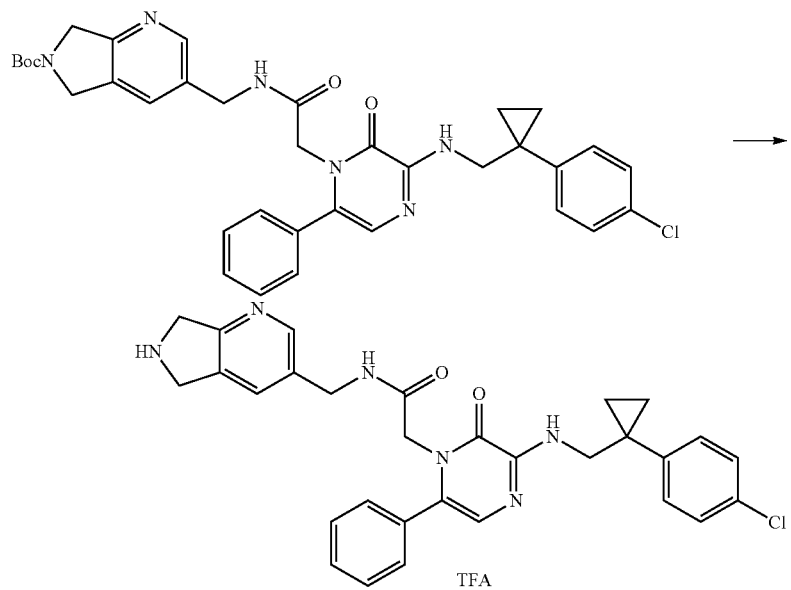

TFA

Step 4: Deprotection of tert-butyl 3-((2-(3-(((1-(4-chlorophenyl)cyclopropyl)methyl)amino)-2-oxo-6-phenylpyrazin-1(2H)-yl)acetamido)methyl)-5,7-dihydro-6H-pyrrolo[3,4-b]pyridine-6-carboxylate (67 mg, 0.1 mmol) was conducted according to Example 25, step 1.

Example 30

Preparation of N-((1H-Pyrrolo[3,2-c]Pyridin-2-yl)Methyl)-2-(3-(((1-(4-Chlorophenyl)Cyclopropyl)Methyl)Amino)-6-(1-Methyl-1H-Pyrazol-4-yl)-2-Oxopyrazin-1(2H)-yl)Acetamide Trifluoroacetate (Compound 65)

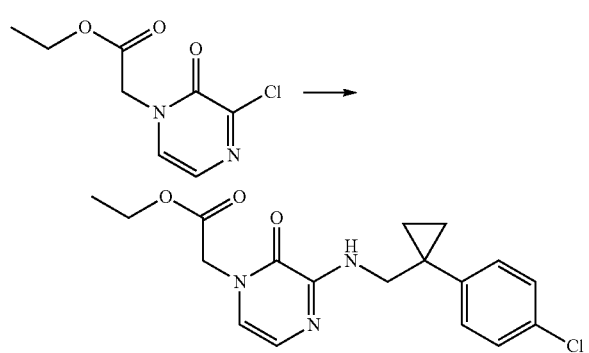

Step 1: To a solution of ethyl 2-(3-chloro-2-oxopyrazin-1(2H)-yl)acetate (100 mg, 0.46 mmol) in acetonitrile (5 mL, 0.09 M) was added (1-(4-chlorophenyl)cyclopropyl)methanamine (91 mg, 0.5 mmol), DIEA (0.28 mL, 1.61 mmol), and NaI (138 mg, 0.92 mmol). After stirring for 18 h at 70° C., the reaction mixture was washed with H₂O and extracted with EtOAc. The organic layer was dried over anhyd Na₂SO₄, filtered, and concd under vacuum. The residue was purified by chromatography (0-100% EtOAc-heptanes) to give ethyl 2-(3-(((1-(4-chlorophenyl)cyclopropyl)methyl)amino)-2-oxopyrazin-1(2H)-yl)acetate (80 mg, 48% yield).

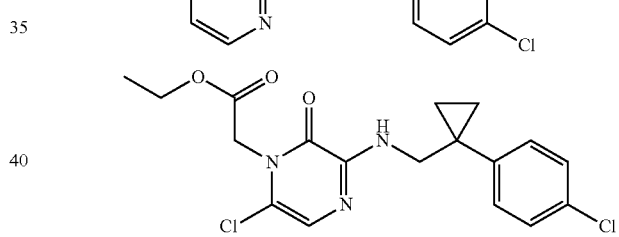

Step 2: To a solution of ethyl 2-(3-(((1-(4-chlorophenyl)cyclopropyl)methyl)amino)-2-oxopyrazin-1(2H)-yl)acetate (80 mg, 0.22 mmol) in acetonitrile (2 mL, 0.1 M) was added NCS (30 mg, 0.23 mmol) slowly. After stirring for 1.5 h at 70° C., the reaction mixture was concd and the residue was purified by chromatography (0-100% EtOAc-heptanes) to give ethyl 2-(6-chloro-3-(((1-(4-chlorophenyl)cyclopropyl)methyl)amino)-2-oxopyrazin-1(2H)-yl)acetate (69 mg, 79% yield).

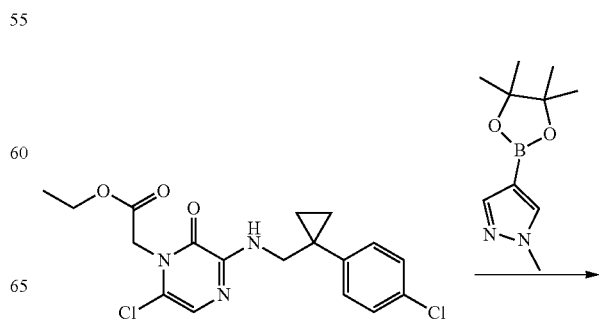

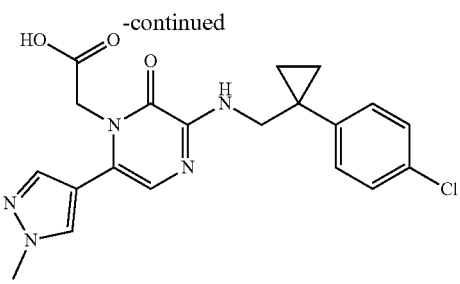

Step 3: To a solution of ethyl 2-(6-chloro-3-(((1-(4-chlorophenyl)cyclopropyl)methyl)amino)-2-oxopyrazin-1(2H)-yl)acetate (69 mg, 0.17 mmol), 1-methyl-4-(4,4,5,5-tetramethyl-1,3,2-dioxaborolan-2-yl)-1H-pyrazole (44 mg, 0.21 mmol), K₂CO₃ (72 mg, 0.52 mmol) in dioxane (2.4 mL) and H₂O (0.6 mL) was added Pd(PPh₃)₄ (72 mg, 0.52 mmol) under N₂. After stirring for 18 h at 100° C., the reaction mixture was diluted with methanol and concd. The residue was taken up in MeOH, filtered (0.2 μm syringe filter), and the filtrate was concd under vacuum. The residue was purified by chromatography (0-20% MeOH—CH₂Cl₂) to give 2-(3-(((1-(4-chlorophenyl)cyclopropyl)methyl)amino)-6-(1-methyl-1H-pyrazol-4-yl)-2-oxopyrazin-1(2H)-yl)acetic acid (43 mg, 60% yield).

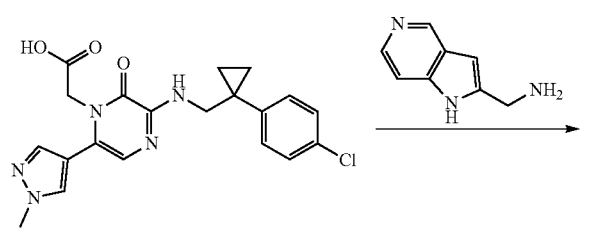

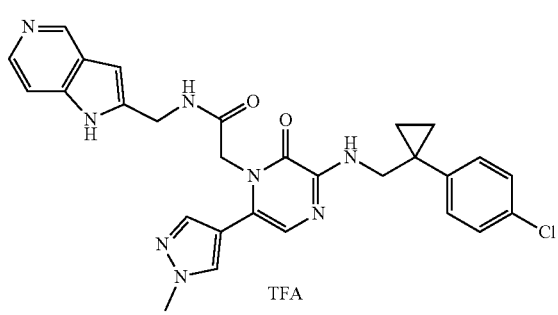

TFA

Step 4: N-((1H-Pyrrolo[3,2-c]pyridin-2-yl)methyl)-2-(3-(((1-(4-chlorophenyl)cyclopropyl)-methyl)amino)-6-(1-methyl-1H-pyrazol-4-yl)-2-oxopyrazin-1(2??)-yl)acetamide trifluoroacetate was synthesized from 2-(3-(((1-(4-chlorophenyl)cyclopropyl)methyl)amino)-6-(1-methyl-1H-pyrazol-4-yl)-2-oxopyrazin-1(2H)-yl)acetic acid (43 mg, 0.1 mmol) according to Example 23, step 3.

Example 31

Preparation of 2-(6-(1-Methyl-1H-Pyrazol-4-yl)-2-Oxo-3-(Phenethylamino)Pyrazin-1(2H)-yl)-N-((4,5,6,7-Tetrahydrothieno[3,2-c]Pyridin-2-yl)Methyl)Acetamide (Compound 78)

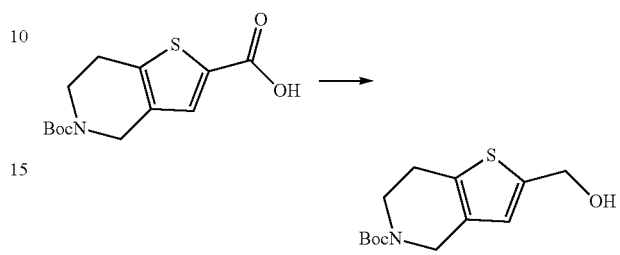

Step 1: A stirred solution of 5-(tert-butoxycarbonyl)-4,5,6,7-tetrahydrothieno[3,2-c]pyridine-2-carboxylic acid (1.01 g, 3.58 mmol) in THF (7.5 mL) was set under N₂ atmosphere. A solution of 1 M BH₃.THF (14 mL, 14 mmol) was added dropwise at 0° C. The reaction was stirred at RT for 16 h. Sat. aq NaHCO₃ was added dropwise at 0° C. The reaction mixture was extracted with EtOAc 3 times. The organic layers were combined, washed with brine, dried over Na₂SO₄, vacuum filtered, and evaporated under reduced pressure. The crude product was dissolved in CH₂Cl₂ and adsorbed onto silica gel. Purification by chromatography (0-100% EtOAc-hexanes) afforded tert-butyl 2-(hydroxymethyl)-6,7-dihydrothieno[3,2-c]pyridine-5(4H)-carboxylate (905 mg, 94% yield).

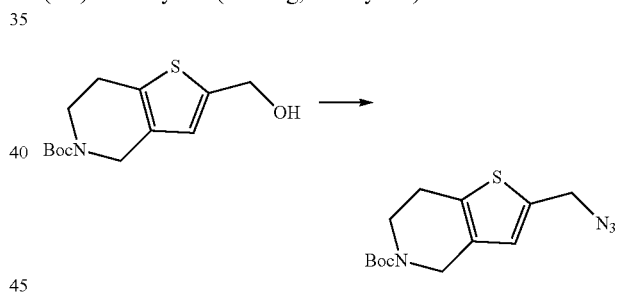

Step 2: To a stirred solution of tert-butyl 2-(hydroxymethyl)-6,7-dihydrothieno[3,2-c]pyridine-5(4H)-carboxylate (197 mg, 0.73 mmol) in THF (3.7 mL) was added DIAD (0.3 mL, 1.53 mmol) and PPh₃ (386 mg, 1.47 mmol) at RT. After purging with N₂, DPPA (0.32 mL, 1.48 mmol) was added at 0° C. The reaction was stirred at RT for 5 h and quenched with water. The reaction mixture was extracted with EtOAc 3 times. The organic layers were combined, washed with brine, dried over Na₂SO₄, vacuum filtered, and evaporated under reduced pressure. The crude product was dissolved in CH₂Cl₂ and adsorbed onto silica gel. Purification by chromatography (0-10% EtOAc-hexane) afforded tert-butyl 2-(azidomethyl)-6,7-dihydrothieno[3,2-c]pyridine-5(4H)-carboxylate (97 mg, 45% yield).

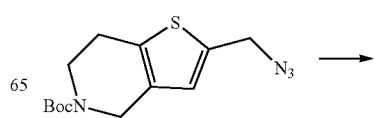

-continued

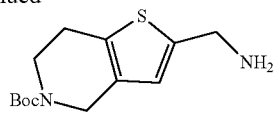

Step 3: To a stirred solution of tert-butyl 2-(azidomethyl)-6,7-dihydrothieno[3,2-c]pyridine-5(4H)-carboxylate (97.2 mg, 0.33 mmol) in THF (1.2 mL) and water (0.14 mL) was added PPh₃ (132 mg, 0.50 mmol). The reaction was stirred at RT for 16 h and quenched with 1 N KHSO₄. The resulting mixture was washed with diethyl ether 3 times. The pH of the aqueous layer was adjusted to 12 by adding 5 N NaOH solution. The basic aqueous layer was extracted with EtOAc 3 times. The organic layers were combined, washed with brine, dried over Na₂SO₄, vacuum filtered, and evaporated under reduced pressure. The crude product was dissolved in CH₂Cl₂ and adsorbed onto silica gel. Purification by chromatography (0-10% 7 N NH₃ in MeOH—CH₂Cl₂) afforded tert-butyl 2-(aminomethyl)-6,7-dihydrothieno[3,2-c]pyridine-5(4H)-carboxylate (61.2 mg, 69% yield).

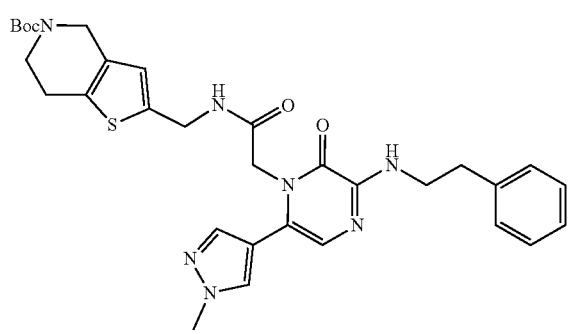

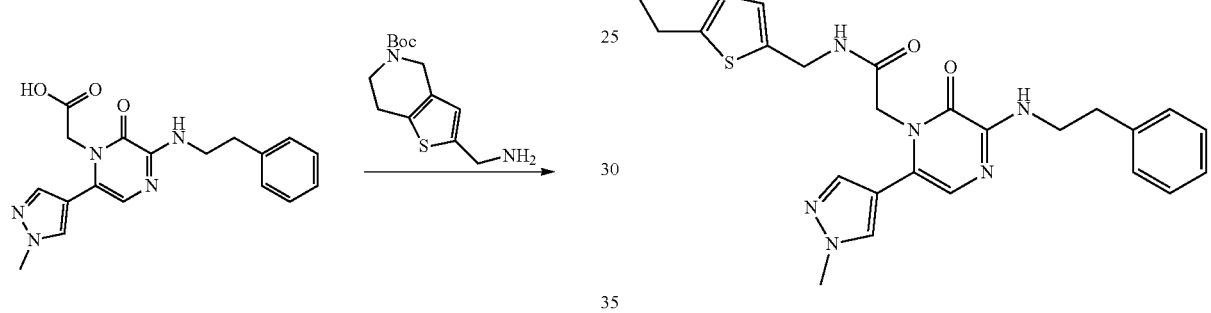

Step 4: To a stirred solution of 2-(6-(1-methyl-1H-pyrazol-4-yl)-2-oxo-3-(phenethylamino)pyrazin-1(2H)-yl)acetic acid (31.4 mg, 0.09 mmol, prepared using the procedure given for Example 7, steps 1-4, Example 8, step 1, and Example 3, step 3 using the appropriate starting materials) and tert-butyl 2-(aminomethyl)-6,7-dihydrothieno[3,2-c]pyridine-5(4H)-carboxylate (30 mg, 0.11 mmol) in DMF (1 mL) was added DIEA (50 μL, 0.29 mmol) at RT. After purging with N₂ and cooled to 0° C., HATU (37 mg, 0.097 mmol) was added. The reaction was stirred at RT for 16 h and evaporated under reduced pressure. The crude product was dissolved in CH₂Cl₂ and adsorbed onto silica gel. Purification by chromatography (0-10% MeOH—CH₂Cl₂) afforded tert-butyl 2-((2-(6-(1-methyl-1H-pyrazol-4-yl)-2-oxo-3-(phenethylamino)pyrazin-1(2H)-yl)acetamido)methyl)-6,7-dihydrothieno[3,2-c]pyridine-5(4H)-carboxylate (38.7 mg, 72% yield).

Step 5: To a stirred solution of tert-butyl 2-((2-(6-(1-methyl-1H-pyrazol-4-yl)-2-oxo-3-(phenethylamino)pyrazin-1(2H)-yl)acetamido)methyl)-6,7-dihydrothieno[3,2-c]pyridine-5(4H)-carboxylate (38.7 mg, 0.064 mmol) in CH₂Cl₂ (1 mL) was added TES (100 μL, 0.63 mmol) at RT and followed by TFA (1 mL) at 0° C. The reaction mixture was stirred at RT for 4 h. Volatiles were evaporated under reduced pressure. The crude product was purified by chromatography using (0-10% 7 N NH₃ in MeOH—CH₂Cl₂) affording 2-(6-(1-methyl-1H-pyrazol-4-yl)-2-oxo-3-(phenethylamino)pyrazin-1(2H)-yl)-N-((4,5,6,7-tetrahydrothieno[3,2-c]pyridin-2-yl)methyl)acetamide (25.3 mg, 78% yield).

The following compound was prepared according to the foregoing procedure using the appropriate amine starting material:

| Compound Name | Cmp No. |
|---|---|
| 2-(6-(1-Methyl-1H-pyrazol-4-yl)-2-oxo-3-(phenethylamino)pyrazin-1(2H)-yl)-N-((4,5,6,7-tetrahydrothieno[2,3-c]pyridin-2-yl)methyl)acetamide | 79 |

Example 32

Preparation of 2-(6-(1-Methyl-1H-Pyrazol-4-yl)-2-Oxo-3-(Phenethylamino)Pyrazin-1(2H)-yl)-N-((1,2,3,4-Tetrahydroisoquinolin-6-yl)Methyl)Acetamide (Compound 80)

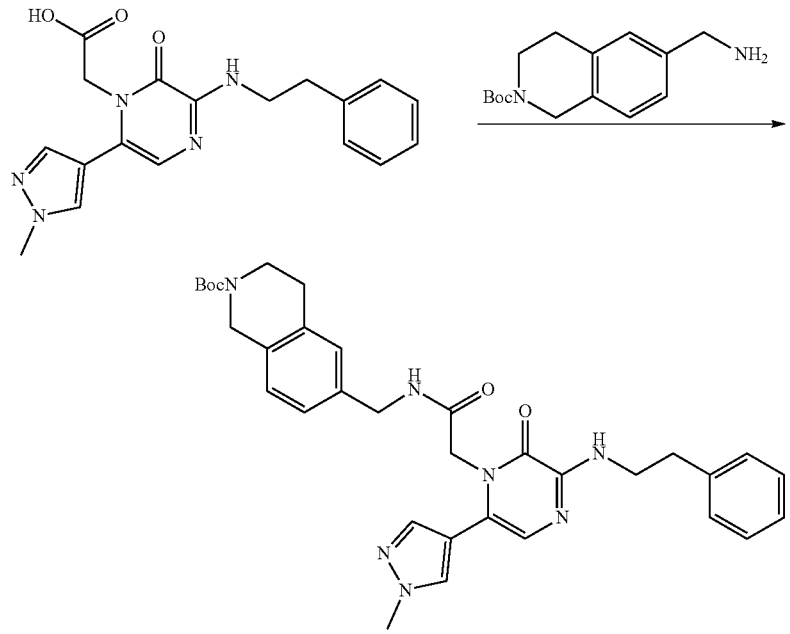

Step 1: tert-Butyl 6-((2-(6-(1-methyl-1H-pyrazol-4-yl)-2-oxo-3-(phenethylamino)pyrazin-1(2H)-yl)acetamido)methyl)-3,4-dihydroisoquinoline-2(1H)-carboxylate was synthesized according to Example 31, step 4.

Step 2: The title compound was synthesized according to Example 31, step 5.

Example 33

Preparation of 2-(2-Oxo-3-(Phenethylamino)-6-Phenylpyrazin-1(2H)-yl)-N-((4,5,6,7-Tetrahydrothieno[2,3-c]Pyridin-2-yl)Methyl)Acetamide (Compound 83)

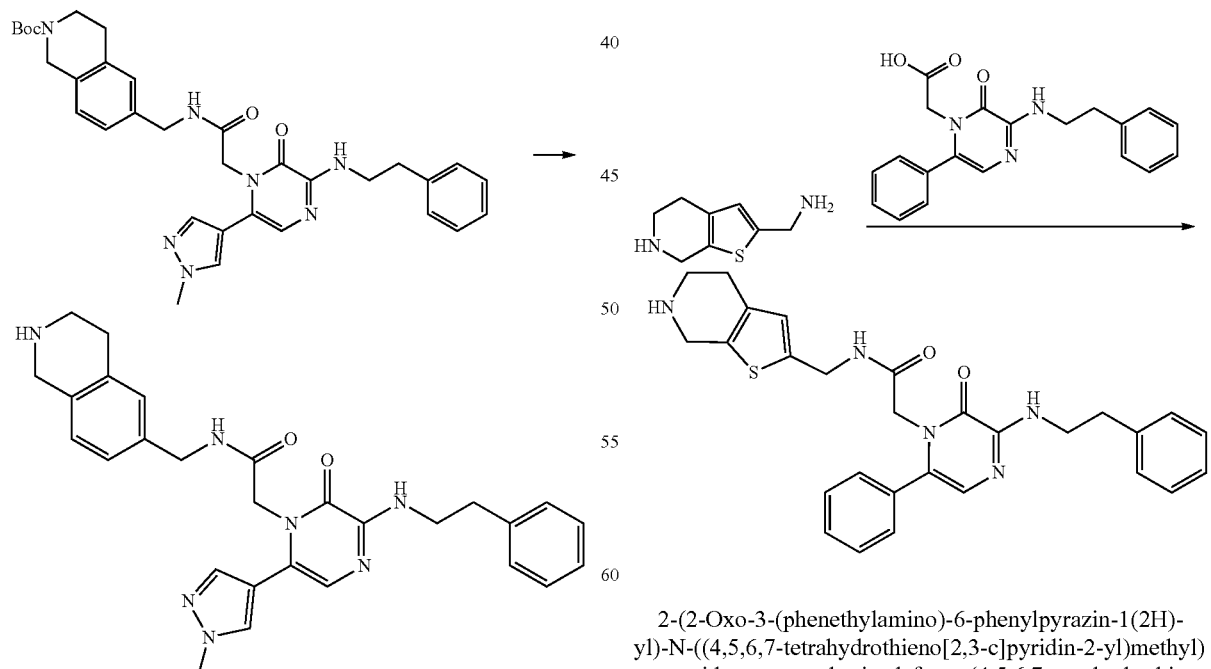

2-(2-Oxo-3-(phenethylamino)-6-phenylpyrazin-1(2H)-yl)-N-((4,5,6,7-tetrahydrothieno[2,3-c]pyridin-2-yl)methyl)acetamide was synthesized from (4,5,6,7-tetrahydrothieno[2,3-c]pyridin-2-yl)methanamine (35 mg, 0.2 mmol) and 2-(2-oxo-3-(phenethylamino)-6-phenylpyrazin-1(2H)-yl)acetic acid (60 mg, 0.17 mmol, prepared according to

Example 34

Preparation of N-((3-Chloro-1H-Pyrrolo[2,3-b]Pyridin-5-yl)Methyl)-2-(6-(1-Methyl-1H-Pyrazol-4-yl)-2-Oxo-3-(Phenethylamino)Pyrazin-1(2H)-yl)Acetamide (Compound 81)

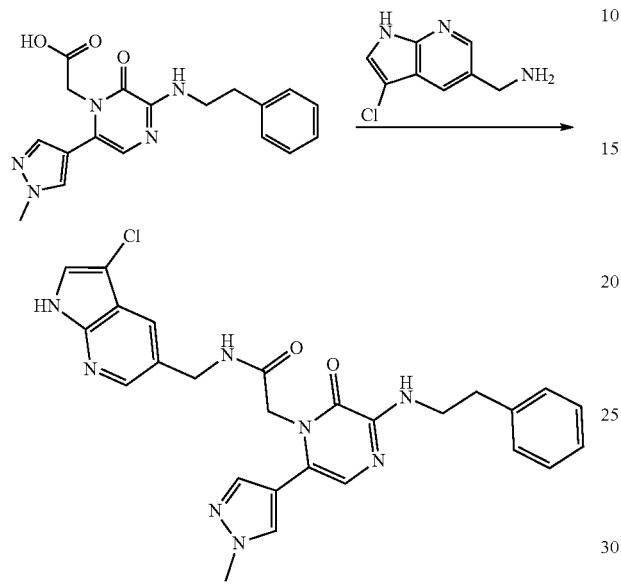

N-((3-Chloro-1H-pyrrolo[2,3-b]pyridin-5-yl)methyl)-2-(6-(1-methyl-1H-pyrazol-4-yl)-2-oxo-3-(phenethylamino)pyrazin-1(2H)-yl)acetamide was synthesized by coupling 2-(6-(1-methyl-1H-pyrazol-4-yl)-2-oxo-3-(phenethylamino)pyrazin-1(2H)-yl)acetic acid with (3-chloro-1H-pyrrolo[2,3-b]pyridin-5-yl)methanamine (described in PCT Publication No. 2019/231935) according to Example 31, step 4 except that the final product was purified by chromatography using (0-10% 7 N NEE in MeOH—CH$_2$Cl$_2$).

The following compound was prepared according to the procedure described in PCT Publication No. 2019/231935, with the appropriate nitrile starting material and purification via reverse-phase HPLC:

| Compound Name | Cmp No. |
|---|---|
| N-((3-Chlorothieno[2,3-b]pyridin-5-yl)methyl)-2-(6-(1-methyl-1H-pyrazol-4-yl)-2-oxo-3-(phenethylamino)pyrazin-1(2H)-yl)acetamide | 82 |

Example 35

Preparation of N-((1H-Pyrrolo[3,2-c]Pyridin-2-yl)Methyl)-2-(6-(2-Fluorophenyl)-2-Oxo-3-(Phenethylamino)Pyrazin-1(2H)-yl)Acetamide Trifluoroacetate (Compound 86)

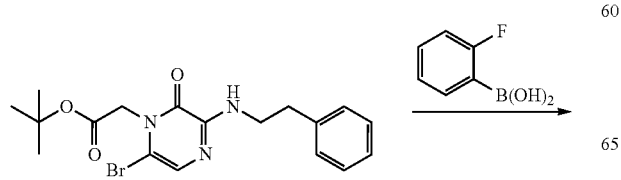

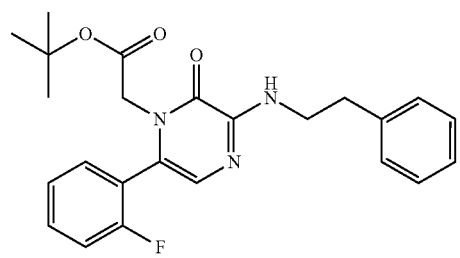

Step 1: A 20 mL pressure vial was charged with tert-butyl 2-(6-bromo-2-oxo-3-(phenethylamino)pyrazin-1(2H)-yl)acetate (61 mg, 0.15 mmol), 4-fluorophenylboronic acid (32 mg, 0.23 mmol), Pd(dppf)Cl$_2$ (11 mg, 0.015 mmol) and K$_2$CO$_3$ (41 mg, 0.3 mmol). The vial was purged with argon, then 1,4-dioxane (1.5 mL) and H$_2$O (150 µL) were added and the reaction vessel sealed and stirred at 80° C. for 12 h. Upon completion by LCMS, the mixture was evaporated to dryness. The crude material was then purified by chromatography (55% EtOAc-heptanes) to afford tert-butyl 2-(6-(2-fluorophenyl)-2-oxo-3-(phenethylamino)pyrazin-1(2H)-yl)acetate as a colorless oil (43 mg, 68% yield).

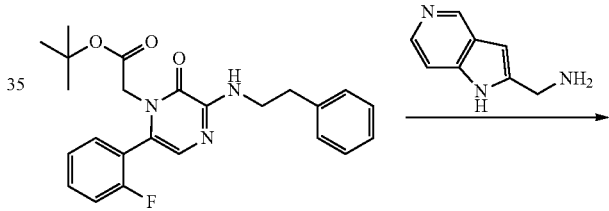

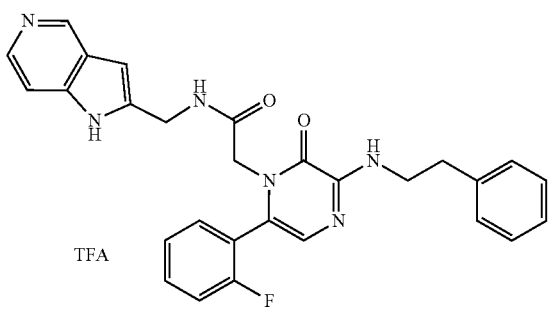

Steps 2-3: The title compound was prepared as a white powder (14 mg, 22% yield) according to the procedure given for Example 3, steps 3-4 using the appropriate amine starting material.

The following compounds were prepared according to the foregoing procedure using the appropriate starting materials:

| Compound Name | Cmp No. |
|---|---|
| N-((1H-Pyrrolo[3,2-c]pyridin-2-yl)methyl)-2-(2-oxo-3-(phenethylamino)-6-(o-tolyl)pyrazin-1(2H)-yl)acetamide trifluoroacetate | 87 |
| N-((1H-Pyrrolo[3,2-c]pyridin-2-yl)methyl)-2-(6-(3-(hydroxymethyl)phenyl)-2-oxo-3-(phenethylamino)pyrazin-1(2H)-yl)acetamide trifluoroacetate | 88 |

Example 36

Preparation of N-((1H-Pyrrolo[3,2-c]Pyridin-2-yl)Methyl)-2-(6-(5-Chlorothiophen-2-yl)-2-Oxo-3-(Phenethylamino)Pyrazin-1(2H)-yl)Acetamide (Compound 89)

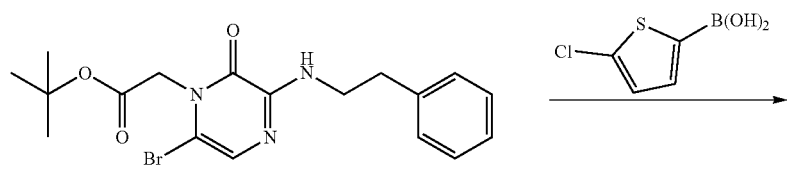

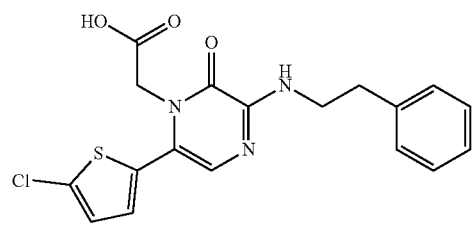

Steps 1-2: 2-(6-(5-Chlorothiophen-2-yl)-2-oxo-3-(phenethylamino)pyrazin-1(2H)-yl)acetic acid was prepared as a colorless oil (9 mg, 52% yield) according to Example 35, steps 1-2 using the appropriate boronic acid.

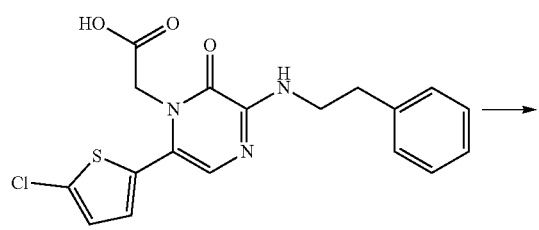

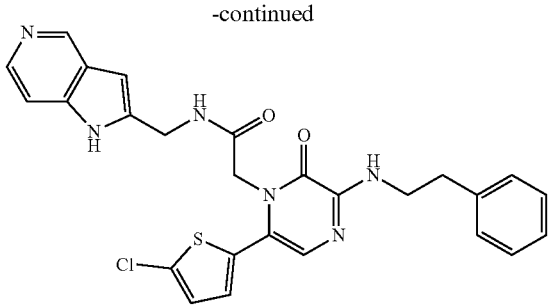

Step 3: The title compound was prepared as a yellow powder (7 mg, 61% yield) according to Example 23, step 3 using the appropriate amine starting material except that the crude material was purification by chromatography (0-10% 7 N NEE in MeOH—CH$_2$Cl$_2$).

The following compounds were prepared according to the foregoing procedure using the appropriate boronic acid and amine starting materials:

| Compound Name | Cmp No. |
| --- | --- |
| N-((1H-pyrrolo[3,2-c]pyridin-2-yl)methyl)-2-(6-(1-(oxetan-3-yl)-1H-pyrazol-4-yl)-2-oxo-3-(phenethylamino)pyrazin-1(2H)-yl)acetamide trifluoroacetate | 90 |
| N-((1H-Pyrrolo[3,2-c]pyridin-2-yl)methyl)-2-(6-(3-(2-hydroxypropan-2-yl)phenyl)-2-oxo-3-(phenethylamino)pyrazin-1(2H)-yl)acetamide | 92 |
| Methyl 2-(3-(1-(2-(((1H-pyrrolo[3,2-c]pyridin-2-yl)methyl)amino)-2-oxoethyl)-6-oxo-5-(phenethylamino)-1,6-dihydropyrazin-2-yl)phenyl)acetate trifluoroacetate | 93 |
| N-((1H-Pyrrolo[3,2-c]pyridin-2-yl)methyl)-2-(2-oxo-3-(phenethylamino)-6-(3-(2,2,2-trifluoro-1-hydroxyethyl)phenyl)pyrazin-1(2H)-yl)acetamide | 97 |
| N-((1H-Pyrrolo[3,2-c]pyridin-2-yl)methyl)-2-(6-(3-(1-hydroxycyclopropyl)phenyl)-2-oxo-3-(phenethylamino)pyrazin-1(2H)-yl)acetamide | 98 |
| N-((1H-Pyrrolo[3,2-c]pyridin-2-yl)methyl)-2-(6-(3-(3-hydroxyoxetan-3-yl)phenyl)-2-oxo-3-(phenethylamino)pyrazin-1(2H)-yl)acetamide | 99 |

The following compounds were prepared according to the foregoing procedure using the appropriate boronic acid and amine starting materials and purification via column chromatography (amine, MeOH—CH$_2$Cl$_2$):

| Compound Name | Cmp No. |
| --- | --- |
| N-((1H-Pyrrolo[3,2-c]pyridin-2-yl)methyl)-2-(6-(4-fluorophenyl)-2-oxo-3-(phenethylamino)pyrazin-1(2H)-yl)acetamide | 106 |
| N-((1H-Pyrrolo[3,2-c]pyridin-2-yl)methyl)-2-(6-(2,5-difluorophenyl)-2-oxo-3-(phenethylamino)pyrazin-1(2H)-yl)acetamide | 107 |
| N-((1H-Pyrrolo[3,2-c]pyridin-2-yl)methyl)-2-(6-(2,5-dimethylphenyl)-2-oxo-3-(phenethylamino)pyrazin-1(2H)-yl)acetamide | 108 |

Example 37

Preparation of N-((1H-Pyrrolo[3,2-c]Pyridin-2-yl)Methyl)-2-(2-Oxo-3-(Phenethylamino)-6-(3-(Prop-1-en-2-yl)Phenyl)Pyrazin-1(2H)-yl)Acetamide (Compound 91)

The title compound was isolated as a side-product (38 mg, 49% yield) from the preparation of N-((1H-pyrrolo[3,2-c]pyridin-2-yl)methyl)-2-(6-(3-(2-hydroxypropan-2-yl)phenyl)-2-oxo-3-(phenethylamino)pyrazin-1(2H)-yl)acetamide.

Example 38

Preparation of 2-(3-(1-(2-(((1H-Pyrrolo[3,2-c]Pyridin-2-yl)Methyl)Amino)-2-Oxoethyl)-6-Oxo-5-(Phenethylamino)-1,6-Dihydropyrazin-2-yl)Phenyl)Acetic Acid Trifluoroacetate (Compound 94)

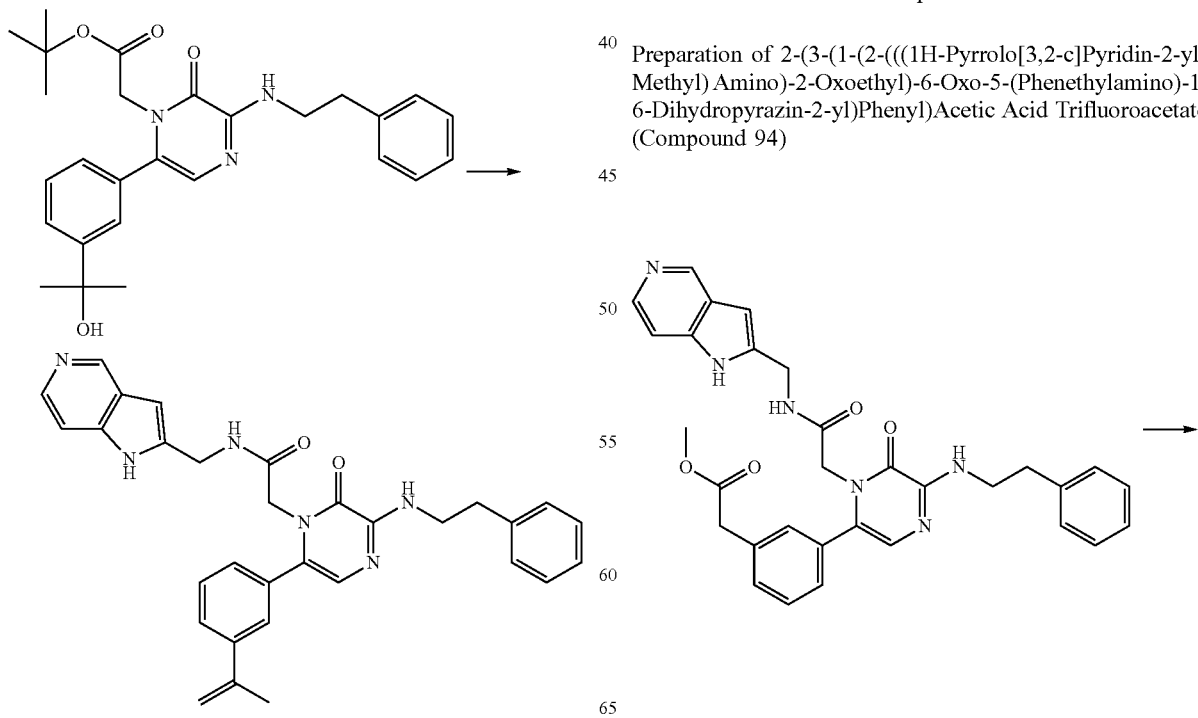

-continued

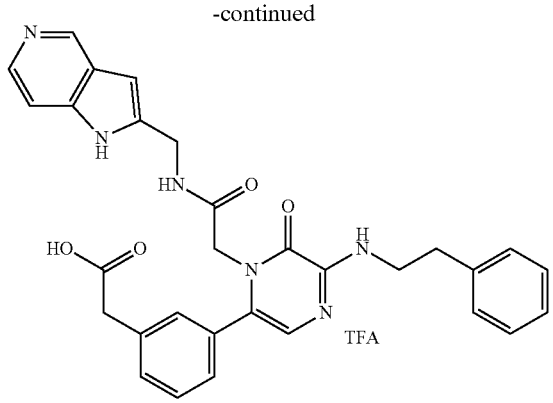

The title compound was prepared as a white powder (48 mg, 53% yield) from methyl 2-(3-(1-(2-(((1H-pyrrolo[3,2-c]pyridin-2-yl)methyl)amino)-2-oxoethyl)-6-oxo-5-(phenethylamino)-1,6-dihydropyrazin-2-yl)phenyl)acetate using the procedure given for Example 10.

Example 39

Preparation of N-((1H-Pyrrolo[3,2-c]Pyridin-2-yl)Methyl)-2-(6-(3-(Methylsulfonamidomethyl)Phenyl)-2-Oxo-3-(Phenethylamino)Pyrazin-1(2H)-yl)Acetamide (Compound 95)

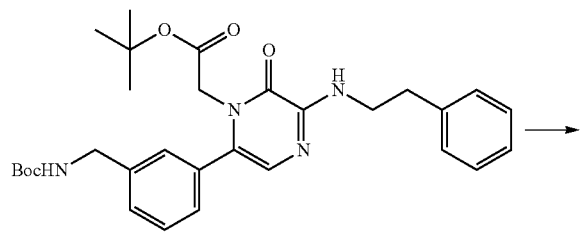

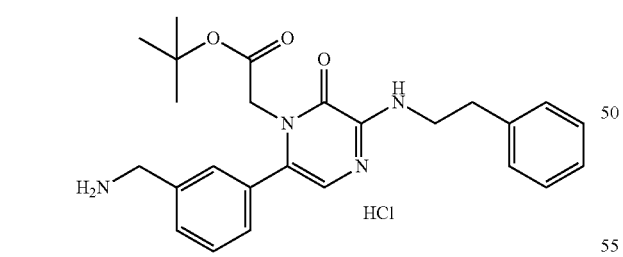

Step 1: tert-Butyl 2-(6-(3-((((tert-butoxycarbonyl)amino)methyl)phenyl)-2-oxo-3-(phenethylamino)pyrazin-1(2H)-yl)acetate (240 mg, 0.45 mmol, prepared according to Example 36, step 1) was dissolved in EtOAc (5 mL) and cooled to 0° C. HCl gas was bubbled in and the resulting solution allowed to stand at RT for 1 h. The reaction mixture was then concentrated, taken up in MeCN/H$_2$O and lyophilized to afford tert-butyl 2-(6-(3-(aminomethyl)phenyl)-2-oxo-3-(phenethyl amino)pyrazin-1(2H)-yl)acetate hydrochloride (212 mg, 100% yield) as a white solid.

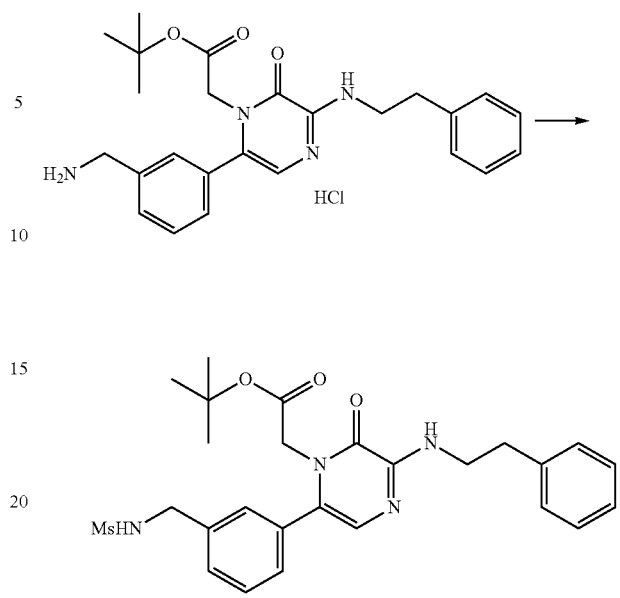

Step 2: tert-Butyl 2-(6-(3-(aminomethyl)phenyl)-2-oxo-3-(phenethylamino)pyrazin-1(2H)-yl)acetate hydrochloride (70 mg, 0.15 mmol) was suspended in CH$_2$Cl$_2$ (1.5 mL) and treated with Et$_3$N (73 µL, 0.5 mmol). After 5 min, methanesulfonyl chloride (12 µL, 0.15 mmol) was added and the reaction mixture was stirred for 1 h. Upon completion, the reaction was diluted with CH$_2$Cl$_2$, then washed with sat. NH$_4$Cl and brine. The organic layer was then dried over Na$_2$SO$_4$, filtered and concentrated to afford tert-butyl 2-(6-(3-(methylsulfonamidomethyl)phenyl)-2-oxo-3-(phenethylamino)pyrazin-1(2H)-yl)acetate. The crude product was carried as is to the next step.

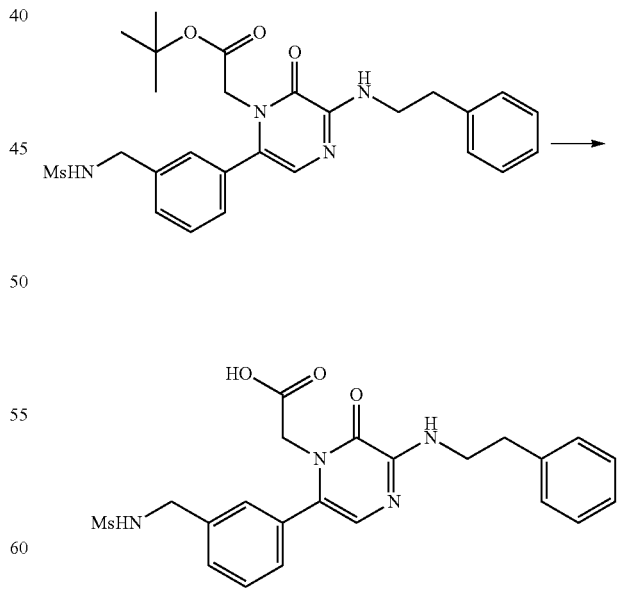

Step 3: 2-(6-(3-(Methylsulfonamidomethyl)phenyl)-2-oxo-3-(phenethylamino)pyrazin-1(2H)-yl)acetic acid was prepared as a colorless oil according to the procedure given for Example 3, step 3.

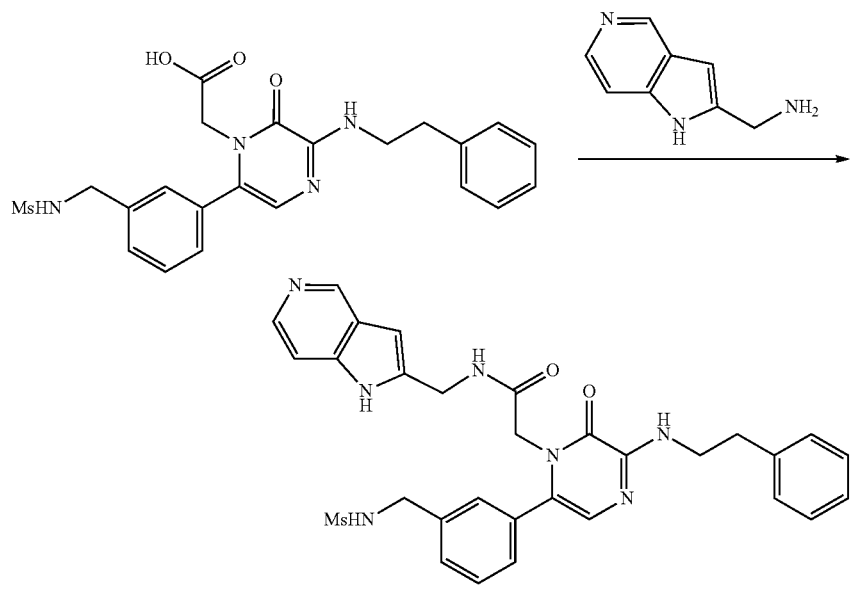

Step 4: A 20 mL reaction vial was charged with 2-(6-(3-(methylsulfonamidomethyl)phenyl)-2-oxo-3-(phenethylamino)pyrazin-1(2H)-yl)acetic acid (68 mg, 0.15 mmol), NHS (21 mg, 0.18 mmol) and $CH_2Cl_2$ (1.5 mL). DCC (35 mg, 0.17 mmol) was added in a single portion, followed by 5-(aminomethyl)-6-methylpyridin-2-amine (26 mg, 0.18 mmol) in DMF (1 mL) after 10 min. The reaction mixture was then stirred at RT until completion, filtered through Celite® with $CH_2Cl_2$ and concentrated. The resulting residue was purified by chromatography (0-10% 7 N $NH_3$ in MeOH—$CH_2Cl_2$) to afford the title compound as a white powder (4.2 mg, 5% yield over 3 steps).

Example 40

Preparation of N-((1H-Pyrrolo[3,2-c]Pyridin-2-yl)Methyl)-2-(6-(3-(Aminomethyl)Phenyl)-2-Oxo-3-(Phenethylamino) Pyrazin-1(2H)-yl)Acetamide (Compound 96)

The title compound was prepared as an off-white powder (6 mg, 16% yield) from tert-butyl 2-(6-(3-(aminomethyl)phenyl)-2-oxo-3-(phenethylamino)pyrazin-1(2H)-yl)acetate hydrochloride according to Example 39, steps 3-4.

Example 40

Preparation of N-((1H-Pyrrolo[3,2-c]Pyridin-2-yl)Methyl)-2-(6-(3-(1-Hydroxyethyl)Phenyl)-2-Oxo-3-(Phenethylamino)Pyrazin-1(2H)-yl)Acetamide (Compound 100)

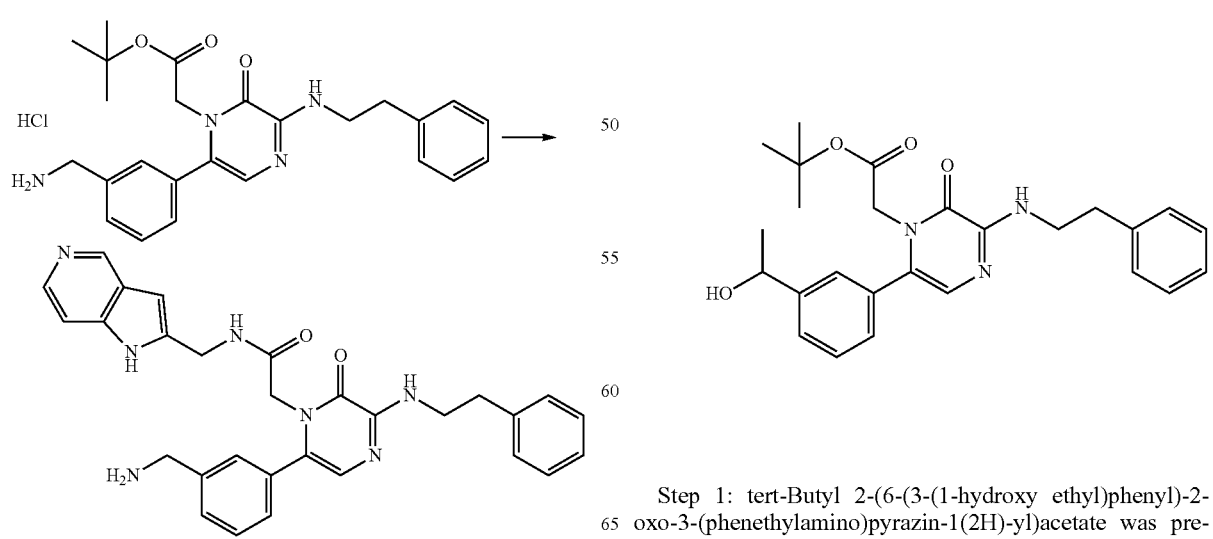

Step 1: tert-Butyl 2-(6-(3-(1-hydroxy ethyl)phenyl)-2-oxo-3-(phenethylamino)pyrazin-1(2H)-yl)acetate was prepared as a white powder (33 mg, 57% yield) according to Example 35, step 1 using the appropriate boronic acid.

159

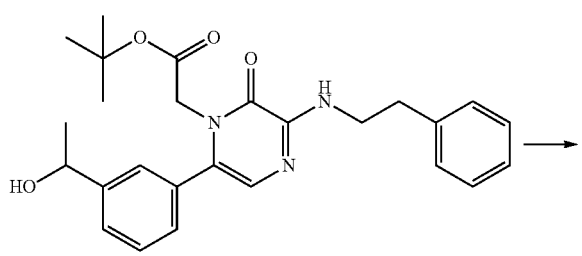

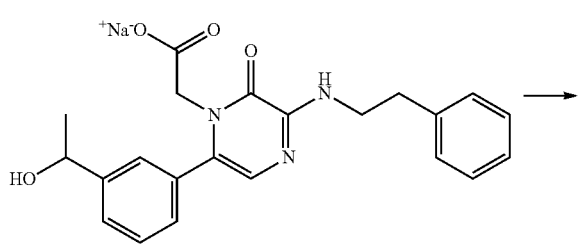

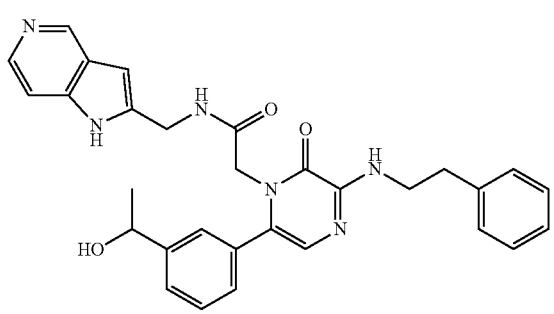

Step 2: tert-Butyl 2-(6-(3-(1-hydroxy ethyl)phenyl)-2-oxo-3-(phenethylamino)pyrazin-1(2H)-yl)acetate (33 mg, 0.07 mmol) was dissolved in MeOH (1 mL) and treated with 1 N NaOH (1 mL). Upon completion, the reaction mixture was concd under vacuum then taken up in a minimal amount of DMF and filtered through a fine filter funnel and carried to the next step.

Step 3: The title compound was prepared as a white powder (9 mg, 25% yield over 2 steps) according to Example 39, step 4.

160

Example 41

Preparation of N-((6-Amino-2-Methylpyridin-3-yl)Methyl)-2-(6-(2-Aminopyridin-4-yl)-2-Oxo-3-(Phenethylamino)Pyrazin-1(2H)-yl)Acetamide (Compound 84)

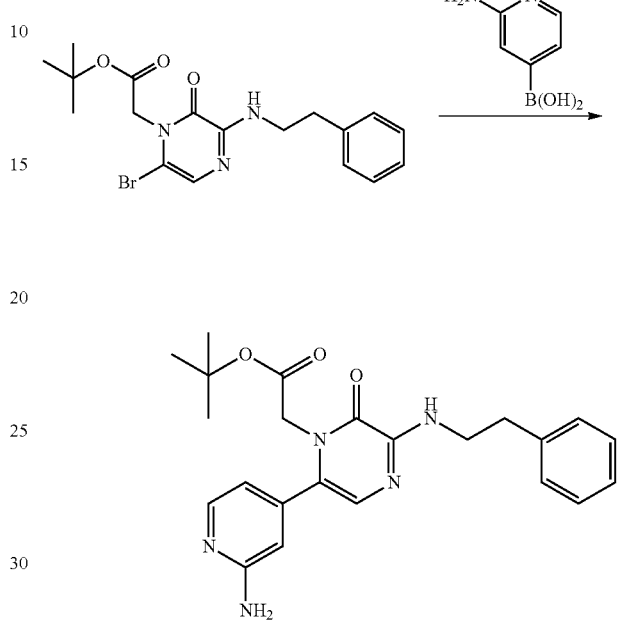

Step 1: A 20 mL pressure vial was charged with tert-butyl 2-(6-bromo-2-oxo-3-(phenethylamino)pyrazin-1(2H)-yl)acetate (41 mg, 0.1 mmol), (2-aminopyridin-4-yl)boronic acid (21 mg, 0.15 mmol), Pd-XPhos-G2 (4 mg, 0.005 mmol) and K₃PO₄ (43 mg, 0.2 mmol). The vial was purged with argon, then 1,4-dioxane (1 mL) and H₂O (100 μL) were added and the reaction vessel sealed and stirred at 80° C. for 16 h. LCMS showed conversion to both the desired product and the de-halogenated starting material. The mixture was evaporated to dryness and purified by chromatography (amine column, 50% EtOAc-hexanes) to afford tert-butyl 2-(6-(2-aminopyridin-4-yl)-2-oxo-3-(phenethylamino)pyrazin-1(2H)-yl)acetate as a yellow solid (21 mg, 43% yield).

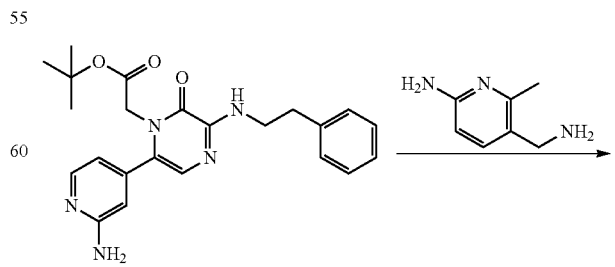

161

-continued

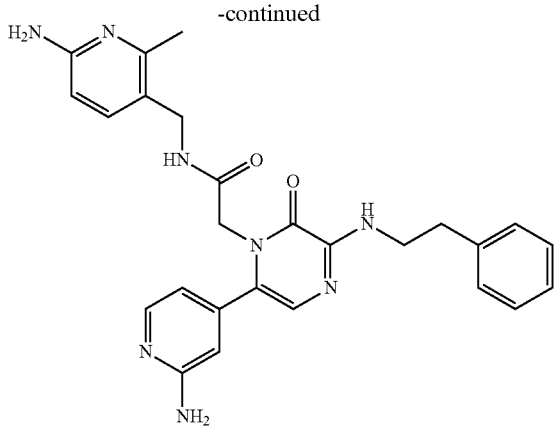

Steps 2-3: The title compound was prepared as a yellow powder (35 mg, 72% yield) according to Example 36, steps 2-3 using the appropriate amine starting material. The following compounds were prepared according to the foregoing procedure using the appropriate boronic acid and amine starting materials and purification via amine column chromatography (MeOH—CH$_2$Cl$_2$):

| Compound Name | Cmp No. |
|---|---|
| N-((1H-Pyrrolo[3,2-c]pyridin-2-yl)methyl)-2-(6-(1-methyl-1H-pyrazol-4-yl)-2-oxo-3-(phenethylamino)pyrazin-1(2H)-yl)acetamide | 101 |
| N-((1H-Pyrrolo[3,2-c]pyridin-2-yl)methyl)-2-(2-oxo-3-(phenethylamino)-6-(1H-pyrazol-4-yl)pyrazin-1(2H)-yl)acetamide | 102 |
| N-((1H-Pyrrolo[3,2-c]pyridin-2-yl)methyl)-2-(6-(1-isopropyl-1H-pyrazol-4-yl)-2-oxo-3-(phenethylamino)pyrazin-1(2H)-yl)acetamide | 103 |
| N-((1H-Pyrrolo[3,2-c]pyridin-2-yl)methyl)-2-(6-(1,3-dimethyl-1H-pyrazol-4-yl)-2-oxo-3-(phenethylamino)pyrazin-1(2H)-yl)acetamide | 104 |
| N-((1H-Pyrrolo[3,2-c]pyridin-2-yl)methyl)-2-(6-(1-methyl-1H-pyrazol-5-yl)-2-oxo-3-(phenethylamino)pyrazin-1(2H)-yl)acetamide | 105 |
| N-((1H-Pyrrolo[3,2-c]pyridin-2-yl)methyl)-2-(6-(1-cyclobutyl-1H-pyrazol-4-yl)-2-oxo-3-(phenethylamino)pyrazin-1(2H)-yl)acetamide | 110 |
| tert-Butyl 3-(4-(1-(2(((1H-pyrrolo[3,2-c]pyridin-2-yl)methyl)amino)-2-oxoethyl)-6-oxo-5-(phenethylamino)-1,6-dihydropyrazin-2-yl)-1H-pyrazol-1-yl)azetidine-1-carboxylate | 111 |
| N-((1H-Pyrrolo[3,2-c]pyridin-2-yl)methyl)-2-(6-(1-(difluoromethyl)-1H-pyrazol-4-yl)-2-oxo-3-(phenethylamino)pyrazin-1(2H)-yl)acetamide | 113 |
| N-((1H-Pyrrolo[3,2-c]pyridin-2-yl)methyl)-2-(6-(1-cyclopropyl-3-methyl-1H-pyrazol-4-yl)-2-oxo-3-(phenethylamino)pyrazin-1(2H)-yl)acetamide | 114 |
| N-((1H-Pyrrolo[3,2-c]pyridin-2-yl)methyl)-2-(6-(5,6-dihydro-4H-pyrrolo[1,2-b]pyrazol-3-yl)-2-oxo-3-(phenethylamino)pyrazin-1(2H)-yl)acetamide | 115 |
| N-((1H-Pyrrolo[3,2-c]pyridin-2-yl)methyl)-2-(2-oxo-3-(phenethylamino)-6-(4,5,6,7-tetrahydropyrazolo[1,5-α] pyridin-3-yl)pyrazin-1(2H)-yl)acetamide | 116 |

The following compound was prepared according to the foregoing procedure using the appropriate boronic acid and amine starting material and purification via prep-HPLC:

| Compound Name | Cmp No. |
|---|---|
| 2-(6-(1H-Indol-7-yl)-2-oxo-3-(phenethylamino)pyrazin-1(2H)-yl)-N-((6-amino-2-methylpyridin-3-yl)methyl)acetamide trifluoroacetate | 85 |

162

Example 42

Preparation of N-((1H-Pyrrolo[3,2-c]Pyridin-2-yl)Methyl)-2-(6-(1-(Azetidin-3-yl)-1H-Pyrazol-4-yl)-2-Oxo-3-(Phenethylamino)Pyrazin-1(2H)-yl)Acetamide Hydrochloride (Compound 112)

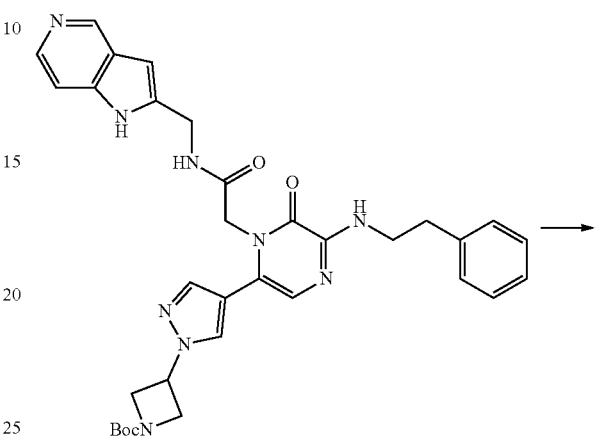

-continued

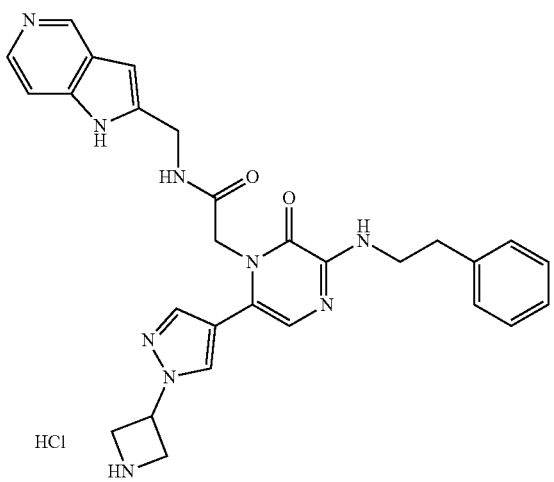

HCl tert-Butyl 3-(4-(1-(2-(((1H-pyrrolo[3,2-b]pyridin-2-yl) methyl)amino)-2-oxoethyl)-6-oxo-5-(phenethylamino)-1,6-dihydropyrazin-2-yl)-1H-pyrazol-1-yl)azetidine-1-carboxylate (851477, 19 mg, 0.03 mmol, prepared according to Example 40 using appropriate boronic acid) was treated with 3 M HCl in iPrOH (1 mL) and allowed to stir for 1 h then concd under vacuum. The residue was then re-dissolved in acetonitrile/H$_2$O and lyophilized to afford the title compound as a white powder (16 mg, 100% yield).

Example 43

Preparation of N-((1H-Pyrrolo[3,2-c]Pyridin-2-yl)Methyl)-2-(6-Bromo-2-Oxo-3-(Phenethylamino)Pyrazin-1(2H)-yl) Acetamide (Compound 109)

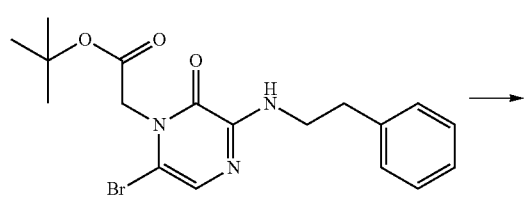

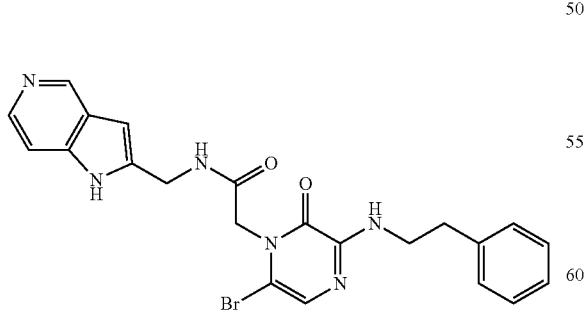

The title compound was prepared from tert-butyl 2-(6-bromo-2-oxo-3-(phenethylamino)pyrazin-1(2H)-yl)acetate as a white powder (250 mg, 52% yield) according to Example 36, steps 2-3.

Example 44

Preparation of N-((1H-Pyrrolo[3,2-c]Pyridin-2-yl)Methyl)-2-(6-Butoxy-2-Oxo-3-(Phenethylamino)Pyrazin-1(2H)-yl) Acetamide (Compound 162)

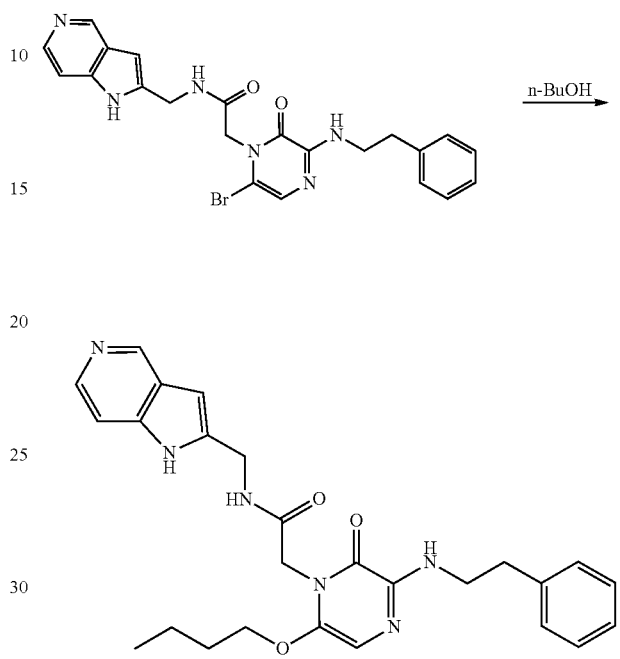

The title compound was prepared from N-((1H-pyrrolo [3,2-c]pyridin-2-yl)methyl)-2-(6-bromo-2-oxo-3-(phenethylamino)pyrazin-1(2H)-yl)acetamide as a white powder (4 mg, 9% yield) according to Example 35, step 1 except in neat n-BuOH (1 mL) and purified by chromatography (amine column, MeOH—CH$_2$Cl$_2$).

Example 45

Preparation of (4-(2-(((1H-Pyrrolo[3,2-c]Pyridin-2-yl) Methyl)Amino)-2-Oxoethyl)-3-Oxo-5-Phenyl-3,4-Dihydropyrazin-2-yl)Glycine Trifluoroacetate (Compound 118)

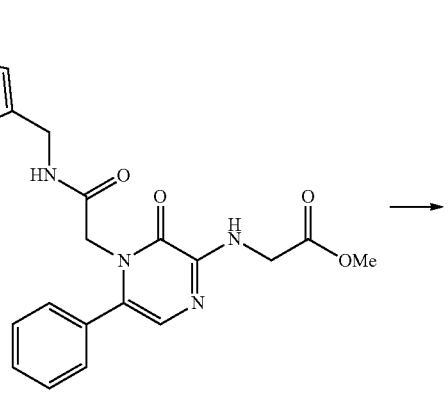

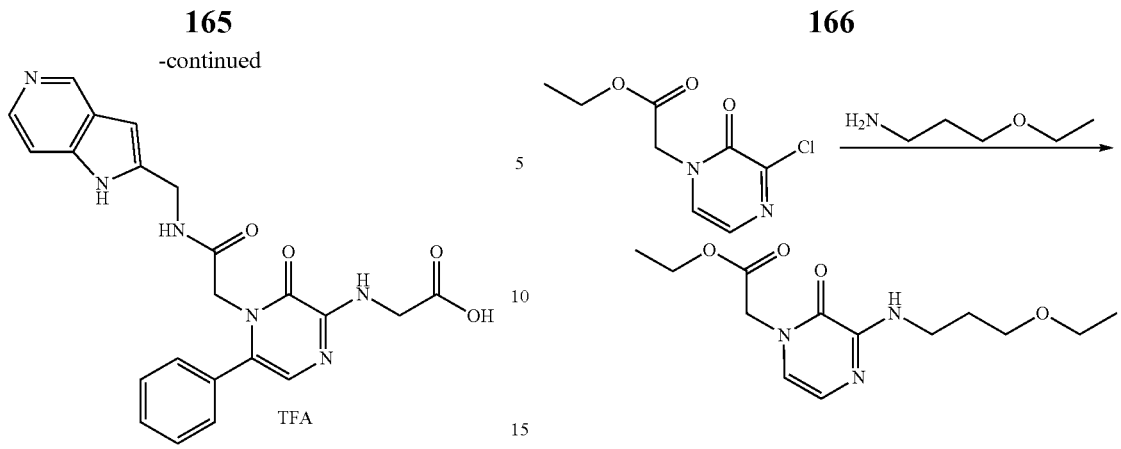

The title compound was prepared as a white powder (16 mg, 26% yield) from ethyl (4-(2-(((1H-pyrrolo[3,2-c]pyridin-2-yl)methyl)amino)-2-oxoethyl)-3-oxo-5-phenyl-3,4-dihydropyrazin-2-yl)glycinate according to the procedure given for Example 10.

The following compound was prepared according to the foregoing procedure using the appropriate starting material:

| Compound Name | Cmp No. |
| --- | --- |
| (4-(2-(((1H-Pyrrolo[3,2-c]pyridin-2-yl)methyl)amino)-2-oxoethyl)-3-oxo-5-phenyl-3,4-dihydropyrazin-2-yl)-L-tyrosine trifluoroacetate | 119 |

Example 45

Preparation of N-((1H-Pyrrolo[3,2-c]Pyridin-2-yl)Methyl)-2-(3-((3-Ethoxypropyl)Amino)-2-Oxo-6-Phenylpyrazin-1(2H)-yl)Acetamide Trifluoroacetate (Compound 126)

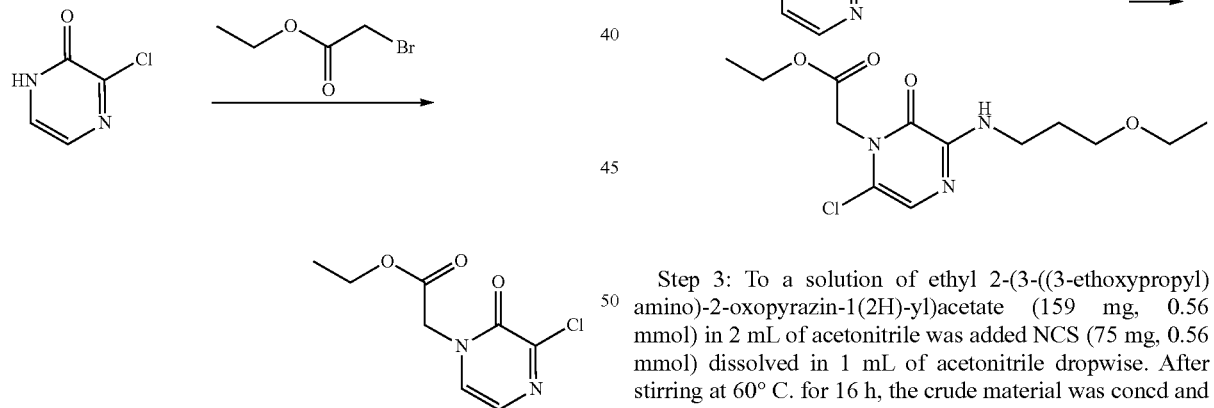

Step 1: 3-Chloropyrazin-2(1H)-one (5 g, 38 mmol), ethyl 2-bromoacetate (4.4 mL, 42 mmol), and potassium carbonate (11.2 g, 81 mmol) were dissolved in DMF (76 mL). The reaction was stirred at RT for 1 h. The crude material was diluted with 200 mL of EtOAc, washed with 200 mL of 1 N HCl and 200 mL brine. The organic layer was dried with Na$_2$SO$_4$ and concd under vacuum. The residue was purified by chromatography (0-100% EtOAc-heptanes) to afford ethyl 2-(3-chloro-2-oxopyrazin-1(2H)-yl)acetate (5.23 g, 63% yield).

Step 2: Ethyl 2-(3-chloro-2-oxopyrazin-1(2H)-yl)acetate (250 mg, 1.15 mmol), 3-ethoxypropan-1-amine (131 mg, 1.27 mmol), and DIEA (400 uL, 2.3 mmol) were dissolved in acetonitrile (5 mL). After stirring at 65° C. for 2 h, the crude material was concd and purified by chromatography (0-100% EtOAc-heptanes) to afford ethyl 2-(3-((3-ethoxypropyl)amino)-2-oxopyrazin-1(2H)-yl)acetate (159 mg, 48% yield).

Step 3: To a solution of ethyl 2-(3-((3-ethoxypropyl)amino)-2-oxopyrazin-1(2H)-yl)acetate (159 mg, 0.56 mmol) in 2 mL of acetonitrile was added NCS (75 mg, 0.56 mmol) dissolved in 1 mL of acetonitrile dropwise. After stirring at 60° C. for 16 h, the crude material was concd and purified by chromatography (0-100% EtOAc-heptanes) to afford ethyl 2-(6-chloro-3-((3-ethoxypropyl)amino)-2-oxopyrazin-1(2H)-yl)acetate (143 mg, 80% yield).

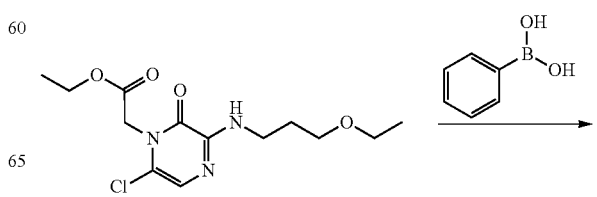

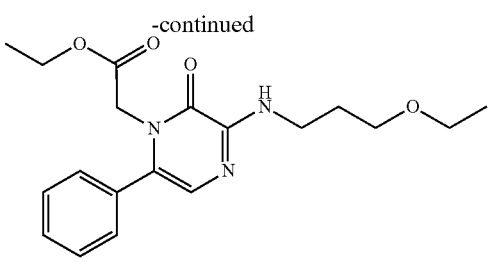

Step 4: Ethyl 2-(6-chloro-3-((3-ethoxypropyl)amino)-2-oxopyrazin-1(2H)-yl)acetate (45 mg, 0.14 mmol), phenylboronic acid (26 mg, 21 mmol), tetrakis(triphenylphosphine)palladium(0) (16 mg, 14 μmol), and potassium carbonate (58 mg, 0.43 mmol) in 1.1 mL dioxane and 0.4 mL water. The reaction was purged with nitrogen for 2 minutes, heated up to 100° C. and allowed to stir for 1 h. The crude material was concd and purified on silica gel chromatography (0-20% MeOH—CH₂Cl₂) to afford ethyl 2-(3-((3-ethoxypropyl)amino)-2-oxo-6-phenylpyrazin-1(2H)-yl)acetate (18.5 mg, 40% yield).

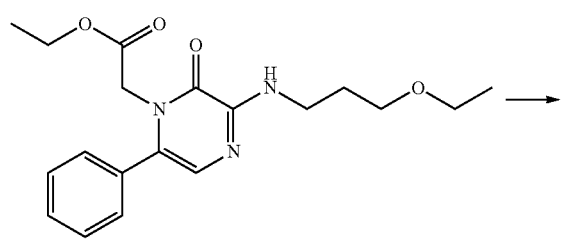

Step 5: Ethyl 2-(3-((3-ethoxypropyl)amino)-2-oxo-6-phenylpyrazin-1(2H)-yl)acetate (18.5 mg, 51.5 μmol) and potassium hydroxide (8.6 mg, 154 μmol) were dissolved in 416 μL of THF and 100 μL of water. The reaction was heated up to 60° C. and allowed to stir for 1 h. The crude 2-(3-((3-ethoxypropyl)amino)-2-oxo-6-phenylpyrazin-1(2H)-yl)acetic acid (17 mg, 100% yield) was concd and used in the next reaction without further purification.

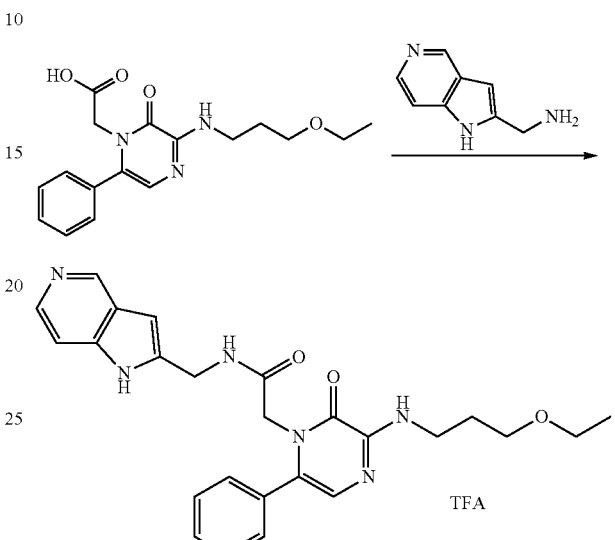

Step 6: 2-(3-((3-Ethoxypropyl)amino)-2-oxo-6-phenylpyrazin-1(2H)-yl)acetic acid (25 mg, 75.5 μmol), 1H-pyrrolo[3,2-c]pyridin-2-yl)methanamine (17 mg, 113 μmol), HATU (42 mg, 113 μmol), and DIEA (80 uL, 453 μmol) were dissolved in DMF (750 μL). After stirring for 2 h, the crude material was purified using reverse-phase HPLC to give N-((1H-pyrrolo[3,2-b]pyridin-2-yl)methyl)-2-(3-((3-ethoxypropyl)amino)-2-oxo-6-phenylpyrazin-1(2H)-yl)acetamide trifluoroacetate (17 mg, 49% yield) as a white solid.

The following compound was prepared according to the foregoing procedure using the appropriate boronate starting material:

| Compound Name | Cmp No. |
|---|---|
| N-((1H-Pyrrolo[3,2-c]pyridin-2-yl)methyl)-2-(3-((3-ethoxypropyl)amino)-6-(1-methyl-1H-pyrazol-4-yl)-2-oxopyrazin-1(2H)-yl)acetamide trifluoroacetate | 129 |

The following compounds were prepared according to the foregoing procedure using the appropriate amine starting material and boronate starting materials. Equivalents of the boronates were changed from 1.5 equiv to 1.3 equiv:

| Compound Name | Cmp No. |
|---|---|
| N-((1H-Pyrrolo[3,2-c]pyridin-2-yl)methyl)-2-(3-((3,3-difluoropropyl)amino)-6-(1-methyl-1H-pyrazol-4-yl)-2-oxopyrazin-1(2H)-yl)acetamide trifluoroacetate | 125 |
| N-((1H-Pyrrolo[3,2-c]pyridin-2-yl)methyl)-2-(3-((3,3-difluoropropyl)amino)-2-oxo-6-phenylpyrazin-1(2H)-yl)acetamide trifluoroacetate | 127 |

Example 46

Preparation of N-((1H-Pyrrolo[3,2-c]Pyridin-2-yl)Methyl)-2-(3-((4-Methoxybutyl)Amino)-6-(1-Methyl-1H-Pyrazol-4-yl)-2-Oxopyrazin-1(2H)-yl)Acetamide Trifluoroacetate (Compound 122)

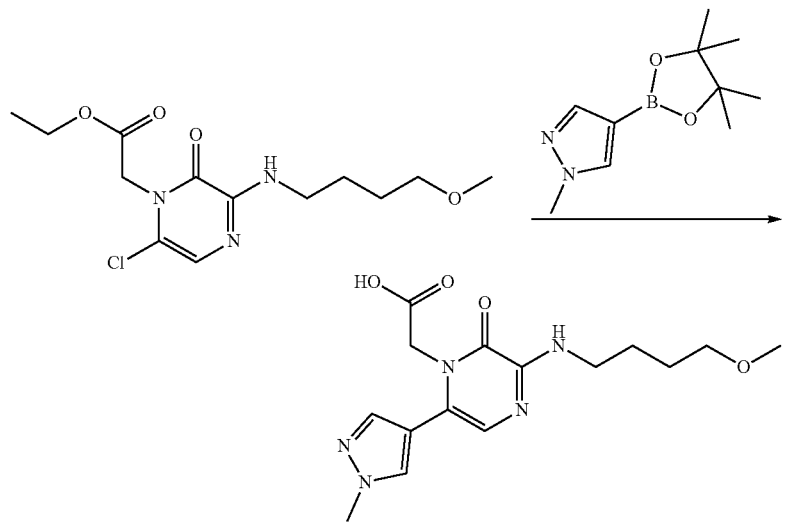

Step 1: Ethyl 2-(6-chloro-3-((4-methoxybutyl)amino)-2-oxopyrazin-1(2H)-yl)acetate (50 mg, 0.157 mmol, prepared according to Example 45, steps 1-3 using appropriate amine), 1-methyl-4-(4,4,5,5-tetramethyl-1,3,2-dioxaborolan-2-yl)-1H-pyrazole (40 mg, 0.188 mmol), tetrakis(triphenyiphosphine)palladium(0) (18 mg, 16 μmol), and potassium carbonate (65 mg, 0.47 mmol) in 1 mL dioxane and 0.4 mL water. The reaction was purged with nitrogen for 2 minutes, heated up to 100° C. and allowed to stir for 1 h. The crude material was concd and purified by chromatography (0-20% MeOH—$CH_2Cl_2$) to afford 2-(3-((4-methoxybutyl)amino)-6-(1-methyl-1H-pyrazol-4-yl)-2-oxopyrazin-1(2H)-yl)acetic acid (30 mg, 57% yield).

Step 2: 2-(3-((4-Methoxybutyl)amino)-6-(1-methyl-1H-pyrazol-4-yl)-2-oxopyrazin-1(2?7)-yl)acetic acid (15 mg, 44.8 μmol), 1H-pyrrolo[3,2-c]pyridin-2-yl)methanamine (7 mg, 44.8 μmol), HATU (25 mg, 67.2 μmol), and DIEA (46 uL, 268 μmol) were dissolved in DMF (500 μL), After stirring for 1 h, the crude material was purified using reverse-phase HPLC to give N-((1H-pyrrolo[3,2-b]pyridin-2-yl)methyl)-2-(3-((4-methoxybutyl)amino)-6-(1-methyl-1H-pyrazol-4-yl)-2-oxopyrazin-1(2H)-yl)acetamide trifluoroacetic acid (14 mg, 70% yield) as a white solid.

Example 47

Preparation of N-((1H-Pyrrolo[3,2-c]Pyridin-2-yl)Methyl)-2-(3-((2,2-Difluoro-2-Phenylethyl)Amino)-6-(1-Methyl-1H-Pyrazol-4-yl)-2-Oxopyrazin-1(2H)-yl)Acetamide Trifluoroacetate (Compound 123)

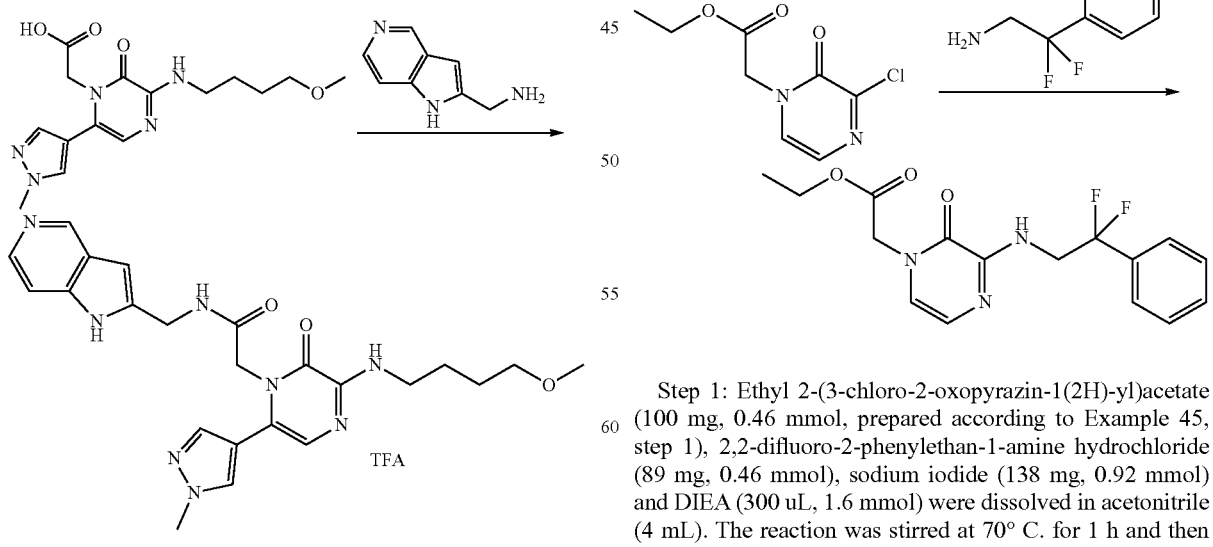

Step 1: Ethyl 2-(3-chloro-2-oxopyrazin-1(2H)-yl)acetate (100 mg, 0.46 mmol, prepared according to Example 45, step 1), 2,2-difluoro-2-phenylethan-1-amine hydrochloride (89 mg, 0.46 mmol), sodium iodide (138 mg, 0.92 mmol) and DIEA (300 uL, 1.6 mmol) were dissolved in acetonitrile (4 mL). The reaction was stirred at 70° C. for 1 h and then 20 min at 130° C. via microwave irradiation. The crude material was diluted with 50 mL EtOAc and washed with 50 mL 1 N HCl and 50 mL brine. The organic layer was dried with sodium sulfate and concd to afford ethyl 2-(3-((2,2-difluoro-2-phenylethyl)amino)-2-oxopyrazin-1(2H)-yl)acetate (72.5 mg, 50% yield).

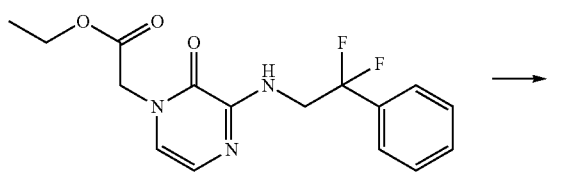

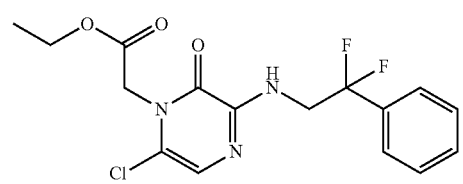

Step 2: Ethyl 2-(6-chloro-3-((2,2-difluoro-2-phenylethyl)amino)-2-oxopyrazin-1(2H)-yl)acetate (34.8 mg, 44% yield) was synthesized from ethyl 2-(3-((2,2-difluoro-2-phenylethyl)amino)-2-oxopyrazin-1(2H)-yl)acetate according to Example 45, step 3.

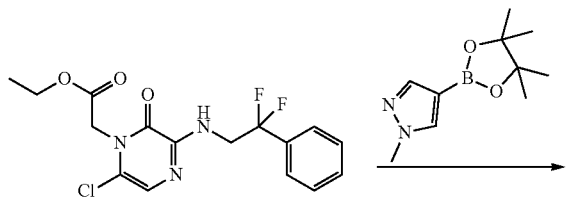

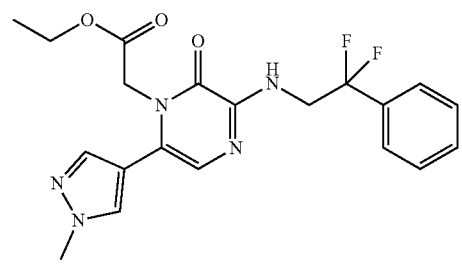

Step 3: Ethyl 2-(6-chloro-3-((2,2-difluoro-2-phenylethyl)amino)-2-oxopyrazin-1(2H)-yl)acetate (34.8 mg, 93.8 µmol), 1-methyl-4-(4,4,5,5-tetramethyl-1,3,2-dioxaborolan-2-yl)-1H-pyrazole (24 mg, 115 µmol), tetrakis(triphenylphosphine)palladium(0) (18 mg, 9.4 µmol), and potassium carbonate (38 mg, 281 µmol) were dissolved in 800 µL dioxane and 200 µL water. The reaction was purged with nitrogen for 2 minutes, heated up to 100° C. and allowed to stir for 0.5 h. The crude material was concd and purified by chromatography (0-100% EtOAc-heptanes) to afford ethyl 2-(3-((2,2-difluoro-2-phenylethyl)amino)-6-(1-methyl-1H-pyrazol-4-yl)-2-oxopyrazin-1(2H)-yl(acetate (20 mg, 51% yield).

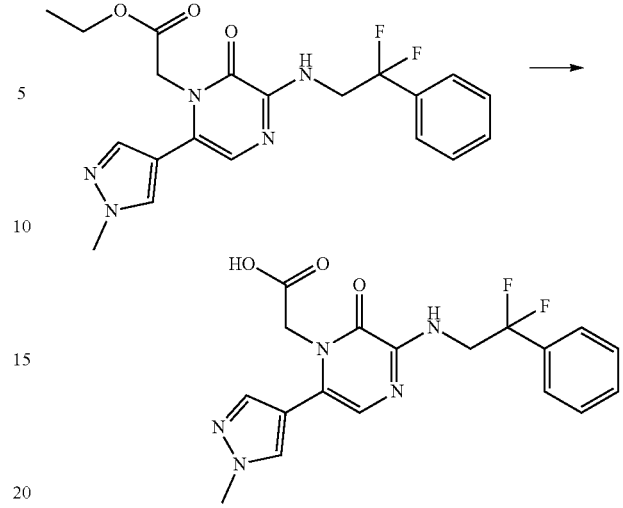

Step 4: Ethyl 2-(3-((2,2-difluoro-2-phenylethyl)amino)-6-(1-methyl-1H-pyrazol-4-yl)-2-oxopyrazin-1(2H)-yl(acetate (20 mg, 47.9 µmol) and potassium hydroxide (8 mg, 148 µmol) were dissolved in 800 µL of THF and 200 µL of water. The reaction was heated up to 40° C. and allowed to stir for 2 h. The crude 2-(3-((2,2-difluoro-2-phenylethyl)amino)-6-(1-methyl-1H-pyrazol-4-yl)-2-oxopyrazin-1(2H)-yl)acetic acid (18.7 mg, 100% yield) was concd and used in the next reaction without further purification.

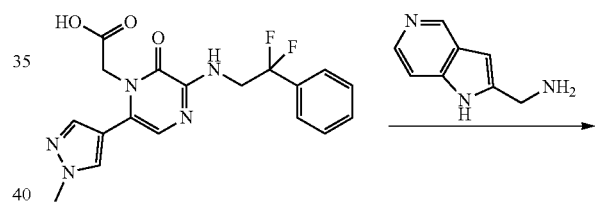

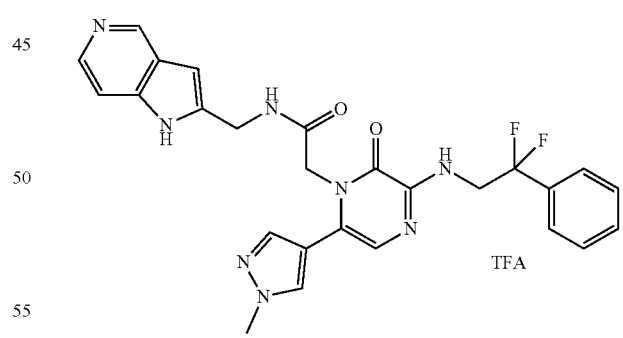

Step 5: 2-(3-((2,2-Difluoro-2-phenylethyl)amino)-6-(1-methyl-1H-pyrazol-4-yl)-2-oxopyrazin-1(2H)-yl)acetic acid (18.7 mg, 47.9 µmol), 1H-pyrrolo[3,2-c]pyridin-2-yl)methanamine (8 mg, 52.7 µmol), HATU (27 mg, 52.7 µmol), and DIEA (50 uL, 288 µmol) were dissolved in DMF (500 µL). After stirring for 1 h, the crude material was purified using reverse-phase HPLC to give N-((1H-pyrrolo[3,2-c]pyridin-2-yl)methyl)-2-(3-((2,2-difluoro-2-phenylethyl)amino)-6-(1-methyl-1H-pyrazol-4-yl)-2-oxopyrazin-1(2H)-yl)acetamide trifluoroacetate (13 mg, 52% yield) as a white solid.

Example 48

Preparation of N-((1H-Pyrrolo[3,2-c]Pyridin-2-yl)Methyl)-2-(3-Methyl-2,6-Dioxo-5-(Phenethylamino)-3,6-Dihydropyrimidin-1(2H)-yl)Acetamide (Compound 161)

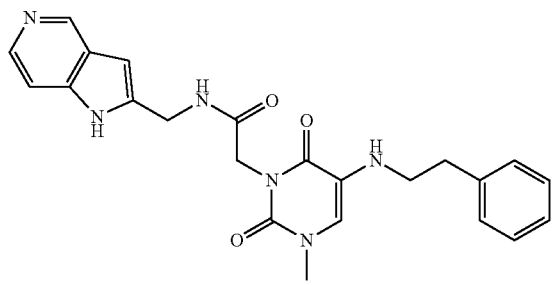 [SMILES: Cn1cc(NCCc2ccccc2)c(=O)n(CC(=O)NCc2cc3cnccc3[nH]2)c1=O]

N-((1H-Pyrrolo[3,2-c]pyridin-2-yl)methyl)-2-(3-methyl-2,6-di oxo-5-(phenethylamino)-3,6-dihydropyrimidin-1 (2H)-yl)acetamide was synthesized according to the procedures for Example 17 except that in step 5, the coupling was performed using the procedure from Example 1, step 4. The product was purified by chromatography (amine column, hepanes then 0-20% MeOH—CH$_2$Cl$_2$).

Example 49

Preparation of N-((1H-Pyrrolo[2,3-b]Pyridin-5-yl)Methyl)-2-(6-(1-Methyl-1H-Pyrazol-4-yl)-2-Oxo-3-(Phenethylamino)Pyrazin-1(2H)-yl)Acetamide (Compound 131)

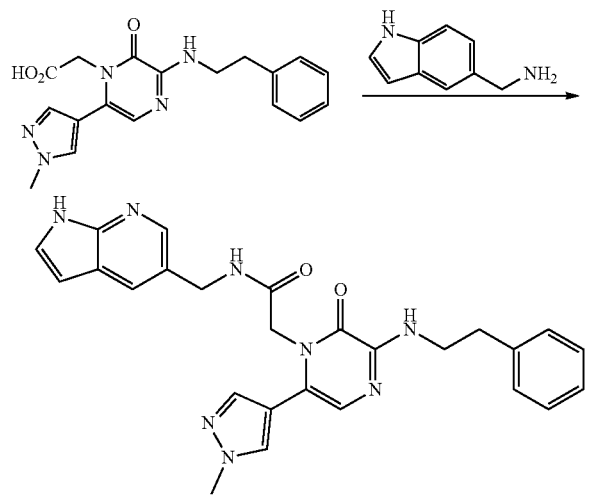

To a solution of 2-(6-(1-methyl-1H-pyrazol-4-yl)-2-oxo-3-(phenethylamino)pyrazin-1(2H)-yl)acetic acid (25 mg, 0.07 mmol, prepared according to Example 41) and (1H-pyrrolo[2,3-b]pyridin-5-yl)methanamine (13 mg, 0.085 mmol) in DMF (0.23 mL) was added HATU (40 mg, 0.11 mmol) and DIEA (60 µL, 0.35 mmol). The reaction was stirred at RT until completion, concentrated, and the residue was purified by chromatography (amine column: hepanes then 0-20% MeOH—CH$_2$Cl$_2$) to afford N-((1H-pyrrolo[2,3-b]pyridin-5-yl)methyl)-2-(6-(1-methyl-1H-pyrazol-4-yl)-2-oxo-3-(phenethylamino)pyrazin-1(2H)-yl)acetamide (15.9 mg, 47% yield).

The following compound was prepared according to the foregoing procedure using the appropriate amine starting material:

| Compound Name | Cmp No. |
| --- | --- |
| N-(Furo[3,2-c]pyridin-2-ylmethyl)-2-(6-(1-methyl-1H-pyrazol-4-yl)-2-oxo-3-(phenethylamino)pyrazin-1(2H)-yl)acetamide | 132 |

Example 50

Preparation of N-((7-Chloro-1H-Benzo[d]Imidazol-5-yl)Methyl)-2-(6-(1-Methyl-1H-Pyrazol-4-yl)-2-Oxo-3-(Phenethylamino)Pyrazin-1(2H)-yl)Acetamide (Compound 130)

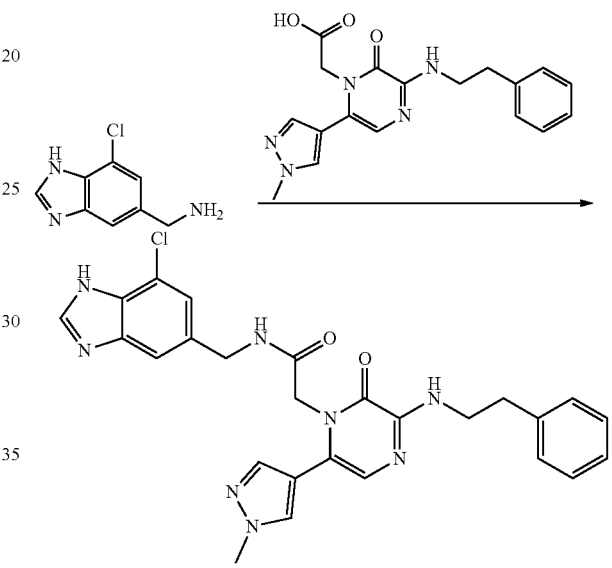

N-((7-chloro-1H-benzo[d]imidazol-5-yl)methyl)-2-(6-(1-methyl-1H-pyrazol-4-yl)-2-oxo-3-(phenethylamino) pyrazin-1(2H)-yl)acetamide was synthesized from (7-chloro-1H-benzo[d]imidazol-5-yl)methanamine (prepared according to the procedure described in PCT Publication No. WO 2019/231935) according to Example 41.

Example 51

Preparation of 2-(6-(1-Methyl-1H-Pyrazol-4-yl)-2-Oxo-3-(Phenethylamino)Pyrazin-1(2H)-yl)-N-(Thieno[3,2-c]Pyridin-2-Ylmethyl)Acetamide (Compound 133)

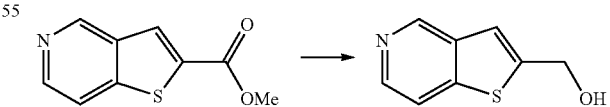

Step 1: A solution of methyl-thieno[3,2-c]pyridine carboxylate (200 mg, 1 mmol, 1 equiv) in anhydrous tetrahydrofuran (3.3 mL, 0.3 M) was cooled to 0° C. and lithium aluminum hydride (60 mg, 1.55 mmol, 1.5 equiv) was added. After stirring for 1 h, the reaction mixture was quenched with saturated ammonium chloride and filtered. The filtrate was diluted with EtOAc and washed with brine.

The organic layer was concentrated to afford the product which was carried forward without further purification.

Step 2: A solution of thieno[3,2-c]pyridin-2-ylmethanol (165 mg, 1 mmol) and diphenylphosphoryl azide (323 µL, 1.5 mmol) in anhydrous tetrahydrofuran (2.5 mL, 0.4 M) was cooled to 0° C. and DBU (224 µL, 1.5 mmol) was added. The reaction mixture was sealed and warmed to 65° C. for 16 h. The reaction mixture was then partitioned between diethyl ether and water and the aqueous layer was extracted with diethyl ether two times. The combined organic extracts were washed with brine, dried over $Na_2SO_4$, concentrated and purified by chromatography (0-100% EtOAc-heptanes) to afford 2-(azidomethyl)thieno[3,2-c]pyridine (126 mg, 66% yield over 2 steps) as a white solid.

Step 3: To a solution of 2-(azidomethyl)thieno[3,2-c]pyridine (126 mg, 0.66 mmol) and triphenylphosphine (350 mg, 1.3 mmol) in anhydrous tetrahydrofuran (2.2 mL, 0.3 M), 28% ammonium hydroxide in water (84 µL, 7.9 M) was added. The reaction mixture was sealed and warmed to 40° C. for 16 h. The reaction mixture was cooled to RT, concd, and purified by chromatography (0-20% MeOH—$CH_2Cl_2$) to afford thieno[3,2-c]pyridin-2-ylmethanamine (92 mg, 85% yield) as a white solid.

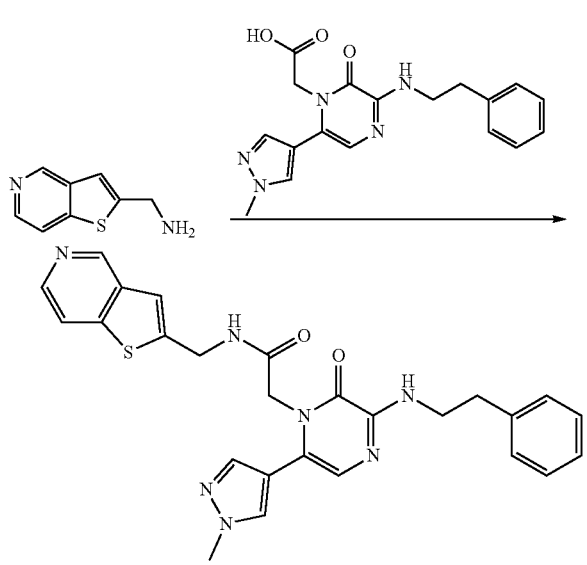

Step 4: 2-(6-(1-Methyl-1H-pyrazol-4-yl)-2-oxo-3-(phenethylamino)pyrazin-1(2H)-yl)-N-(thieno[3,2-c]pyridin-2-ylmethyl)acetamide was synthesized from thieno[3,2-c]pyridin-2-ylmethanamine according to Example 41.

Example 52

Preparation of N-((1H-Pyrrolo[3,2-c]Pyridin-2-yl)Methyl)-2-(5-(Isopropylamino)-2-(Methylthio)-6-Oxopyrimidin-1(6H)-yl)Acetamide (Compound 158)

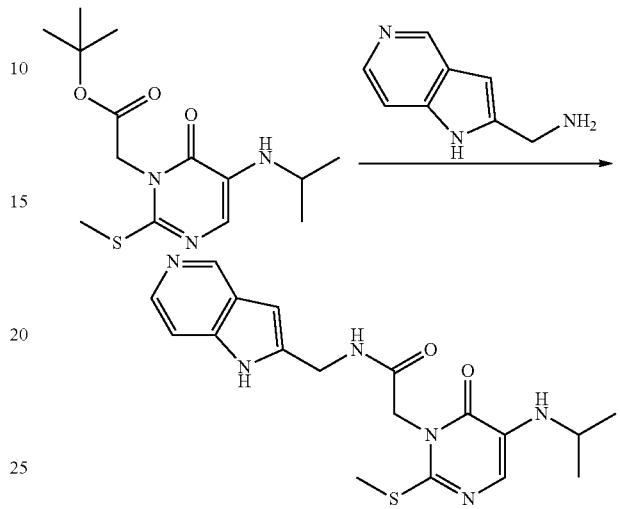

Steps 1-2: The title compound was synthesized according to the procedure given for Example 4 using (1H-pyrrolo[3,2-c]pyridin-2-yl)methanamine.

Example 53

Preparation of N-((1H-Pyrrolo[3,2-c]Pyridin-2-yl)Methyl)-2-(2-(Isopropylamino)-6-Oxo-5-(((1-Phenylcyclobutyl)Methyl)Amino)Pyrimidin-1(6H)-yl)Acetamide Di-Trifluoroacetate (Compound 157)

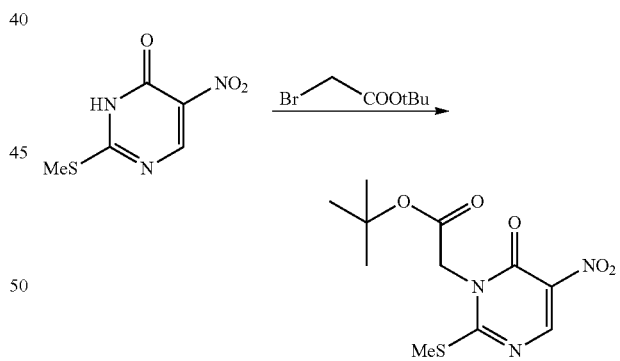

Step 1: To a solution of 2-(methylthio)-5-nitropyrimidin-4(3H)-one (550 mg, 2.67 mmol) in THF (20 mL) and DMF (5 mL) was added tert-butyl 2-bromoacetate (1 mL) followed by $CaH_2$ (powder, 335 mg, 7.97 mmol). After stirring at 80° C. for 4 h, 3 mL of DMF was added followed by tert-butyl 2-bromoacetate (0.5 mL). After stirring at 100° C. for 2 h, the reaction mixture was slowly quenched with ice cold water and extracted with EtOAc (2×10 mL). The organic extracts were dried over anhyd $NaSO_4$, filtered, and concd. The residue was purified by chromatography (0-100% EtOAc-heptanes) to yield tert-butyl 2-(2-(methylthio)-5-nitro-6-oxopyrimidin-1(6H)-yl)acetate (300 mg, 37% yield) as a yellow solid.

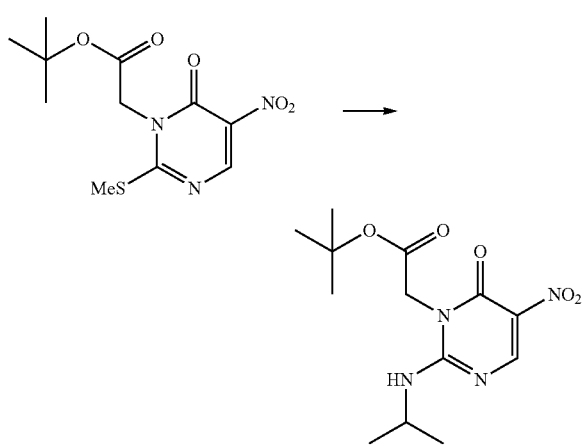

Step 2: To a suspension of tert-butyl 2-(2-(methylthio)-5-nitro-6-oxopyrimidin-1(6H)-yl)acetate (100 mg, 0.33 mmol) in acetonitrile (2 mL) was added isopropylamine (0.1 mL), and DIEA (0.2 mL). After stirring at 40° C. for 1 h, the reaction mixture was concentrated and used in the next step without further purification.

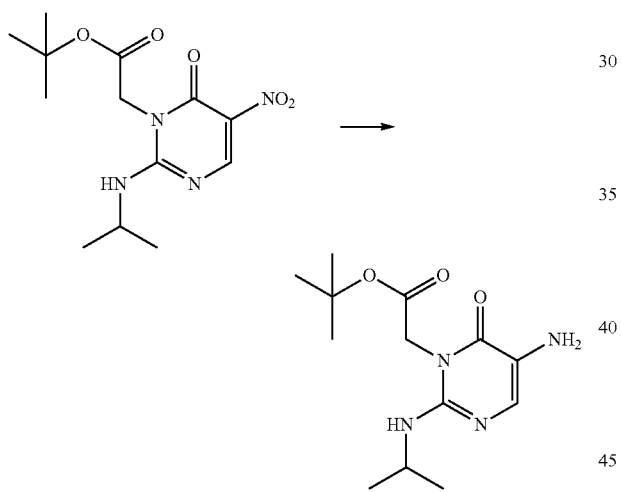

Step 3: To a solution of tert-butyl 2-(2-(isopropylamino)-5-nitro-6-oxopyrimidin-1(6H)-yl)acetate (103 mg, 0.33 mmol) in MeOH (10 mL, 0.03 M) was added 10% Pd/C (20 mg) and stirred under $H_2$ atmosphere for 1 h. The reaction mixture was filtered through Celite® rinsed with MeOH and concentrated. The crude material was used in the next step without further purification.

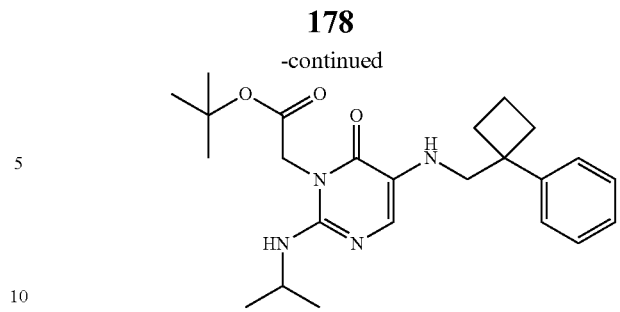

Step 4: To a suspension of tert-butyl 2-(5-amino-2-(isopropylamino)-6-oxopyrimidin-1(6H)-yl)acetate (80 mg, 0.28 mmol) in DCE (2 mL) was added acetic acid (0.05 mL) followed by 1-phenylcyclobutane-1-carbaldehyde (200 mg, 1.28 mmol). After stirring at 40° C. for 10 min, the reaction mixture was concd under vacuum on the 40° C. water bath. The residue was dissolved in DCE (2 mL) followed by the addition of sodium triacetoxyborohydride (250 mg, 4.2 mmol). After stirring at 40° C. for 20 min, the crude mixture was poured into saturated $NaHCO_3$ (10 mL) and extracted with $CH_2Cl_2$ (3×20 mL). The organic extracts were dried over anhyd $NaSO_4$, filtered, and concd. The residue was purified by chromatography (1% 7 $NNH_3$ in MeOH-EtOAc) to yield tert-butyl 2-(2-(isopropylamino)-6-oxo-5-(((1-phenylcyclobutyl)methyl)amino)pyrimidin-1(6H)-yl)acetate (25 mg, 18% yield over 3 steps).

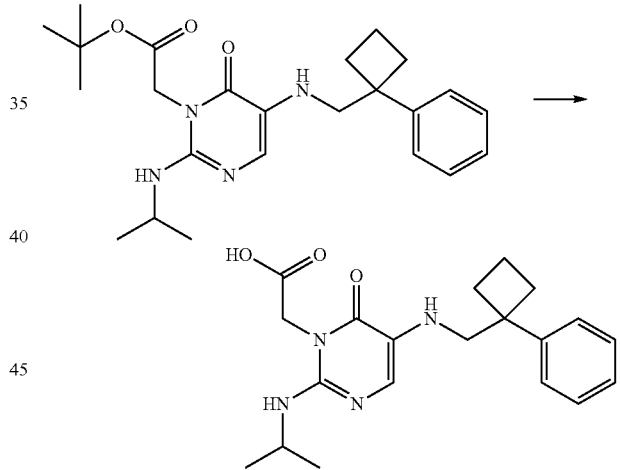

Step 5: tert-Butyl 2-(2-(isopropylamino)-6-oxo-5-(((1-phenylcyclobutyl)methyl)amino)-pyrimidin-1(6H)-yl)acetate (23 mg, 0.054 mmol) was dissolved in TFA (2 mL) and the reaction mixture was stirred at RT for 45 min. The reaction mixture was concd under vacuum and used in the next step without further purification.

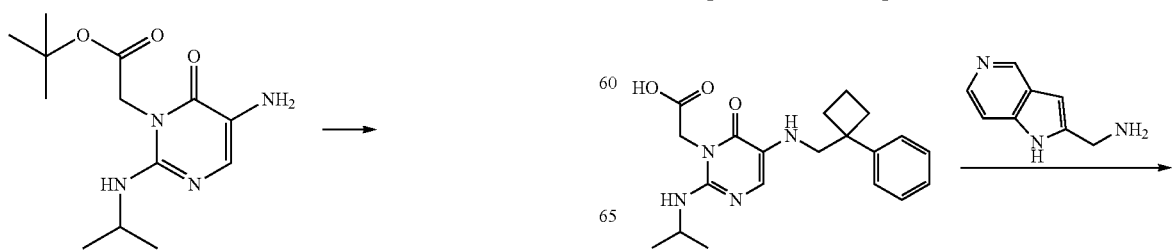

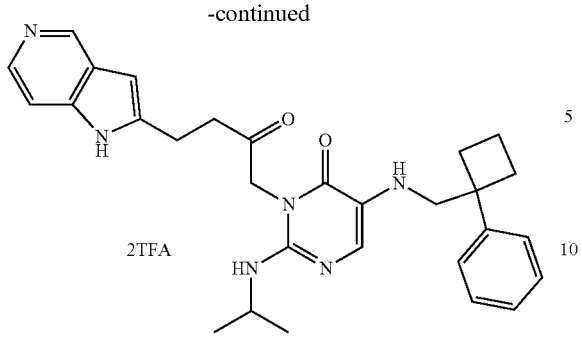

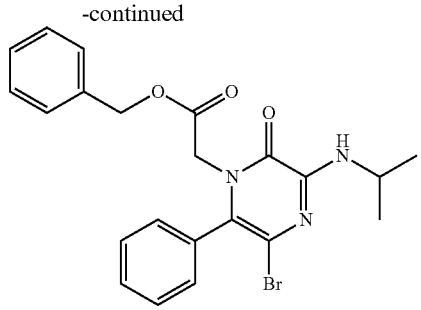

Step 6: To a solution of 2-(2-(isopropylamino)-6-oxo-5-(((1-phenylcyclobutyl)methyl)amino)-pyrimidin-1(6H)-yl)acetic acid (25 mg, 0.069 mmol) in DMF (0.5 mL) and DIEA (0.2 mL) was added NHS (12 mg, 0.1 mmol), DCC (20 mg, 0.1 mmol), and 1H-pyrrolo[3,2-c]pyridin-2-yl)methanamine (20 mg, 0.13 mmol). After stirring at RT for 36 h, the reaction mixture was filtered and washed with $CH_2Cl_2$. The filtrate was concentrated and purified using reverse-phase HPLC to give N-((1H-pyrrolo[3,2-c]pyridin-2-yl)methyl)-2-(2-(isopropylamino)-6-oxo-5-(((1-phenylcyclobutyl)methyl)amino)pyrimidin-1(6H)-yl)acetamide di-trifluoroacetate (9 mg, 33% yield over two steps) as a white solid.

The following compound was prepared according to the foregoing procedure using the appropriate aldehyde starting material:

| Compound Name | Cmp No. |
| --- | --- |
| N-((1H-Pyrrolo[3,2-c]pyridin-2-yl)methyl)-2-(5-(diphenethylamino)-2-(isopropylamino)-6-oxopyrimidin-1(6H)-yl)acetamide | 159 |

The following compound was prepared according to the foregoing procedure using the appropriate aldehyde starting material except that the amide coupling reaction in step 6 was conducted according to the procedure given in Example 4:

| Compound Name | Cmp No. |
| --- | --- |
| N-((1H-Pyrrolo[3,2-c]pyridin-2-yl)methyl)-2-(2-(isopropylamino)-6-oxo-5-(phenethylamino)pyrimidin-1(6H)-yl)acetamide | 160 |

Step 1: To a solution of benzyl 2-(3,5-dibromo-2-oxo-6-phenylpyrazin-1(2H)-yl)acetate (200 mg, 0.42 mmol) in acetonitrile (5 mL, 0.08 M) was added isopropyl amine (37 mg, 0.63 mmol) and DIEA (108 mg, 0.84 mmol). After stirring for 6 h at 70° C., the reaction mixture was evaporated to dryness, washed with water, and extracted with EtOAc. The organic layer was dried over anhyd $Na_2SO_4$, filtered and concd under vacuum. The residue was purified by chromatography (20% EtOAc-hexanes) giving benzyl 2-(5-bromo-3-(isopropylamino)-2-oxo-6-phenylpyrazin-1(2H)-yl)acetate (177 mg, 92% yield).

Example 54

Preparation of N-((1H-Pyrrolo[3,2-c]Pyridin-2-yl)Methyl)-2-(3-(Isopropylamino)-2-Oxo-6-Phenylpyrazin-1(2H)-yl) Acetamide (Compound 134)

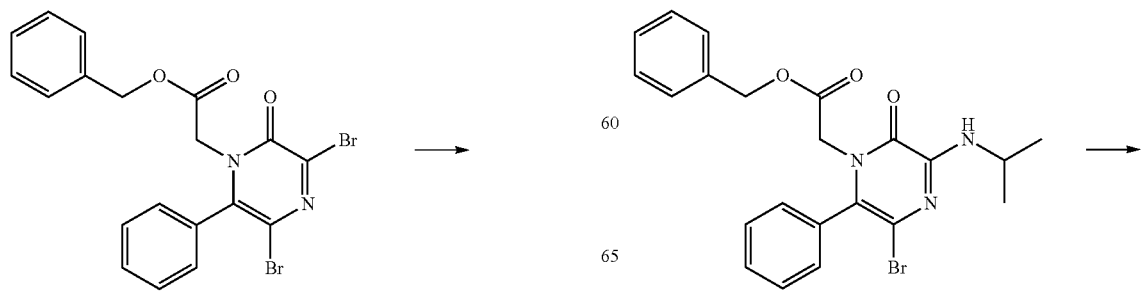

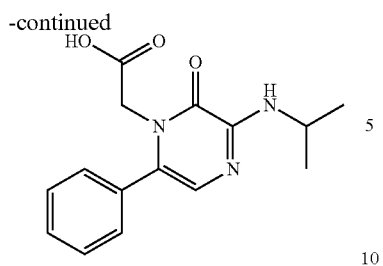

Step 2: A solution of benzyl 2-(5-bromo-3-(isopropylamino)-2-oxo-6-phenylpyrazin-1(2H)-yl)acetate (170 mg, 0.37 mmol) and DIEA (96 mg, 0.74 mmol) in MeOH (5 mL) was degassed with a stream of Ar for 1 min. 10% Pd/C (40 mg) was added, a vacuum was pulled for 1 min, and the mixture was hydrogenated overnight at 120 psi. The catalyst was removed by filtration and the solution was evaporated to give 2-(3-(isopropylamino)-2-oxo-6-phenylpyrazin-1(2H)-yl) acetic acid (106 mg, 100% yield) which was used in the next step without further purification.

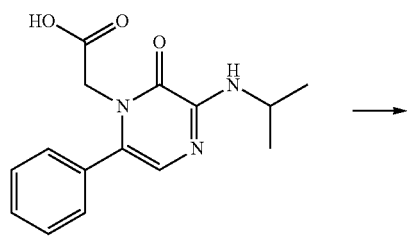

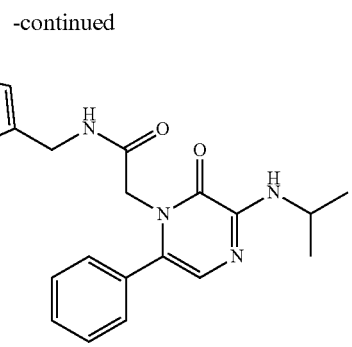

Step 3: To a solution of 2-(3-(isopropylamino)-2-oxo-6-phenylpyrazin-1(2H)-yl)acetic acid (106 mg, 0.37 mmol) in DMF (3 mL) was added NHS (51 mg, 0.44 mmol) with stirring until dissolved followed by DCC (91 mg, 0.44 mmol) with stirring for an additional 15 min. 1H-pyrrolo[3,2-c]pyridin-2-yl)methanamine (65 mg, 0.44 mmol) was added and stirred overnight at RT. The mixture was evaporated to dryness and the residue was swirled and sonicated in 3% 7 N $NH_3$ in $CH_2Cl_2$ (5 mL). The mixture was filtered, evaporated to dryness, and purified by chromatography (3% 7 N $NH_3$ in MeOH—$CH_2Cl_2$) giving N-((1H-pyrrolo[3,2-c]pyridine-2-yl)methyl)-2-(3-(isopropylamino)-2-oxo-6-phenylpyrazin-1(2H)-yl)acetamide (69 mg, 45% yield) as an off white solid.

The following compounds were prepared according to the foregoing procedure using appropriate amine starting materials:

| Compound Name | Cmp No. |
|---|---|
| N-((1H-Pyrrolo[3,2-c]pyridin-2-yl)methyl)-2-(3-((2-methylphenethyl)amino)-2-oxo-6-phenylpyrazin-1(2H)-yl)acetamide | 135 |
| N-((1H-Pyrrolo[3,2-c]pyridin-2-yl)methyl)-2-(3-((3-methoxyphenethyl)amino)-2-oxo-6-phenylpyrazin-1(2H)-yl)acetamide | 136 |
| N-((1H-Pyrrolo[3,2-c]pyridin-2-yl)methyl)-2-(3-((3-methylphenethyl)amino)-2-oxo-6-phenylpyrazin-1(2H)-yl)acetamide | 137 |
| N-((1H-Pyrrolo[3,2-c]pyridin-2-yl)methyl)-2-(3-((4-methylphenethyl)amino)-2-oxo-6-phenylpyrazin-1(2H)-yl)acetamide | 138 |
| N-((1H-Pyrrolo[3,2-c]pyridin-2-yl)methyl)-2-(2-oxo-6-phenyl-3-(3-phenylazetidin-1-yl)pyrazin-1(2H)-yl)acetamide | 139 |
| N-((1H-Pyrrolo[3,2-c]pyridin-2-yl)methyl)-2-(2-oxo-6-phenyl-3-(4-phenylpiperidin-1-yl)pyrazin-1(2H)-yl)acetamide | 140 |
| N-((1H-Pyrrolo[3,2-c]pyridin-2-yl)methyl)-2-(3-((2-methoxyphenethyl)amino)-2-oxo-6-phenylpyrazin-1(2H)-yl)acetamide | 141 |
| N-((1H-Pyrrolo[3,2-c]pyridin-2-yl)methyl)-2-(3-((4-methoxyphenethyl)amino)-2-oxo-6-phenylpyrazin-1(2H)-yl)acetamide | 142 |
| (R)-N-((1H-Pyrrolo[3,2-c]pyridin-2-yl)methyl)-2-(2-oxo-6-phenyl-3-(3-phenylpyrrolidin-1-yl)pyrazin-1(2H)-yl)acetamide | 143 |
| N-((1H-Pyrrolo[3,2-c]pyridin-2-yl)methyl)-2-(3-((2-fluorophenethyl)amino)-2-oxo-6-phenylpyrazin-1(2H)-yl)acetamide | 144 |
| N-((1H-Pyrrolo[3,2-c]pyridin-2-yl)methyl)-2-(3-((3-fluorophenethyl)amino)-2-oxo-6-phenylpyrazin-1(2H)-yl)acetamide | 145 |
| N-((1H-Pyrrolo[3,2-c]pyridin-2-yl)methyl)-2-(3-((4-fluorophenethyl)amino)-2-oxo-6-phenylpyrazin-1(2H)-yl)acetamide | 146 |
| N-((1H-Pyrrolo[3,2-c]pyridin-2-yl)methyl)-2-(3-(methylamino)-2-oxo-6-phenylpyrazin-1(2H)-yl)acetamide | 148 |
| N-((1H-Pyrrolo[3,2-c]pyridin-2-yl)methyl)-2-(3-(azetidin-1-yl)-2-oxo-6-phenylpyrazin-1(2H)-yl)acetamide | 149 |

Example 55

Preparation of N-((1H-Pyrrolo[3,2-c]Pyridin-2-yl)Methyl)-2-(3-((4-Fluorobenzyl)Amino)-2-Oxo-6-Phenylpyrazin-1(2H)-yl)Acetamide (Compound 147)

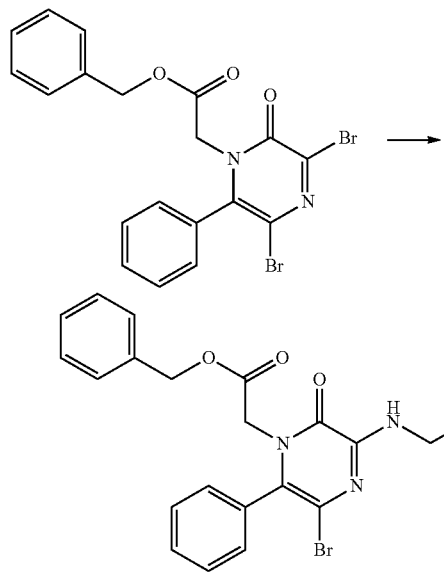

Step 1: Benzyl 2-(5-bromo-3-((4-fluorobenzyl)amino)-2-oxo-6-phenylpyrazin-1(2H)-yl)acetate was prepared according to the Example 54, step 1.

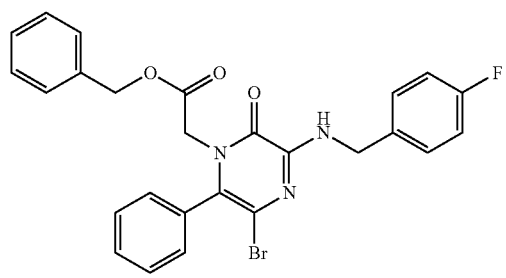

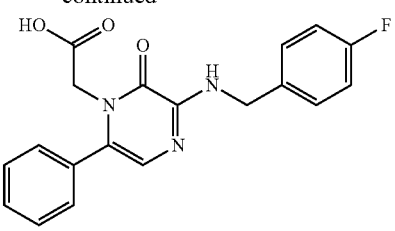

Step 2: 2-(3-((4-Fluorobenzyl)amino)-2-oxo-6-phenylpyrazin-1(2H)-yl)acetic acid was prepared according to Example 54, step 2 except that the reaction time was reduced to 3 h and the catalyst load was reduced by half.

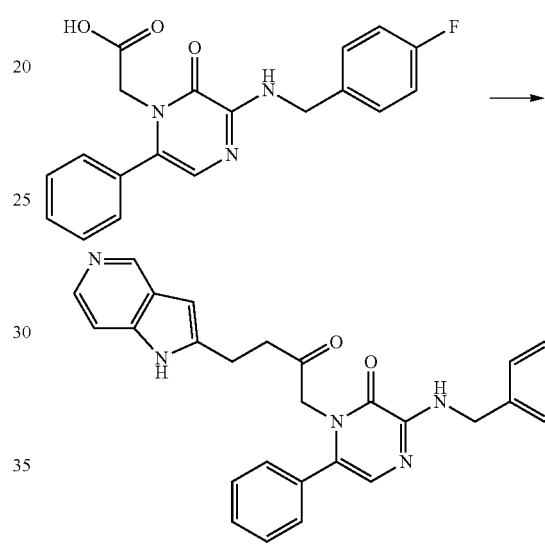

Step 3: N-((1H-Pyrrolo[3,2-c]pyridin-2-yl)methyl)-2-(3-((4-fluorobenzyl)amino)-2-oxo-6-phenylpyrazin-1(2H)-yl)acetamide was prepared according to Example 54, step 3.

The following compounds were prepared according to the foregoing procedure using appropriate amine starting materials:

| Compound Name | Cmp No. |
| --- | --- |
| N-((1H-Pyrrolo[3,2-c]pyridin-2-yl)methyl)-2-(3-((4-methoxybenzyl)amino)-2-oxo-6-phenylpyrazin-1(2H)-yl)acetamide | 150 |
| N-((1H-Pyrrolo[3,2-c]pyridin-2-yl)methyl)-2-(3-((3-fluorobenzyl)amino)-2-oxo-6-phenylpyrazin-1(2H)-yl)acetamide | 151 |
| N-((1H-Pyrrolo[3,2-c]pyridin-2-yl)methyl)-2-(2-oxo-6-phenyl-3-((3-(trifluoromethyl)benzyl)amino)pyrazin-1(2H)-yl)acetamide | 152 |
| N-((1H-Pyrrolo[3,2-c]pyridin-2-yl)methyl)-2-(3-((3-methoxybenzyl)amino)-2-oxo-6-phenylpyrazin-1(2H)-yl)acetamide | 153 |
| N-((1H-Pyrrolo[3,2-c]pyridin-2-yl)methyl)-2-(3-((3,5-difluorobenzyl)amino)-2-oxo-6-phenylpyrazin-1(2H)-yl)acetamide | 154 |
| N-((1H-Pyrrolo[3,2-c]pyridin-2-yl)methyl)-2-(3-((3-methylbenzyl)amino)-2-oxo-6-phenylpyrazin-1(2H)-yl)acetamide | 155 |
| (S)-N-((1H-Pyrrolo[3,2-c]pyridin-2-yl)methyl)-2-(2-oxo-6-phenyl-3-((1-phenylethyl)amino)pyrazin-1(2H)-yl)acetamide | 156 |

Table 1 lists compounds of the Examples described above, as well as additional compounds that may be prepared according to methods analogous to those described for the compounds above and other methods known to a person having skill in the art. In some embodiments, the compound is selected from Table 1.

TABLE 1

Exemplary compounds of Structures (I), (II), (III), and (IV)

| Cmp No. | Structure | Salt | Exact Observed Mass (ES+; M + H) | Exact Calc. Mass |
|---|---|---|---|---|
| 1 | 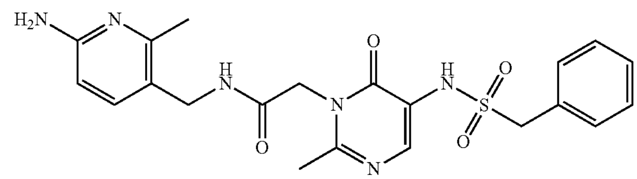 [SMILES: Cc1nc(N)ccc1CNC(=O)Cn1c(C)ncc(NS(=O)(=O)Cc2ccccc2)c1=O] | TFA | 457.05 | 456.16 |
| 2 | 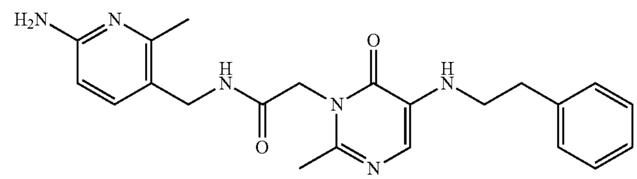 [SMILES: Cc1nc(N)ccc1CNC(=O)Cn1c(C)ncc(NCCc2ccccc2)c1=O] | TFA | 407.16 | 406.21 |
| 3 | 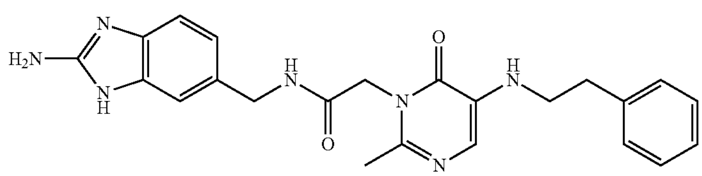 [SMILES: Cc1ncc(NCCc2ccccc2)c(=O)n1CC(=O)NCc1ccc2nc(N)[nH]c2c1] | TFA | 432.12 | 431.21 |
| 4 | 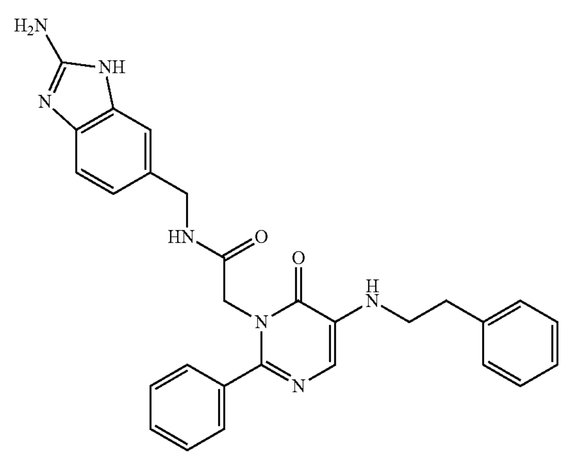 [SMILES: Nc1nc2ccc(CNC(=O)Cn3c(-c4ccccc4)ncc(NCCc4ccccc4)c3=O)cc2[nH]1] | TFA | 494.10 | 493.22 |
| 5 | 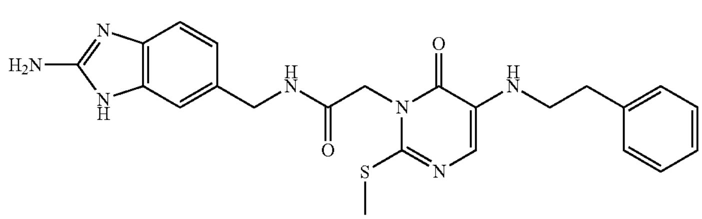 [SMILES: CSc1ncc(NCCc2ccccc2)c(=O)n1CC(=O)NCc1ccc2nc(N)[nH]c2c1] | — | 464.06 | 463.18 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 6 | 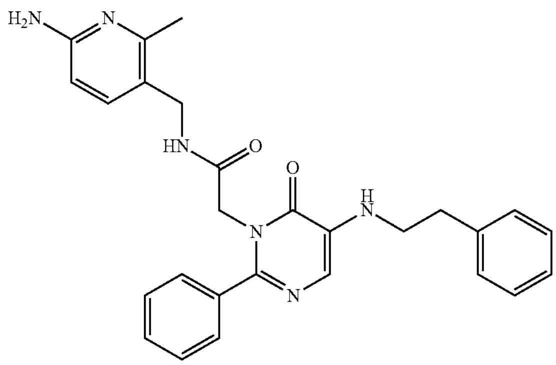 [SMILES: Cc1nc(N)ccc1CNC(=O)Cn1c(-c2ccccc2)ncc(NCCc2ccccc2)c1=O] | — | 469.11 | 468.23 |
| 7 | 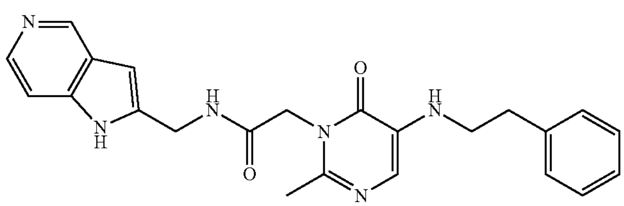 [SMILES: Cc1ncc(NCCc2ccccc2)c(=O)n1CC(=O)NCc1cc2cnccc2[nH]1] | — | 417.09 | 416.20 |
| 8 | 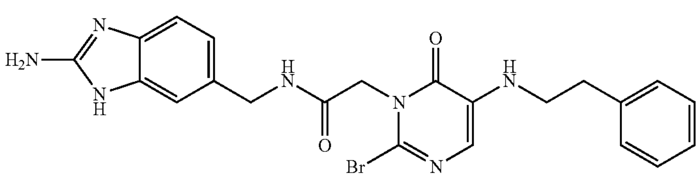 [SMILES: Nc1nc2ccc(CNC(=O)Cn3c(Br)ncc(NCCc4ccccc4)c3=O)cc2[nH]1] | — | 495.97 | 495.10 |
| 9 | 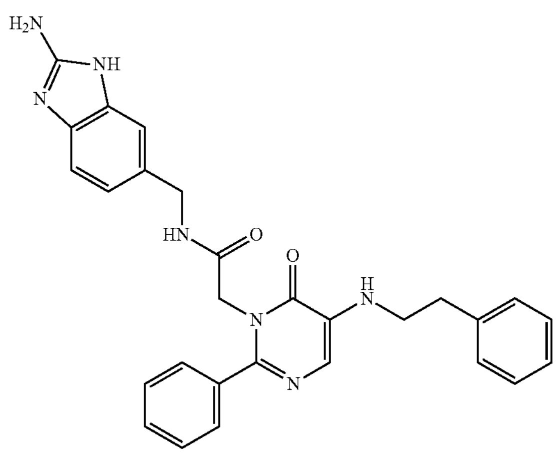 [SMILES: Nc1nc2ccc(CNC(=O)Cn3c(-c4ccccc4)ncc(NCCc4ccccc4)c3=O)cc2[nH]1] | — | 491.99 (ES−) | 493.22 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 10 | 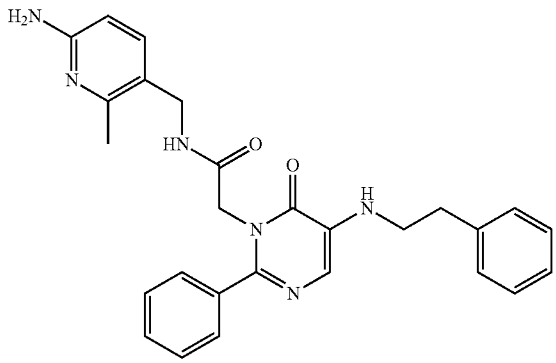 [SMILES: Cc1nc(N)ccc1CNC(=O)Cn1c(-c2ccccc2)ncc(NCCc2ccccc2)c1=O] | — | 469.11 | 468.23 |
| 11 | 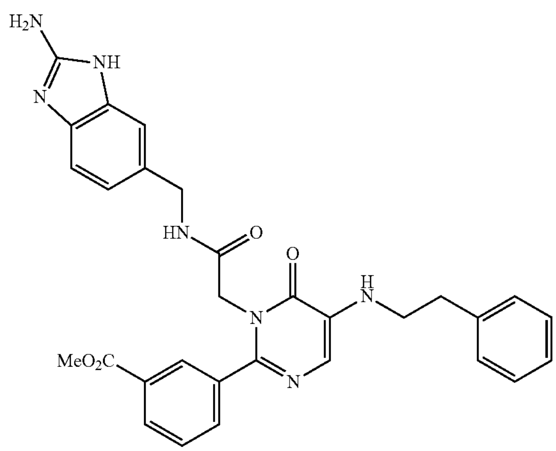 [SMILES: COC(=O)c1cccc(-c2ncc(NCCc3ccccc3)c(=O)n2CC(=O)NCc2ccc3nc(N)[nH]c3c2)c1] | — | 551.94 | 551.23 |
| 12 | 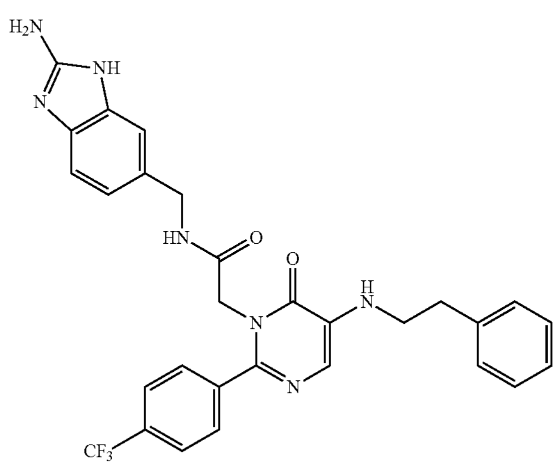 [SMILES: Nc1nc2ccc(CNC(=O)Cn3c(-c4ccc(C(F)(F)F)cc4)ncc(NCCc4ccccc4)c3=O)cc2[nH]1] | TFA | 561.89 | 561.21 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 13 | 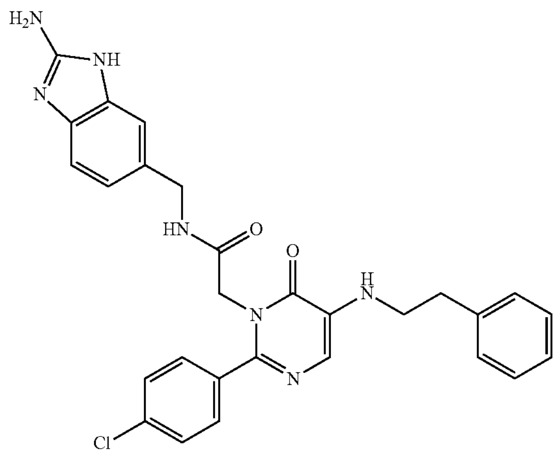 [SMILES: Nc1nc2ccc(CNC(=O)Cn3c(-c4ccc(Cl)cc4)ncc(NCCc4ccccc4)c3=O)cc2[nH]1] | TFA | 527.92 | 527.18 |
| 14 | 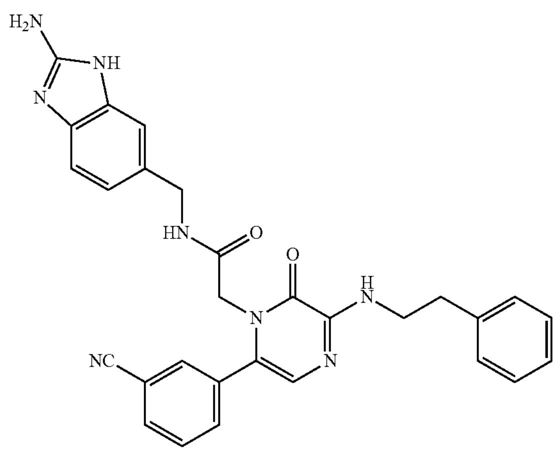 [SMILES: N#Cc1cccc(-c2cnc(NCCc3ccccc3)c(=O)n2CC(=O)NCc2ccc3nc(N)[nH]c3c2)c1] | — | 518.95 | 518.22 |
| 15 | 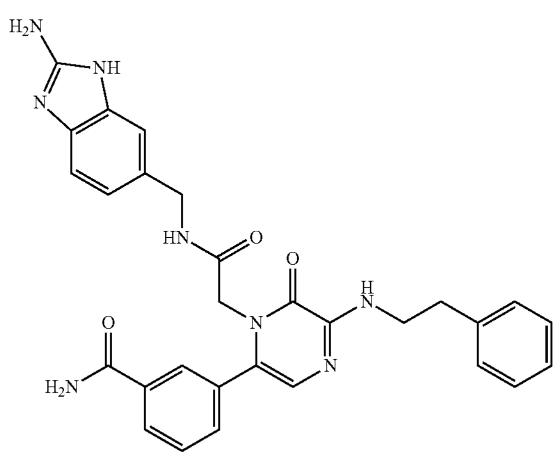 [SMILES: NC(=O)c1cccc(-c2cnc(NCCc3ccccc3)c(=O)n2CC(=O)NCc2ccc3nc(N)[nH]c3c2)c1] | TFA | 535.10 (ES−) | 536.23 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 16 | 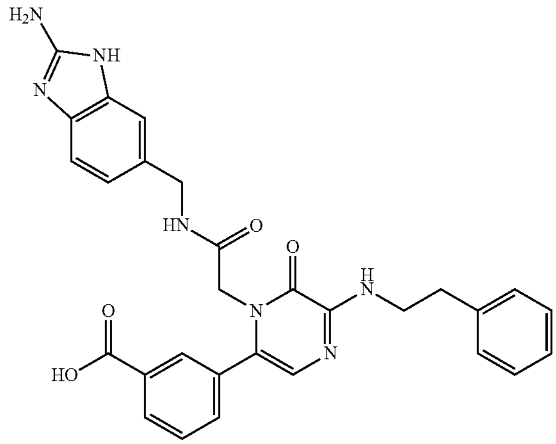 [SMILES: Nc1nc2ccc(CNC(=O)Cn3c(-c4cccc(C(=O)O)c4)cnc(NCCc4ccccc4)c3=O)cc2[nH]1] | TFA | 536.18 (ES−) | 537.21 |
| 17 | 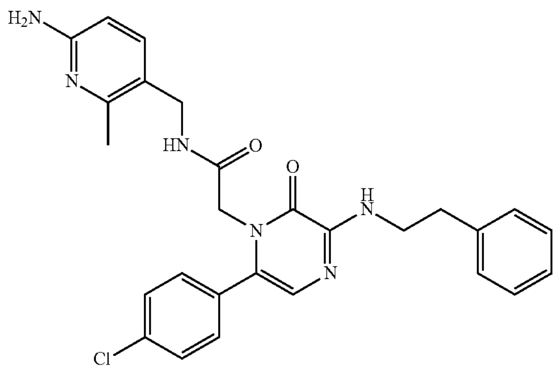 [SMILES: Cc1nc(N)ccc1CNC(=O)Cn1c(-c2ccc(Cl)cc2)cnc(NCCc2ccccc2)c1=O] | TFA | 503.13 | 502.19 |
| 18 | 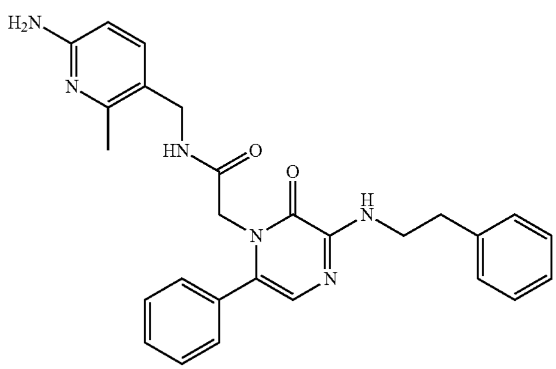 [SMILES: Cc1nc(N)ccc1CNC(=O)Cn1c(-c2ccccc2)cnc(NCCc2ccccc2)c1=O] | 2TFA | 470.15 | 469.22 |
| 19 | 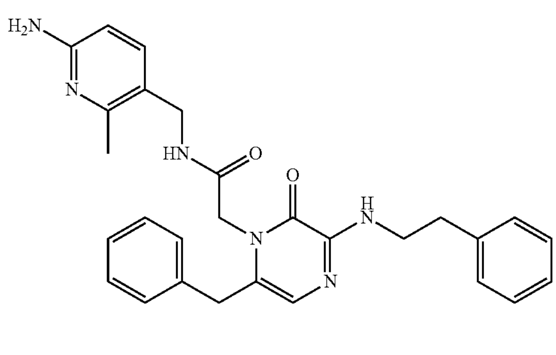 [SMILES: Cc1nc(N)ccc1CNC(=O)Cn1c(Cc2ccccc2)cnc(NCCc2ccccc2)c1=O] | TFA | 483.16 | 482.24 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 20 | 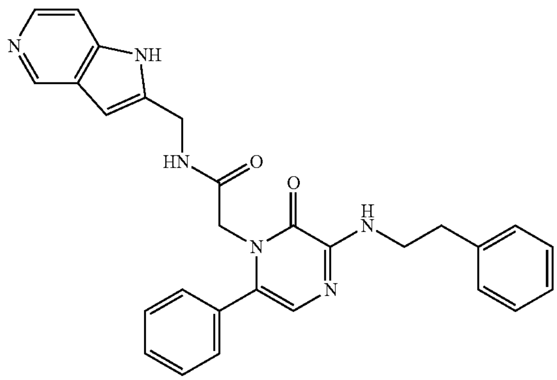 [SMILES: O=C(Cn1c(-c2ccccc2)cnc(NCCc2ccccc2)c1=O)NCc1cc2cnccc2[nH]1] | TFA | 479.16 | 478.21 |
| 21 | 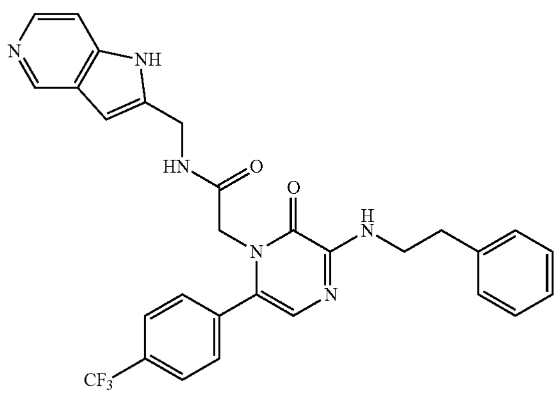 [SMILES: O=C(Cn1c(-c2ccc(C(F)(F)F)cc2)cnc(NCCc2ccccc2)c1=O)NCc1cc2cnccc2[nH]1] | TFA | 547.09 | 546.20 |
| 22 | 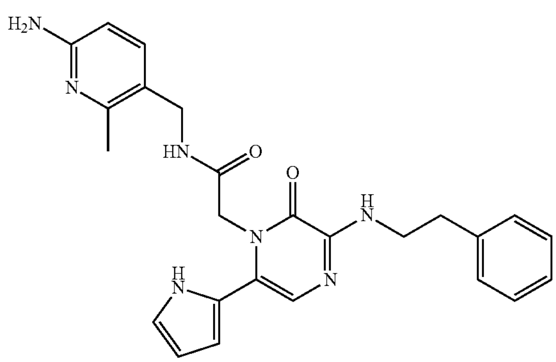 [SMILES: Cc1nc(N)ccc1CNC(=O)Cn1c(-c2ccc[nH]2)cnc(NCCc2ccccc2)c1=O] | — | 458.12 | 457.22 |
| 23 | 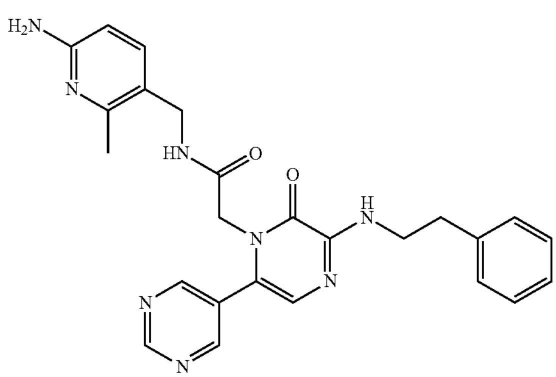 [SMILES: Cc1nc(N)ccc1CNC(=O)Cn1c(-c2cncnc2)cnc(NCCc2ccccc2)c1=O] | — | 471.19 | 470.22 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 24 | 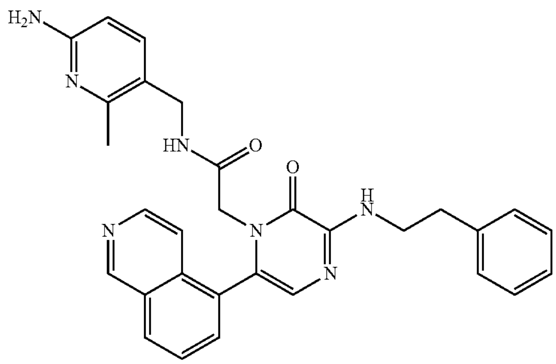 [SMILES: Cc1nc(N)ccc1CNC(=O)Cn1c(-c2cccc3cnccc23)cnc(NCCc2ccccc2)c1=O] | — | 520.18 | 519.24 |
| 25 | 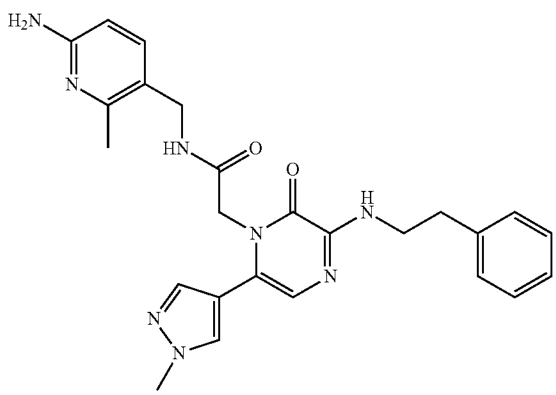 [SMILES: Cc1nc(N)ccc1CNC(=O)Cn1c(-c2cnn(C)c2)cnc(NCCc2ccccc2)c1=O] | — | 473.18 | 472.23 |
| 26 | 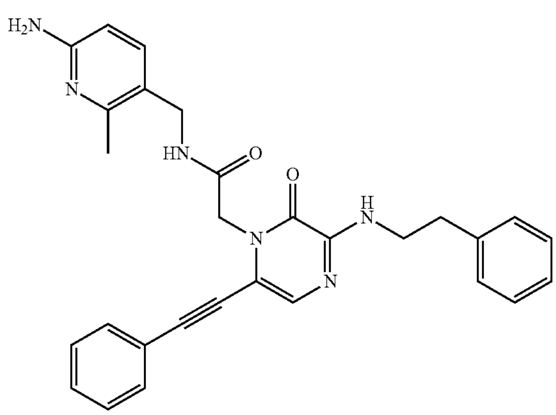 [SMILES: Cc1nc(N)ccc1CNC(=O)Cn1c(C#Cc2ccccc2)cnc(NCCc2ccccc2)c1=O] | — | 493.06 | 492.23 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 27 | 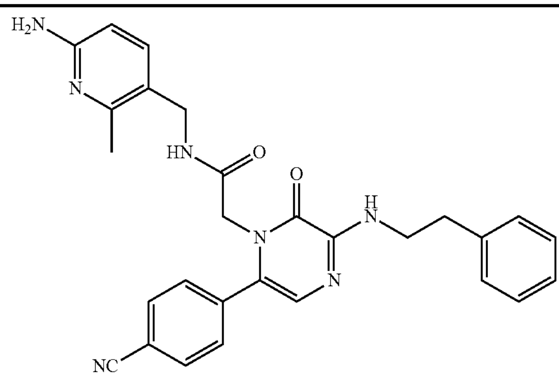 | — | 494.16 | 493.22 |
| 28 | 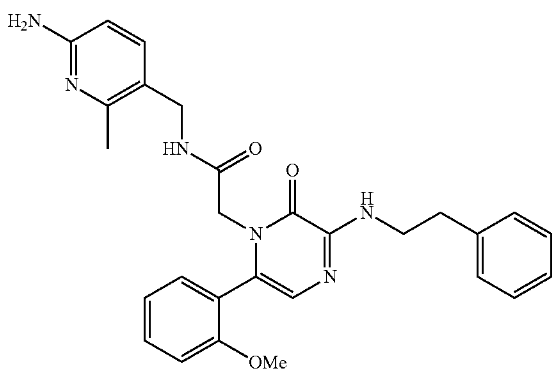 [SMILES: COc1ccccc1-c1cnc(NCCc2ccccc2)c(=O)n1CC(=O)NCc1ccc(N)nc1C] | HCl | 499.14 | 498.24 |
| 29 | 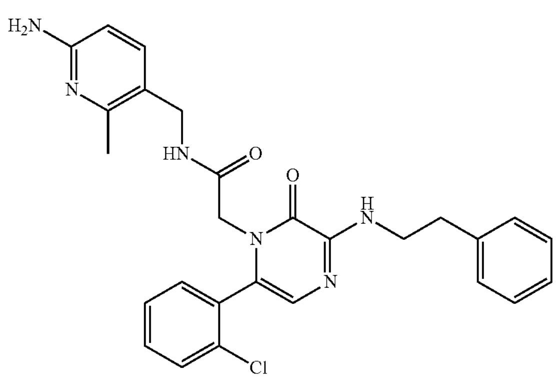 [SMILES: Cc1nc(N)ccc1CNC(=O)Cn1c(-c2ccccc2Cl)cnc(NCCc2ccccc2)c1=O] | — | 503.14 | 502.19 |
| 30 | 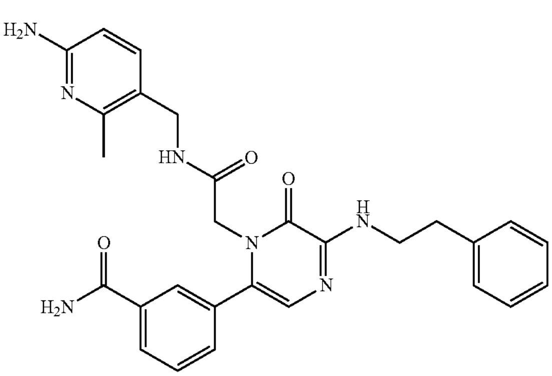 [SMILES: Cc1nc(N)ccc1CNC(=O)Cn1c(-c2cccc(C(N)=O)c2)cnc(NCCc2ccccc2)c1=O] | HCl | 512.12 | 511.23 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 31 | 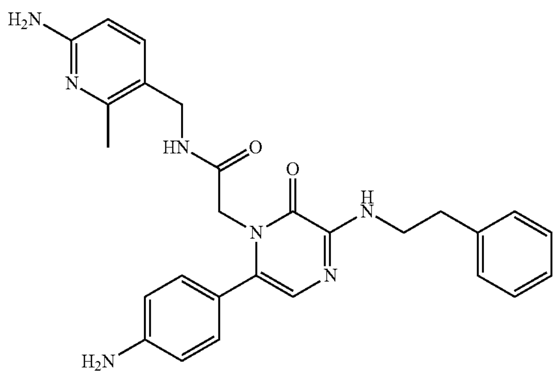 [SMILES: Cc1nc(N)ccc1CNC(=O)Cn1c(-c2ccc(N)cc2)cnc(NCCc2ccccc2)c1=O] | — | 484.18 | 483.24 |
| 32 | 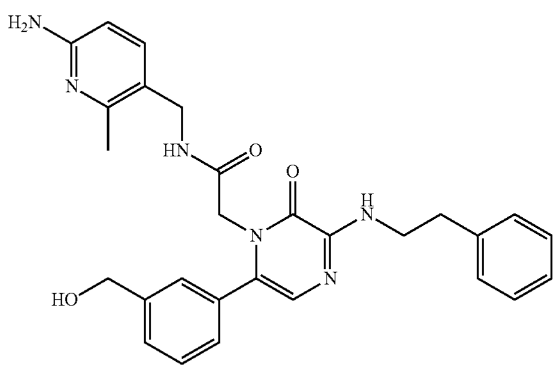 [SMILES: Cc1nc(N)ccc1CNC(=O)Cn1c(-c2cccc(CO)c2)cnc(NCCc2ccccc2)c1=O] | — | 499.15 | 498.24 |
| 33 | 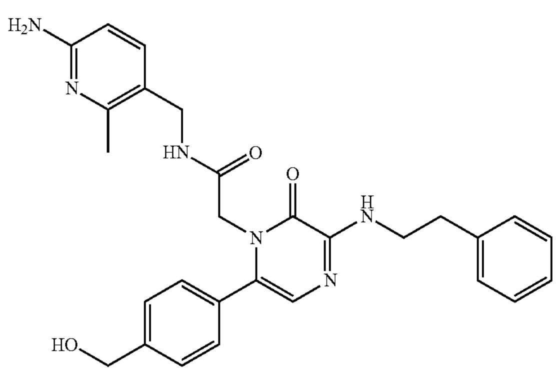 [SMILES: Cc1nc(N)ccc1CNC(=O)Cn1c(-c2ccc(CO)cc2)cnc(NCCc2ccccc2)c1=O] | — | 499.15 | 498.24 |
| 34 | 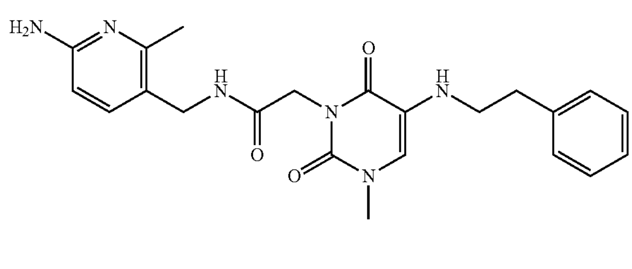 [SMILES: Cc1nc(N)ccc1CNC(=O)Cn1c(=O)c(NCCc2ccccc2)cn(C)c1=O] | — | 423.13 | 422.21 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 35 | 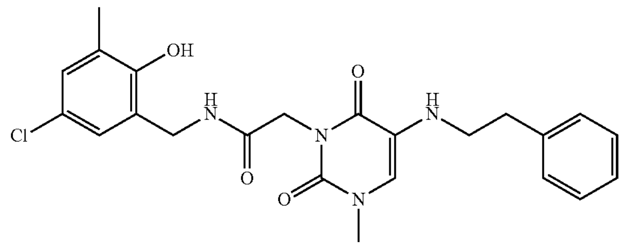 [SMILES: Cc1cc(Cl)cc(CNC(=O)Cn2c(=O)c(NCCc3ccccc3)cn(C)c2=O)c1O] | TFA | 457.00 | 456.16 |
| 36 | 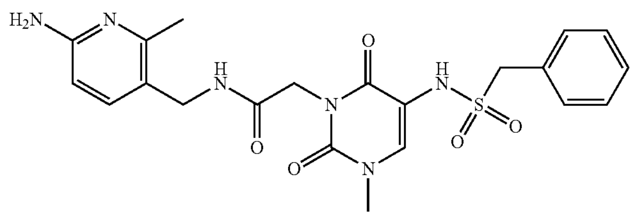 [SMILES: Cc1nc(N)ccc1CNC(=O)Cn1c(=O)c(NS(=O)(=O)Cc2ccccc2)cn(C)c1=O] | TFA | 473.06 | 472.15 |
| 37 | 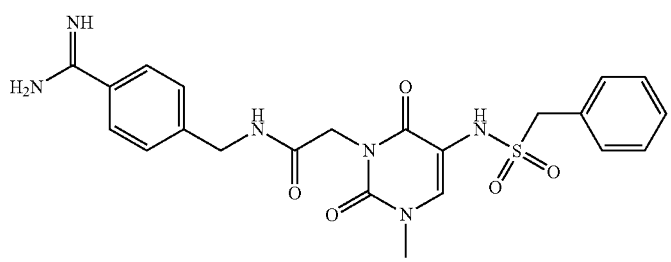 [SMILES: Cn1cc(NS(=O)(=O)Cc2ccccc2)c(=O)n(CC(=O)NCc2ccc(C(=N)N)cc2)c1=O] | TFA | 485.04 | 484.15 |
| 38 | 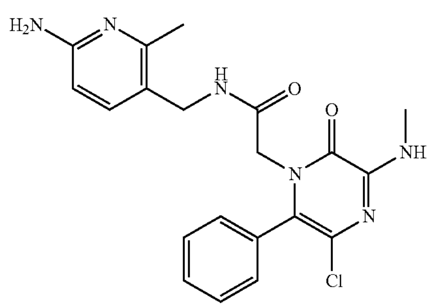 [SMILES: CNc1nc(Cl)c(-c2ccccc2)n(CC(=O)NCc2ccc(N)nc2C)c1=O] | — | 413.00 | 412.14 |
| 39 | 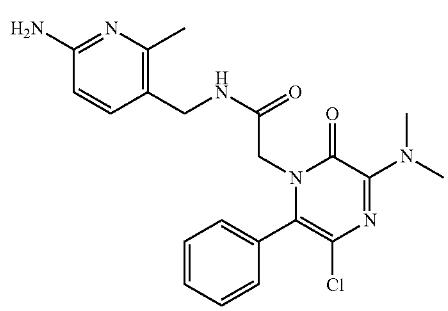 [SMILES: Cc1nc(N)ccc1CNC(=O)Cn1c(-c2ccccc2)c(Cl)nc(N(C)C)c1=O] | — | 427.01 | 426.16 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 40 | 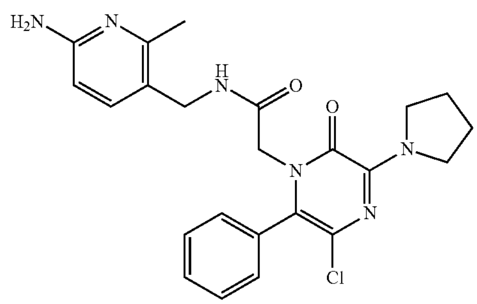 [SMILES: Cc1nc(N)ccc1CNC(=O)Cn1c(-c2ccccc2)c(Cl)nc(N2CCCC2)c1=O] | — | 453.06 | 452.17 |
| 41 | 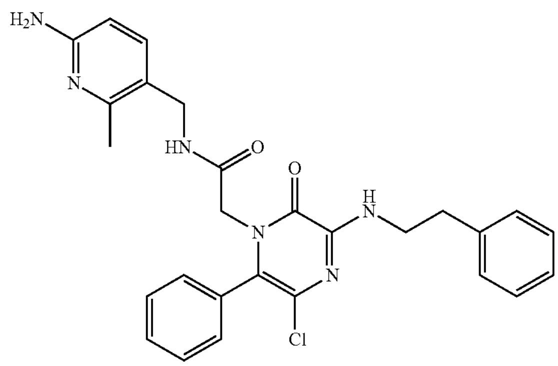 [SMILES: Cc1nc(N)ccc1CNC(=O)Cn1c(-c2ccccc2)c(Cl)nc(NCCc2ccccc2)c1=O] | — | 503.13 | 502.19 |
| 42 | 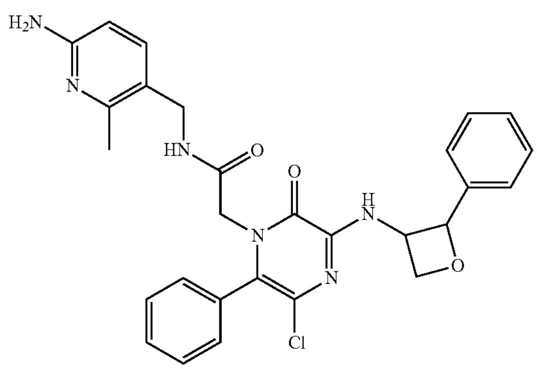 [SMILES: Cc1nc(N)ccc1CNC(=O)Cn1c(-c2ccccc2)c(Cl)nc(NC2COC2c2ccccc2)c1=O] | — | 531.08 | 530.18 |
| 43 | 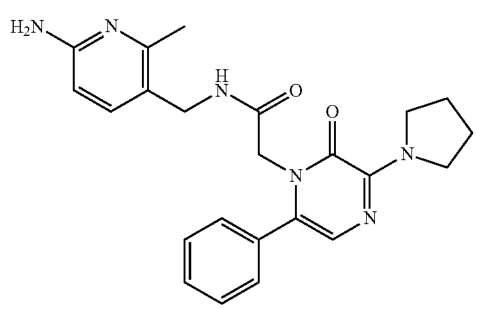 [SMILES: Cc1nc(N)ccc1CNC(=O)Cn1c(-c2ccccc2)cnc(N2CCCC2)c1=O] | — | 419.17 | 418.21 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 44 | 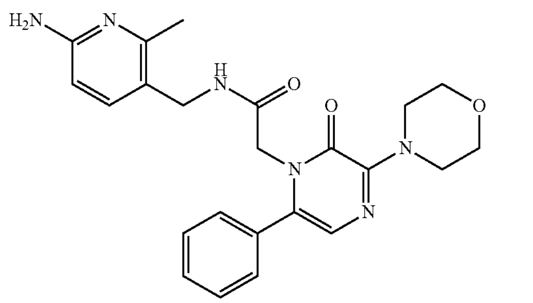 [SMILES: Cc1nc(N)ccc1CNC(=O)Cn1c(-c2ccccc2)cnc(N2CCOCC2)c1=O] | — | 435.16 | 434.21 |
| 45 | 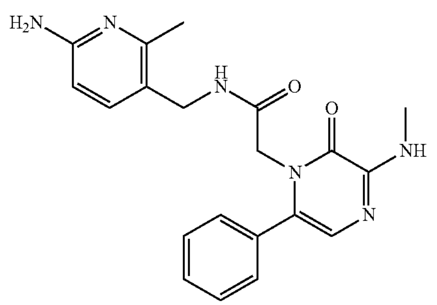 [SMILES: CNc1ncc(-c2ccccc2)n(CC(=O)NCc2ccc(N)nc2C)c1=O] | — | 379.14 | 378.18 |
| 46 | 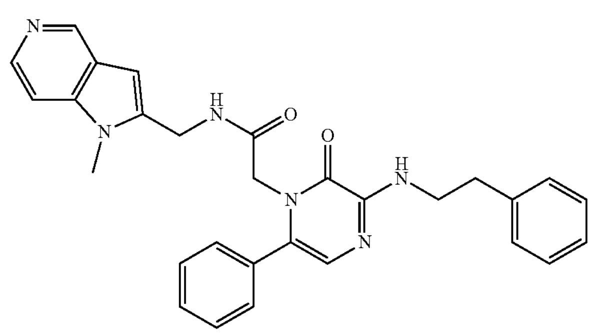 [SMILES: Cn1c(CNC(=O)Cn2c(-c3ccccc3)cnc(NCCc3ccccc3)c2=O)cc2cnccc21] | TFA | 493.14 | 492.23 |
| 47 | 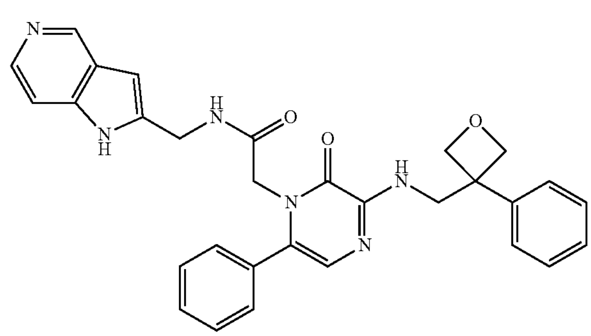 | TFA | 521.17 | 520.22 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 48 | 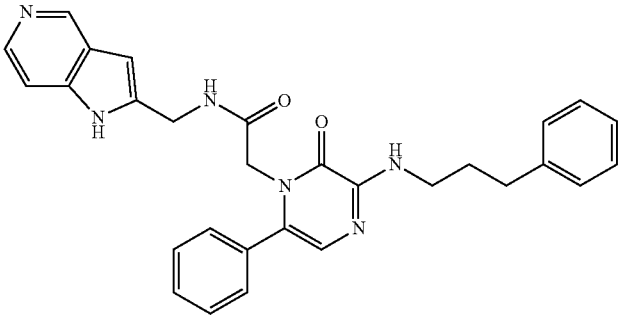 [SMILES: O=C(Cn1c(-c2ccccc2)cnc(NCCCc2ccccc2)c1=O)NCc1cc2cnccc2[nH]1] | TFA | 493.24 | 492.23 |
| 49 | 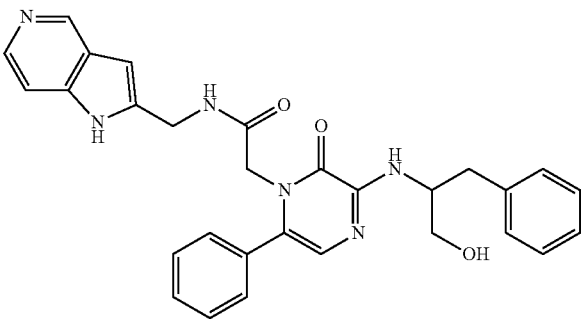 [SMILES: O=C(Cn1c(-c2ccccc2)cnc(NC(CO)Cc2ccccc2)c1=O)NCc1cc2cnccc2[nH]1] | TFA | 509.18 | 508.22 |
| 50 | 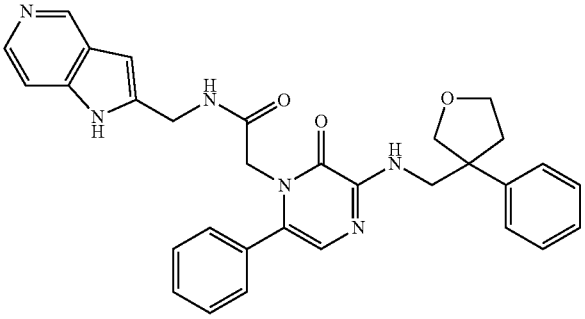 [SMILES: O=C(Cn1c(-c2ccccc2)cnc(NCC2(c3ccccc3)CCOC2)c1=O)NCc1cc2cnccc2[nH]1] | TFA | 535.71 | 534.24 |
| 51 | 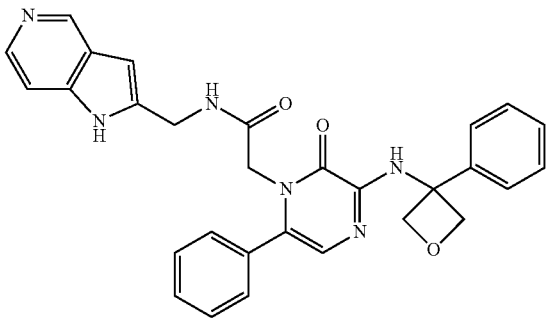 [SMILES: O=C(Cn1c(-c2ccccc2)cnc(NC2(c3ccccc3)COC2)c1=O)NCc1cc2cnccc2[nH]1] | TFA | 507.57 | 506.21 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 52 | 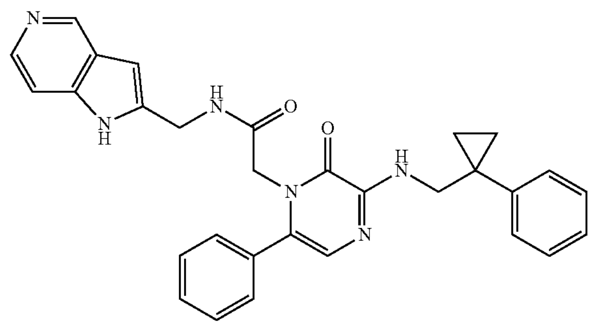 [SMILES: O=C(Cn1c(-c2ccccc2)cnc(NCC2(c3ccccc3)CC2)c1=O)NCc1cc2cnccc2[nH]1] | TFA | 505.17 | 504.23 |
| 53 | 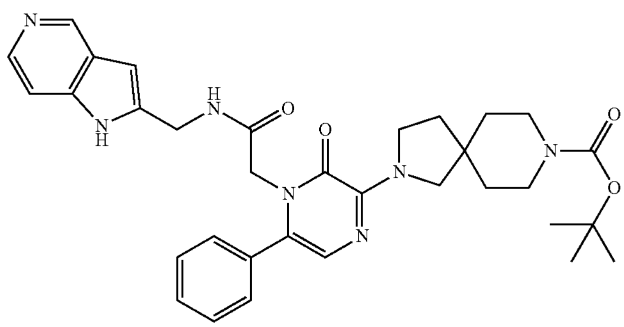 [SMILES: CC(C)(C)OC(=O)N1CCC2(CC1)CCN(c1ncc(-c3ccccc3)n(CC(=O)NCc3cc4cnccc4[nH]3)c1=O)C2] | — | 598.22 | 597.31 |
| 54 | 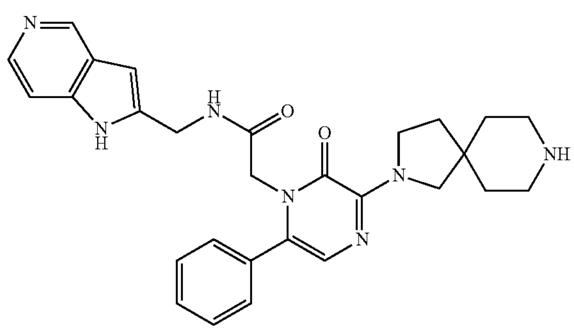 [SMILES: O=C(Cn1c(-c2ccccc2)cnc(N2CCC3(CCNCC3)C2)c1=O)NCc1cc2cnccc2[nH]1] | 2TFA | 498.17 | 497.25 |
| 55 | 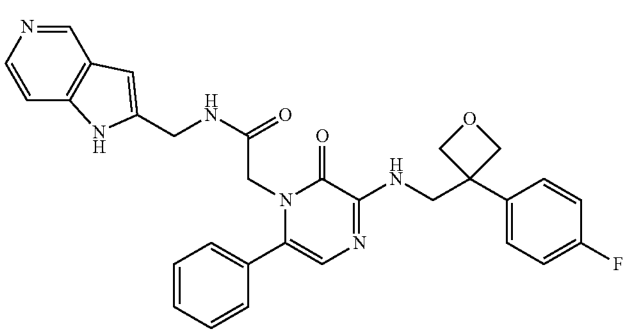 [SMILES: O=C(Cn1c(-c2ccccc2)cnc(NCC2(c3ccc(F)cc3)COC2)c1=O)NCc1cc2cnccc2[nH]1] | TFA | 539.17 | 538.21 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 56 | 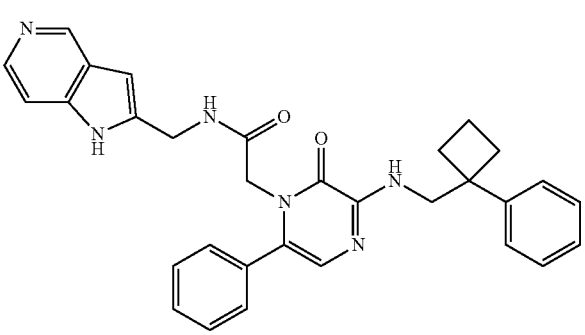 [SMILES: O=C(Cn1c(-c2ccccc2)cnc(NCC2(c3ccccc3)CCC2)c1=O)NCc1cc2cnccc2[nH]1] | TFA | 519.15 | 518.24 |
| 57 | 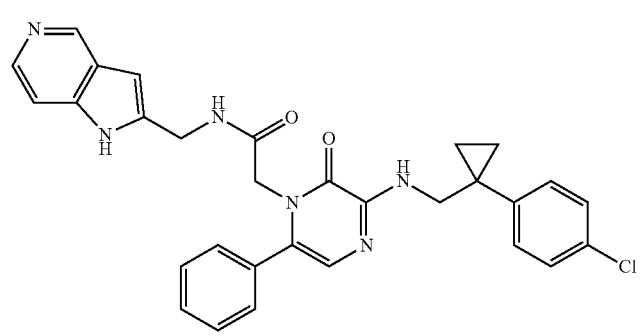 [SMILES: O=C(Cn1c(-c2ccccc2)cnc(NCC2(c3ccc(Cl)cc3)CC2)c1=O)NCc1cc2cnccc2[nH]1] | TFA | 539.09 | 538.19 |
| 58 | 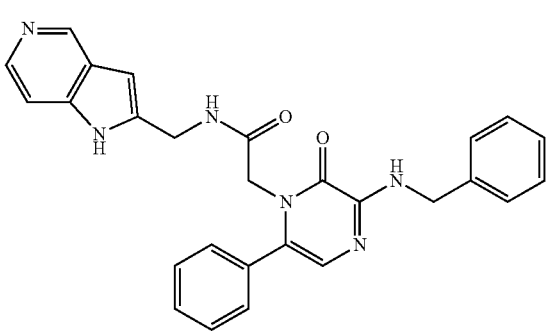 [SMILES: O=C(Cn1c(-c2ccccc2)cnc(NCc2ccccc2)c1=O)NCc1cc2cnccc2[nH]1] | TFA | 465.49 | 464.20 |
| 59 | 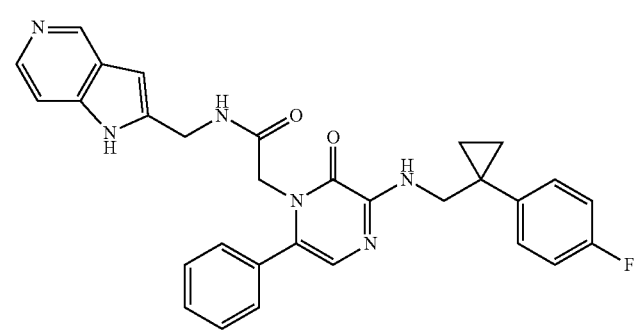 [SMILES: O=C(Cn1c(-c2ccccc2)cnc(NCC2(c3ccc(F)cc3)CC2)c1=O)NCc1cc2cnccc2[nH]1] | TFA | 523.58 | 522.22 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 60 | 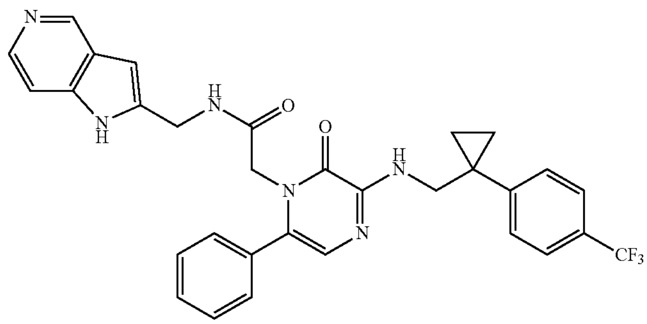 [SMILES: O=C(Cn1c(-c2ccccc2)cnc(NCC2(c3ccc(C(F)(F)F)cc3)CC2)c1=O)NCc1cc2cnccc2[nH]1] | TFA | 573.39 | 572.21 |
| 61 | 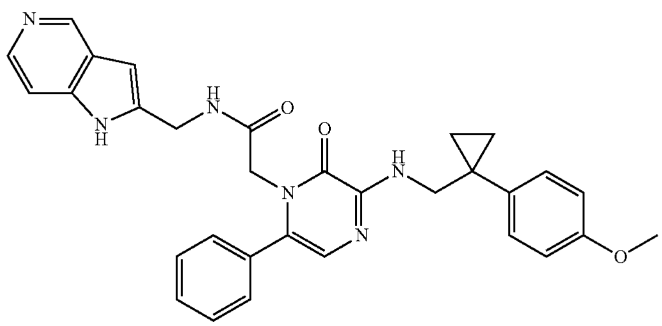 [SMILES: COc1ccc(C2(CNc3ncc(-c4ccccc4)n(CC(=O)NCc4cc5cnccc5[nH]4)c3=O)CC2)cc1] | TFA | 535.71 | 534.24 |
| 62 | 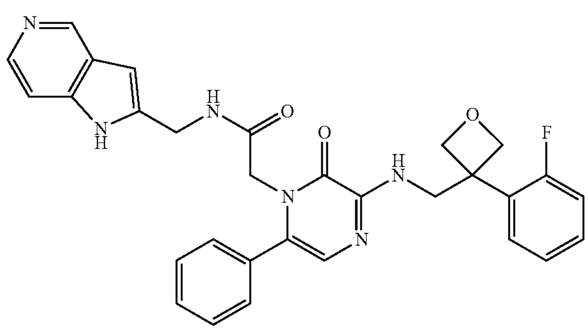 [SMILES: O=C(Cn1c(-c2ccccc2)cnc(NCC2(c3ccccc3F)COC2)c1=O)NCc1cc2cnccc2[nH]1] | TFA | 539.02 | 538.21 |
| 63 | 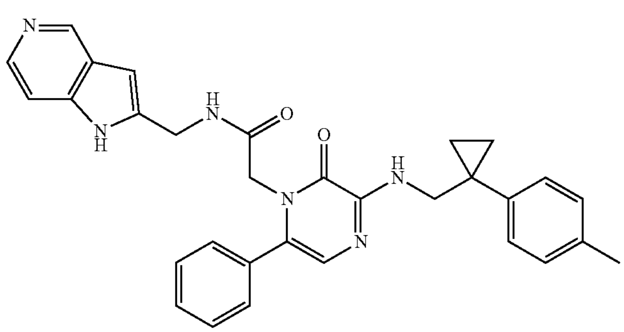 [SMILES: Cc1ccc(C2(CNc3ncc(-c4ccccc4)n(CC(=O)NCc4cc5cnccc5[nH]4)c3=O)CC2)cc1] | TFA | 519.14 | 518.24 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 64 | 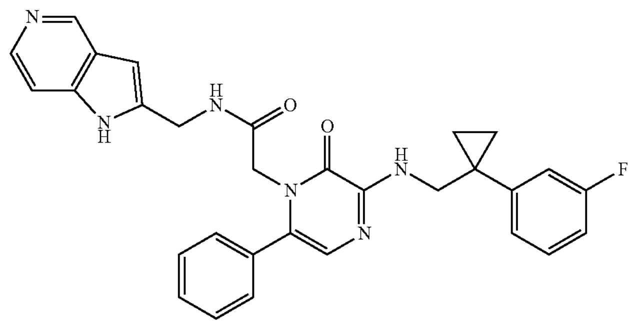 [SMILES: O=C(Cn1c(-c2ccccc2)cnc(NCC2(c3cccc(F)c3)CC2)c1=O)NCc1cc2cnccc2[nH]1] | — | 523.12 | 522.22 |
| 65 | 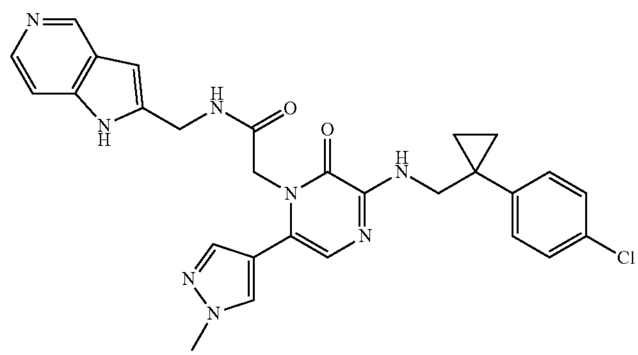 [SMILES: Cn1cc(-c2cnc(NCC3(c4ccc(Cl)cc4)CC3)c(=O)n2CC(=O)NCc2cc3cnccc3[nH]2)cn1] | TFA | 543.08 | 542.19 |
| 66 | 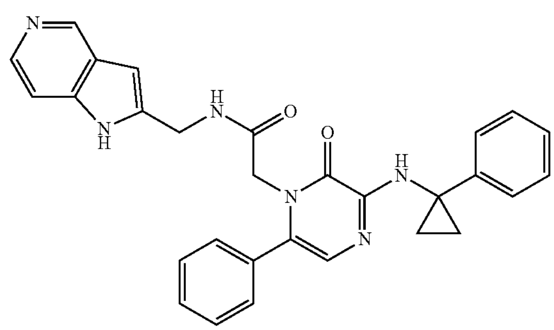 [SMILES: O=C(Cn1c(-c2ccccc2)cnc(NC2(c3ccccc3)CC2)c1=O)NCc1cc2cnccc2[nH]1] | TFA | 491.07 | 490.21 |
| 67 | 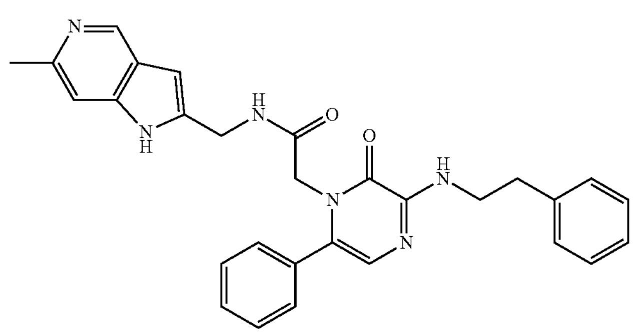 [SMILES: Cc1cc2[nH]c(CNC(=O)Cn3c(-c4ccccc4)cnc(NCCc4ccccc4)c3=O)cc2cn1] | TFA | 493.07 | 492.23 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 68 | 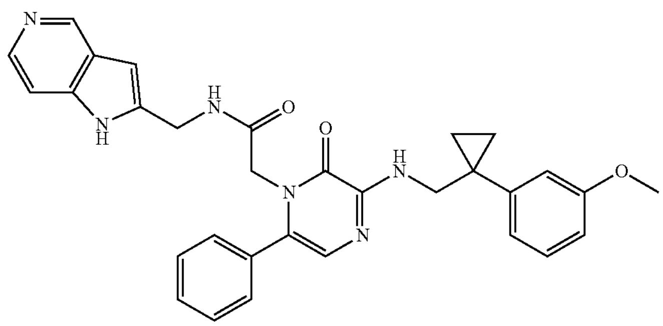 [SMILES: COc1cccc(C2(CNc3ncc(-c4ccccc4)n(CC(=O)NCc4cc5cnccc5[nH]4)c3=O)CC2)c1] | TFA | 535.11 | 534.24 |
| 69 | 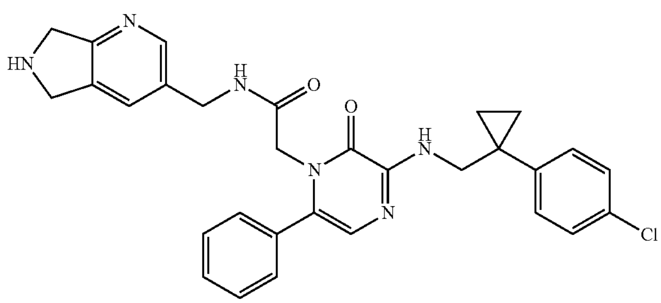 [SMILES: O=C(Cn1c(-c2ccccc2)cnc(NCC2(c3ccc(Cl)cc3)CC2)c1=O)NCc1cnc2c(c1)CNC2] | TFA | 541.06 | 540.20 |
| 70 | 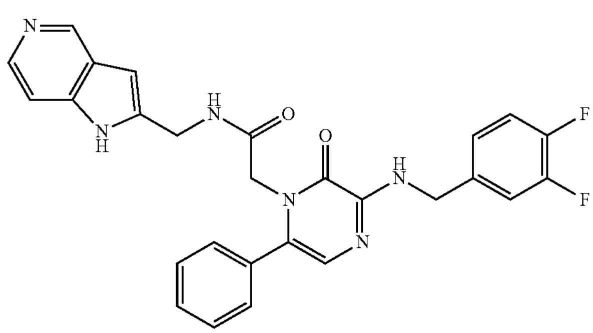 [SMILES: O=C(Cn1c(-c2ccccc2)cnc(NCc2ccc(F)c(F)c2)c1=O)NCc1cc2cnccc2[nH]1] | TFA | 501.02 | 500.18 |
| 71 | 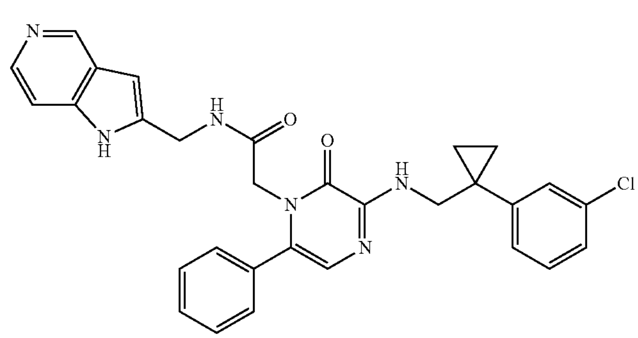 [SMILES: O=C(Cn1c(-c2ccccc2)cnc(NCC2(c3cccc(Cl)c3)CC2)c1=O)NCc1cc2cnccc2[nH]1] | TFA | 538.98 | 538.19 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 72 | 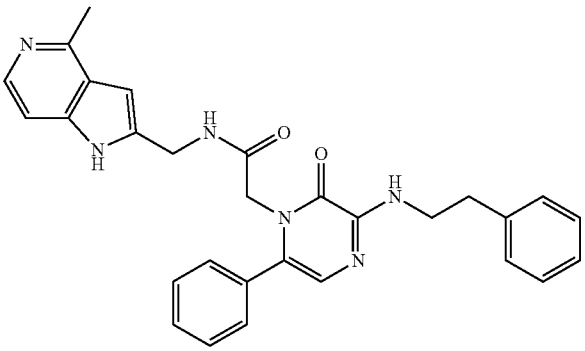 [SMILES: Cc1nccc2[nH]c(CNC(=O)Cn3c(-c4ccccc4)cnc(NCCc4ccccc4)c3=O)cc12] | TFA | 493.06 | 492.23 |
| 73 | 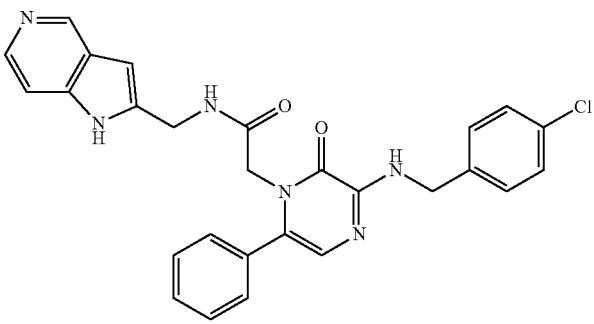 [SMILES: O=C(Cn1c(-c2ccccc2)cnc(NCc2ccc(Cl)cc2)c1=O)NCc1cc2cnccc2[nH]1] | TFA | 498.94 | 498.16 |
| 74 | 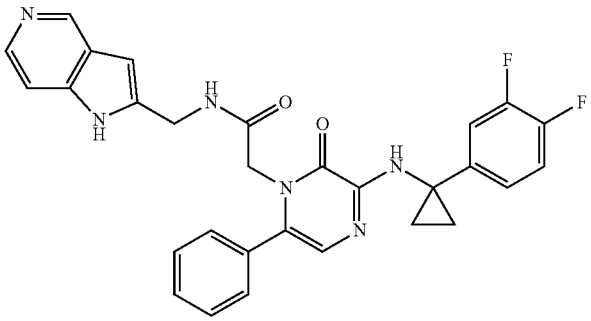 [SMILES: O=C(Cn1c(-c2ccccc2)cnc(NC2(c3ccc(F)c(F)c3)CC2)c1=O)NCc1cc2cnccc2[nH]1] | TFA | 526.98 | 526.19 |
| 75 | 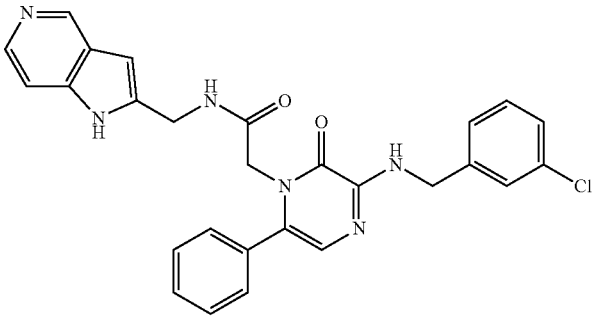 [SMILES: O=C(Cn1c(-c2ccccc2)cnc(NCc2cccc(Cl)c2)c1=O)NCc1cc2cnccc2[nH]1] | TFA | 499.07 | 498.16 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 76 | 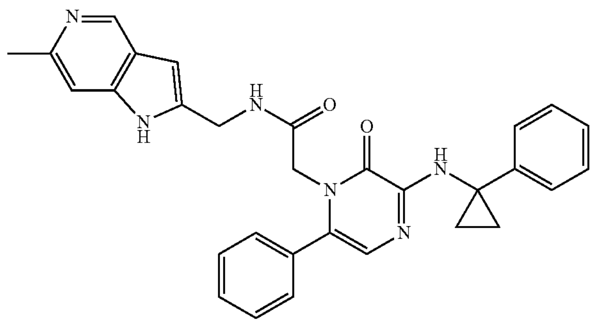 [SMILES: Cc1cc2[nH]c(CNC(=O)Cn3c(-c4ccccc4)cnc(NC4(c5ccccc5)CC4)c3=O)cc2cn1] | TFA | 505.13 | 504.23 |
| 77 | 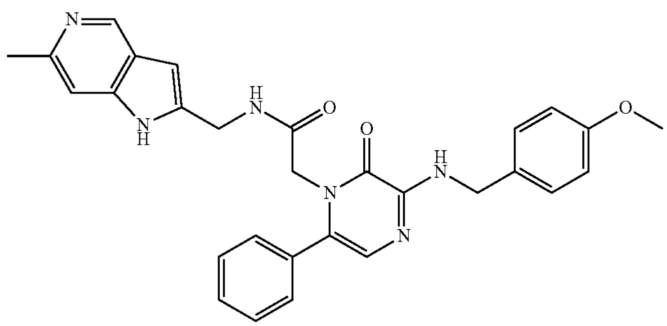 | TFA | 509.15 | 508.22 |
| 78 | 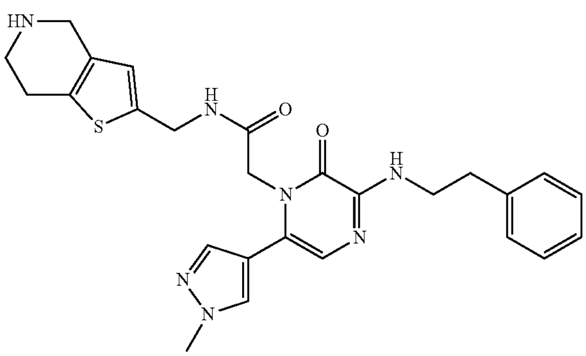 [SMILES: Cn1cc(-c2cnc(NCCc3ccccc3)c(=O)n2CC(=O)NCc2cc3c(s2)CCNC3)cn1] | — | 504.51 | 503.21 |
| 79 | 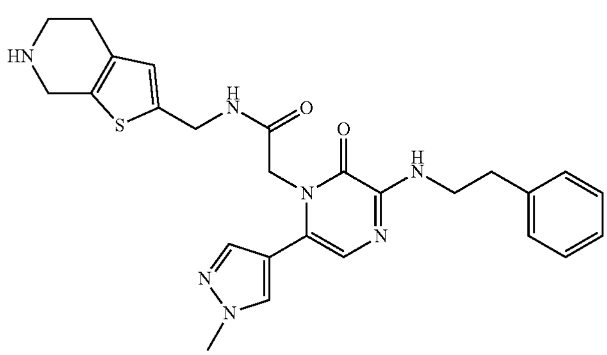 [SMILES: Cn1cc(-c2cnc(NCCc3ccccc3)c(=O)n2CC(=O)NCc2cc3c(s2)CNCC3)cn1] | — | 504.51 | 503.21 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 80 | 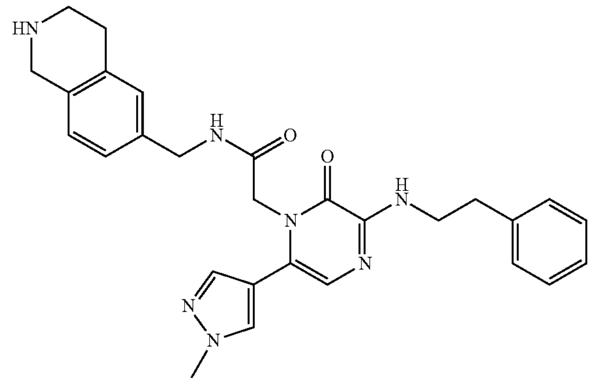 [SMILES: Cn1cc(-c2cnc(NCCc3ccccc3)c(=O)n2CC(=O)NCc2ccc3c(c2)CCNC3)cn1] | — | 498.21 | 497.25 |
| 81 | 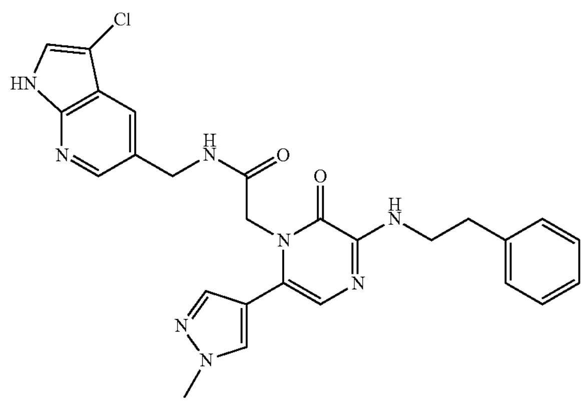 [SMILES: Cn1cc(-c2cnc(NCCc3ccccc3)c(=O)n2CC(=O)NCc2cnc3[nH]cc(Cl)c3c2)cn1] | — | 517.11 | 516.18 |
| 82 | 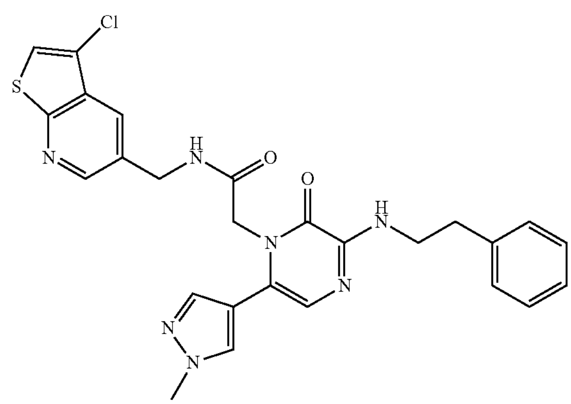 [SMILES: Cn1cc(-c2cnc(NCCc3ccccc3)c(=O)n2CC(=O)NCc2cnc3scc(Cl)c3c2)cn1] | — | 533.93 | 533.14 |
| 83 | 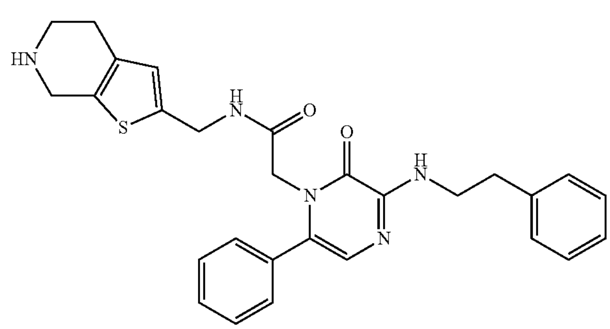 [SMILES: O=C(Cn1c(-c2ccccc2)cnc(NCCc2ccccc2)c1=O)NCc1cc2c(s1)CNCC2] | — | 500.09 | 499.20 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 84 | 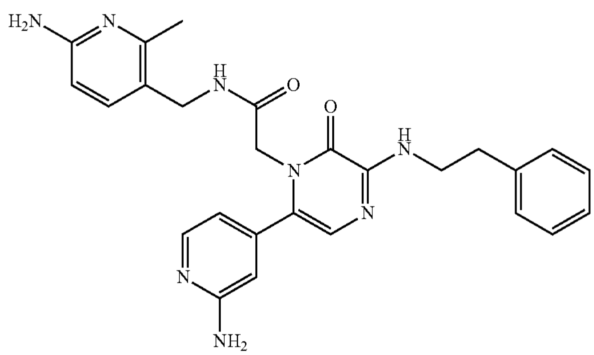 [SMILES: Cc1nc(N)ccc1CNC(=O)Cn1c(-c2ccnc(N)c2)cnc(NCCc2ccccc2)c1=O] | — | 485.47 | 484.6 |
| 85 | 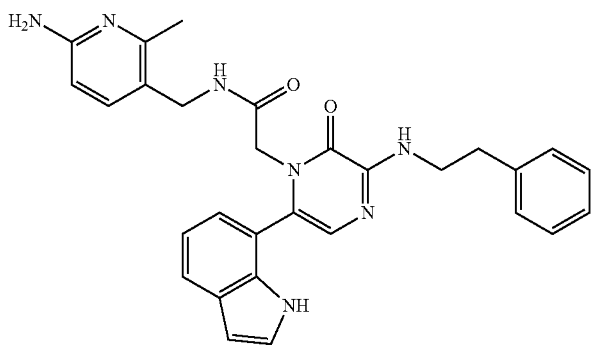 [SMILES: Cc1nc(N)ccc1CNC(=O)Cn1c(-c2cccc3cc[nH]c23)cnc(NCCc2ccccc2)c1=O] | TFA | 508.24 | 507.6 |
| 86 | 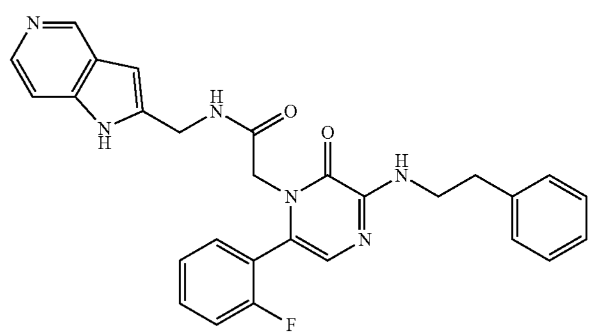 [SMILES: O=C(Cn1c(-c2ccccc2F)cnc(NCCc2ccccc2)c1=O)NCc1cc2cnccc2[nH]1] | TFA | 497.15 | 496.5 |
| 87 | 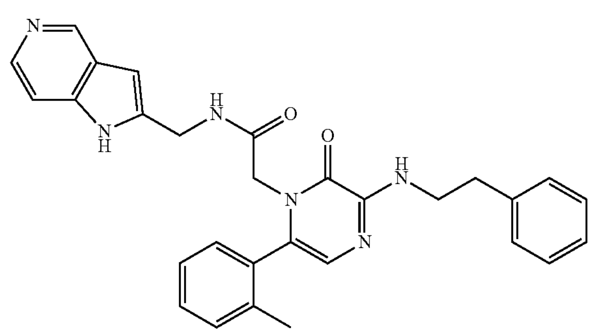 [SMILES: Cc1ccccc1-c1cnc(NCCc2ccccc2)c(=O)n1CC(=O)NCc1cc2cnccc2[nH]1] | TFA | 493.15 | 492.6 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 88 | 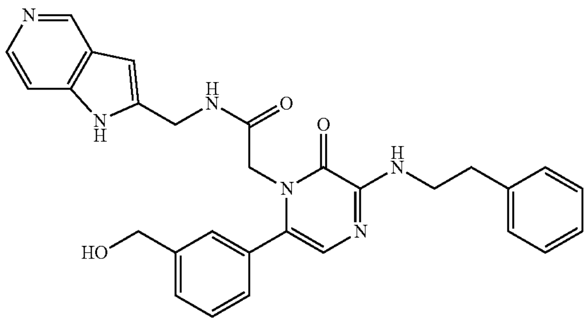 [SMILES: O=C(Cn1c(-c2cccc(CO)c2)cnc(NCCc2ccccc2)c1=O)NCc1cc2cnccc2[nH]1] | TFA | 509.13 | 508.6 |
| 89 | 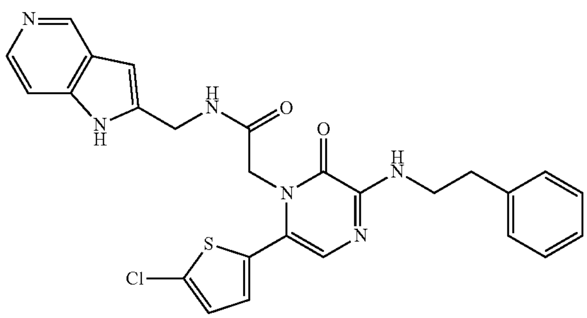 [SMILES: O=C(Cn1c(-c2ccc(Cl)s2)cnc(NCCc2ccccc2)c1=O)NCc1cc2cnccc2[nH]1] | — | 519.05 | 519 |
| 90 | 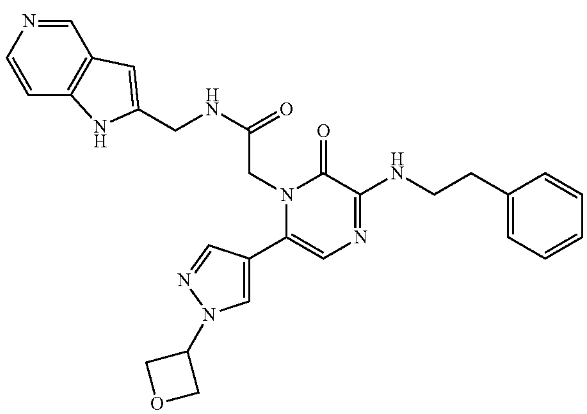 [SMILES: O=C(Cn1c(-c2cnn(C3COC3)c2)cnc(NCCc2ccccc2)c1=O)NCc1cc2cnccc2[nH]1] | TFA | 525.16 | 524.6 |
| 91 | 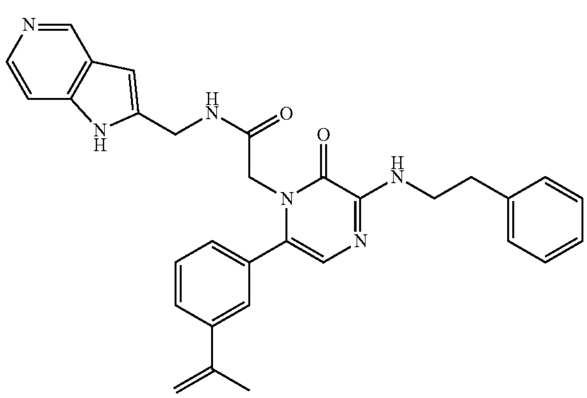 [SMILES: C=C(C)c1cccc(-c2cnc(NCCc3ccccc3)c(=O)n2CC(=O)NCc2cc3cnccc3[nH]2)c1] | — | 519.20 | 518.6 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 92 | 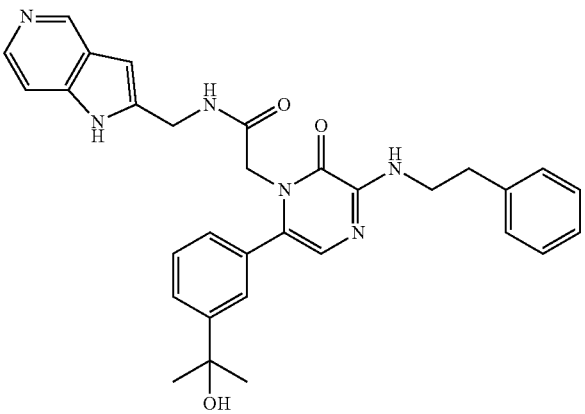 [SMILES: CC(C)(O)c1cccc(-c2cnc(NCCc3ccccc3)c(=O)n2CC(=O)NCc2cc3cnccc3[nH]2)c1] | — | 537.18 | 536.6 |
| 93 | 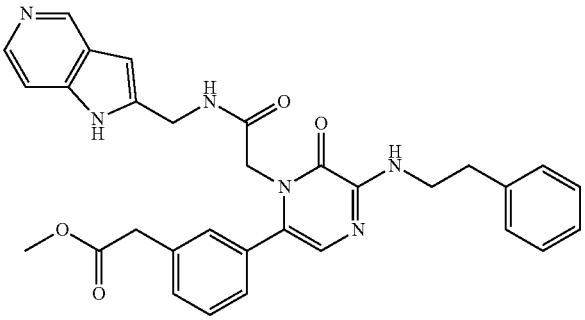 [SMILES: COC(=O)Cc1cccc(-c2cnc(NCCc3ccccc3)c(=O)n2CC(=O)NCc2cc3cnccc3[nH]2)c1] | TFA | 551.25 | 550.6 |
| 94 | 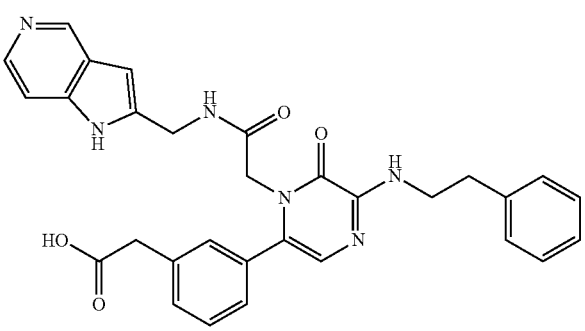 [SMILES: O=C(O)Cc1cccc(-c2cnc(NCCc3ccccc3)c(=O)n2CC(=O)NCc2cc3cnccc3[nH]2)c1] | TFA | 537.22 | 536.6 |
| 95 | 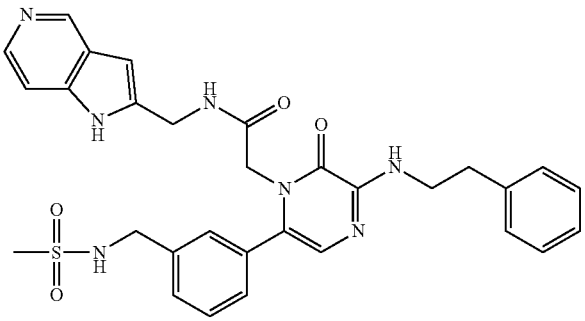 [SMILES: CS(=O)(=O)NCc1cccc(-c2cnc(NCCc3ccccc3)c(=O)n2CC(=O)NCc2cc3cnccc3[nH]2)c1] | — | 586.24 | 585.7 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 96 | 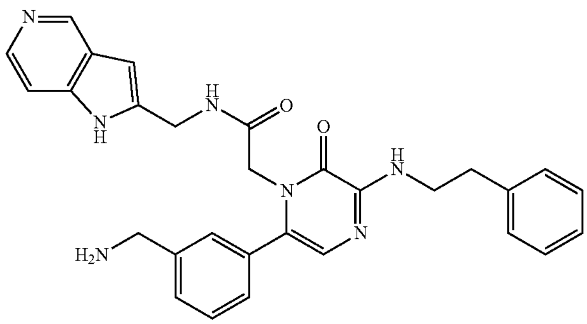 | — | 508.26 | 507.6 |
| 97 | 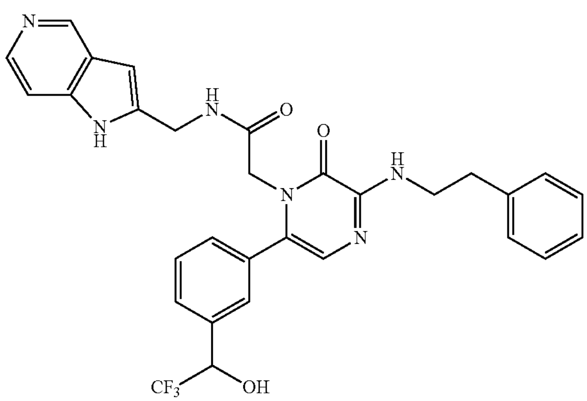 [SMILES: O=C(Cn1c(-c2cccc(C(O)C(F)(F)F)c2)cnc(NCCc2ccccc2)c1=O)NCc1cc2cnccc2[nH]1] | — | 577.59 | 576.6 |
| 98 | 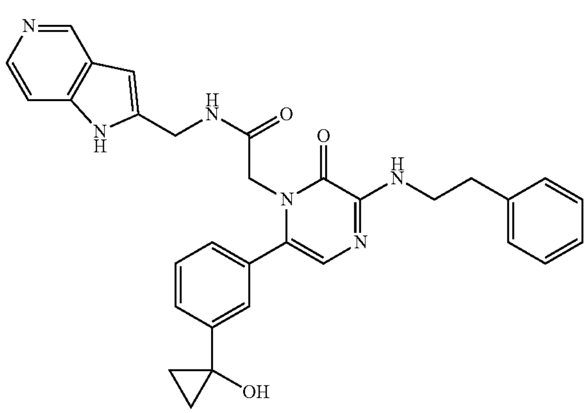 [SMILES: O=C(Cn1c(-c2cccc(C3(O)CC3)c2)cnc(NCCc2ccccc2)c1=O)NCc1cc2cnccc2[nH]1] | — | 577.59 | 576.6 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 99 | 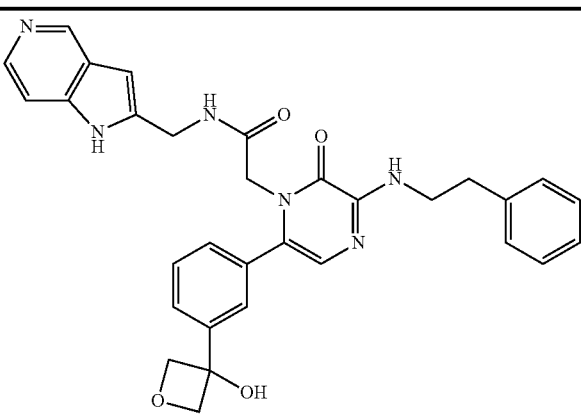 | — | 551.61 | 550.6 |
| 100 | 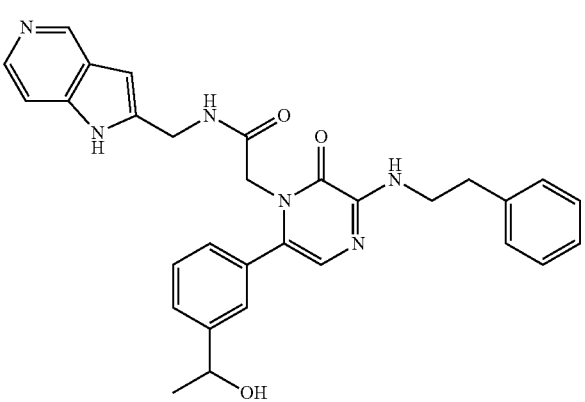 [SMILES: CC(O)c1cccc(-c2cnc(NCCc3ccccc3)c(=O)n2CC(=O)NCc2cc3cnccc3[nH]2)c1] | — | 523.62 | 522.6 |
| 101 | 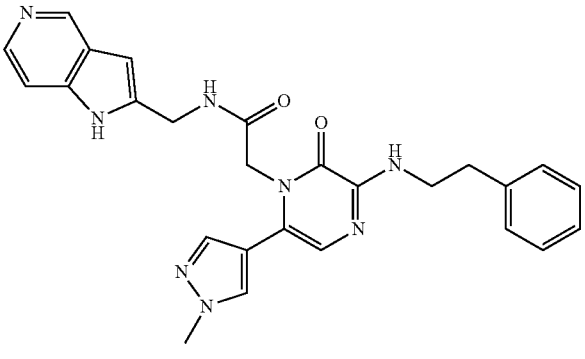 [SMILES: Cn1cc(-c2cnc(NCCc3ccccc3)c(=O)n2CC(=O)NCc2cc3cnccc3[nH]2)cn1] | — | 483.14 | 482.5 |
| 102 | 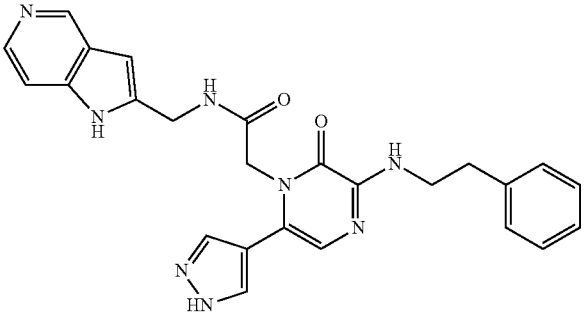 [SMILES: O=C(Cn1c(-c2cn[nH]c2)cnc(NCCc2ccccc2)c1=O)NCc1cc2cnccc2[nH]1] | — | 469.17 | 468.5 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 103 | 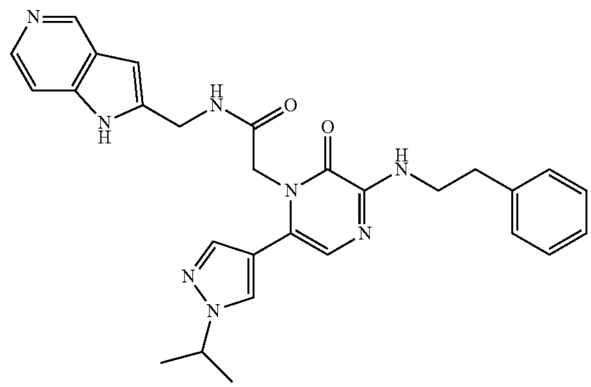 [SMILES: CC(C)n1cc(-c2cnc(NCCc3ccccc3)c(=O)n2CC(=O)NCc2cc3cnccc3[nH]2)cn1] | — | 511.16 | 510.6 |
| 104 | 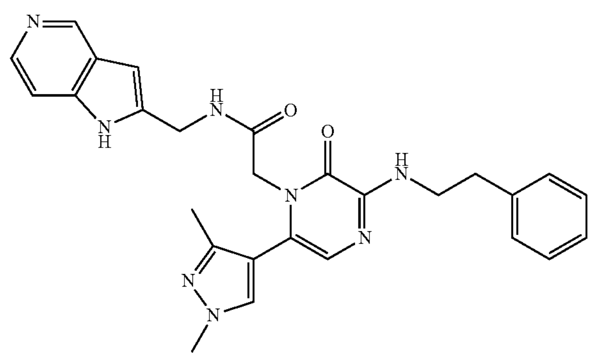 [SMILES: Cc1nn(C)cc1-c1cnc(NCCc2ccccc2)c(=O)n1CC(=O)NCc1cc2cnccc2[nH]1] | — | 497.18 | 496.6 |
| 105 | 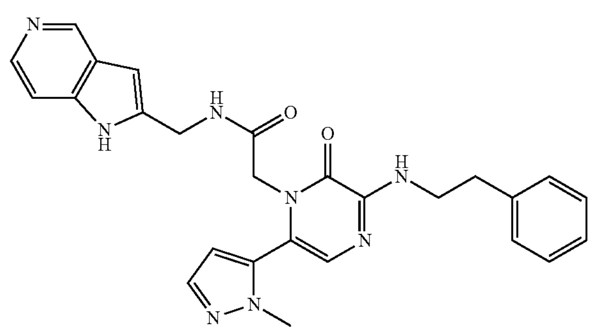 [SMILES: Cn1nccc1-c1cnc(NCCc2ccccc2)c(=O)n1CC(=O)NCc1cc2cnccc2[nH]1] | — | 483.17 | 482.5 |
| 106 | 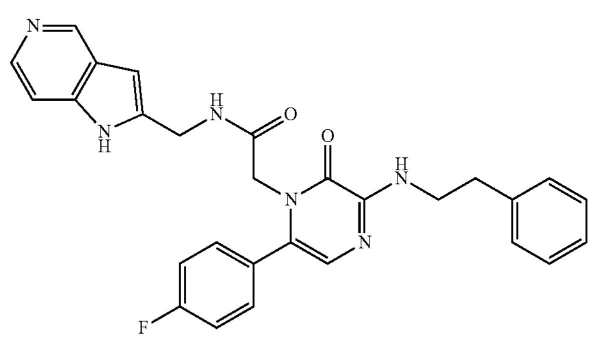 [SMILES: O=C(Cn1c(-c2ccc(F)cc2)cnc(NCCc2ccccc2)c1=O)NCc1cc2cnccc2[nH]1] | — | 497.51 | 496.5 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 107 | 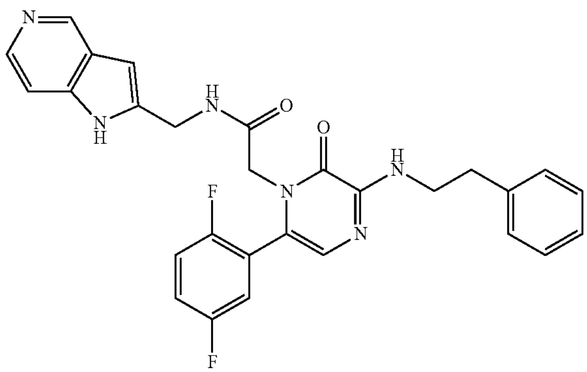 [SMILES: O=C(Cn1c(-c2cc(F)ccc2F)cnc(NCCc2ccccc2)c1=O)NCc1cc2cnccc2[nH]1] | — | 515.53 | 514.5 |
| 108 | 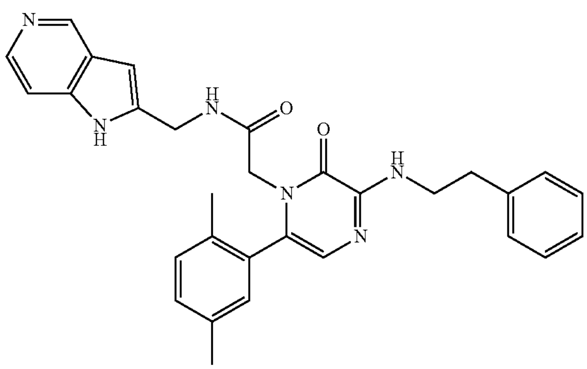 [SMILES: Cc1ccc(C)c(-c2cnc(NCCc3ccccc3)c(=O)n2CC(=O)NCc2cc3cnccc3[nH]2)c1] | — | 507.48 | 506.6 |
| 109 | 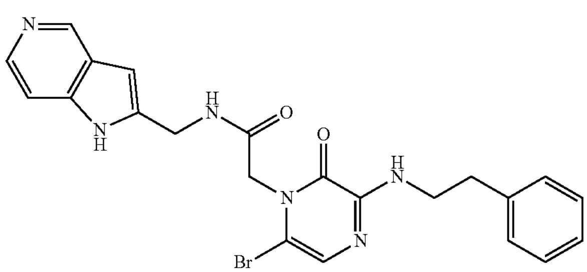 [SMILES: O=C(Cn1c(Br)cnc(NCCc2ccccc2)c1=O)NCc1cc2cnccc2[nH]1] | — | 480.97 | 481.3 |
| 110 | 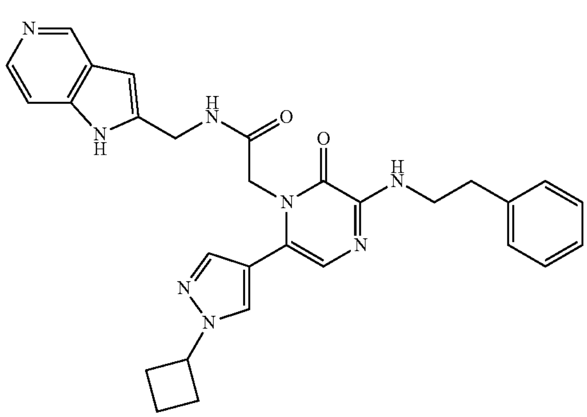 [SMILES: O=C(Cn1c(-c2cnn(C3CCC3)c2)cnc(NCCc2ccccc2)c1=O)NCc1cc2cnccc2[nH]1] | — | 523.06 | 522.6 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 111 | 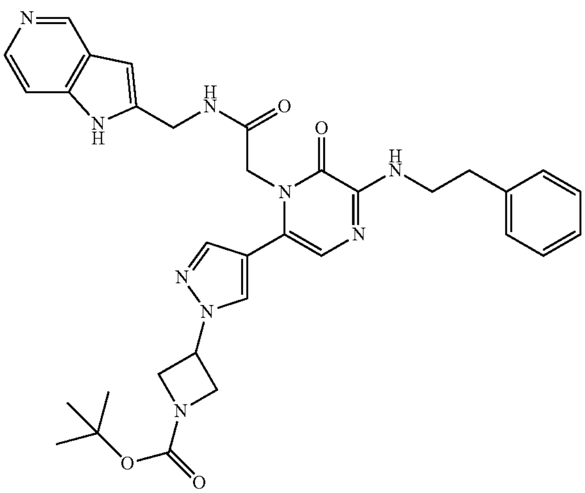 [SMILES: CC(C)(C)OC(=O)N1CC(n2cc(-c3cnc(NCCc4ccccc4)c(=O)n3CC(=O)NCc3cc4cnccc4[nH]3)cn2)C1] | — | 624.06 | 623.7 |
| 112 | 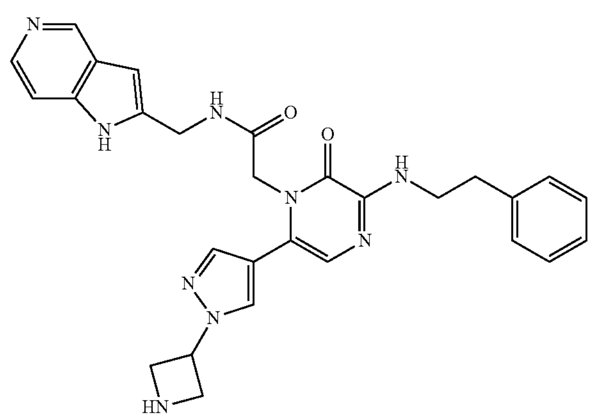 [SMILES: O=C(Cn1c(-c2cnn(C3CNC3)c2)cnc(NCCc2ccccc2)c1=O)NCc1cc2cnccc2[nH]1] | HCl | 524.04 | 523.6 |
| 113 | 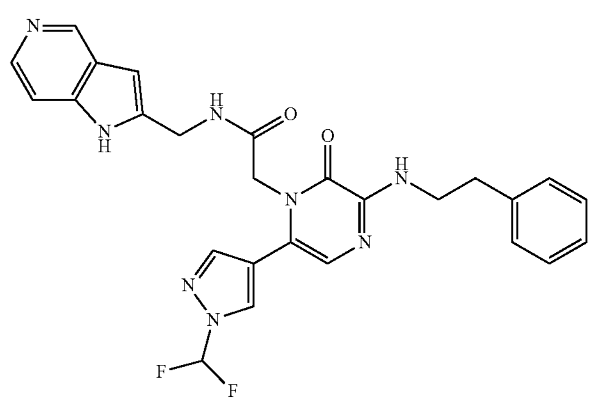 [SMILES: O=C(Cn1c(-c2cnn(C(F)F)c2)cnc(NCCc2ccccc2)c1=O)NCc1cc2cnccc2[nH]1] | — | 519.00 | 518.5 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 114 | 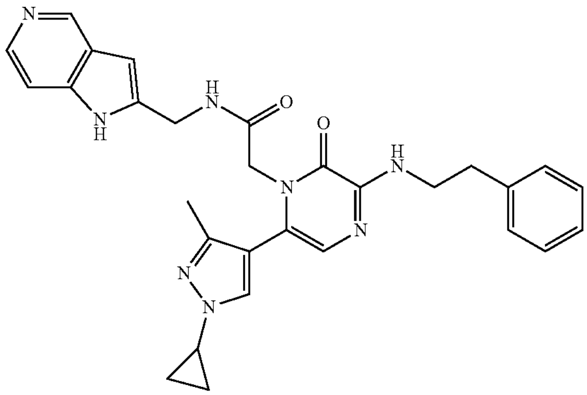 [SMILES: Cc1nn(C2CC2)cc1-c1cnc(NCCc2ccccc2)c(=O)n1CC(=O)NCc1cc2cnccc2[nH]1] | — | 523.04 | 522.6 |
| 115 | 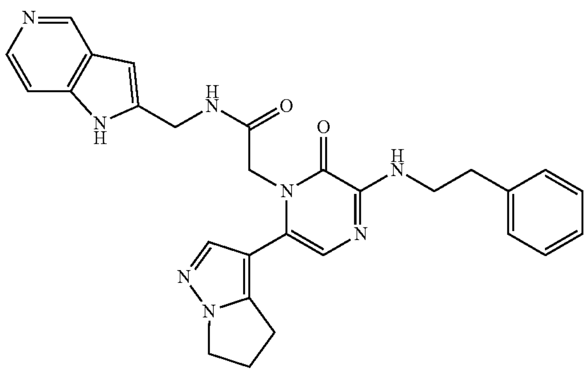 [SMILES: O=C(Cn1c(-c2cnn3c2CCC3)cnc(NCCc2ccccc2)c1=O)NCc1cc2cnccc2[nH]1] | — | 509.03 | 508.6 |
| 116 | 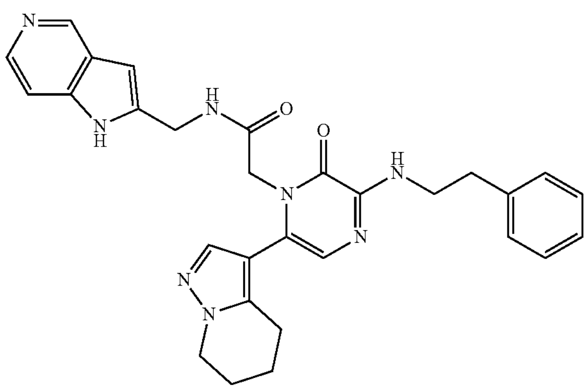 [SMILES: O=C(Cn1c(-c2cnn3c2CCCC3)cnc(NCCc2ccccc2)c1=O)NCc1cc2cnccc2[nH]1] | — | 523.05 | 522.6 |
| 117 | 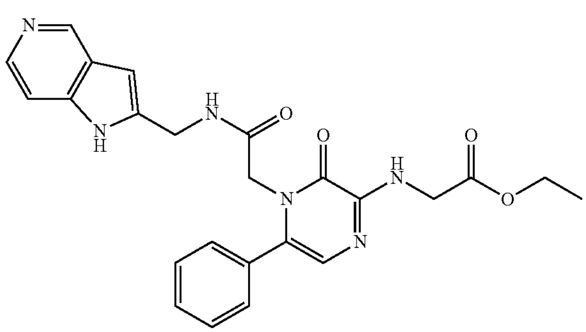 [SMILES: CCOC(=O)CNc1ncc(-c2ccccc2)n(CC(=O)NCc2cc3cnccc3[nH]2)c1=O] | — | 461.18 | 460.49 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 118 | 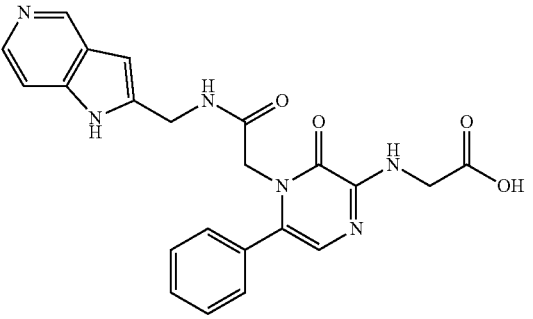 [SMILES: O=C(O)CNc1ncc(-c2ccccc2)n(CC(=O)NCc2cc3cnccc3[nH]2)c1=O] | TFA | 433.15 | 432.4 |
| 119 | 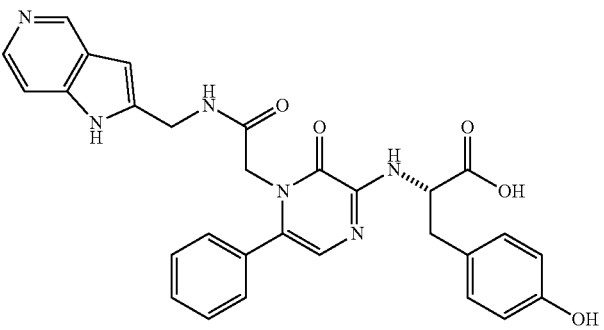 | TFA | 539.12 | 538.6 |
| 120 | 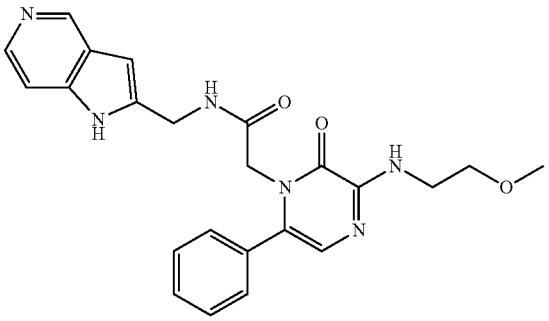 [SMILES: COCCNc1ncc(-c2ccccc2)n(CC(=O)NCc2cc3cnccc3[nH]2)c1=O] | TFA | 433.18 | 432.19 |
| 121 | 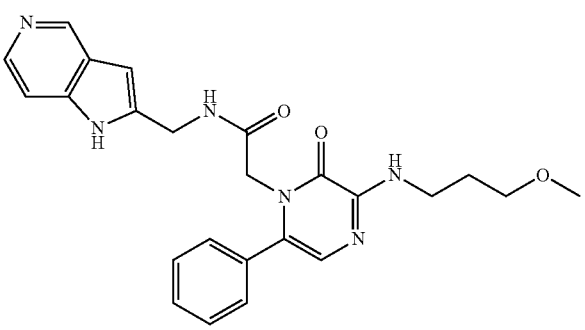 [SMILES: COCCCNc1ncc(-c2ccccc2)n(CC(=O)NCc2cc3cnccc3[nH]2)c1=O] | TFA | 447.19 | 446.21 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 122 | 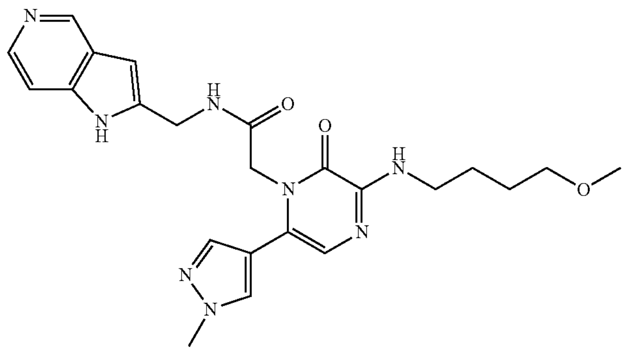 [SMILES: COCCCCNc1ncc(-c2cnn(C)c2)n(CC(=O)NCc2cc3cnccc3[nH]2)c1=O] | TFA | 465.20 | 464.23 |
| 123 | 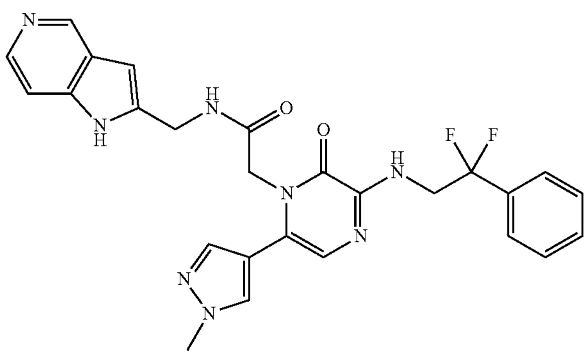 [SMILES: Cn1cc(-c2cnc(NCC(F)(F)c3ccccc3)c(=O)n2CC(=O)NCc2cc3cnccc3[nH]2)cn1] | TFA | 519.14 | 518.2 |
| 124 | 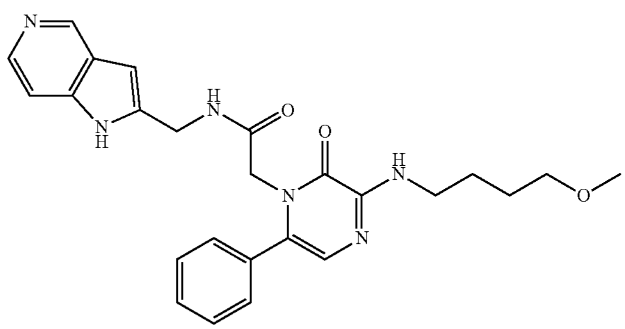 | TFA | 461.65 | 460.22 |
| 125 | 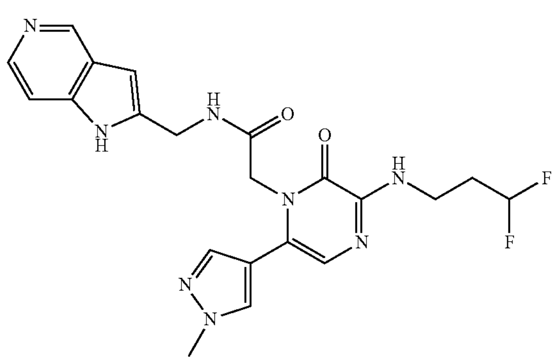 [SMILES: Cn1cc(-c2cnc(NCCC(F)F)c(=O)n2CC(=O)NCc2cc3cnccc3[nH]2)cn1] | TFA | 457.44 | 456.18 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 126 | 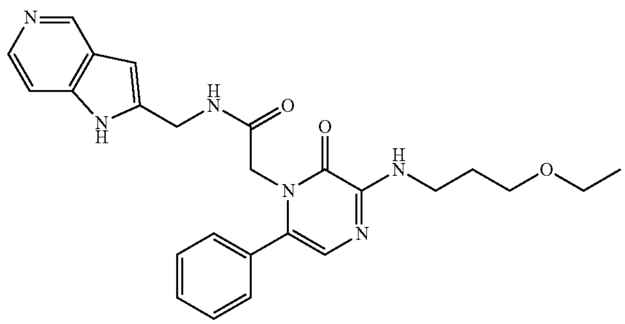 [SMILES: CCOCCCNc1ncc(-c2ccccc2)n(CC(=O)NCc2cc3cnccc3[nH]2)c1=O] | TFA | 461.55 | 460.22 |
| 127 | 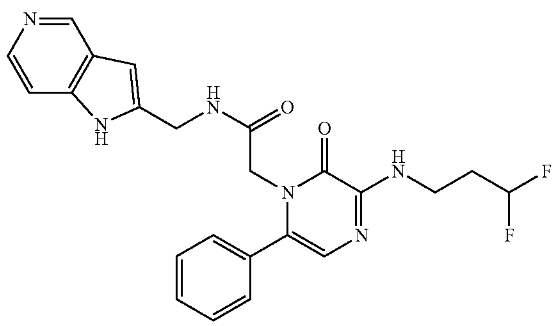 [SMILES: O=C(Cn1c(-c2ccccc2)cnc(NCCC(F)F)c1=O)NCc1cc2cnccc2[nH]1] | TFA | 453.42 | 452.18 |
| 128 | 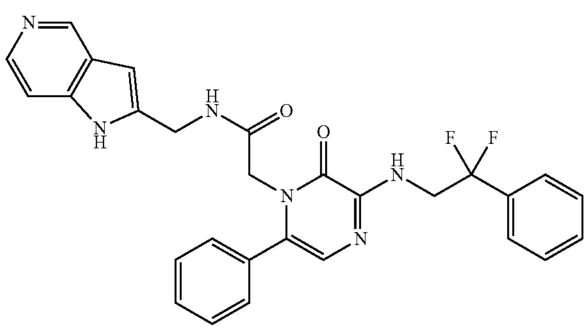 [SMILES: O=C(Cn1c(-c2ccccc2)cnc(NCC(F)(F)c2ccccc2)c1=O)NCc1cc2cnccc2[nH]1] | TFA | 515.53 | 514.19 |
| 129 | 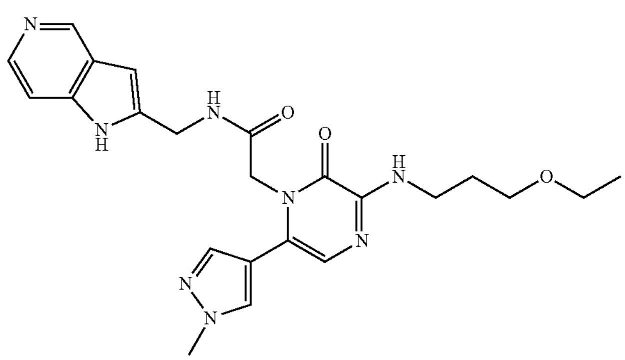 [SMILES: CCOCCCNc1ncc(-c2cnn(C)c2)n(CC(=O)NCc2cc3cnccc3[nH]2)c1=O] | TFA | 465.49 | 464.23 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 130 | 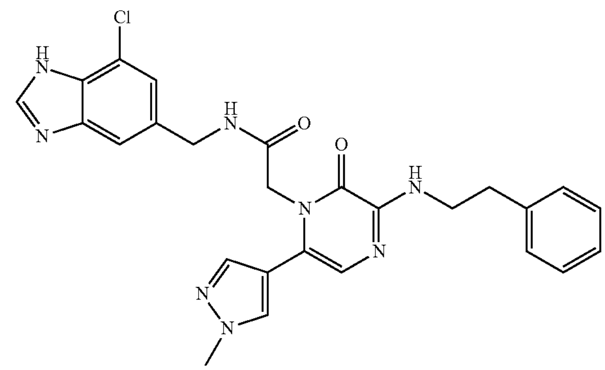 [SMILES: Cn1cc(-c2cnc(NCCc3ccccc3)c(=O)n2CC(=O)NCc2cc(Cl)c3[nH]cnc3c2)cn1] | — | 517.37 | 516.18 |
| 131 | 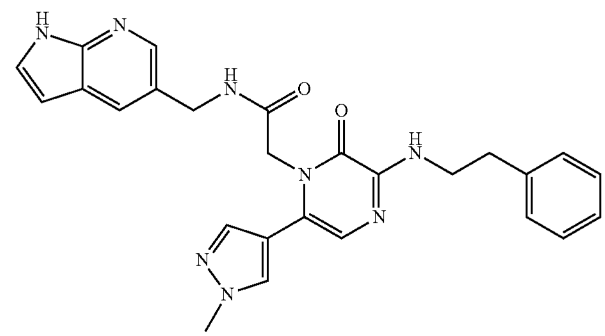 [SMILES: Cn1cc(-c2cnc(NCCc3ccccc3)c(=O)n2CC(=O)NCc2cnc3[nH]ccc3c2)cn1] | — | 483.60 | 482.22 |
| 132 | 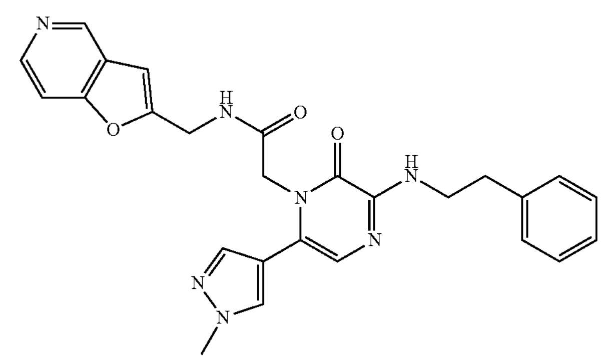 [SMILES: Cn1cc(-c2cnc(NCCc3ccccc3)c(=O)n2CC(=O)NCc2cc3cnccc3o2)cn1] | — | 484.56 | 483.20 |
| 133 | 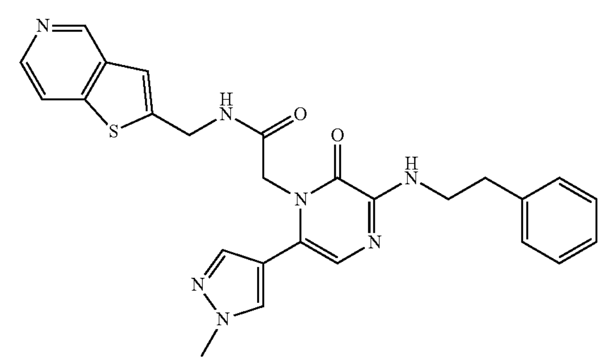 [SMILES: Cn1cc(-c2cnc(NCCc3ccccc3)c(=O)n2CC(=O)NCc2cc3cnccc3s2)cn1] | — | 500.49 | 499.18 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 134 | 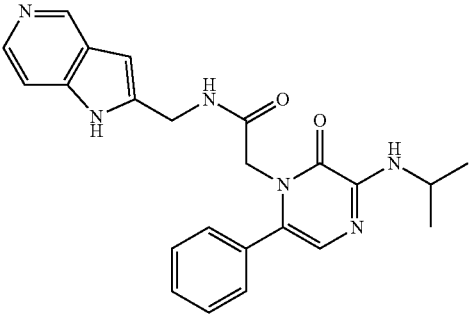 [SMILES: CC(C)Nc1ncc(-c2ccccc2)n(CC(=O)NCc2cc3cnccc3[nH]2)c1=O] | — | 417.23 | 416.20 |
| 135 | 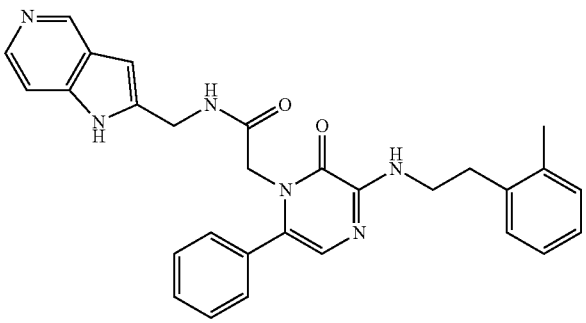 [SMILES: Cc1ccccc1CCNc1ncc(-c2ccccc2)n(CC(=O)NCc2cc3cnccc3[nH]2)c1=O] | — | 493.18 | 492.23 |
| 136 | 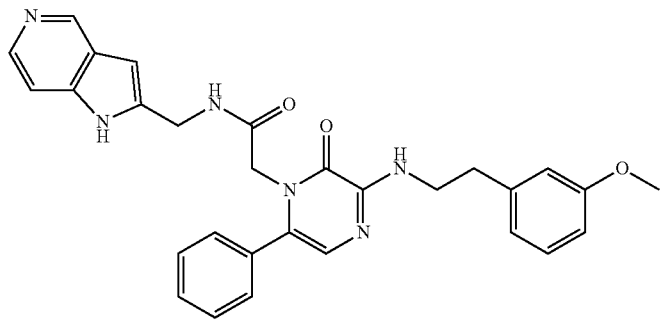 [SMILES: COc1cccc(CCNc2ncc(-c3ccccc3)n(CC(=O)NCc3cc4cnccc4[nH]3)c2=O)c1] | — | 509.17 | 508.22 |
| 137 | 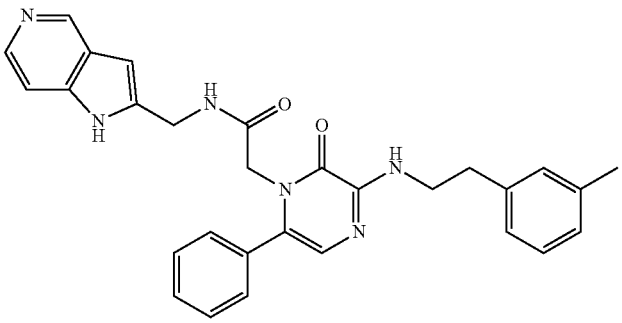 [SMILES: Cc1cccc(CCNc2ncc(-c3ccccc3)n(CC(=O)NCc3cc4cnccc4[nH]3)c2=O)c1] | — | 493.17 | 492.23 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 138 | 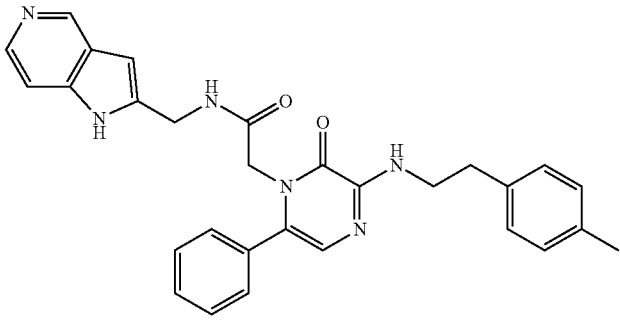 [SMILES: Cc1ccc(CCNc2ncc(-c3ccccc3)n(CC(=O)NCc3cc4cnccc4[nH]3)c2=O)cc1] | — | 493.16 | 492.23 |
| 139 | 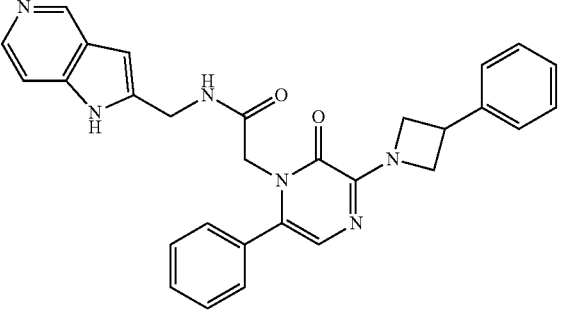 [SMILES: O=C(Cn1c(-c2ccccc2)cnc(N2CC(c3ccccc3)C2)c1=O)NCc1cc2cnccc2[nH]1] | — | 491.18 | 490.21 |
| 140 | 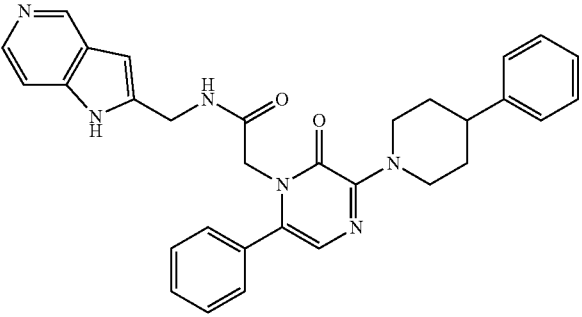 [SMILES: O=C(Cn1c(-c2ccccc2)cnc(N2CCC(c3ccccc3)CC2)c1=O)NCc1cc2cnccc2[nH]1] | — | 519.17 | 518.24 |
| 141 | 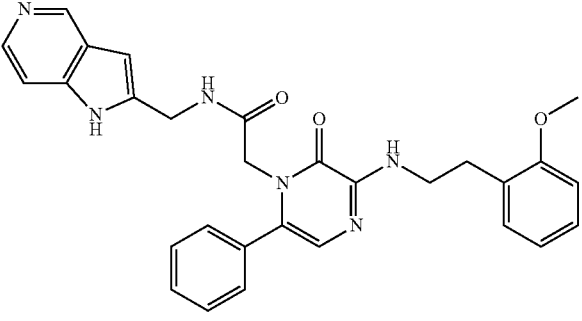 [SMILES: COc1ccccc1CCNc1ncc(-c2ccccc2)n(CC(=O)NCc2cc3cnccc3[nH]2)c1=O] | — | 509.16 | 508.22 |

TABLE 1-continued
Exemplary compounds of Structures (I), (II), (III), and (IV)
| Cmp No. | Structure | Salt | Exact Observed Mass (ES+; M + H) | Exact Calc. Mass |
|---|---|---|---|---|
| 142 | 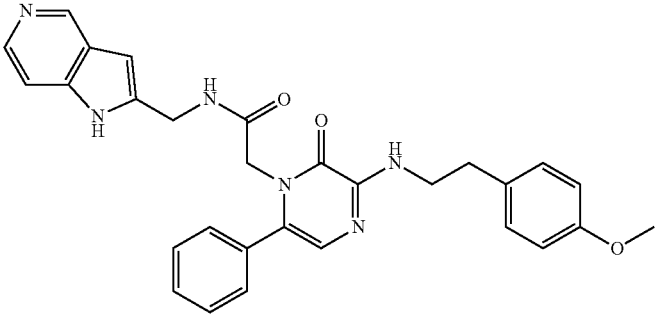 [SMILES: COc1ccc(CCNc2ncc(-c3ccccc3)n(CC(=O)NCc3cc4cnccc4[nH]3)c2=O)cc1] | — | 509.14 | 508.22 |
| 143 | 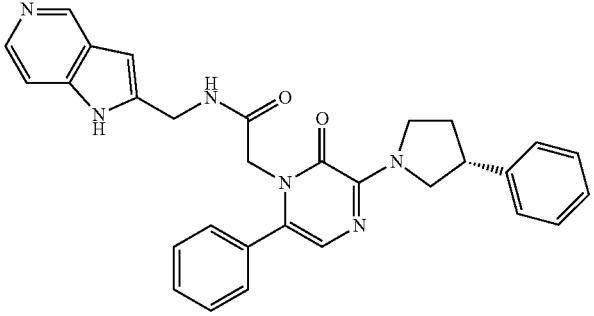 [SMILES: O=C(Cn1c(-c2ccccc2)cnc(N2CC[C@H](c3ccccc3)C2)c1=O)NCc1cc2cnccc2[nH]1] | — | 505.17 | 504.23 |
| 144 | 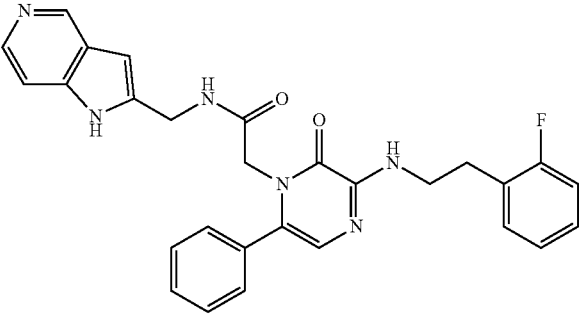 | — | 497.17 | 496.20 |
| 145 | 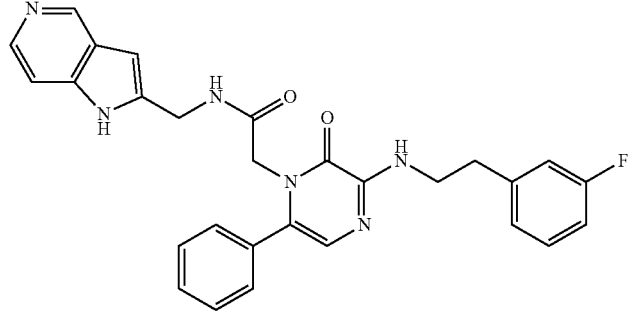 [SMILES: O=C(Cn1c(-c2ccccc2)cnc(NCCc2cccc(F)c2)c1=O)NCc1cc2cnccc2[nH]1] | — | 497.17 | 496.20 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 146 | 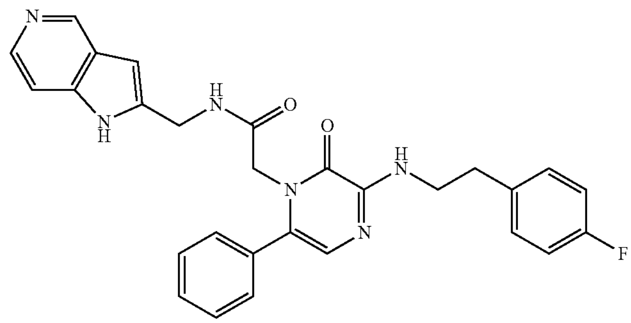 [SMILES: O=C(Cn1c(-c2ccccc2)cnc(NCCc2ccc(F)cc2)c1=O)NCc1cc2cnccc2[nH]1] | — | 497.15 | 496.20 |
| 147 | 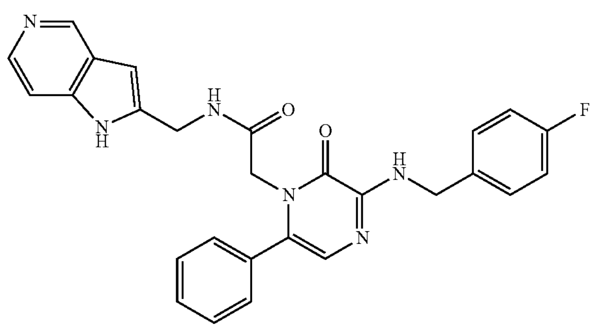 [SMILES: O=C(Cn1c(-c2ccccc2)cnc(NCc2ccc(F)cc2)c1=O)NCc1cc2cnccc2[nH]1] | — | 483.07 | 482.19 |
| 148 | 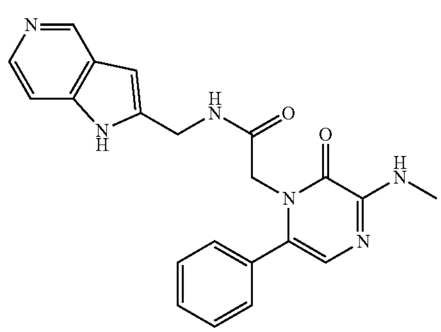 [SMILES: CNc1ncc(-c2ccccc2)n(CC(=O)NCc2cc3cnccc3[nH]2)c1=O] | — | 389.10 | 388.16 |
| 149 | 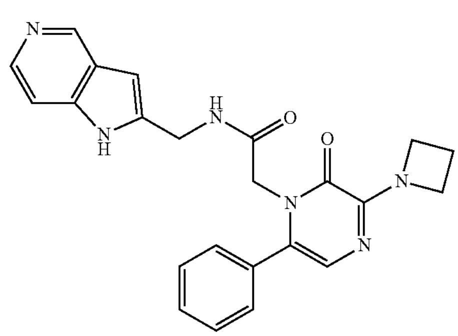 [SMILES: O=C(Cn1c(-c2ccccc2)cnc(N2CCC2)c1=O)NCc1cc2cnccc2[nH]1] | — | 415.12 | 414.18 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 150 | 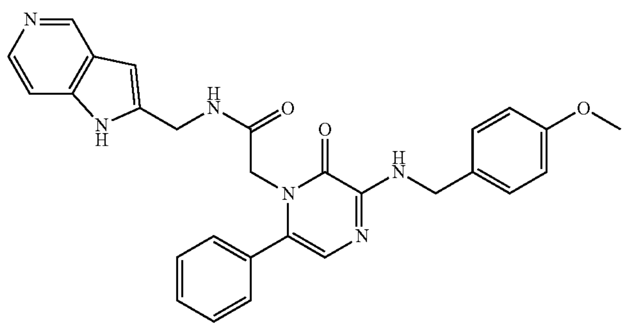 [SMILES: COc1ccc(CNc2ncc(-c3ccccc3)n(CC(=O)NCc3cc4cnccc4[nH]3)c2=O)cc1] | — | 495.06 | 494.21 |
| 151 | 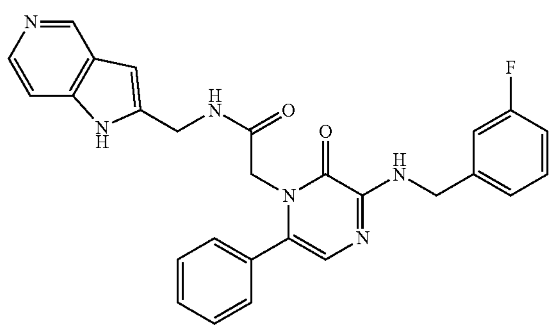 [SMILES: O=C(Cn1c(-c2ccccc2)cnc(NCc2cccc(F)c2)c1=O)NCc1cc2cnccc2[nH]1] | — | 483.06 | 482.19 |
| 152 | 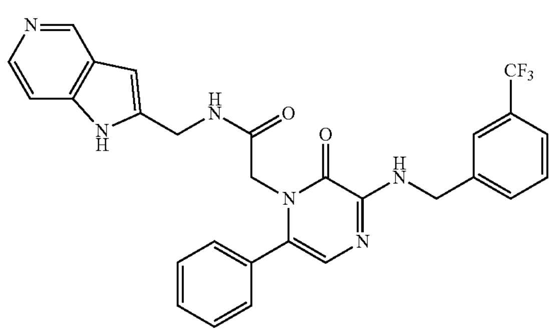 [SMILES: O=C(Cn1c(-c2ccccc2)cnc(NCc2cccc(C(F)(F)F)c2)c1=O)NCc1cc2cnccc2[nH]1] | — | 533.02 | 532.18 |
| 153 | 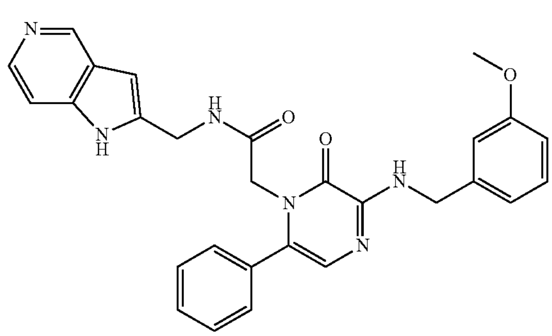 [SMILES: COc1cccc(CNc2ncc(-c3ccccc3)n(CC(=O)NCc3cc4cnccc4[nH]3)c2=O)c1] | — | 495.04 | 494.21 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 154 | 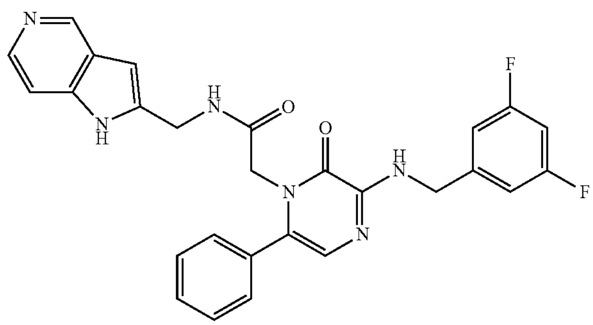 [SMILES: O=C(Cn1c(-c2ccccc2)cnc(NCc2cc(F)cc(F)c2)c1=O)NCc1cc2cnccc2[nH]1] | — | 500.99 | 500.18 |
| 155 | 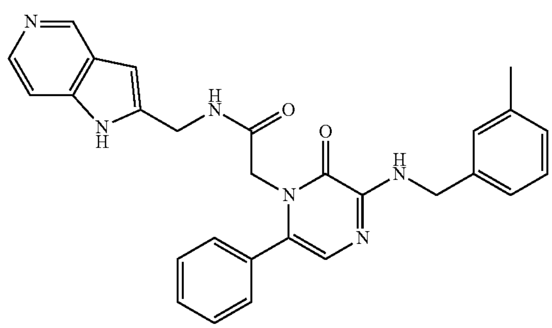 | — | 479.19 | 478.21 |
| 156 | 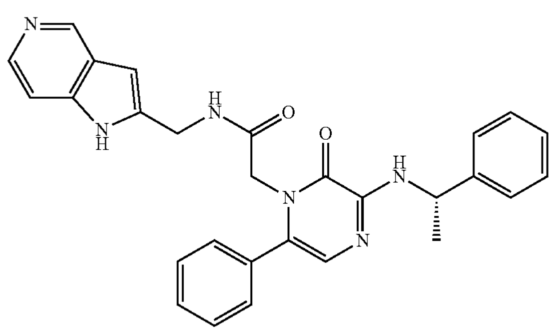 [SMILES: C[C@H](Nc1ncc(-c2ccccc2)n(CC(=O)NCc2cc3cnccc3[nH]2)c1=O)c1ccccc1] | — | 479.22 | 478.21 |
| 157 | 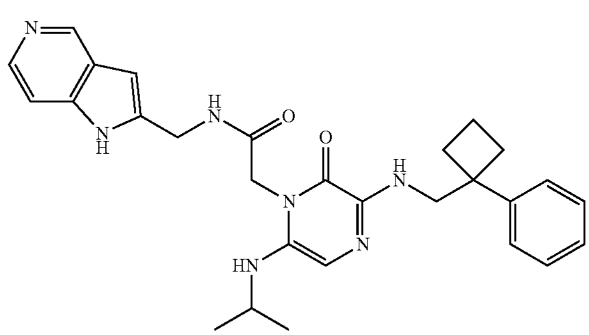 [SMILES: CC(C)Nc1cnc(NCC2(c3ccccc3)CCC2)c(=O)n1CC(=O)NCc1cc2cnccc2[nH]1] | 2TFA | 500.6 | 499.3 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 158 | 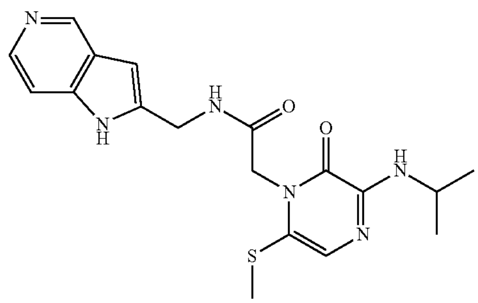 [SMILES: CSc1cnc(NC(C)C)c(=O)n1CC(=O)NCc1cc2cnccc2[nH]1] | — | 387.1 | 386.1 |
| 159 | 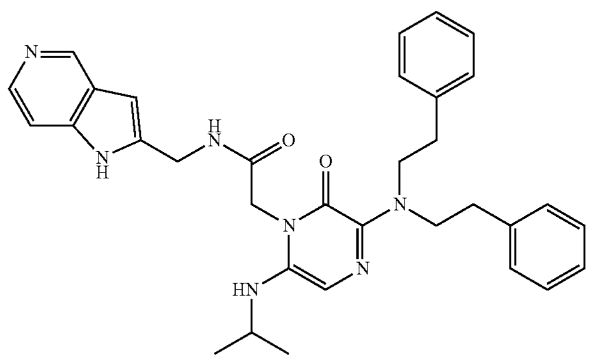 [SMILES: CC(C)Nc1cnc(N(CCc2ccccc2)CCc2ccccc2)c(=O)n1CC(=O)NCc1cc2cnccc2[nH]1] | — | 564.6 | 563.3 |
| 160 | 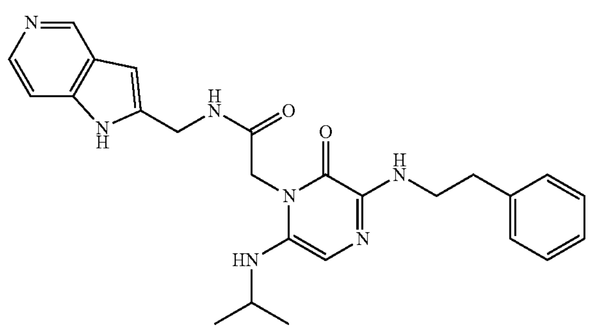 [SMILES: CC(C)Nc1cnc(NCCc2ccccc2)c(=O)n1CC(=O)NCc1cc2cnccc2[nH]1] | — | 460.5 | 459.2 |
| 161 | 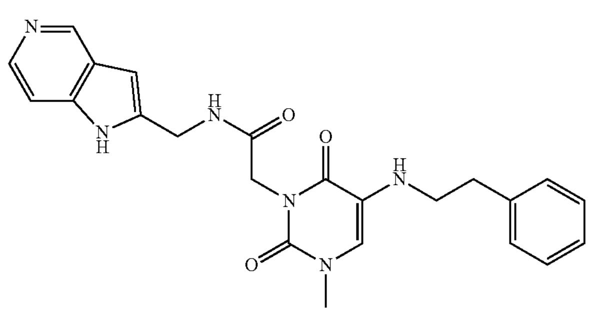 [SMILES: Cn1cc(NCCc2ccccc2)c(=O)n(CC(=O)NCc2cc3cnccc3[nH]2)c1=O] | — | 433.3 | 432.19 |

TABLE 1-continued

Exemplary compounds of Structures (I), (II), (III), and (IV)

| Cmp No. | Structure | Salt | Exact Observed Mass (ES+; M + H) | Exact Calc. Mass |
|---|---|---|---|---|
| 162 | [structure] | — | 475.11 | 474.6 |
| 163 | [structure] | TFA | 553.15 | 552.21 |

Example 56

Enzymatic Assay for MASP-2

The MASP-2 assay utilizes a fluorogenic substrate, based on the cleavage site for its natural substrate C2. The assay is run at room temperature in an assay buffer containing 20 mM HEPES, pH 7.4, 140 mM NaCl and 0.1% Tween 20. Assay parameters are adjusted such that the assay is linear with respect to time, enzyme, and substrate concentrations. Under these optimized assays conditions, $IC_{50}$ values are equivalent to Ki values, except in a few cases of "tight binding" inhibitors. Cases of "tight binding" or possible "slow binding" inhibitors are handled by the methods described in Copeland R. A. (2013) Evaluation of Enzyme Inhibitors in Drug Discovery. 2nd Ed., John Wiley and Sons, Inc., Chapters 5-7.

The MASP-2 assay protocol is carried out as follows. Test compounds are serially diluted in DMSO and then 100 nL of each dilution is transferred to the assay plate(s). 10 µL of Assay Buffer is added, followed by 15 µL of Enzyme MASP-2 (CCP1-CCP2-SP) in Assay Buffer. 15 µL of Substrate in Assay Buffer is then added and mixed to start the reactions. After 20 min at room temperature, 15 µL of a stop solution (0.1 M acetic acid) is added, mixed and the plates are read on a SpectraMax i3x Microplate Reader and exported as Excel files. Each assay plate included a "no inhibitor" (DMSO Only) control, a "no enzyme" control and a reference inhibitor control. % Activity values=100*(average test comp. fluorescence–average "no enzyme" fluorescence)/(average "DMSO only" fluorescence–average "no enzyme" fluorescence). $IC_{50}$ and Ki values are very reproducible, falling well within ±2-fold.

The results of biological assays for the compounds listed in Table 1 are listed in Table 2, below.

TABLE 2

MASP-2 Inhibition for compounds in Table 1

| Compound | MASP-2 $K_i$ (µM) | Compound | MASP-2 $K_i$ (µM) | Compound | MASP-2 $K_i$ (µM) |
|---|---|---|---|---|---|
| 1 | * | 2 | **** | 3 | **** |
| 4 | **** | 5 | **** | 6 | **** |
| 7 | **** | 8 | **** | 9 | **** |
| 10 | **** | 11 | **** | 12 | **** |
| 13 | **** | 14 | **** | 15 | **** |
| 16 | **** | 17 | **** | 18 | **** |
| 19 | **** | 20 | **** | 21 | **** |
| 22 | **** | 23 | **** | 24 | **** |
| 25 | **** | 26 | *** | 27 | **** |
| 28 | **** | 29 | **** | 30 | **** |
| 31 | **** | 32 | **** | 33 | **** |
| 34 | **** | 35 | ** | 36 | * |
| 37 | *** | 38 | *** | 39 | ** |
| 40 | **** | 41 | *** | 42 | *** |
| 43 | **** | 44 | **** | 45 | **** |
| 46 | **** | 47 | **** | 48 | **** |
| 49 | **** | 50 | **** | 51 | **** |
| 52 | **** | 53 | **** | 54 | *** |
| 55 | **** | 56 | **** | 57 | **** |
| 58 | **** | 59 | **** | 60 | **** |
| 61 | **** | 62 | **** | 63 | **** |
| 64 | **** | 65 | **** | 66 | **** |
| 67 | **** | 68 | **** | 69 | **** |
| 70 | **** | 71 | **** | 72 | **** |

TABLE 2-continued

MASP-2 Inhibition for compounds in Table 1

| Compound | MASP-2 K$_i$ (μM) | Compound | MASP-2 K$_i$ (μM) | Compound | MASP-2 K$_i$ (μM) |
|---|---|---|---|---|---|
| 73 | **** | 74 | **** | 75 | **** |
| 76 | **** | 77 | **** | 78 | *** |
| 79 | **** | 80 | ** | 81 | ** |
| 82 | ** | 83 | **** | 84 | **** |
| 85 | **** | 86 | **** | 87 | **** |
| 88 | **** | 89 | **** | 90 | **** |
| 91 | **** | 92 | **** | 93 | **** |
| 94 | **** | 95 | **** | 96 | **** |
| 97 | **** | 98 | **** | 99 | **** |
| 100 | **** | 101 | **** | 102 | **** |
| 103 | **** | 104 | **** | 105 | **** |
| 106 | **** | 107 | **** | 108 | **** |
| 109 | **** | 110 | **** | 111 | **** |
| 112 | **** | 113 | **** | 114 | **** |
| 115 | **** | 116 | **** | 117 | **** |
| 118 | *** | 119 | **** | 120 | **** |
| 121 | **** | 122 | **** | 123 | **** |
| 124 | **** | 125 | **** | 126 | **** |
| 127 | **** | 128 | **** | 129 | **** |
| 130 | ** | 131 | * | 132 | *** |
| 133 | **** | 134 | **** | 135 | **** |
| 136 | **** | 137 | **** | 138 | **** |
| 139 | **** | 140 | **** | 141 | **** |
| 142 | **** | 143 | **** | 144 | **** |
| 145 | **** | 146 | **** | 147 | **** |
| 148 | **** | 149 | **** | 150 | **** |
| 151 | **** | 152 | **** | 153 | **** |
| 154 | **** | 155 | **** | 156 | **** |
| 157 | * | 158 | **** | 159 | * |
| 160 | ** | 161 | **** | 162 | **** |
| 163 | **** | — | — | — | — |

MASP-2 Inhibition K Values:
* K$_i$ greater than 10 μM
** K$_i$ between 2.5-10 μM
*** K$_i$ between 0.5-2.5 μM
**** K$_i$ of less than 0.5 μM
— not tested It is understood that the examples and embodiments described herein are for illustrative purposes only and that various modifications or changes in light thereof will be suggested to persons skilled in the art and are to be included within the spirit and purview of this application and scope of the appended claims. Each reference, including without limitation all patent, patent applications, and publications, cited in the present application is incorporated herein by reference in its entirety for all purposes.

The invention claimed is:

1. A compound having the following Structure (I):

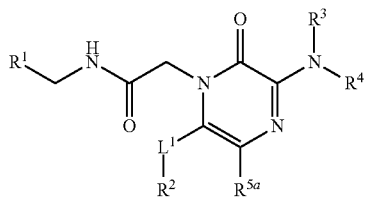

(I)

or a stereoisomer, tautomer, or pharmaceutically acceptable salt thereof, wherein:

$R^1$ is a substituted or unsubstituted heteroaryl, wherein the substituted or unsubstituted heteroaryl is selected from the group consisting of:

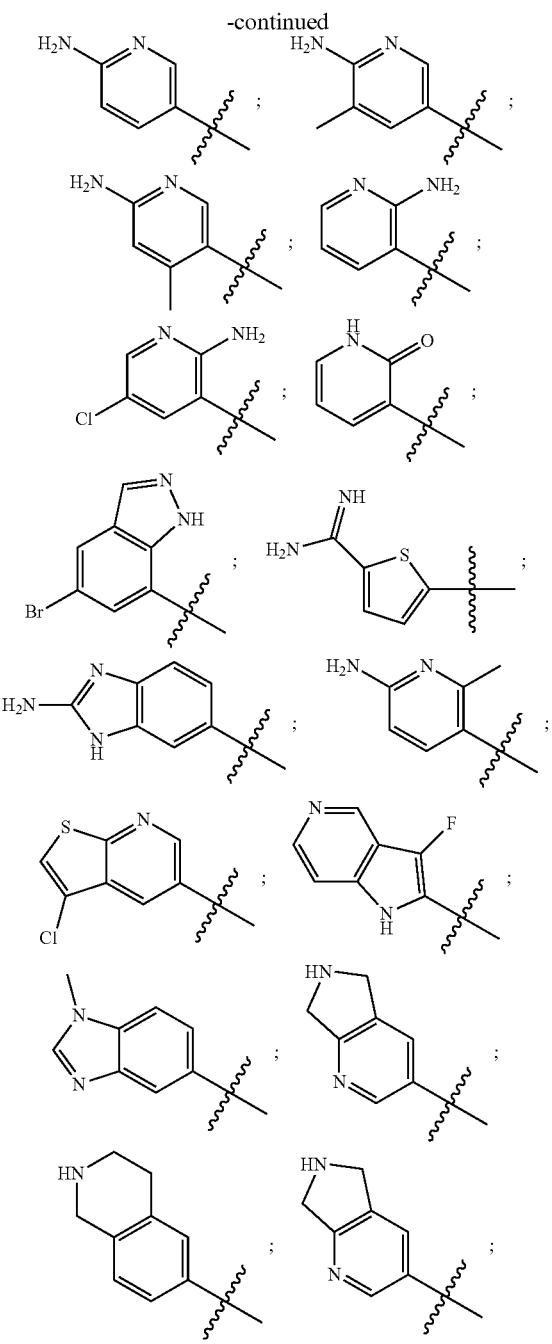

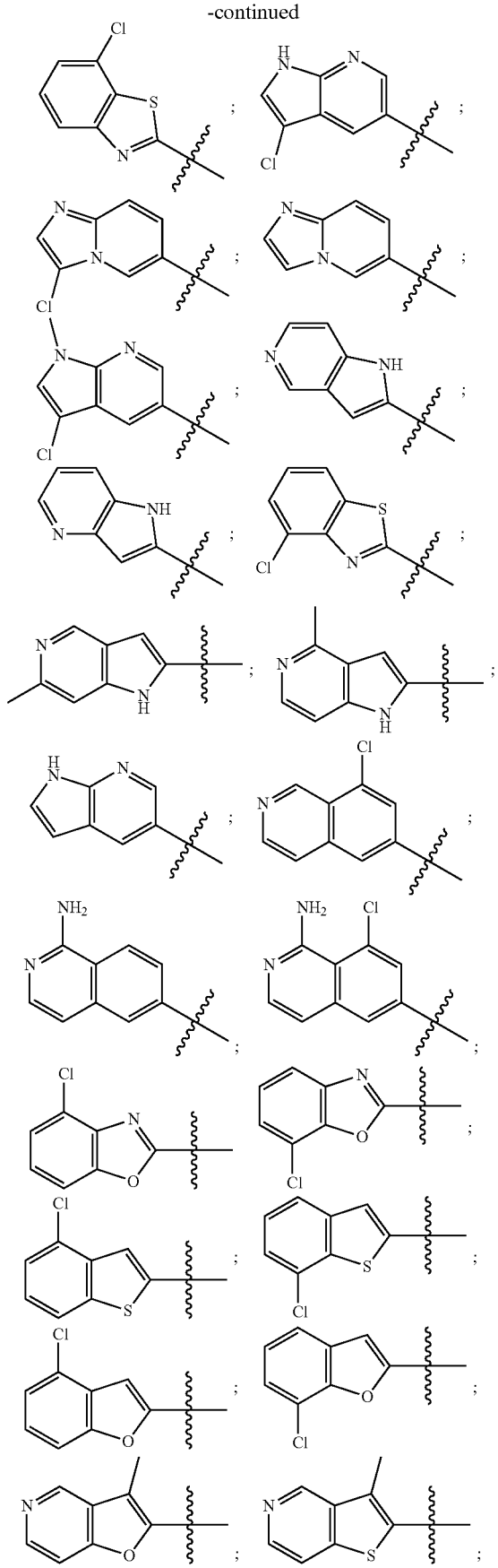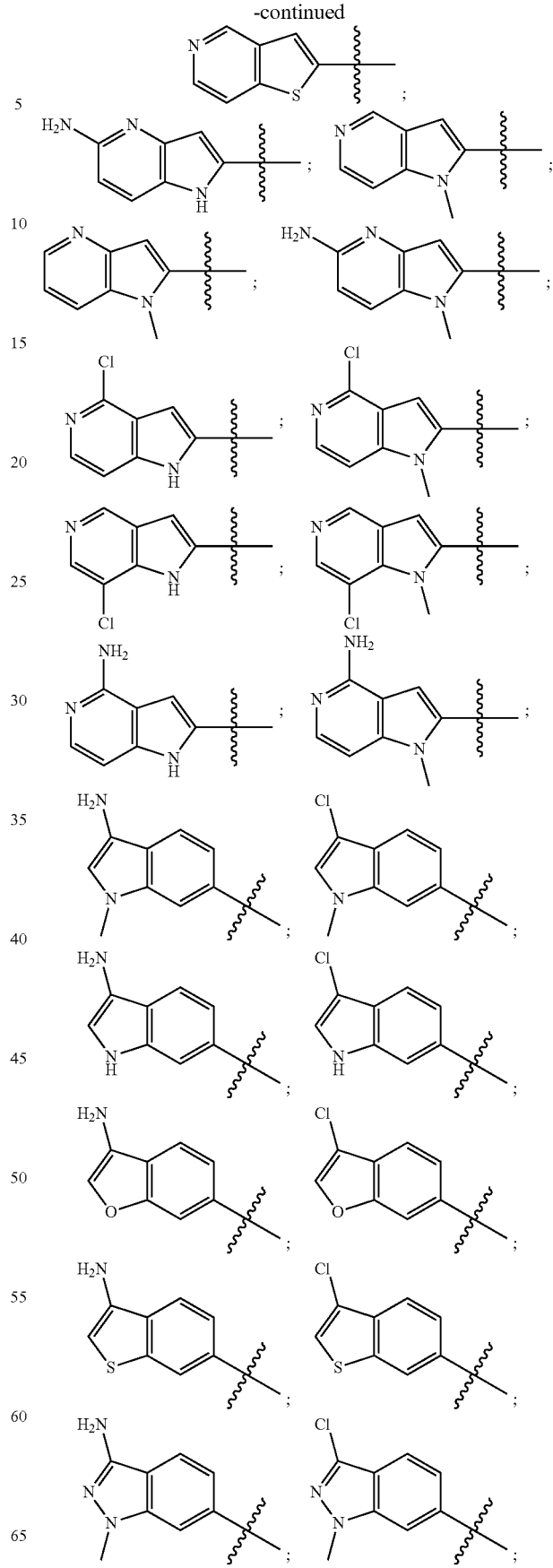

-continued

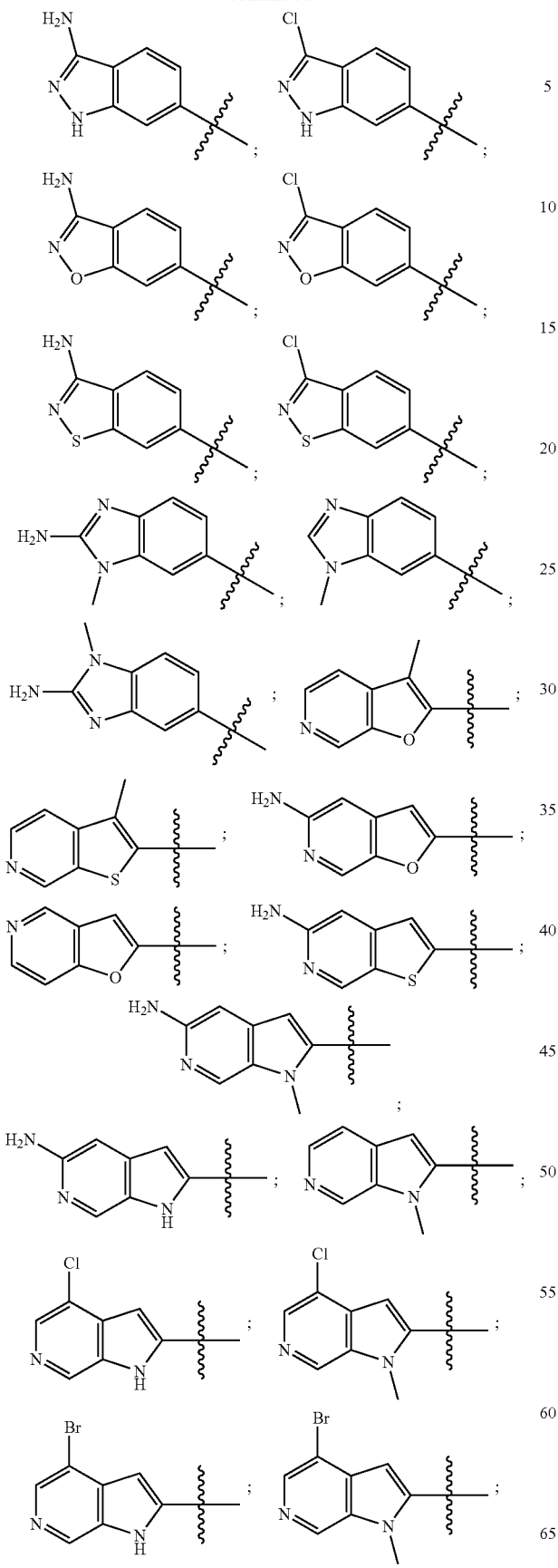

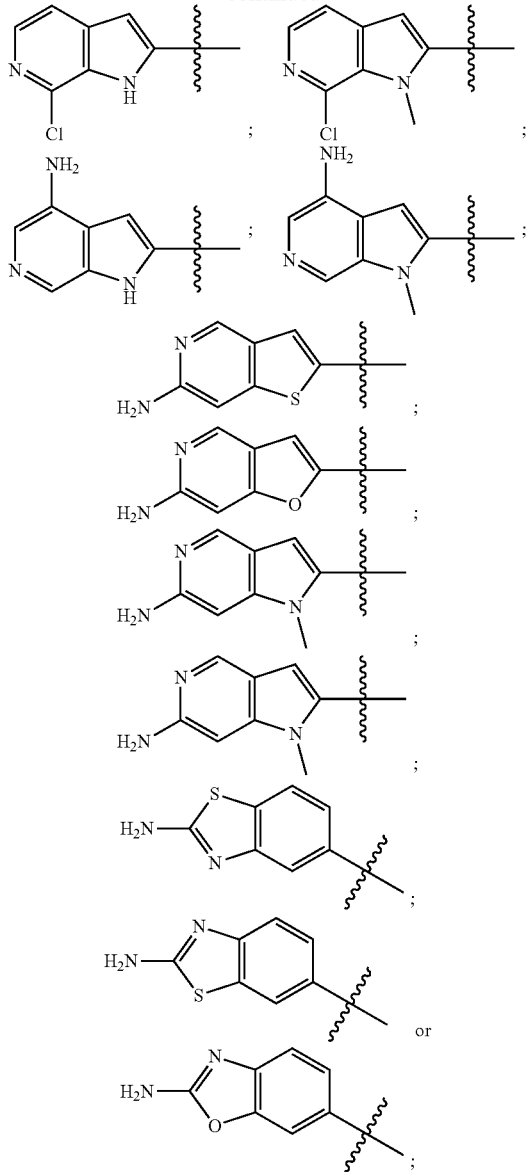

R² is a substituted or unsubstituted aryl, or a substituted or unsubstituted heteroaryl, wherein the substituted aryl of R² is substituted with one or more of $R^{2a}$, $R^{2b}$, $R^{2c}$, $R^{2d}$, or $R^{2e}$ wherein $R^{2a}$, $R^{2b}$, $R^{2c}$, $R^{2d}$, and $R^{2e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxyalkyl, phosphate, phosphonalkyl, phosphoalkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^e$, $C(=NOR^a)NR^bR^e$, $C(=NOC(O)R^a)NR^bR^c$, $C(=NR^a)N(R^b)C(O)OR^a$, $N(R^a)C(=NR^b)NR^aR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^a$, $R^b$, $R^c$, and $R^d$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, and wherein $R^{2a}$, $R^{2b}$, $R^{2c}$, $R^{2d}$, or $R^{2e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NR^fR^g$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{2a}R^{2b}$, $R^{2c}$, $R^{2d}$, or $R^{2e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, wherein the substituted heteroaryl of $R^2$ is substituted with one or more of $R^{2a}$, $R^{2b}$, $R^{2c}$, $R^{2d}$, or $R^{2e}$ wherein $R^{2a}$, $R^{2b}$, $R^{2c}$, $R^{2d}$, and $R^{2e}$ are each independently selected from the group consisting of $C_{1-6}$ alkyl, $C_{1-6}$ deuterated alkyl, $C_{2-6}$ alkenyl, $C_{2-6}$ alkynyl, halo, $C_{1-6}$ haloalkyl, aminylalkyl, hydroxyalkyl, cyano, nitro, $OR^a$, $SR^a$, $C(O)R^a$, $C(O)NR^aR^b$, $C(O)OR^a$, $OC(O)R^a$, $OC(O)OR^a$, $OC(O)NR^aR^b$, $NR^aR^b$, $N(R^a)C(O)R^b$, $N(R^a)C(O)NR^bR^c$, $N(R^a)C(O)OR^b$, $C(=NR^a)NR^bR^c$, $C(=NOR^a)NR^bR^c$, $C(=NOC(O)R^a)NR^bR^c$, $C(=NR^a)N(R^b)C(O)OR^c$, $N(R^a)C(=NR^b)NR^aR^d$, $S(O)R^a$, $S(O)NR^aR^b$, $S(O)_2R^a$, $N(R^a)S(O)_2R^b$, $S(O)_2NR^aR^b$, oxo, substituted or unsubstituted $C_{6-10}$ aryl, substituted or unsubstituted $C_{6-10}$ arylalkyl, substituted or unsubstituted $C_{6-10}$ aryloxy, substituted or unsubstituted $C_{6-10}$ arylalkoxy, substituted or unsubstituted 5-10 membered heteroaryl, substituted or unsubstituted $C_{3-10}$ cycloalkyl, and substituted or unsubstituted 4-10 membered heterocyclyl, wherein $R^a$, $R^b$, $R^c$, and $R^d$, are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl, and wherein $R^{2a}$, $R^{2b}$, $R^{2c}$, $R^{2d}$, or $R^{2e}$ is optionally substituted with one or more substituents selected from the group consisting of halo, CN, $OR^e$, $SR^e$, $C(O)R^e$, $C(O)NR^eR^f$, $C(O)OR^e$, $OC(O)R^e$, $OC(O)NR^eR^f$, $NR^eR^f$, $NR^eC(O)R^f$, $NR^eC(O)NRfR8$, $NR^eC(O)OR^f$, $C(=NR^e)NR^fR^g$, $NR^eC(=NR^f)NR^gR^h$, $S(O)R^e$, $S(O)NR^eR^f$, $S(O)_2R^e$, $NR^eS(O)_2R^f$, $S(O)_2NR^eR^f$ and oxo when $R^{2a}R^{2b}$, $R^{2c}$, $R^{2d}$, or $R^{2e}$ is a substituted $C_{6-10}$ aryl, a substituted $C_{6-10}$ arylalkyl, a substituted $C_{6-10}$ aryloxy, a substituted $C_{6-10}$ arylalkoxy, a substituted 5-10 membered heteroaryl, a substituted $C_{3-10}$ cycloalkyl, and a substituted 4-10 membered heterocyclyl, wherein $R^e$, $R^f$, $R^g$, and $R^h$ are, at each occurrence, independently selected from the group consisting of hydrogen, $C_{1-6}$ alkyl, $C_{2-6}$ alkenyl, $C_{2-6}$ alkynyl, hydroxyl, $C_{1-6}$ alkoxy, aryl, arylalkyl, $C_{1-6}$ haloalkyl, $C_{1-6}$ haloalkoxy, $C_{1-6}$ hydroxyalkyl, cycloalkyl, heterocyclyl, and heteroaryl;

$R^3$ is hydrogen or alkyl;

$R^4$ is alkyl, an arylalkyl, a heterocyclyl substituted with substituents selected from the group consisting of a phenyl or a pyridinyl, or $R^3$ and $R^4$, together with the nitrogen to which they are attached, form a 4-10 membered heterocyclyl;

$R^{5a}$ is hydrogen or halo;

$R^{5b}$ is hydrogen, alkyl, haloalkyl, (C=O)alkyl, (C=O)Oalkyl, (C=O)cycloalkyl, (C=O)Ocycloalkyl, (C=O)aryl, (C=O)Oaryl, (C=O)heteroaryl, (C=O)Oheteroaryl, (C=O)heterocyclyl, (C=O)Oheterocyclyl, an aryl, a heteroaryl, a cycloalkyl, a heterocyclyl, an arylalkyl, a heteroarylalkyl, a cycloalkylalkyl, or a heterocyclylalkyl;

$L^1$ is a direct bond, —$CH_2$—, —$S(O)_t$—, $NR^{5b}$, —O—, —C=C—, or —C≡C—; and t is 0, 1, or 2, and wherein the aryl is a 6- to 18-membered monocyclic, bicyclic, tricyclic, or tetracyclic ring system comprising at least one aromatic ring, and which can comprise fused or bridged ring systems, wherein the heteroaryl of $R^2$, $R^a$, $R^b$, $R^c$, $R^d$, $R^e$, $R^f$, $R^g$, $R^h$, and $R^{5b}$, are a 5- to 14-membered monocyclic, bicyclic, tricyclic, or tetracyclic ring system consisting of at least one aromatic ring, one to thirteen carbon atoms, one to six heteroatoms selected from the group consisting of nitrogen, oxygen, and sulfur, and can comprise fused or bridged ring systems, wherein the cycloalkyl is a non-aromatic 3- to 15-membered monocyclic or polycyclic ring system, which is saturated or unsaturated, and which can comprise fused or bridged ring systems, and wherein the heterocyclyl is a 3- to 18-membered monocyclic, bicyclic, tricyclic, or tetracyclic ring system consisting of two to twelve carbon atoms and from one to six heteroatoms selected from the group consisting of nitrogen, oxygen, and sulfur, and which can comprise fused, bridged, and spiro ring systems, provided that:

A) $R^2$ does not have one of the following structures:

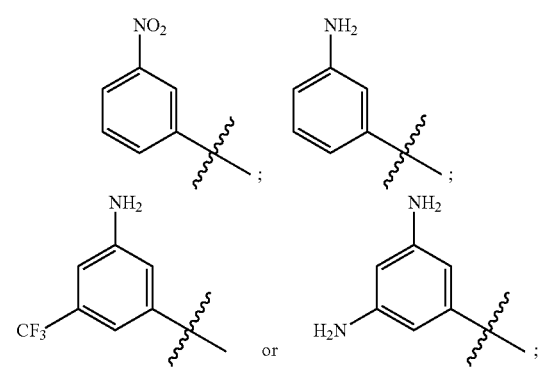

and

B) when $R^2$ is unsubstituted phenyl, $R^1$ does not have one of the following structures:

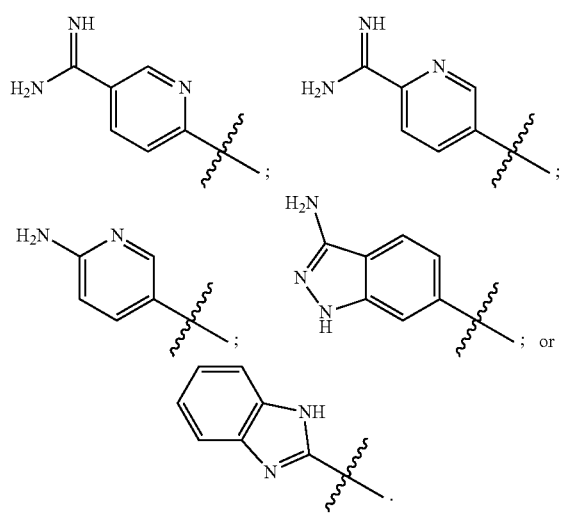
2. The compound of claim 1, wherein the substituted or unsubstituted aryl of R² is a phenyl.
3. The compound of claim 1, wherein R² has one of the following structures:
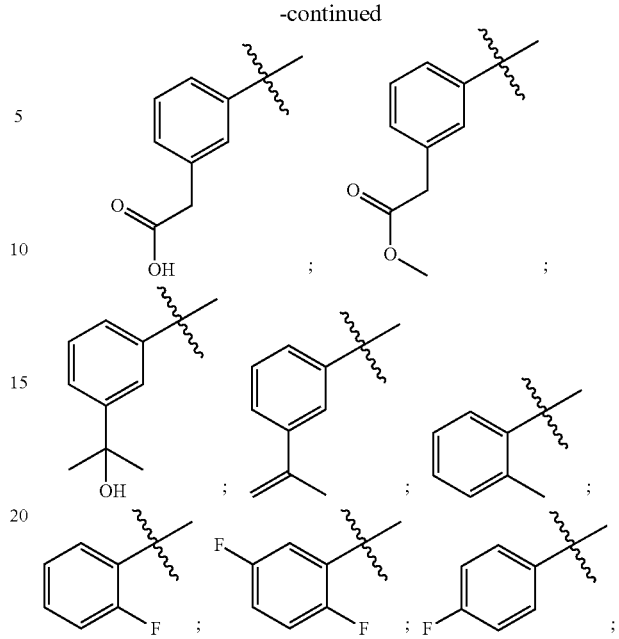
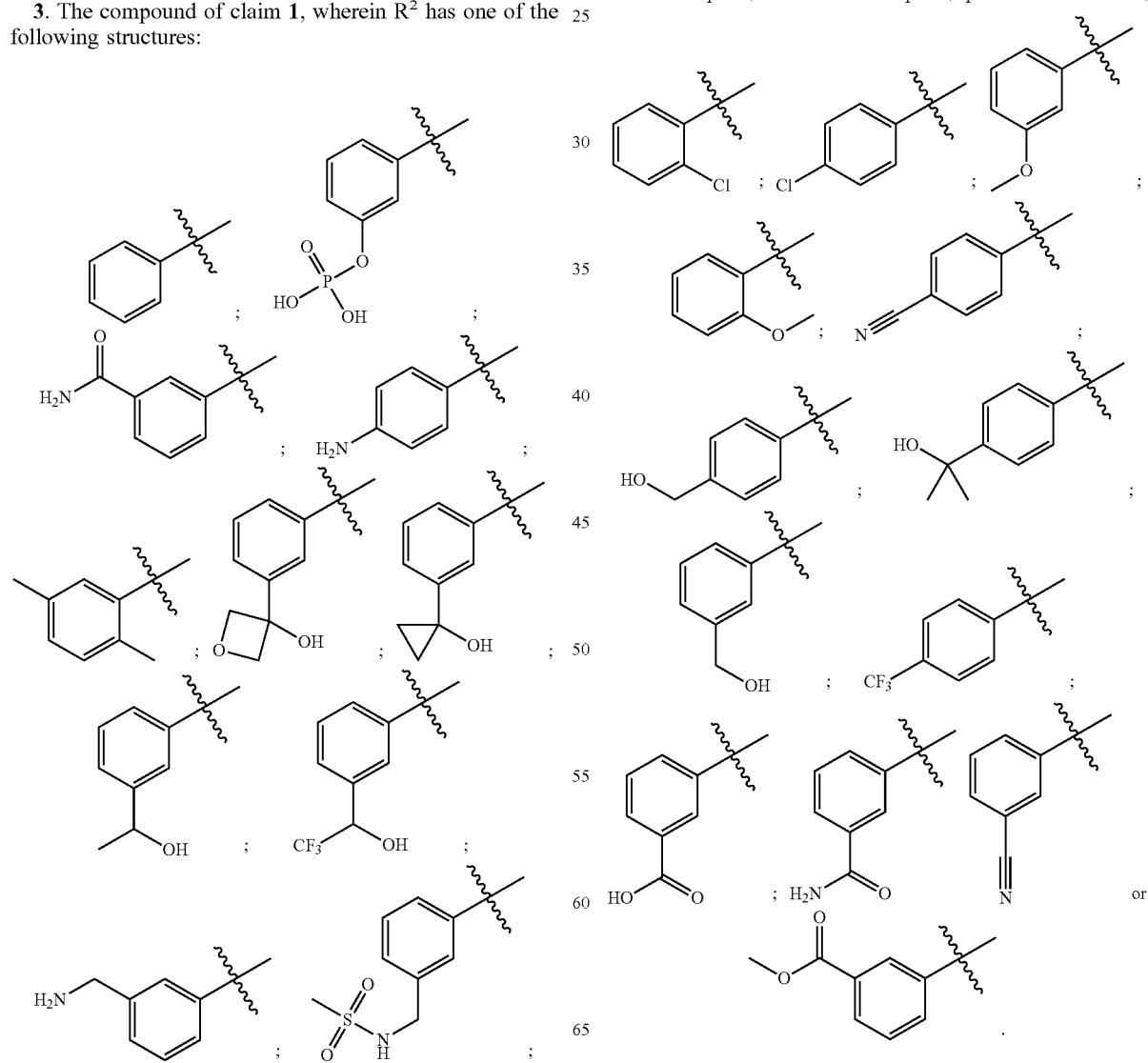

4. The compound of claim 1, wherein the substituted or unsubstituted heteroaryl of R² is a 5-10 membered heteroaryl.

5. The compound of claim 1, wherein the substituted or unsubstituted heteroaryl of R² is a pyridinyl, a pyrrolyl, a pyrimidinyl, an isoquinolinyl, a pyrazolyl, a pyrrolopyridinyl, or a benzoimidazolyl.

6. The compound of claim 1, wherein R² has one of the following structures:

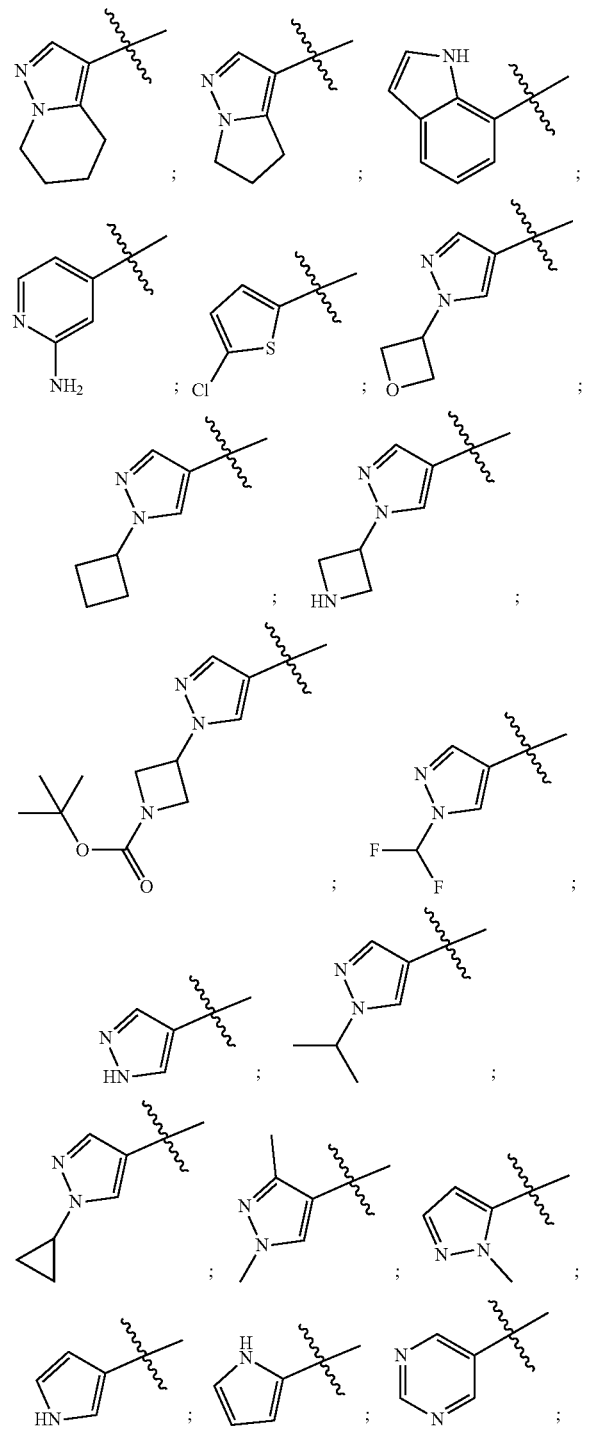

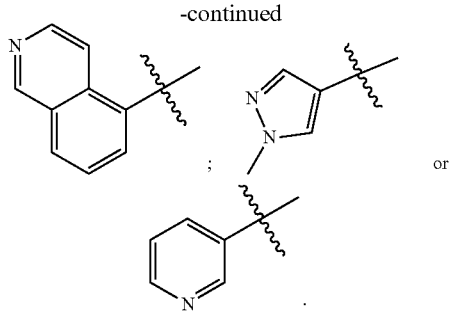

7. The compound of claim 1, wherein R³ is hydrogen or methyl.

8. The compound of claim 1, wherein R³ and R⁴, together with the nitrogen to which they are attached, form a 4-10 membered heterocyclyl, wherein the heterocyclyl is selected from the group consisting of:

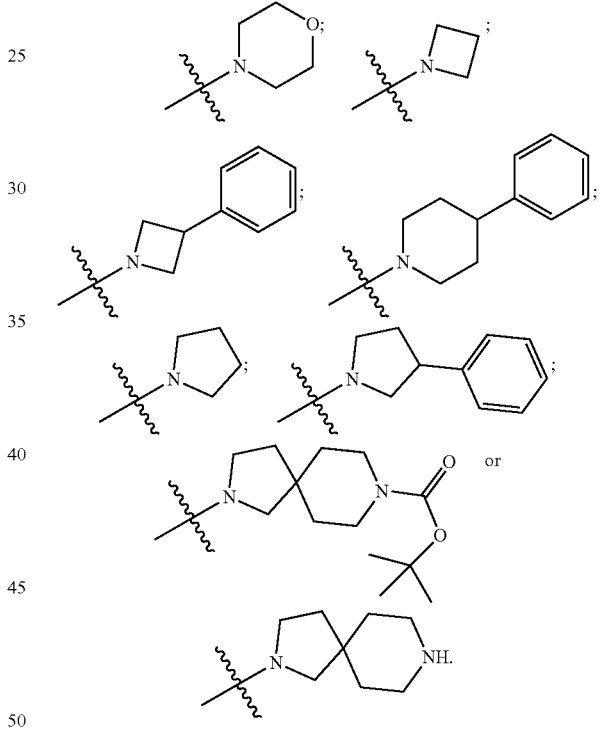

9. The compound of claim 1, wherein R⁴ is methyl or has one of the following structures:

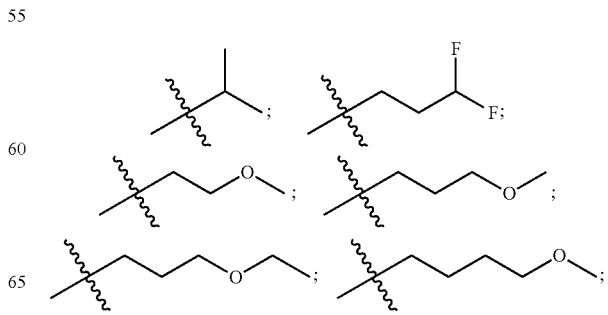

10. The compound of claim 1, wherein R⁴ is an arylalkyl.

11. The compound of claim 1, wherein R⁴ has the following structure:

-continued

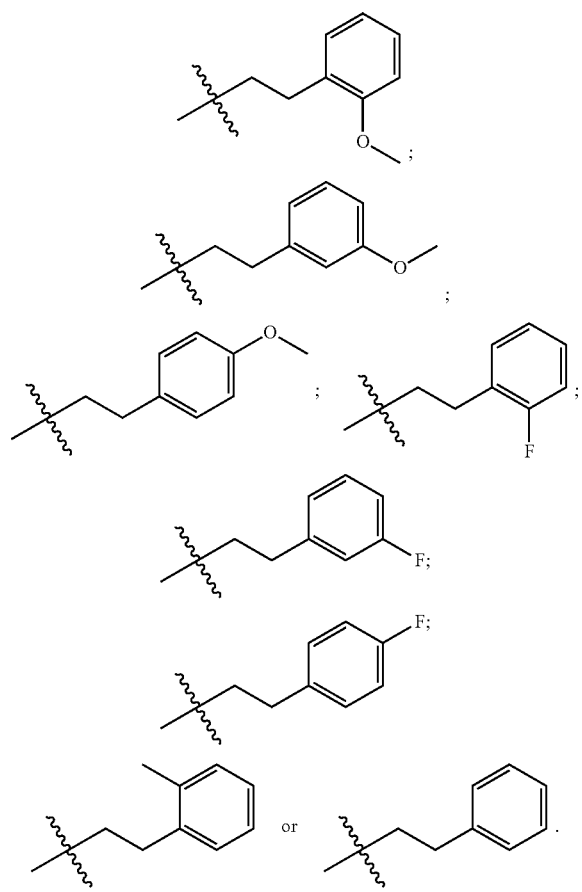

12. The compound of claim 1, wherein R⁴ is a heterocyclyl substituted with substituents selected from the group consisting of a phenyl and a pyridinyl.

13. The compound of claim 1, wherein R⁴ has one of the following structures:

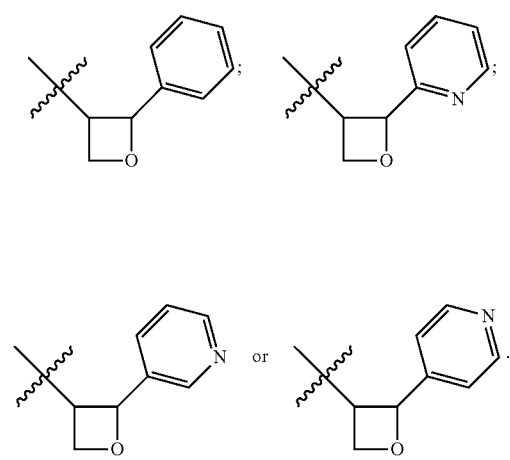

14. The compound of claim 1, wherein $L^1$ is a direct bond, —CH₂—, or —C≡C—.

15. The compound of claim 1, wherein $R^{5a}$ is hydrogen, F, Br, or Cl.

16. A compound of claim 1, having one of the structures:

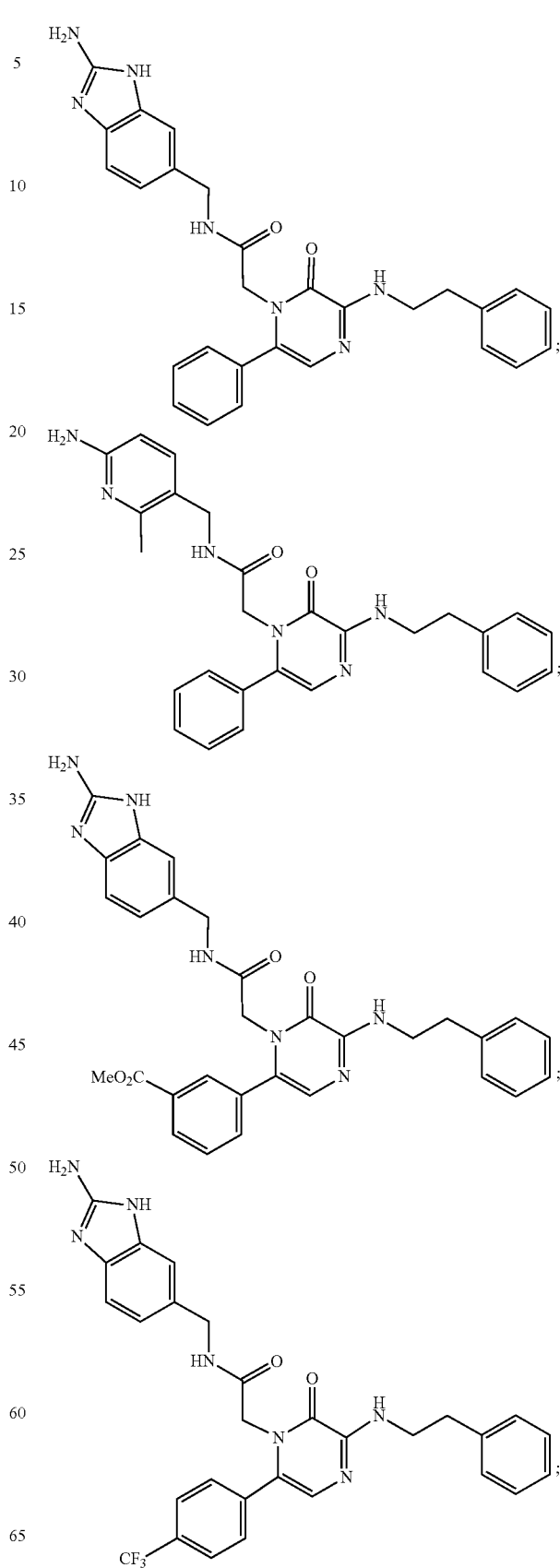

289
-continued
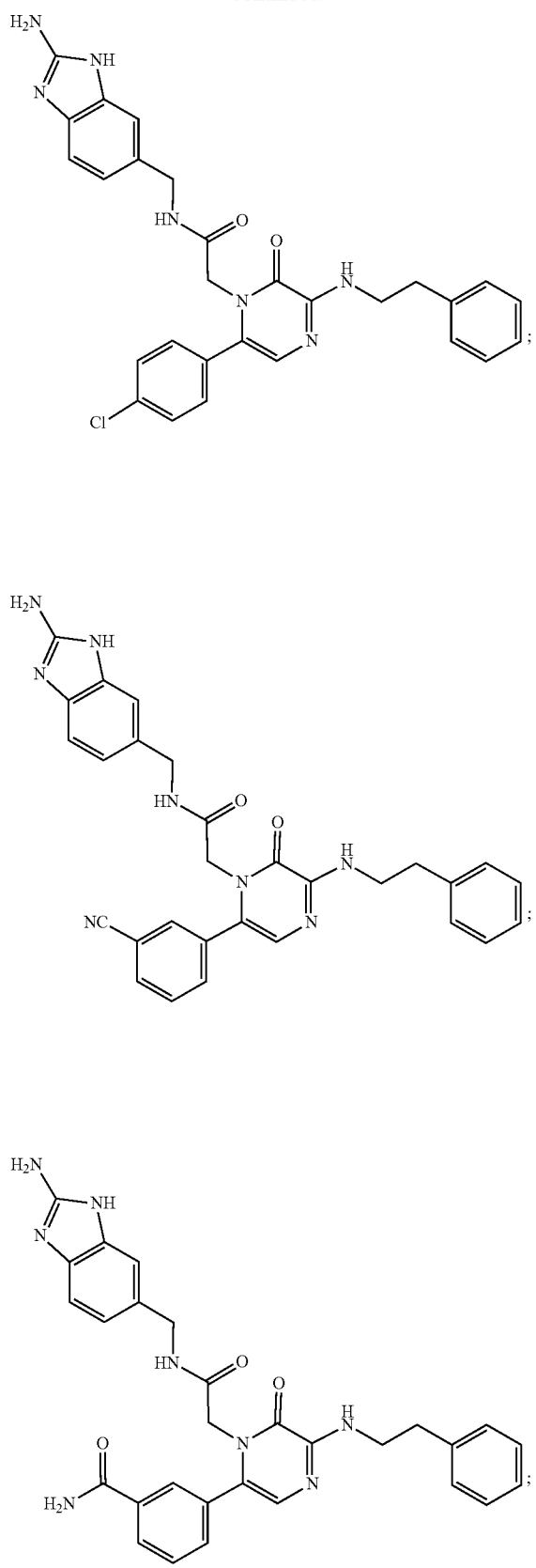
290
-continued
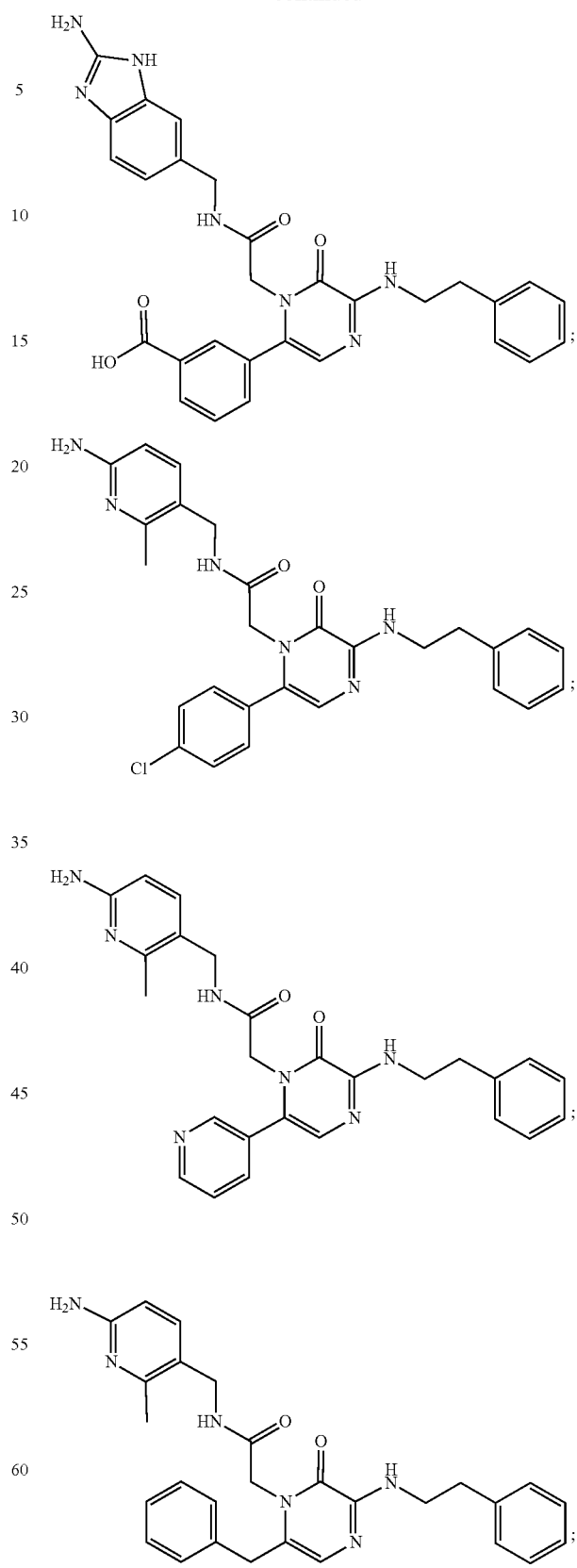

-continued
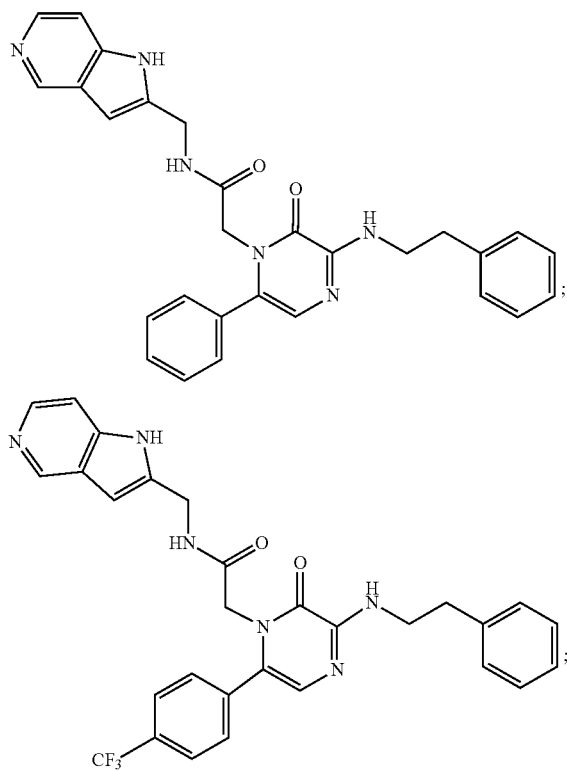
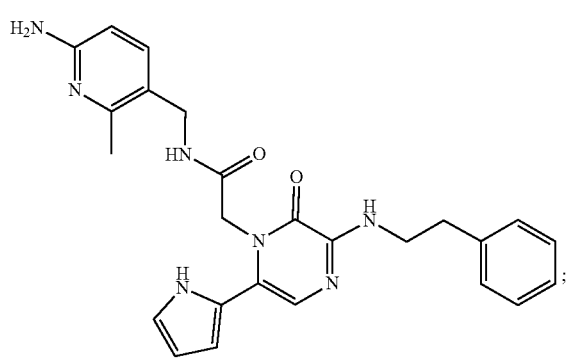
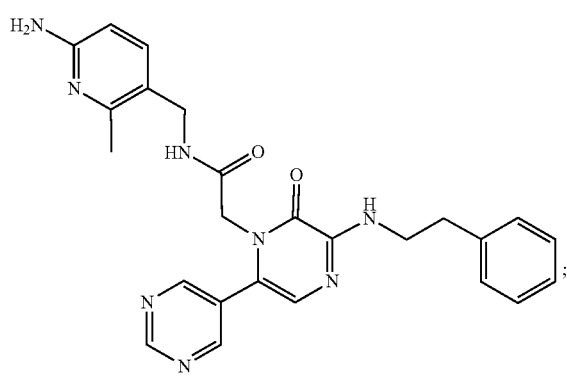
-continued
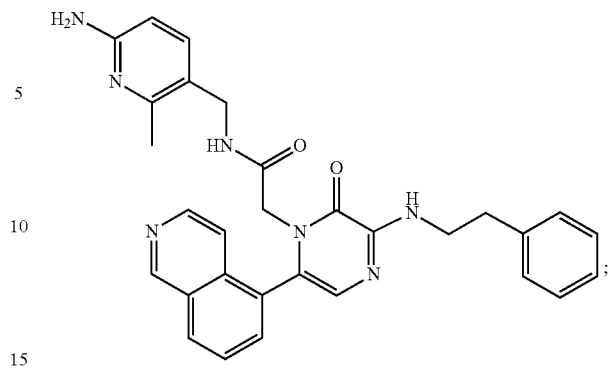
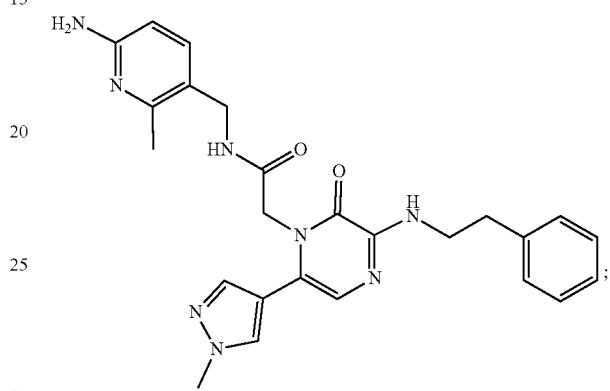
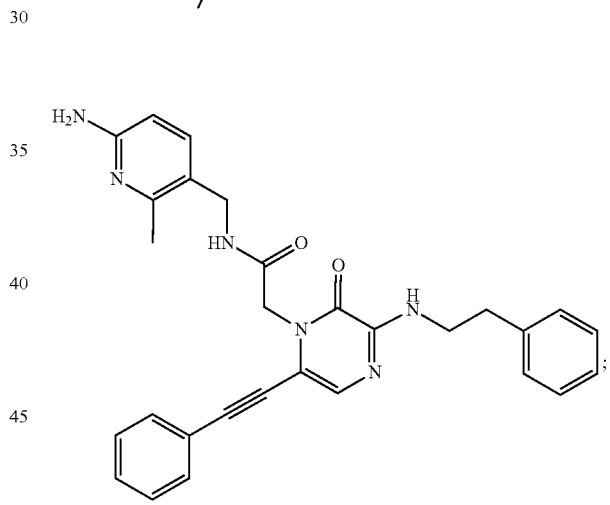
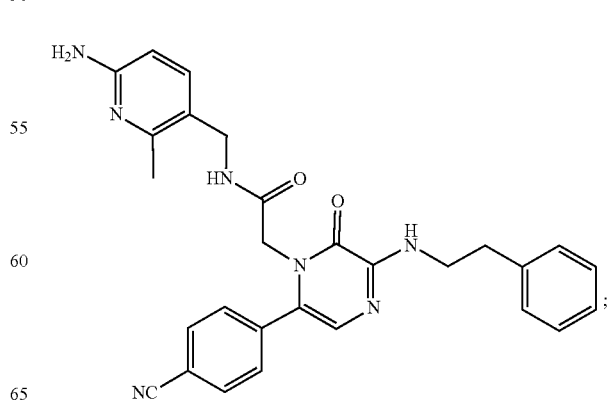

293
-continued
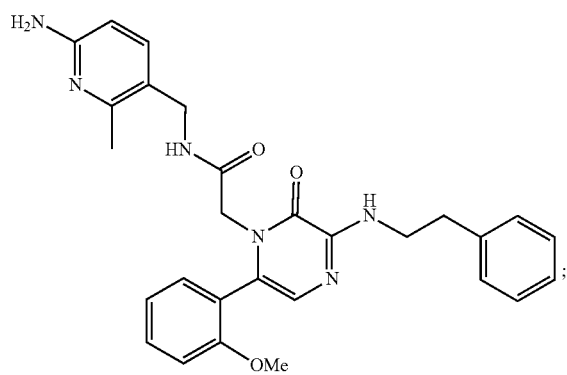
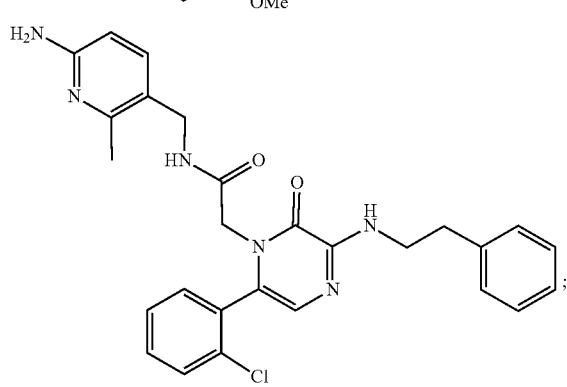
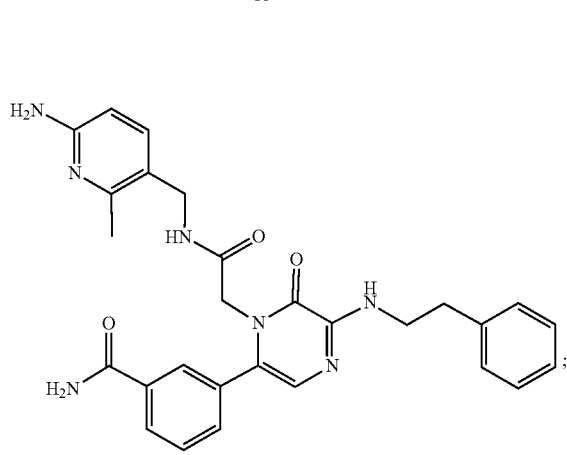
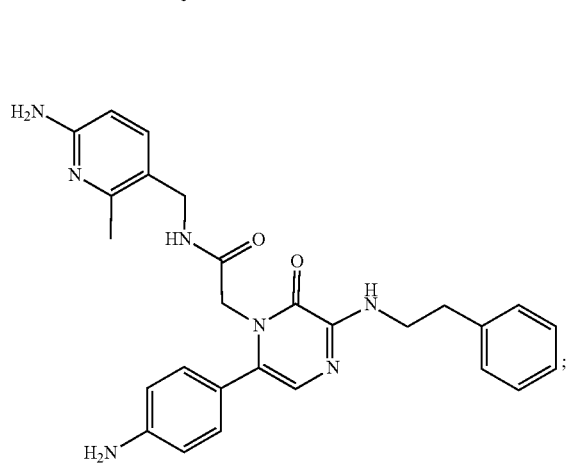
294
-continued
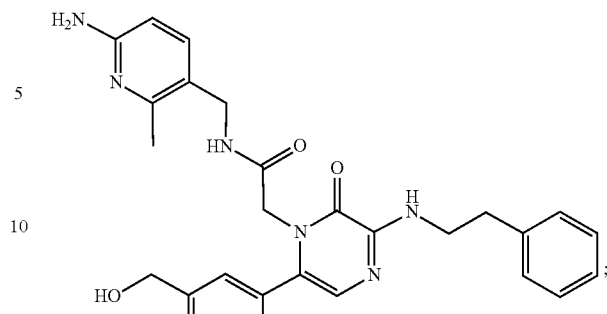
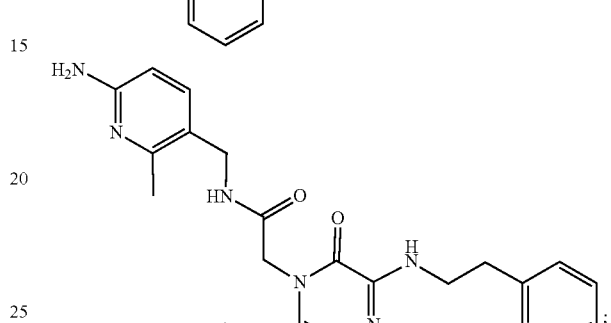
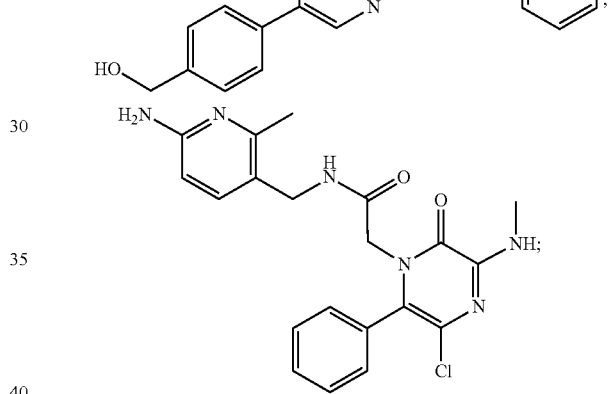
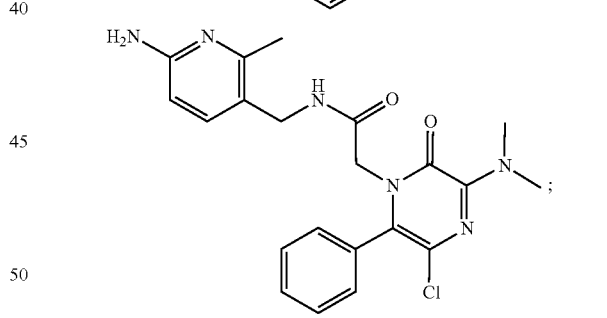
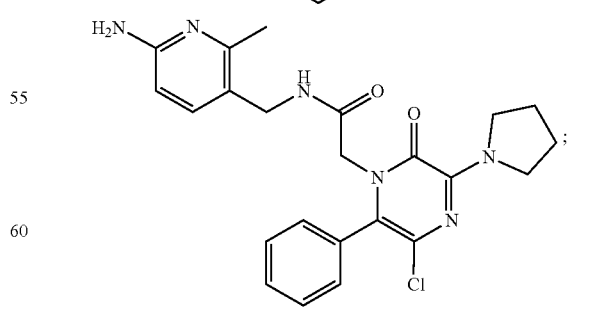

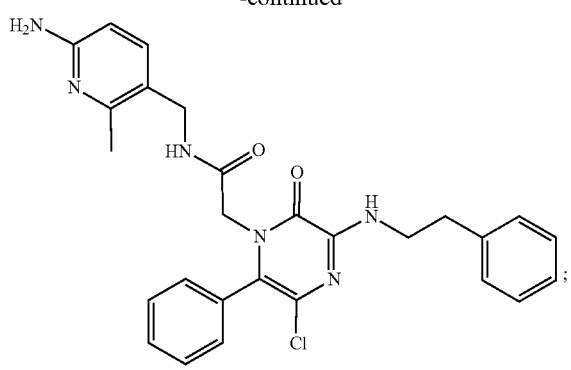
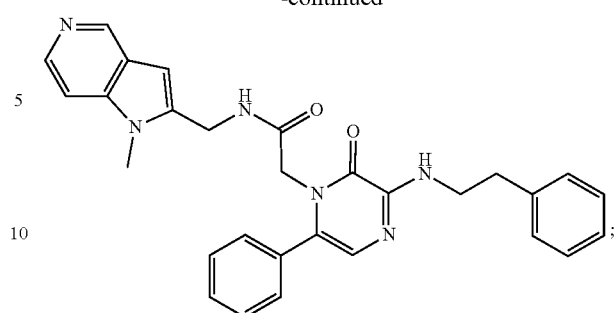
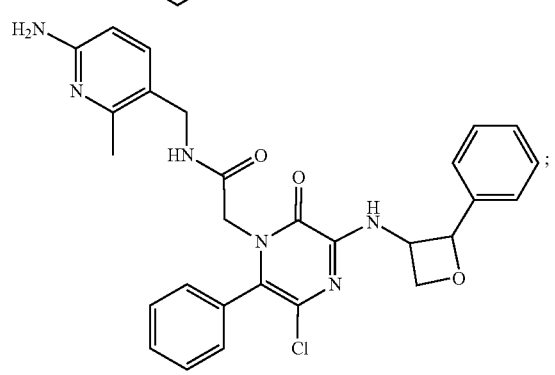
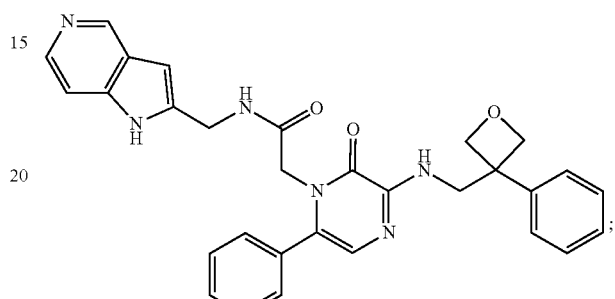
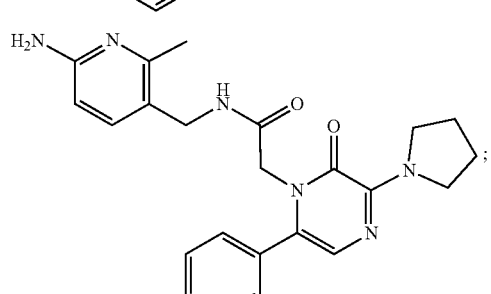
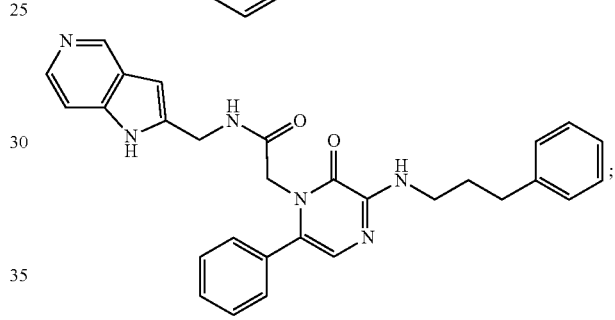
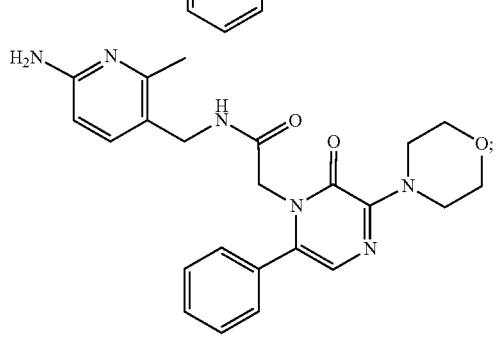
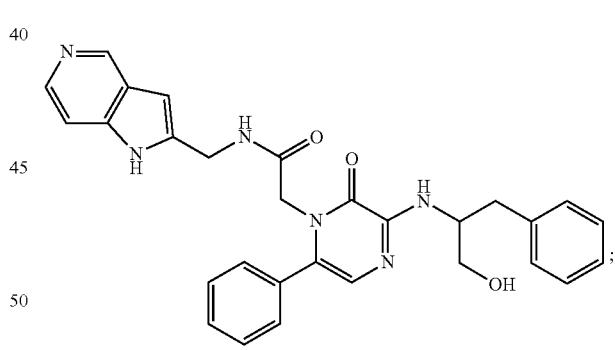
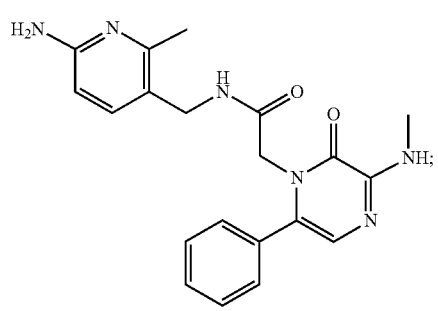
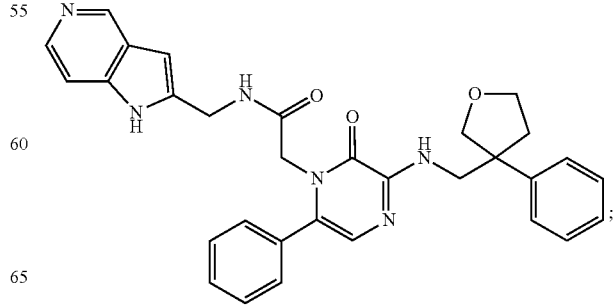

297
-continued
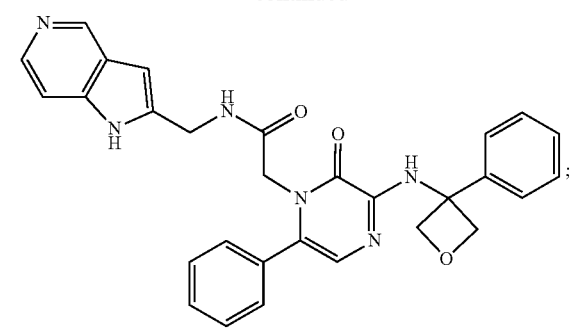
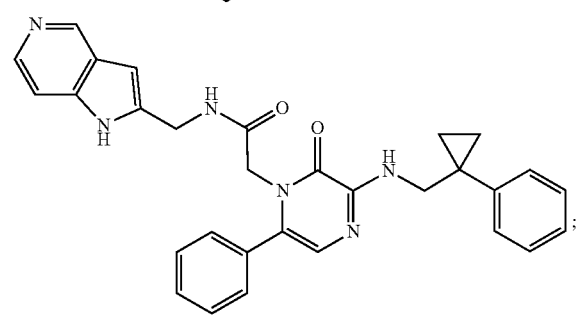
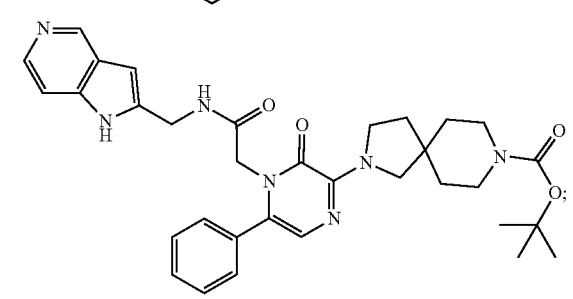
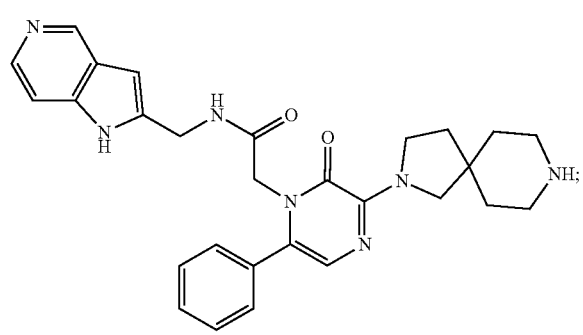
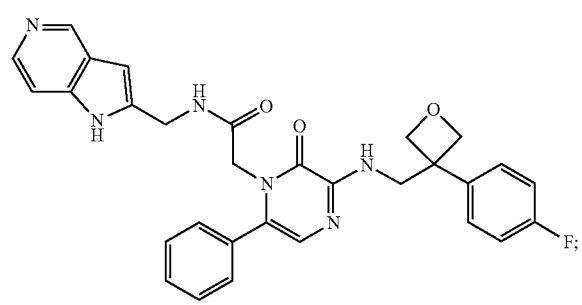
298
-continued
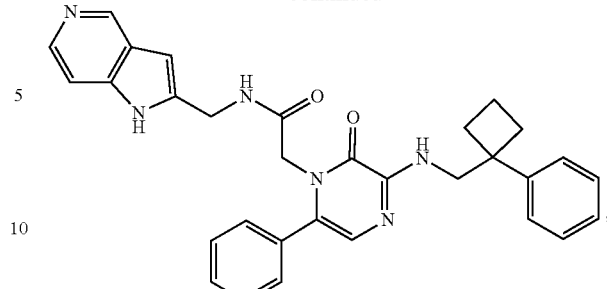
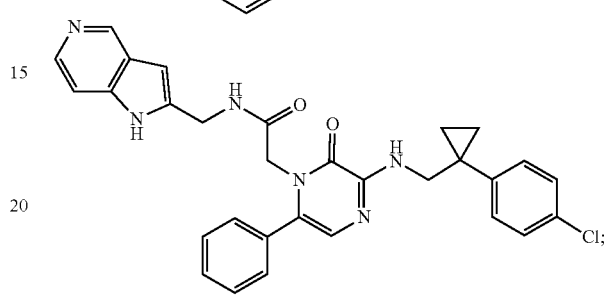
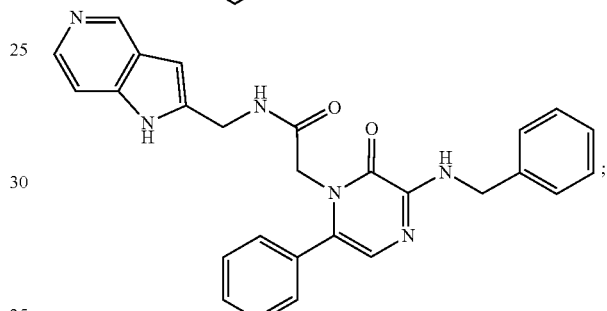
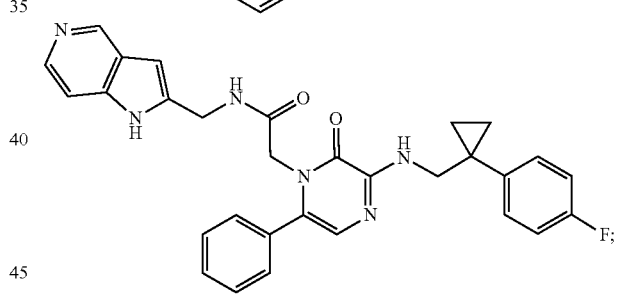
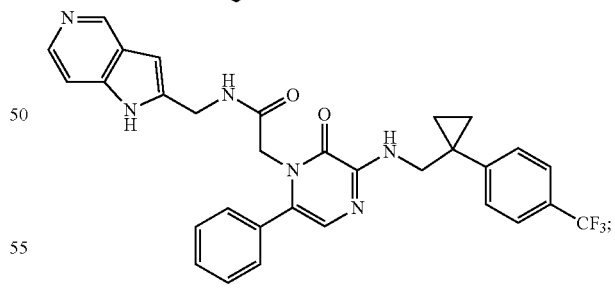
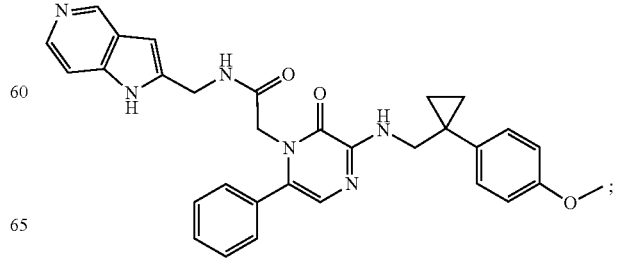

299
-continued
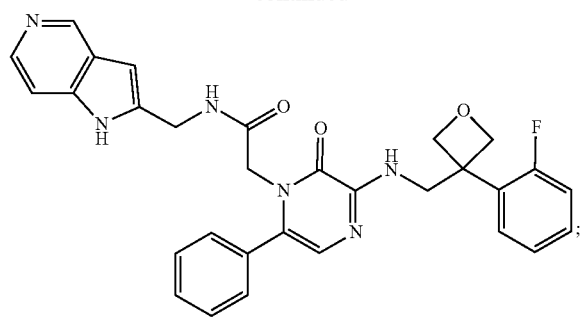
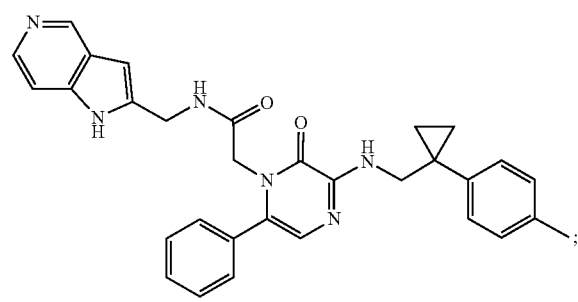
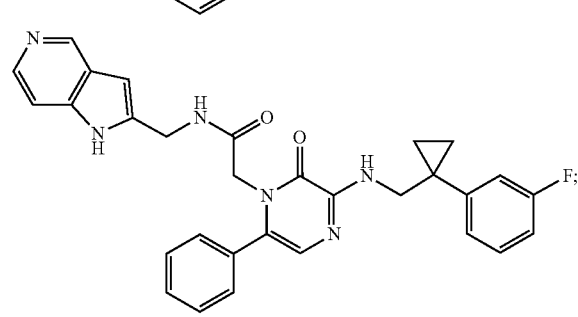
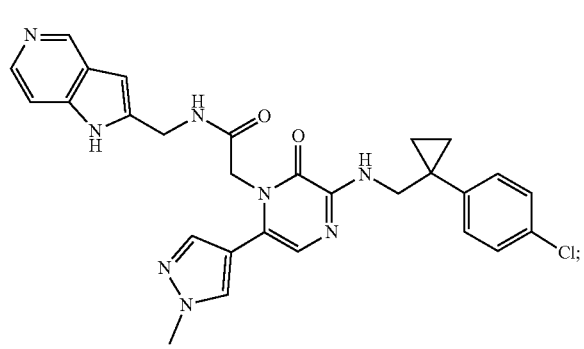
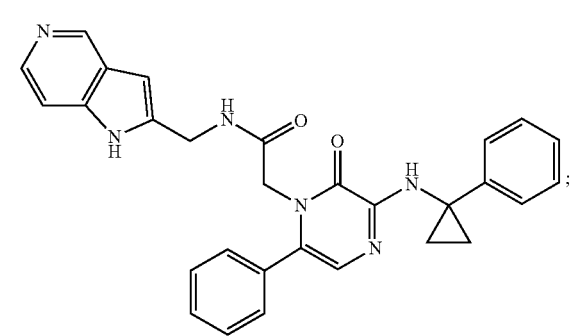
300
-continued
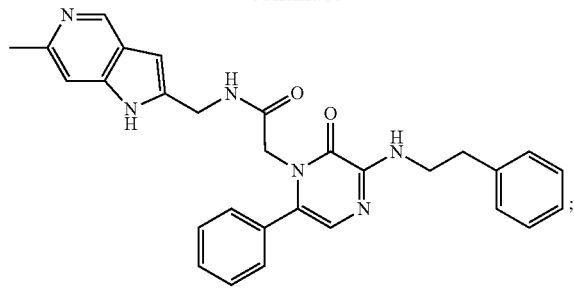
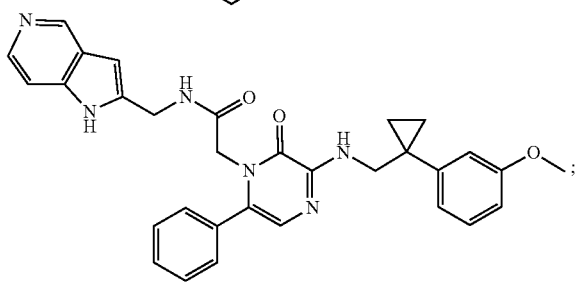
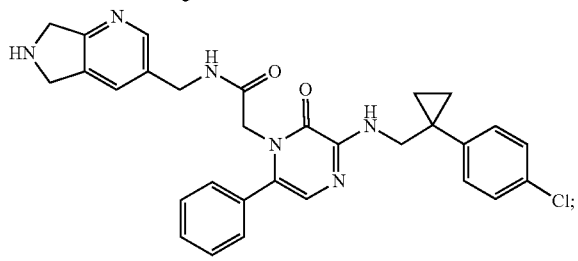
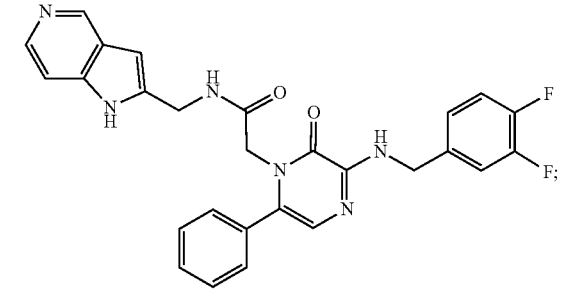
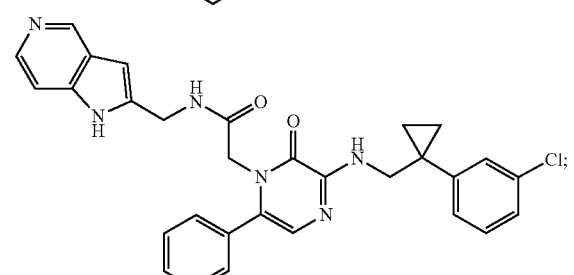
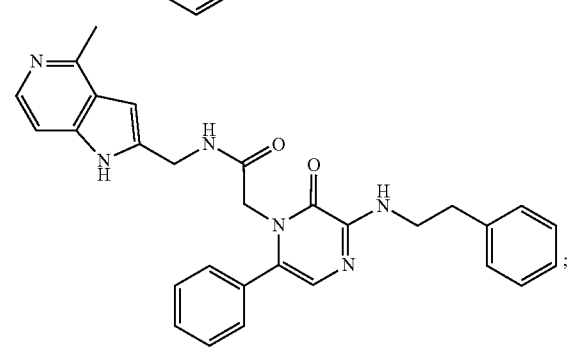

301
-continued
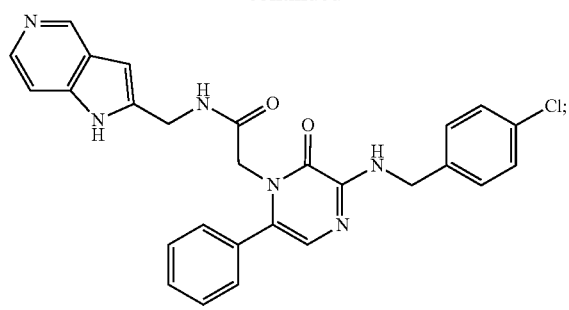
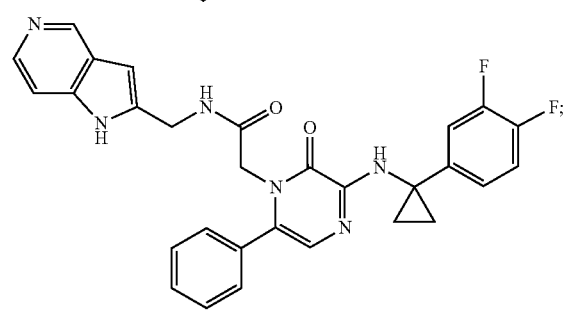
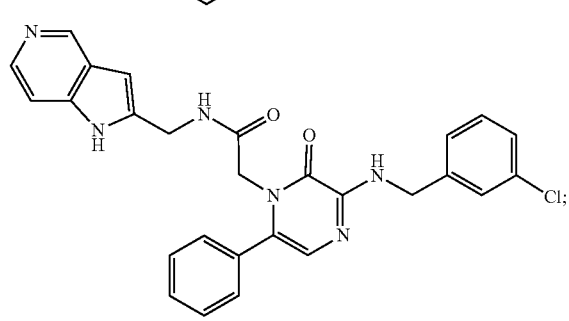
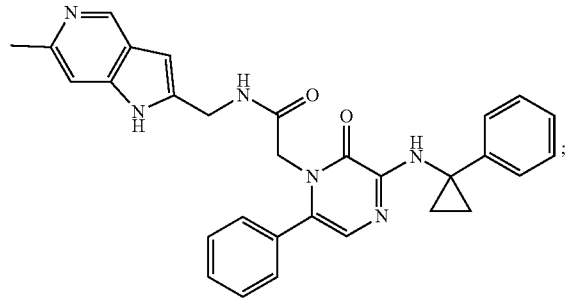
302
-continued
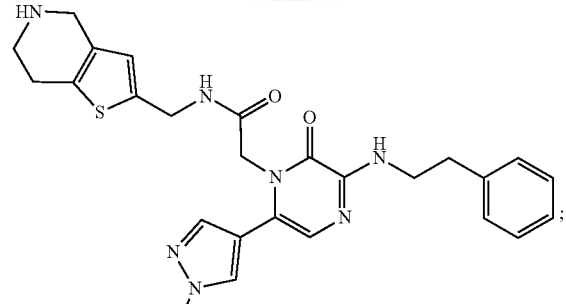
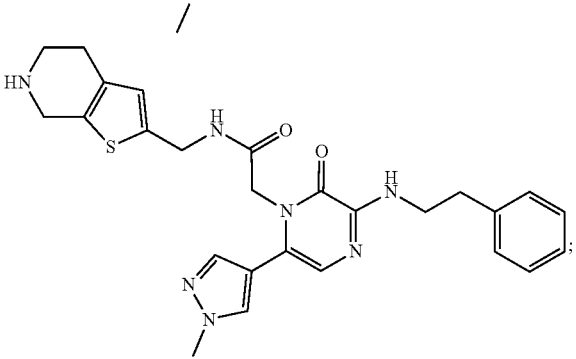
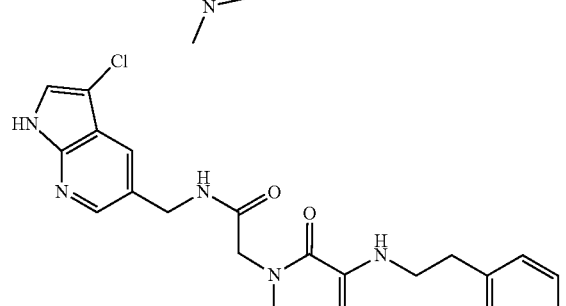
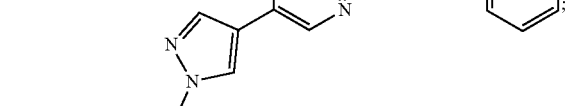
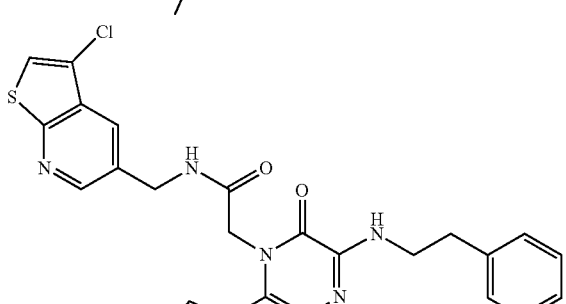
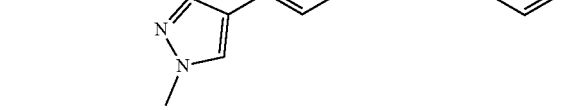

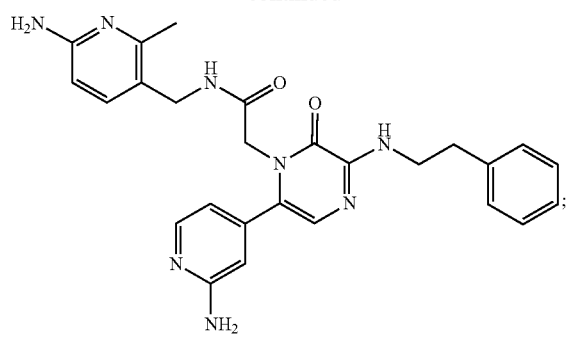
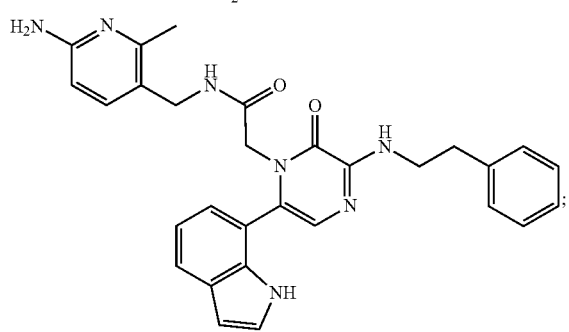
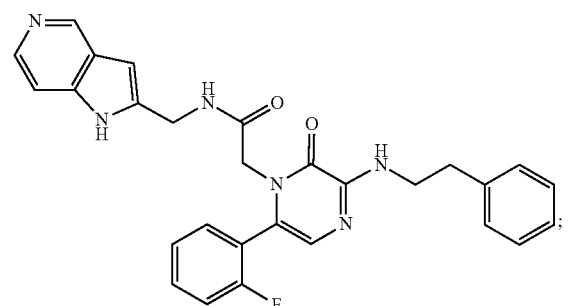
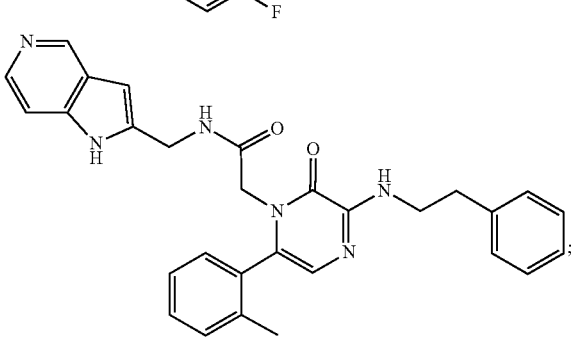
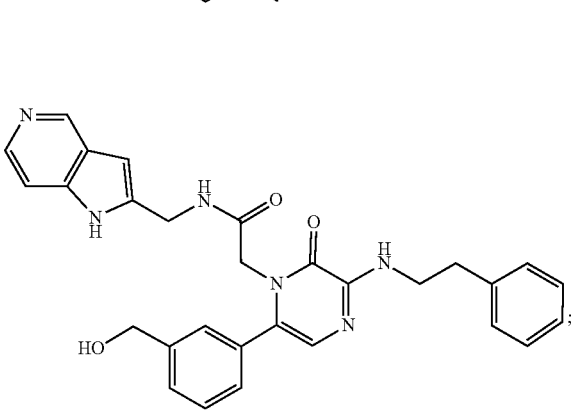
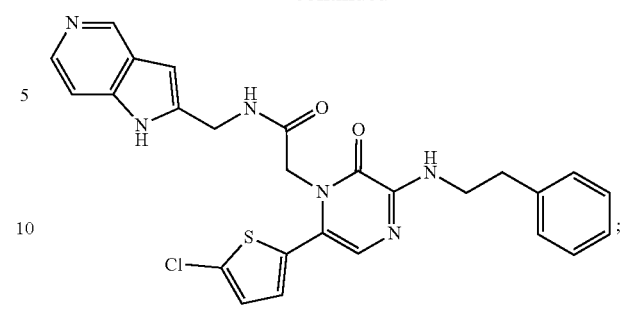
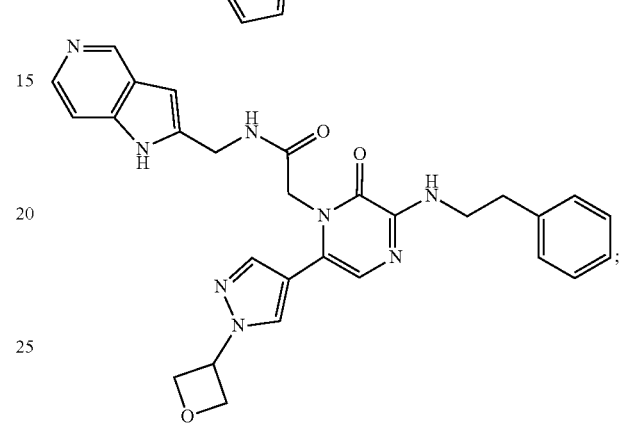
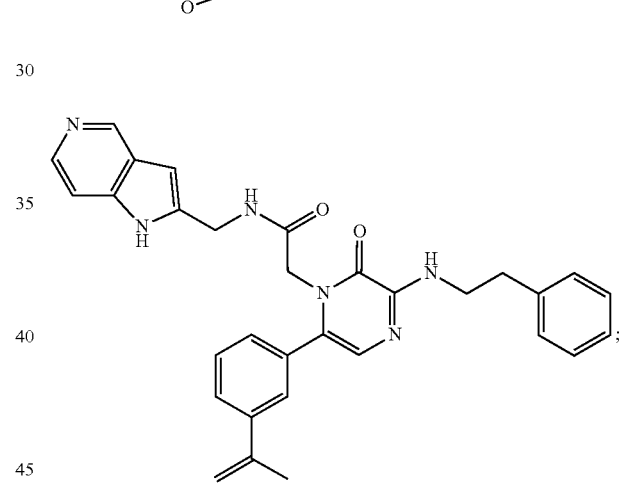
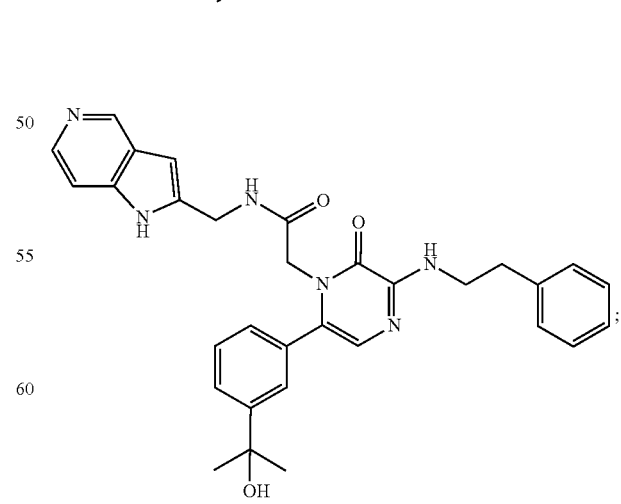

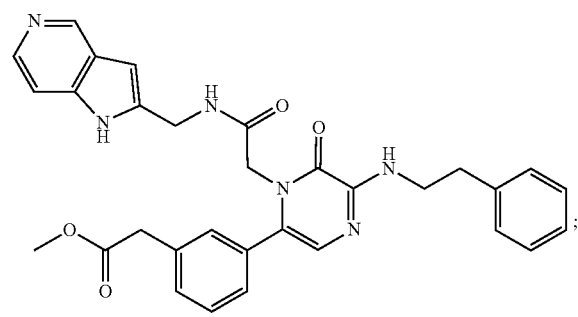
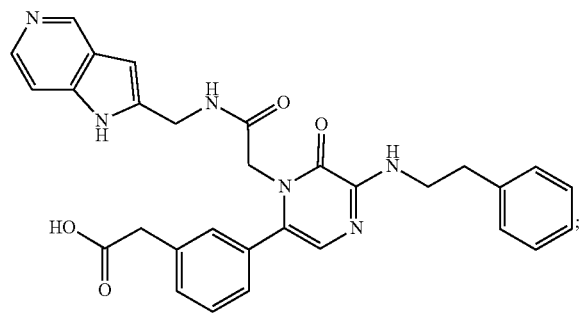
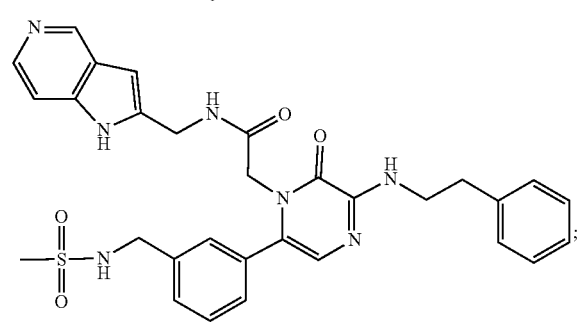
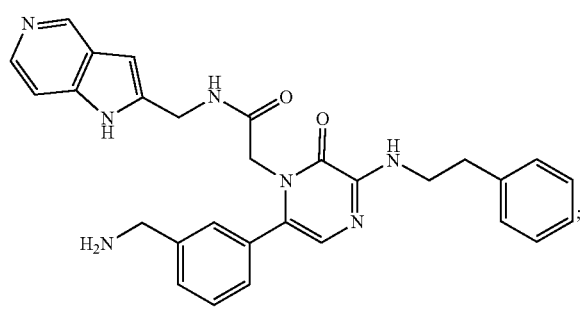
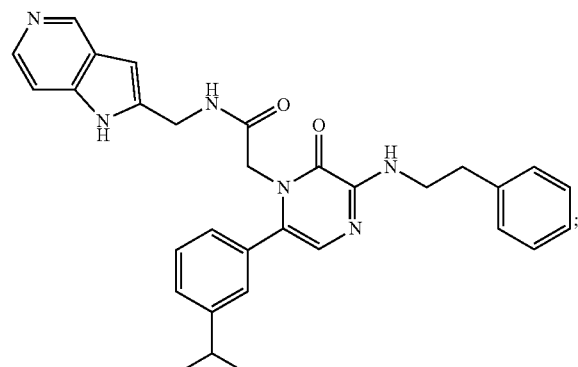
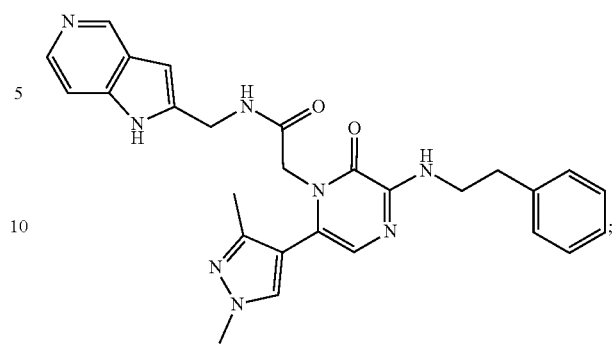
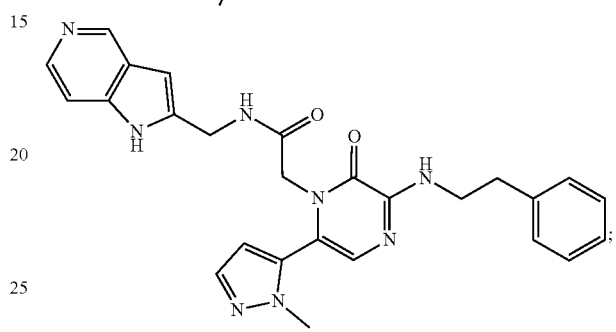
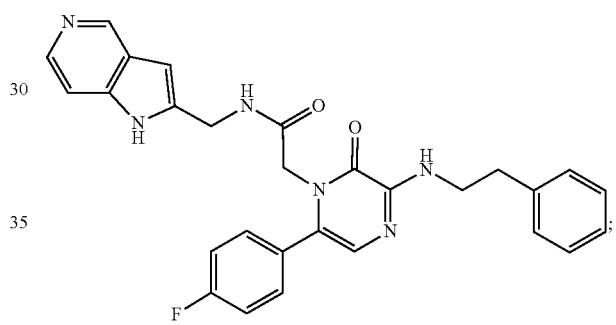
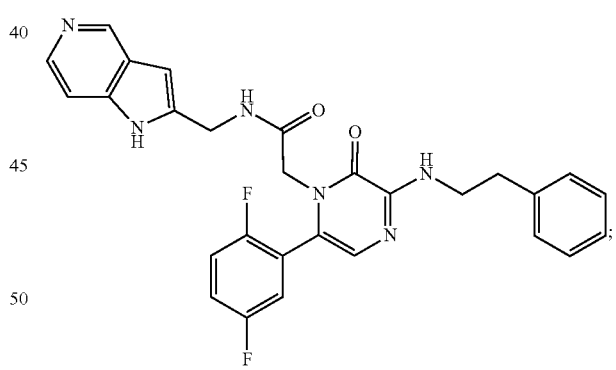
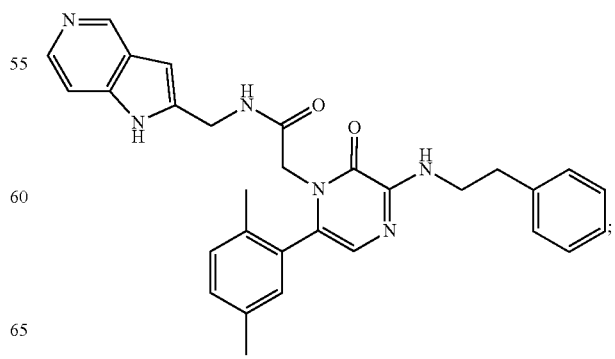

307
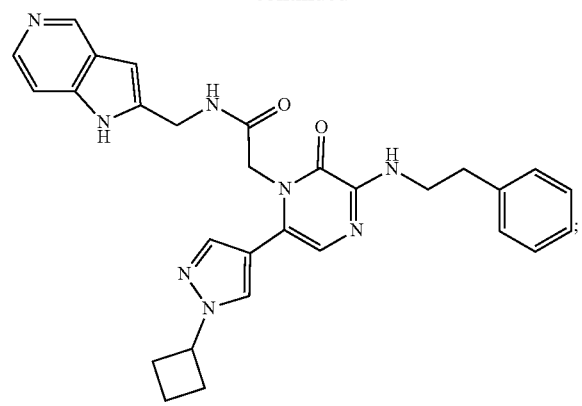
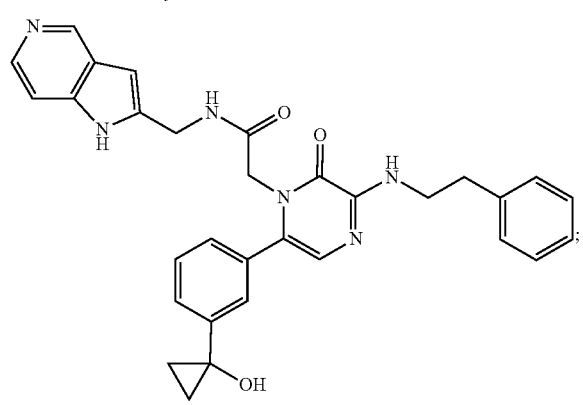
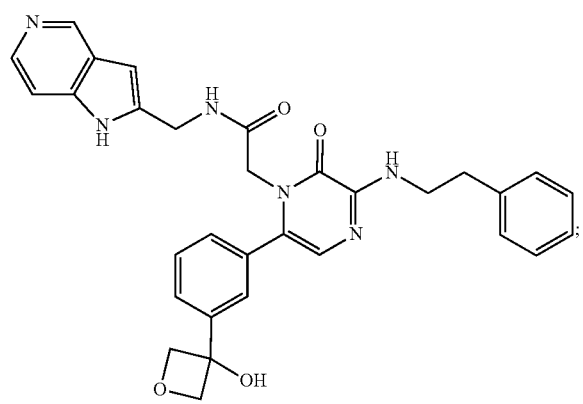
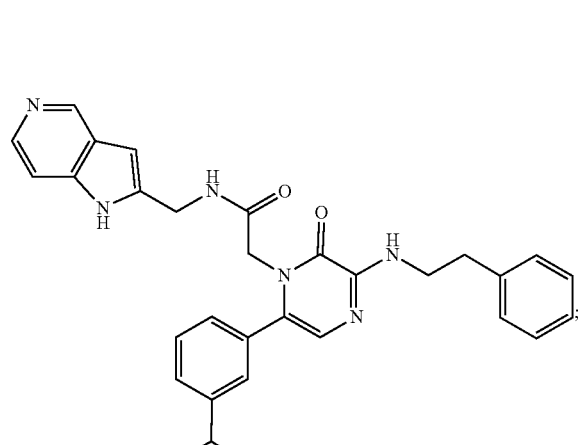
308
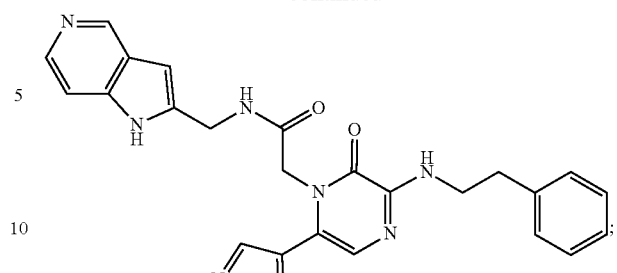
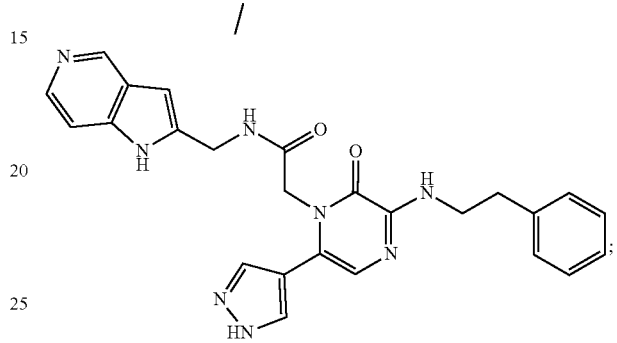
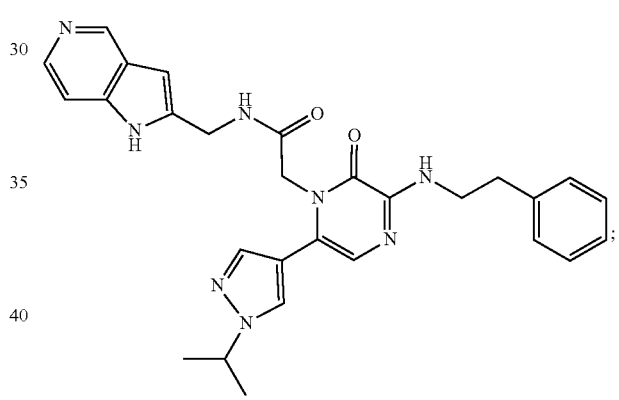
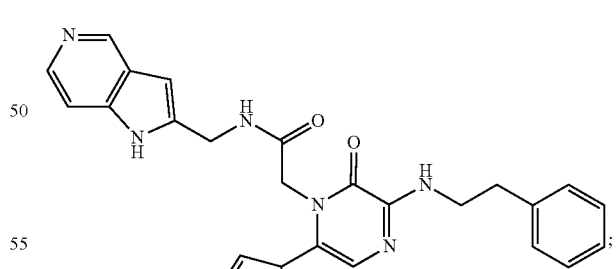
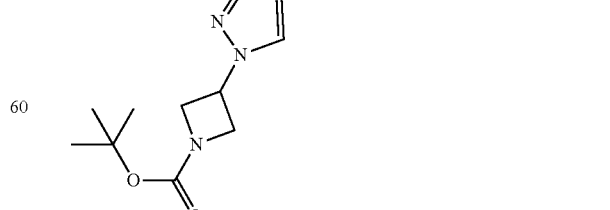

309
-continued
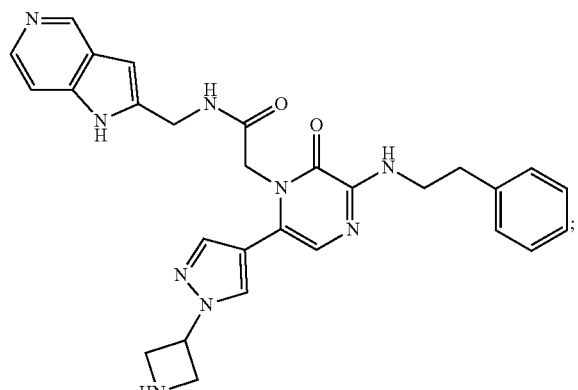
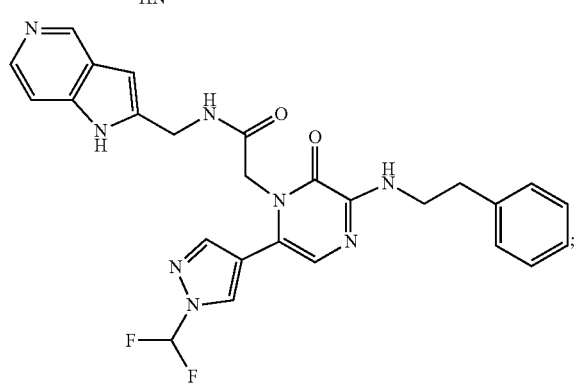
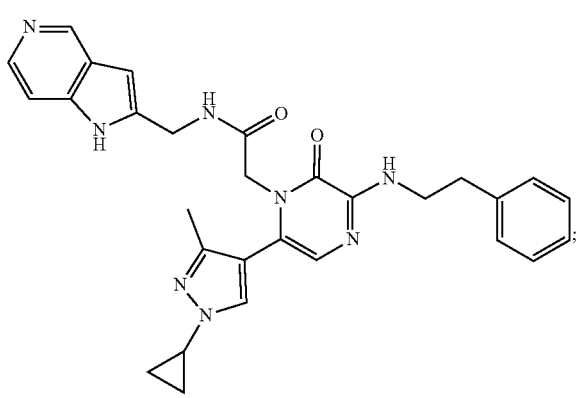
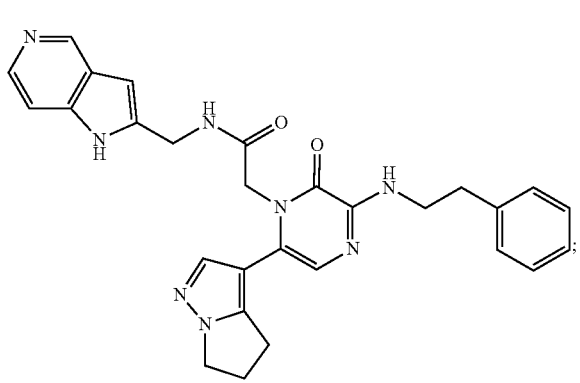
310
-continued
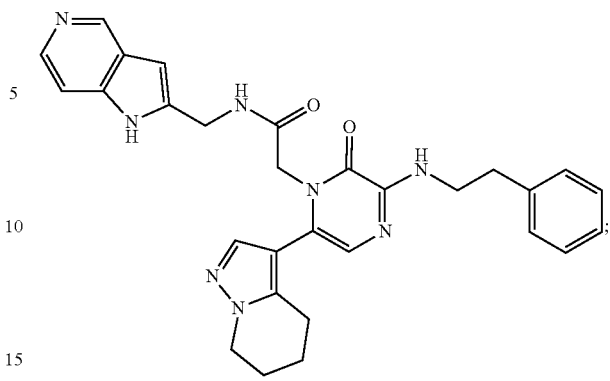
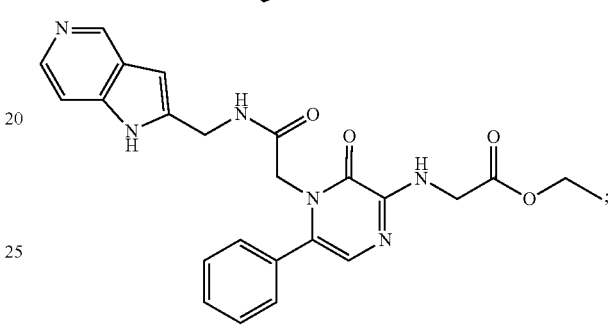
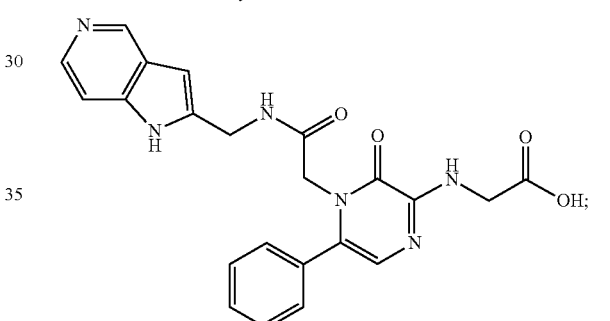
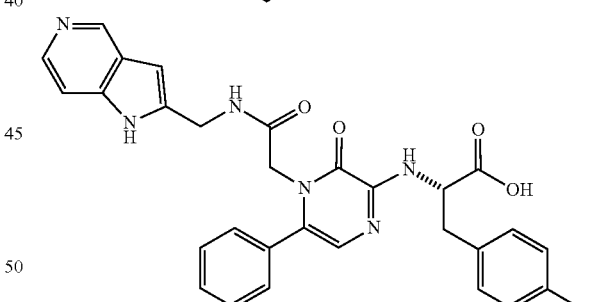
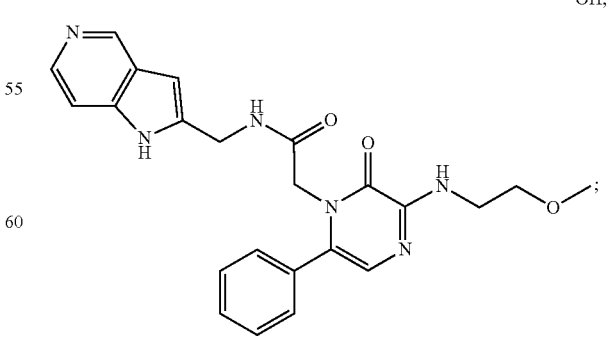

311
-continued
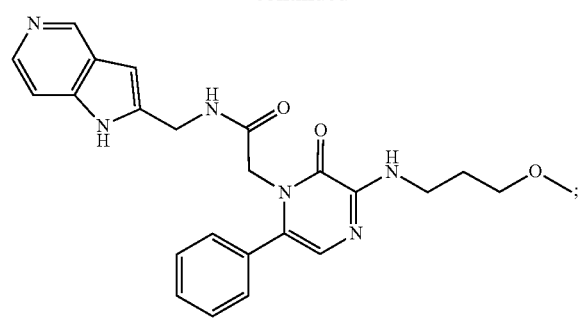
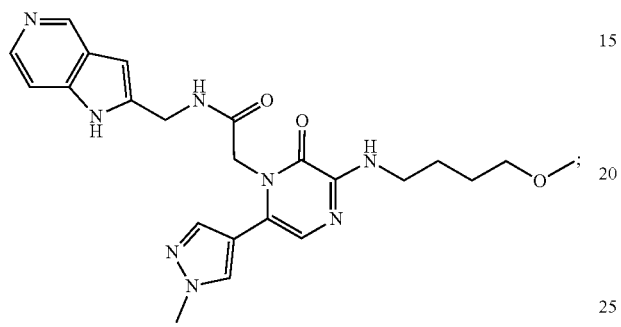
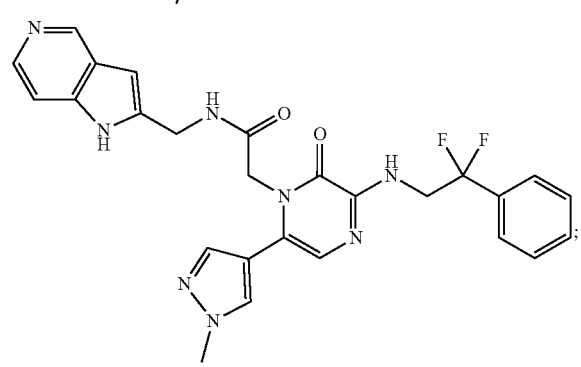
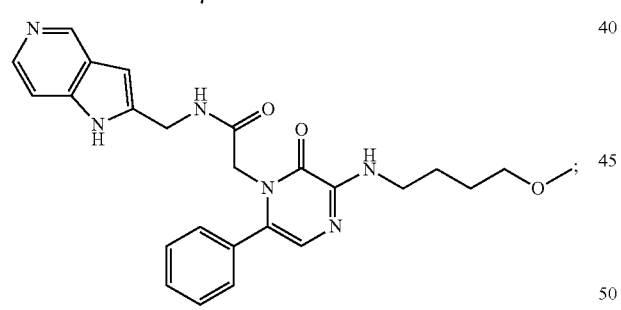
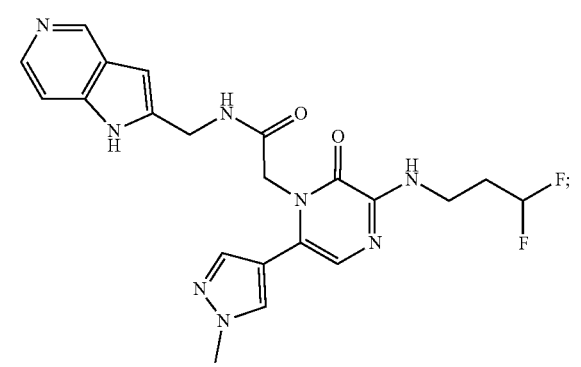
312
-continued
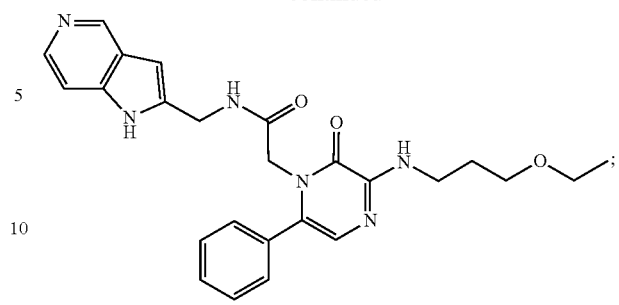
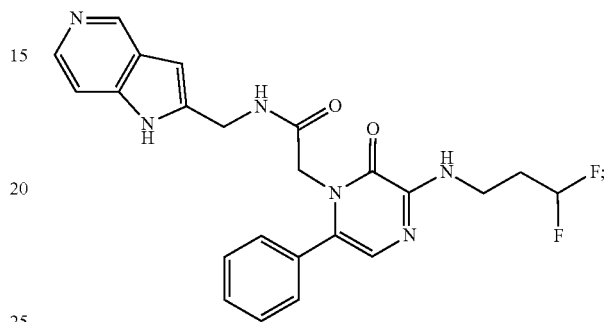
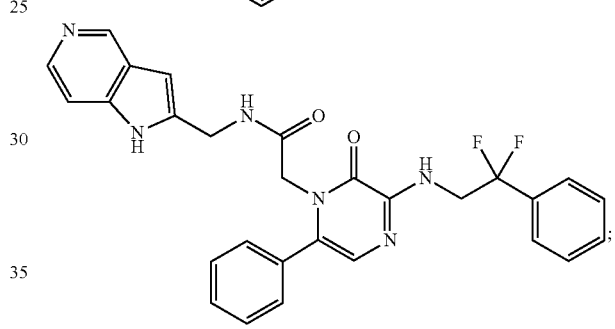
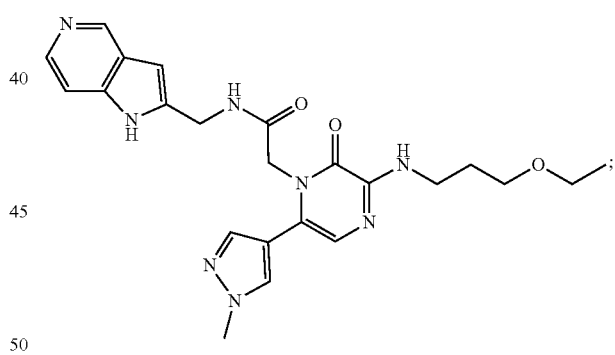
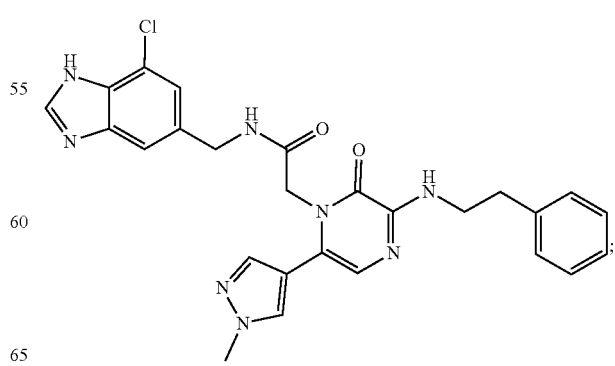

313
-continued
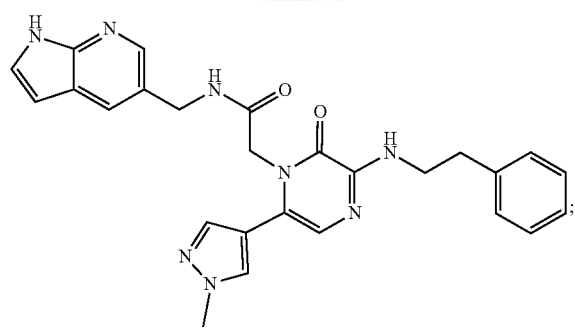
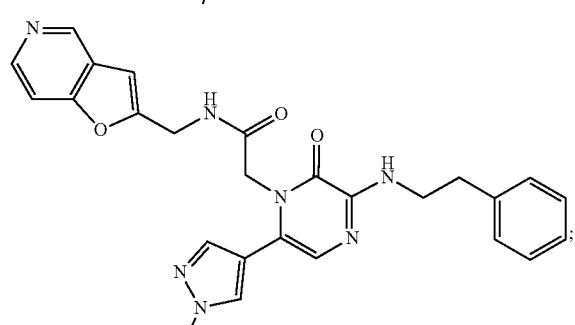
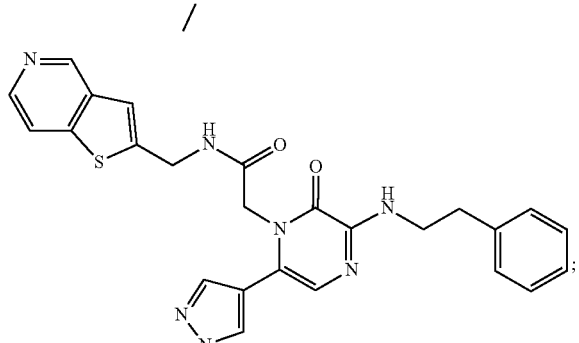
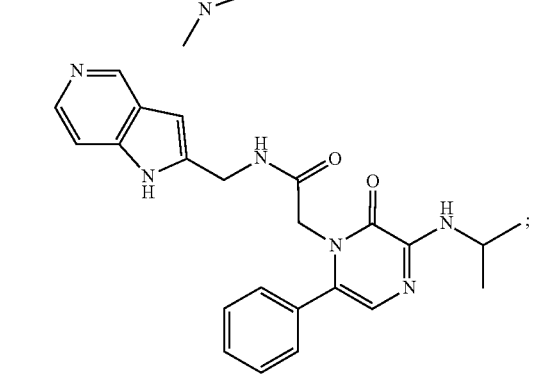
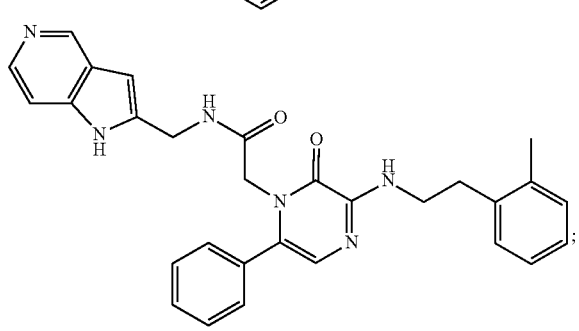
314
-continued
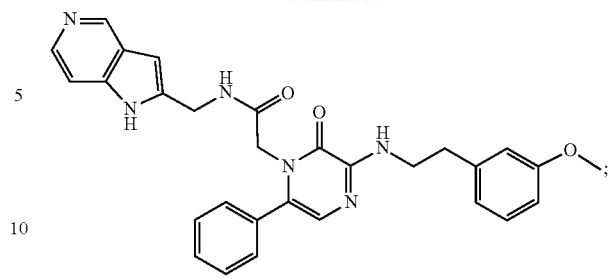
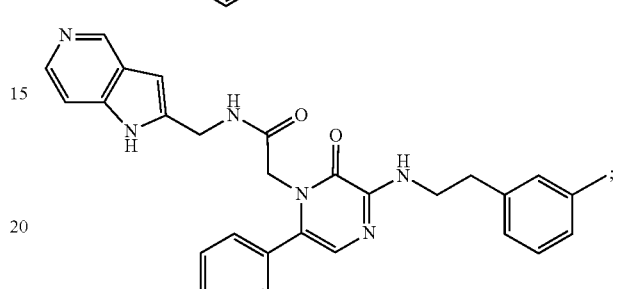
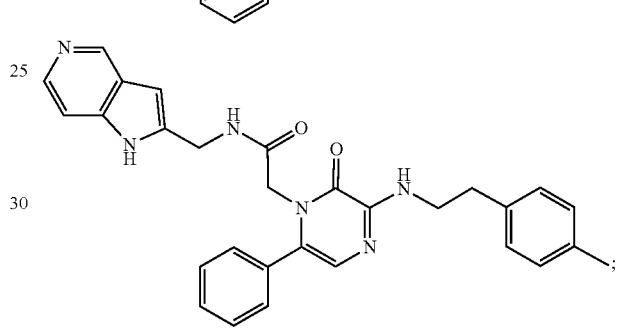
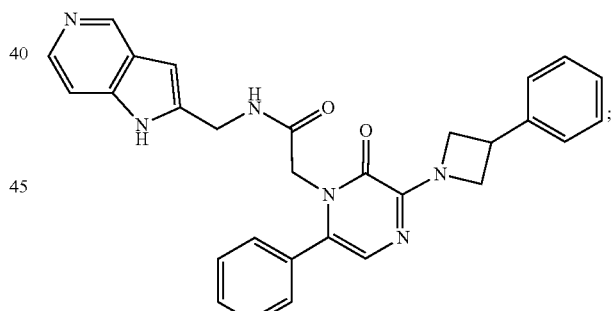
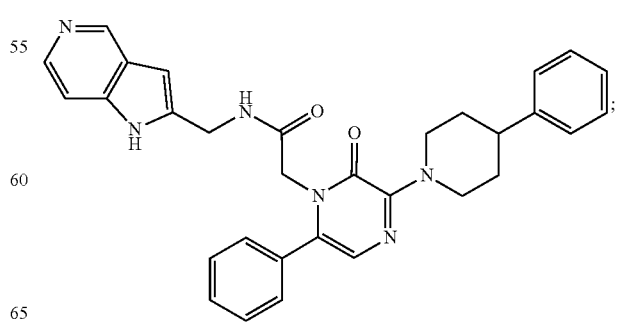

315
-continued
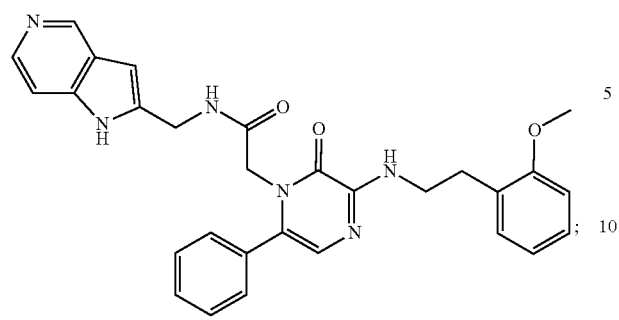
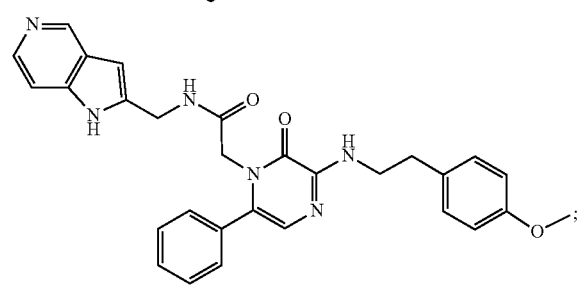
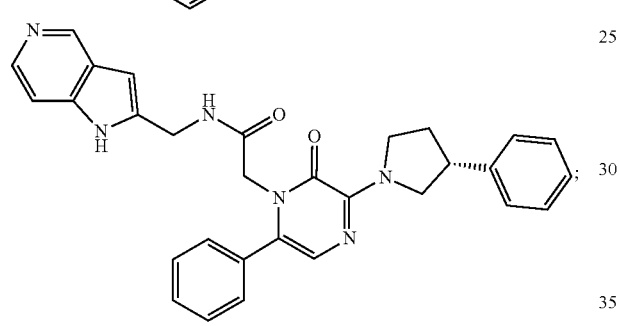
316
-continued
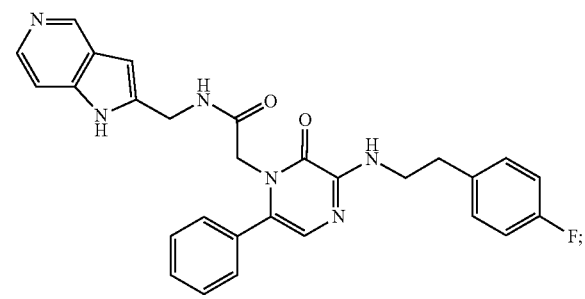
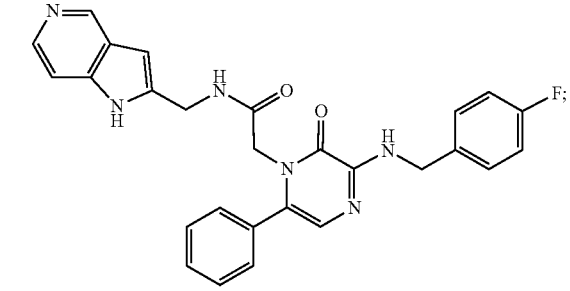
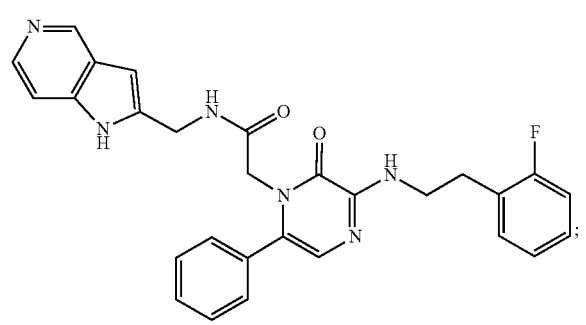
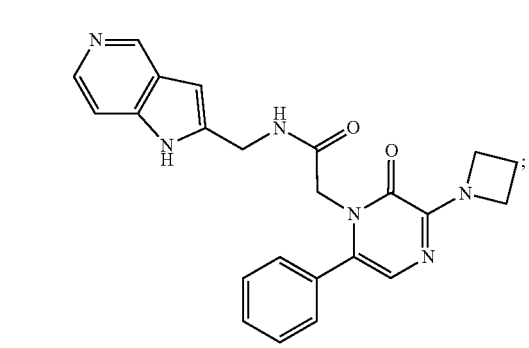
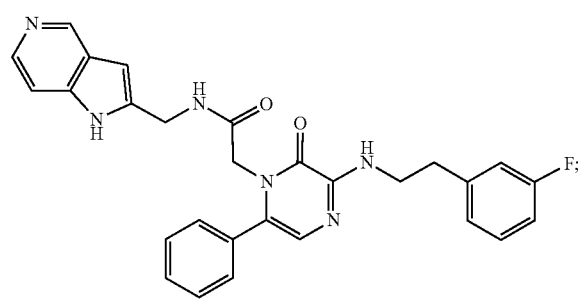
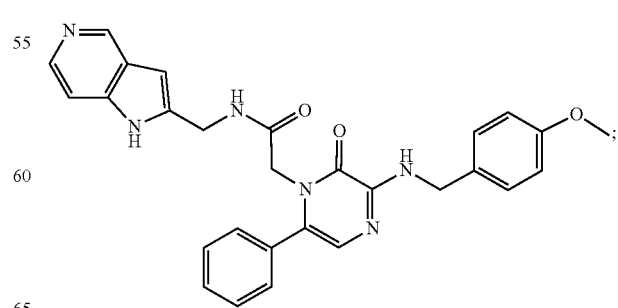

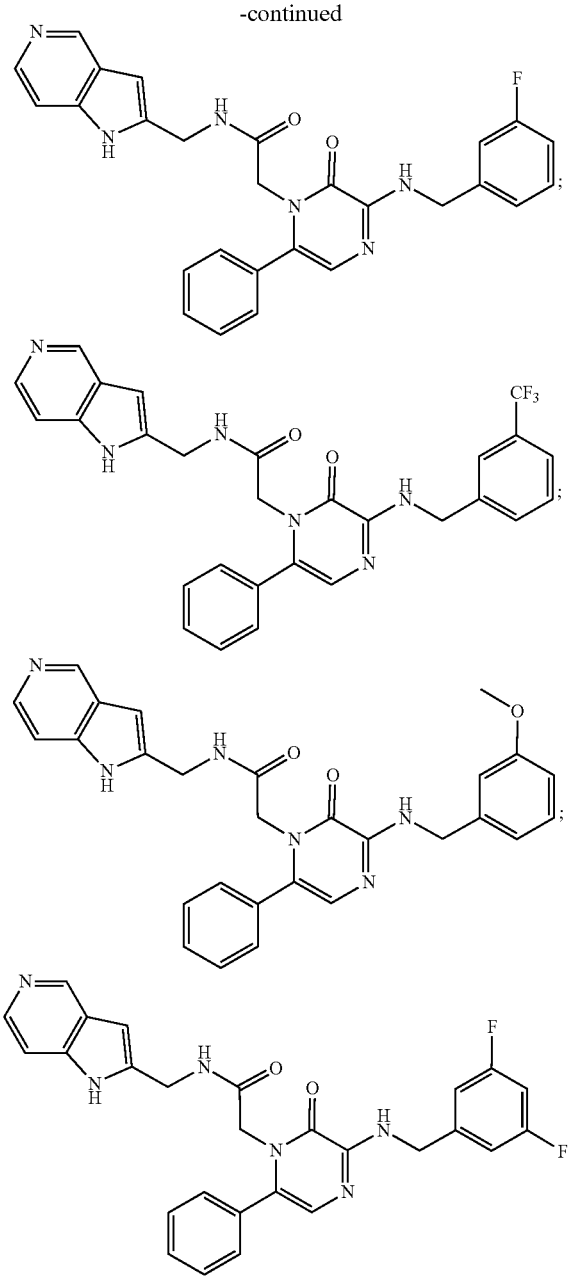
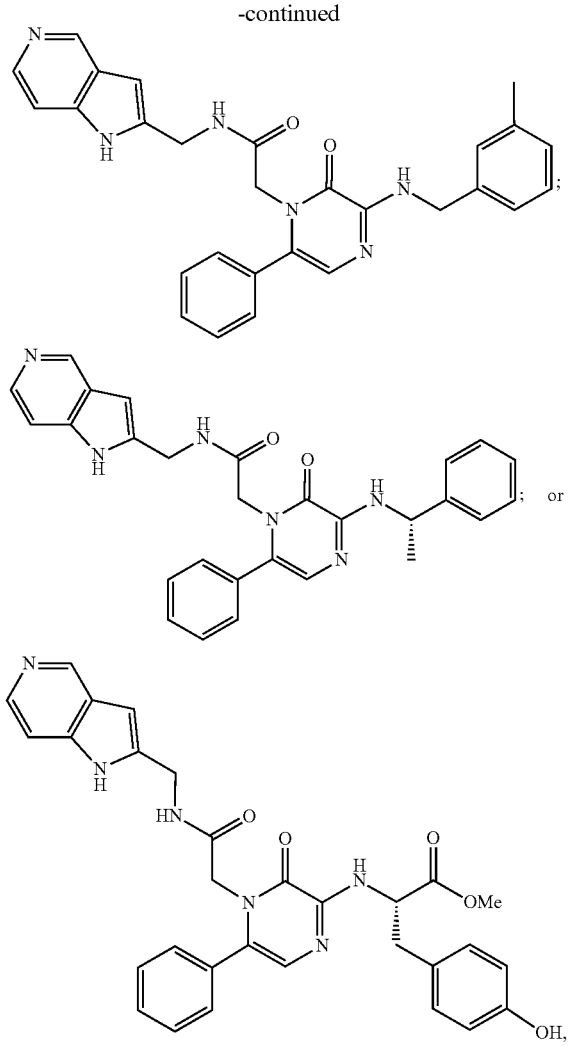
or a stereoisomer, tautomer, or pharmaceutically acceptable salt thereof.
17. A pharmaceutical composition comprising a compound of claim 1, or a stereoisomer, tautomer, or pharmaceutically acceptable salt thereof, and a pharmaceutically acceptable carrier or excipient.
* * * * *

SEQUENCE LISTING

```
<160> NUMBER OF SEQ ID NOS: 1

<210> SEQ ID NO 1
<211> LENGTH: 686
<212> TYPE: PRT
<213> ORGANISM: Homo sapiens

<400> SEQUENCE: 1

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190
```

-continued

Ser Gly Glu Leu Ser Ser Pro Glu Tyr Pro Arg Pro Tyr Pro Lys Leu
        195                 200                 205

Ser Ser Cys Thr Tyr Ser Ile Ser Leu Glu Glu Gly Phe Ser Val Ile
    210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
            275                 280                 285

Trp Lys Ile His Tyr Thr Ser Thr Ala Gln Pro Cys Pro Tyr Pro Met
        290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
            340                 345                 350

Ser Trp Asp Arg Pro Met Pro Ala Cys Ser Ile Val Asp Cys Gly Pro
        355                 360                 365

Pro Asp Asp Leu Pro Ser Gly Arg Val Glu Tyr Ile Thr Gly Pro Gly
    370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
            420                 425                 430

Val Cys Gly Leu Ser Ala Arg Thr Thr Gly Gly Arg Ile Tyr Gly Gly
        435                 440                 445

Gln Lys Ala Lys Pro Gly Asp Phe Pro Trp Gln Val Leu Ile Leu Gly
    450                 455                 460

Gly Thr Thr Ala Ala Gly Ala Leu Leu Tyr Asp Asn Trp Val Leu Thr
465                 470                 475                 480

Ala Ala His Ala Val Tyr Glu Gln Lys His Asp Ala Ser Ala Leu Asp
                485                 490                 495

Ile Arg Met Gly Thr Leu Lys Arg Leu Ser Pro His Tyr Thr Gln Ala
            500                 505                 510

Trp Ser Glu Ala Val Phe Ile His Glu Gly Tyr Thr His Asp Ala Gly
        515                 520                 525

Phe Asp Asn Asp Ile Ala Leu Ile Lys Leu Asn Asn Lys Val Val Ile
    530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575

Gln Arg Gly Phe Leu Ala Arg Asn Leu Met Tyr Val Asp Ile Pro Ile
            580                 585                 590

Val Asp His Gln Lys Cys Thr Ala Ala Tyr Glu Lys Pro Pro Tyr Pro
        595                 600                 605

```
Arg Gly Ser Val Thr Ala Asn Met Leu Cys Ala Gly Leu Glu Ser Gly
    610             615                 620

Gly Lys Asp Ser Cys Arg Gly Asp Ser Gly Gly Ala Leu Val Phe Leu
625             630              635                     640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
                660             665                 670

Ile Asn Tyr Ile Pro Trp Ile Glu Asn Ile Ile Ser Asp Phe
            675             680                 685
```